US012180512B2

(12) United States Patent
Colloca

(10) Patent No.: US 12,180,512 B2
(45) Date of Patent: Dec. 31, 2024

(54) SIMIAN ADENOVIRAL VECTORS WITH TWO EXPRESSION CASSETTES

(71) Applicant: GLAXOSMITHKLINE BIOLOGICALS SA, Rixensart (BE)

(72) Inventor: Stefano Colloca, Rome (IT)

(73) Assignee: GLAXOSMITHKLINE BIOLOGICALS SA, Rixensart (BE)

(*) Notice: Subject to any disclaimer, the term of this patent is extended or adjusted under 35 U.S.C. 154(b) by 0 days.

(21) Appl. No.: 18/453,078

(22) Filed: Aug. 21, 2023

(65) Prior Publication Data
US 2024/0093161 A1    Mar. 21, 2024

Related U.S. Application Data

(63) Continuation of application No. 16/756,377, filed as application No. PCT/EP2018/078210 on Oct. 16, 2018, now abandoned.

(60) Provisional application No. 62/572,944, filed on Oct. 16, 2017.

(51) Int. Cl.
| C12N 15/00 | (2006.01) |
| A61K 39/235 | (2006.01) |
| C12N 7/00 | (2006.01) |
| C12N 15/86 | (2006.01) |
| A61K 39/00 | (2006.01) |

(52) U.S. Cl.
CPC .............. *C12N 7/00* (2013.01); *A61K 39/235* (2013.01); *C12N 15/86* (2013.01); *A61K 2039/5256* (2013.01); *A61K 2039/53* (2013.01); *C12N 2710/10334* (2013.01); *C12N 2710/10342* (2013.01); *C12N 2710/10343* (2013.01); *C12N 2710/16121* (2013.01)

(58) Field of Classification Search
None
See application file for complete search history.

(56) References Cited

U.S. PATENT DOCUMENTS

| 9,580,476 B2 | 2/2017 | Douglas |
| 2010/0143304 A1 | 6/2010 | Lowenstein et al. |
| 2017/0143820 A1 | 5/2017 | Steff |

FOREIGN PATENT DOCUMENTS

| CN | 1965086 A | 5/2007 |
| JP | 2017-523139 A | 8/2017 |
| WO | WO 2005/106002 A2 | 11/2005 |
| WO | WO 2010/086189 A2 | 8/2010 |
| WO | WO 2012/021730 A2 | 2/2012 |
| WO | WO 2012/089833 A2 | 7/2012 |

(Continued)

OTHER PUBLICATIONS

International Search Report and Written Opinion for International Application No. PCT/EP2018/078210 mailed Nov. 28, 2018 (15 pages).

(Continued)

*Primary Examiner* — M Franco G Salvoza
(74) *Attorney, Agent, or Firm* — Birch, Stewart, Kolasch & Birch, LLP

(57) ABSTRACT

A simian adenoviral vector comprising two expression cassettes, wherein each expression cassette comprises a transgene and a promoter, and wherein the first expression cassette is inserted in the E1 region of the simian adenoviral vector, and the second expression cassette is inserted in a region of the adenoviral vector that is compatible with vector replication.

18 Claims, 27 Drawing Sheets
Specification includes a Sequence Listing.

(i) RC1

(ii) RC3:

(iii) RC2:

(56) References Cited

FOREIGN PATENT DOCUMENTS

WO  WO 2015/189425 A1  12/2015
WO  WO 2017/017049 A1  2/2017

OTHER PUBLICATIONS

International Search Report and Written Opinion for PCT Application No. PCT/EP2018/078212 mailed Dec. 5, 2018.
Jin et al., "Identification of Novel Insertion Sites in the Ad5 Genome that Utilize the Ad Splicing Machinery for Therapeutic Gene Expression," Molecular Theraphy (2005), vol. 12, No. 6, pp. 1052-1063.
Li et al., "Modified recombinant adenoviruses increase porcine circovirus 2 capsid protein expression . . . ," Acta Virologica (2016), vol. 60, No. 03, pp. 271-280.
Pierantoni et al., "Mucosal delivery of a vectored RSV vaccine is safe and elicits protective immunity in rodents and nonhuman primates," Molecular Therapy—Methods & Clinical Development (2015), vol. 2, 15018, pp. 1-11.
Sharma et al., "Maternal immunzation with chimpanzee adenovirus expressing RSV fusion protein protects against neonatal RSV pulmonary infection," Vaccine (2014), vol. 32, pp. 5761-5768.
Small et al., "Construction and characterization of E1- and E3-deleted adenovirus vectors . . . ," Human Gene Therapy (2014), vol. 25, No. 4, pp. 328-338.

(i) RC1

(ii) RC3:

(iii) RC2:

SIMIAN ADENOVIRAL VECTORS WITH TWO EXPRESSION CASSETTES

CROSS-REFERENCE TO RELATED APPLICATIONS

This application is a Continuation of copending application Ser. No. 16/756,377 filed Apr. 15, 2020, which is the National Phase under 35 U.S.C. § 371 of International Application No. PCT/EP2018/078210, filed on Oct. 16, 2018, which claims the benefit under 35 U.S.C. § 119(e) to U.S. Provisional Application No. 62/572,944, filed on Oct. 16, 2017, all of which are hereby expressly incorporated by reference into the present application.

REFERENCE TO ELECTRONIC SEQUENCE LISTING

This application contains a Sequence Listing which has been submitted electronically in .XML format and is hereby incorporated by reference in its entirety. Said .XML copy, created on Aug. 21, 2023, is named 2801-0326PUS2_SL.xml and is 138,799 bytes in size. The sequence listing contained in this .XML file is part of the specification and is hereby incorporated by reference herein in its entirety.

FIELD OF THE INVENTION

This invention is in the field of recombinant adenoviral vectors. The invention relates to an adenoviral vector comprising two expression cassettes. In particular, the invention relates to a simian adenovirus such as a chimpanzee (chimp) adenovirus comprising two expression cassettes.

BACKGROUND OF THE INVENTION

Recombinant adenoviruses are useful in gene therapy and as vaccines.

Human adenoviruses have been widely used for gene transfer applications due to their large transgene capacity and ability to achieve highly efficient gene transfer in a variety of target tissues.

However, most humans are exposed to and develop immunity to human adenoviruses. Therefore, there is a demand for vectors which effectively deliver molecules to a target and minimize the effect of pre-existing immunity to human adenovirus serotypes. Simian adenoviruses are effective in this regard; they are sufficiently closely related to human viruses to be effective in inducing immunity to delivered exogenous antigens to which humans have little or no pre-existing immunity. Therefore, viral vectors based on simian adenoviruses can provide an alternative to the use of human derived adenoviral vectors for the development of nucleic acid based vaccines.

Replication defective adenoviruses deliver their genome to the interior of a cell and, because they do not replicate, do not amplify the transgene payload. Typically, the E1 gene is replaced with a transgene cassette comprising a promoter of choice and a nucleic acid sequence corresponding to a gene or genes of interest, resulting in a replication defective recombinant virus.

There is a need in the art for improved recombinant adenoviruses.

SUMMARY OF THE INVENTION

The invention relates to a simian adenoviral vector comprising two expression cassettes. In particular, the invention relates to a simian adenovirus such as a chimpanzee (chimp) adenovirus comprising two expression cassettes. Examples of suitable chimp adenoviruses include ChAd155 and ChAd83.

The adenoviral vectors of the invention are useful as components of immunogenic compositions for the induction of an immune response in a subject, methods for their use in treatment and processes for manufacture.

The term "vector" refers to an agent (such as a plasmid or virus) that contains or carries genetic material and can be used to introduce exogenous genes into an organism. The adenoviral vector of the present invention is derived from a non-human simian adenovirus, also referred to as a "simian adenovirus". Preferably, the simian adenoviral vector of the present invention is a simian adenovirus.

Each expression cassette in the adenoviral vector of the invention comprises a transgene and a promoter. A "transgene" is a nucleic acid sequence, heterologous to the vector sequences flanking the transgene, which encodes a polypeptide of interest. The nucleic acid coding sequence is operatively linked to regulatory components in a manner which permits transgene transcription, translation, and/or expression in a host cell. A "promoter" is a nucleotide sequence that permits the binding of RNA polymerase and directs the transcription of a gene. Typically, a promoter is located in a non-coding region of a gene, proximal to the transcriptional start site.

In adenoviral vectors of the invention, the first expression cassette is inserted in the E1 region of the virus, and the second expression cassette is inserted into a second region of the adenoviral vector.

In a simian adenoviral vector comprising two expression cassettes of the invention, the first expression cassette is inserted in the E1 region of the simian adenoviral vector, and the second expression cassette is inserted in a region of the adenoviral vector that is compatible with vector replication. A region of the adenoviral vector genome is considered "compatible with vector replication" if disruption of this region would not affect the ability of the adenoviral vector to replicate.

Preferably, in adenoviral vectors of the invention, the first expression cassette is inserted in the E1 region of the virus, and the second expression cassette is inserted into the E3, HE1 or HE2 region of the adenoviral vector. As is well known in the art, the E3 genes are expressed in the early phase of transduction to prepare the host cell for viral replication. E3 is involved in immune modulation. The term "HE1" is used to describe a site located between the stop codons of L5 and E4. The term "HE2" has been used to define a site located between the end of the ITR and the cap site of E4 mRNA.

For example, in a ChAd155 adenovirus vector:
HE1 ChAd155: insertion site between bp 34611 and 34612 of SEQ ID NO: 1.
HE2 ChAd155: insertion site between bp 37662 and 37663 of SEQ ID NO: 1.
In another example, in a ChAd83 adenovirus vector:
HE1 ChAd83: insertion site between bp 33535 and 33536 of SEQ ID NO: 2.
HE2 ChAd83: insertion site between bp 36387 and 36388 of SEQ ID NO: 2.

As the first expression cassette is inserted in the E1 region of the adenoviral vector, the native E1 region is deleted. In order to increase the cloning capacity of the vector, the native E3 region can be removed from the adenoviral vector. The native E3 region can be deleted from the adenoviral vector in embodiments of the invention where the second expression cassette is inserted in the E3 region, or in embodiments where the second expression cassette is not inserted into the E3 region. The insertion in HE1 or HE2 site doesn't require deletion of any specific sequence of the vector backbone.

Preferably, the second expression cassette is inserted into the HE1 or HE2 region of the adenoviral vector. Most preferably, the second expression cassette is inserted in the HE2 region of the adenoviral vector. In one embodiment, the native E3 region is deleted from the adenoviral vector to increase the cloning capacity of the vector, and the second expression cassette is inserted in the HE1 or HE2 region of the adenoviral vector.

In embodiments of the invention, the first expression cassette of the adenoviral vector may comprise a human CMV or an enhanced human CMV promoter, and/or the second expression cassette may comprise a human CMV or an enhanced human CMV promoter.

In a preferred embodiment, the first and second expression cassettes comprise different promoters. For example, in one embodiment, the first expression cassette may comprise a human CMV promoter and the second expression cassette an enhanced human CMV promoter (or vice versa).

In one aspect of the invention, there is provided an adenoviral vector of the invention, wherein the first expression cassette is inserted in the E1 region of the virus, and the second expression cassette is inserted in a region of the adenoviral vector that is compatible with vector replication, wherein at least one of the first and second expression cassette comprises an enhanced CMV promoter. In some embodiments, the enhanced hCMV promoter can include a nucleic acid sequence having at least about 90%, at least about 95%, at least about 96%, at least about 97%, at least about 98%, at least about 99%, or more, sequence identity to SEQ ID NO: 6. In some embodiments, the promoter comprises or consists of a nucleic acid sequence of SEQ ID NO: 6.

Adenoviral vectors of the invention are derived from a simian adenoviral vector, for example, from chimpanzees (*Pan troglodytes*), bonobos (*Pan paniscus*), gorillas (*Gorilla gorilla*) and orangutans (*Pongo abelii* and *Pongo pygnaeus*). Chimpanzee adenoviruses include, but are not limited to AdY25, ChAd3, ChAd19, ChAd25.2, ChAd26, ChAd27, ChAd29, ChAd30, ChAd31, ChAd32, ChAd33, ChAd34, ChAd35, ChAd37, ChAd38, ChAd39, ChAd40, ChAd63, ChAd83, ChAd155, ChAd15, SadV41, sAd4310A, sAd4312, SAdV31, SAdV-A1337, ChAdOx1, ChAdOx2 and ChAd157. Preferably, the simian adenoviral vector of the invention is a ChAd83 or ChAd155 adenovirus vector, most preferably a ChAd155 adenovirus vector.

Preferably, the adenoviral vector of the invention has a seroprevalence of less than 30%, preferably less than 10% in human subjects and, most preferably, no seroprevalence in human subjects.

In a preferred embodiment, the simian adenoviral vector of the invention is capable of infecting a mammalian cell.

In one embodiment, the first and second expression cassettes of the adenoviral vector of the invention comprise transgenes from respiratory syncytial virus (RSV). For example, in one embodiment, one of the expression cassettes comprises an RSV F antigen, and the other expression cassette comprises RSV M and N antigens. In such embodiments, the vector preferably encodes an RSV F0ΔTM antigen (fusion (F) protein deleted of the transmembrane and cytoplasmic regions), and RSV M2-1 (transcription antitermination) and N (nucleocapsid) antigens.

The present invention also provides a composition comprising a simian adenoviral vector and a pharmaceutically acceptable excipient.

In addition, the present invention provides a simian adenoviral vector or composition comprising such an adenoviral vector for use as a medicament, a vaccine, and/or for the therapy or prophylaxis of a disease.

The invention also provides a method of inducing an immune response in a subject comprising administering the simian adenoviral vector or composition to the subject.

Figure 1:
FIG. 1: Simian adenoviral constructs with a single expression cassette. Inverted terminal repeats (ITR) flank the 3' and 5' ends; E1 is the early gene 1; CMV is the cytomegalovirus promoter; CASI is the CASI promoter, RG is a model antigen, WPRE is the Woodchuck Hepatitis Posttranscriptional Regulatory Element, ΔE3 denotes that the early gene 3 is deleted; fiber denotes the adenoviral gene encoding the fiber protein and E4 is the early gene 4.
Figure 1:
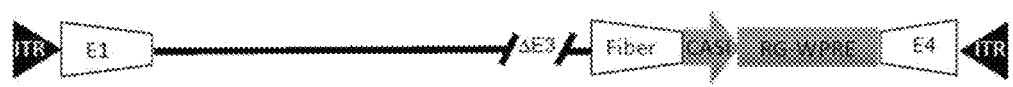
Figure 1:
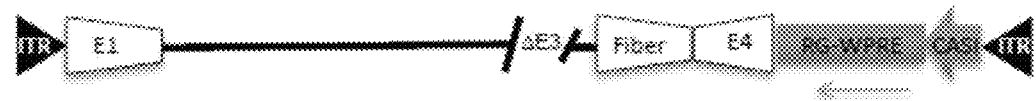

Three different simian adenoviral vectors are shown in FIG. 1. The vector of FIG. 1(*i*) was constructed by inserting a transgene expression cassette in place of the E3 region of the adenoviral genome ("RC1") (top panel), the vector of FIG. 1(*ii*) was formed by inserting a transgene expression cassette in the HE1 region, i.e., between the stop codons of the fiber gene and the E4 region ("RC3") (middle panel), and the vector of FIG. 1(*iii*) was made by inserting a transgene expression cassette in the HE2 region, i.e., between the end of the ITR and the cap site of E4 mRNA ("RC2") (bottom panel).

Figure 2A:
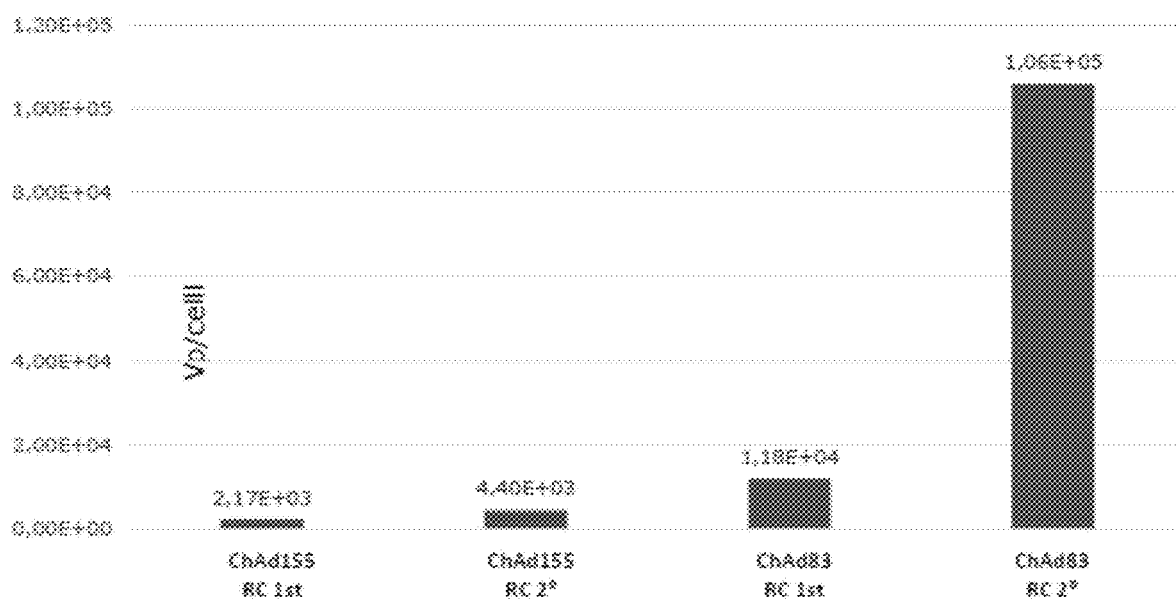

FIG. 2A: Production of ChAd155 and ChAd83 with transgene cassette inserted in E3 and HE2 sites (RC1 and RC2 vectors of FIG. 1) in a primary human cell line.

Figure 2B:
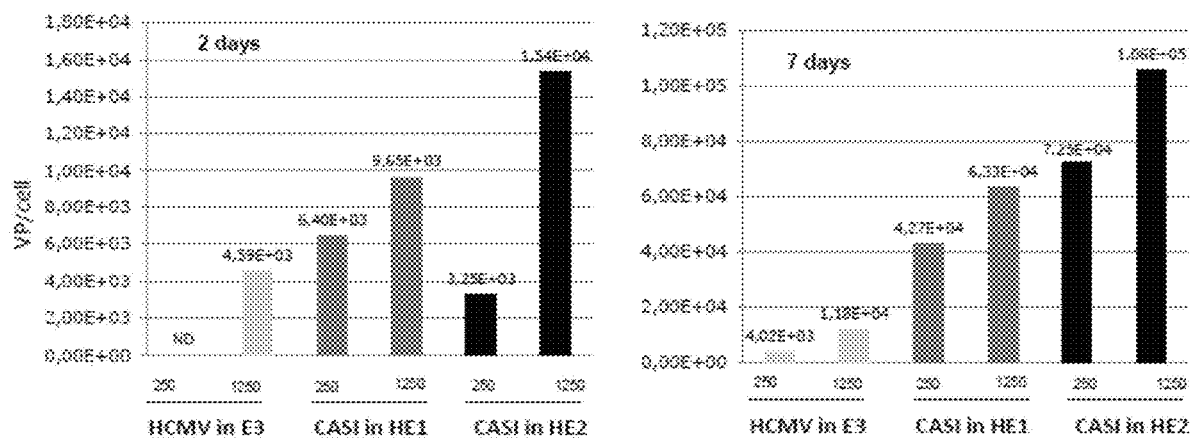

FIG. 2B: Production of ChAd83 with transgene cassette inserted in E3, HE1 and HE2 (the RC1, RC2 and RC3 vectors of FIG. 1) in a human MRC5 cell line at two and seven days post-infection. Cells were infected at multiplicities of infection of 250 and 1250.

Figure 3A:
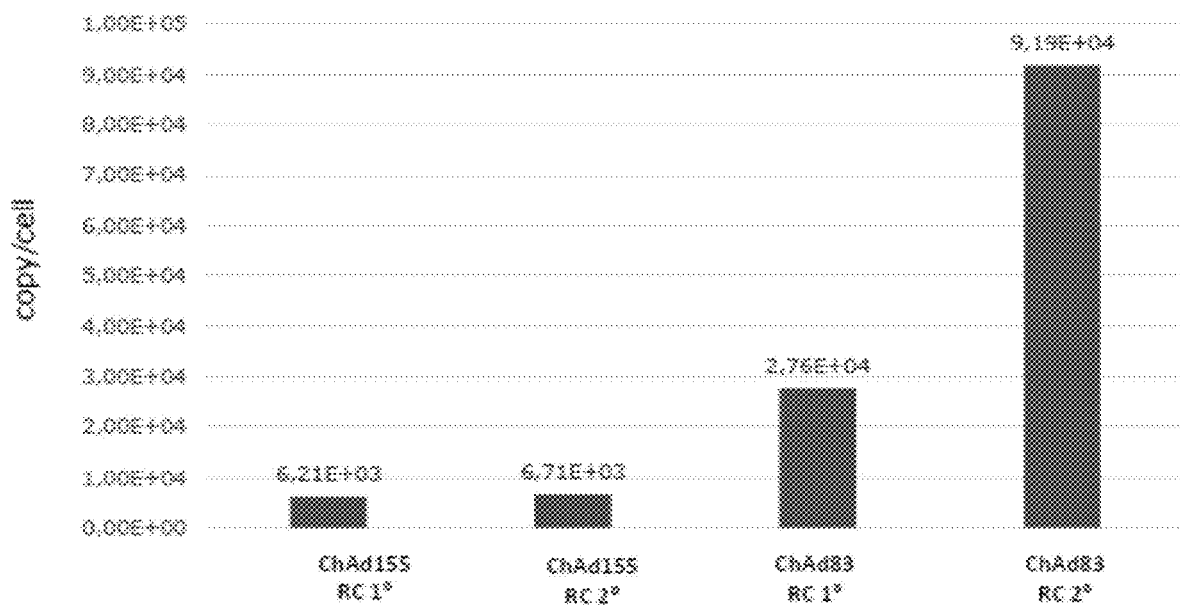

FIG. 3A: Total viral genome copy number of RC1 and RC2 vector (ChAd155 and ChAd83) of FIG. 1 in a primary human cell line.

Figure 3B:
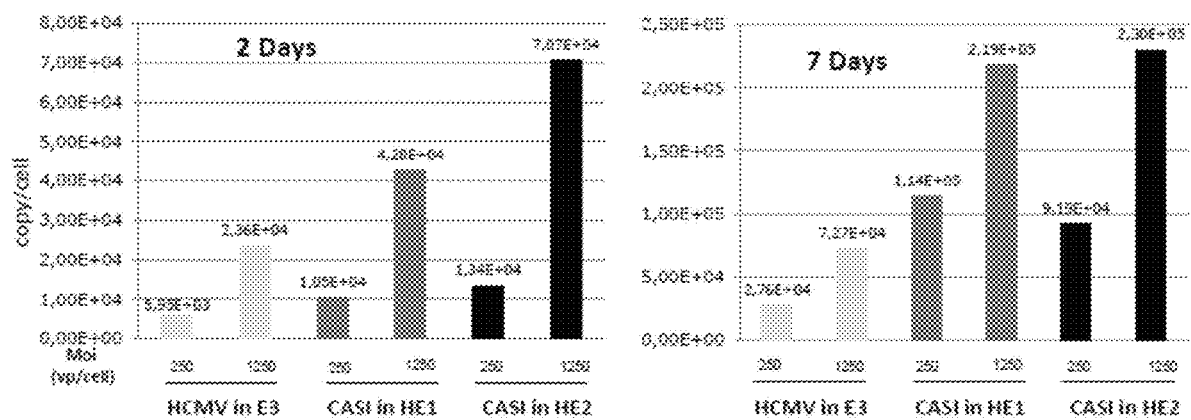

FIG. 3B: Total viral genome copy number of RC1, RC2 and RC3 versions of ChAd83 vector of FIG. 1 in a human MRC5 cell line at two and seven days post-infection. Cells were infected at multiplicities of infection of 250 and 1250.

Figure 4A:
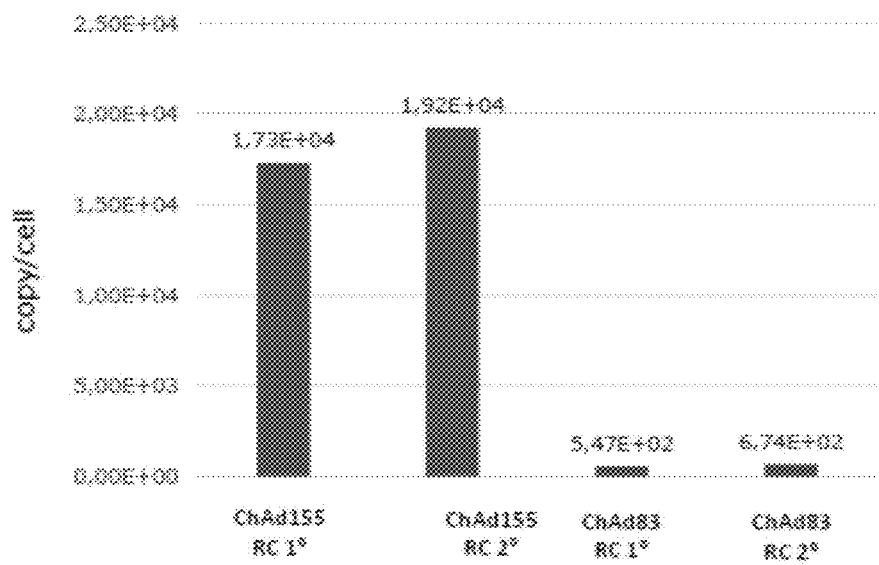
Figure 4B:
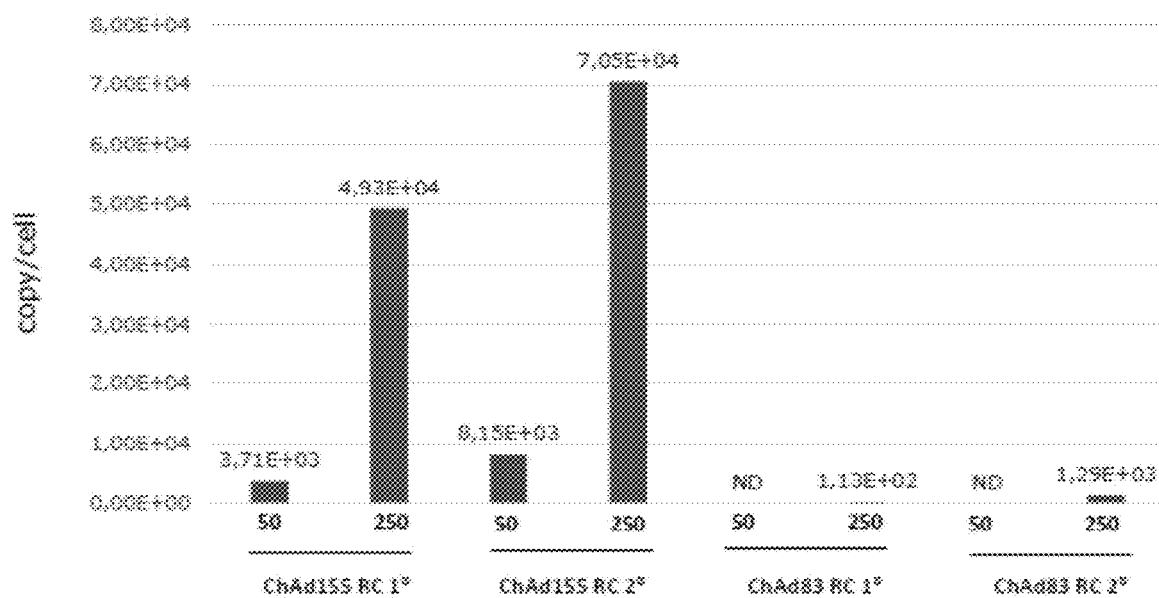

FIG. 4: Total viral genome copy number of ChAd155 RC1 and RC2 and ChAd83 RC1 and RC2 vectors of FIG. 1 in a murine cell line FIG. 4(A), top panel) and in a non-human primate cell line FIG. 4(B), bottom panel). Cells were infected at multiplicities of infection of 50 and 250.

Figure 5A:
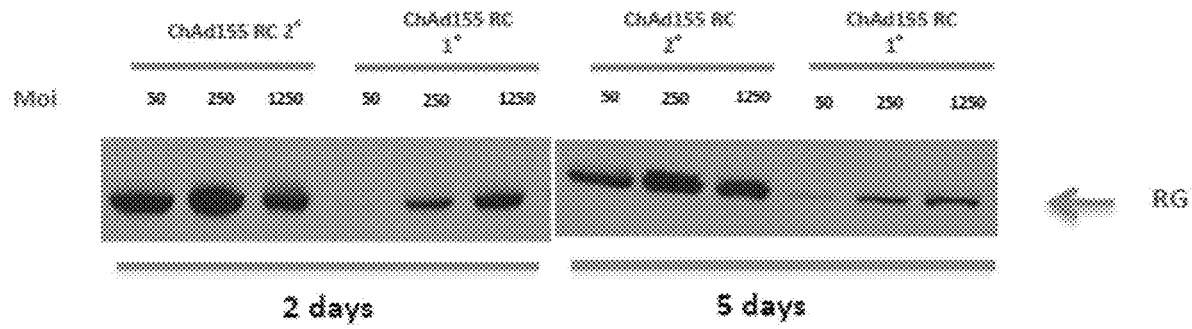
Figure 5B:
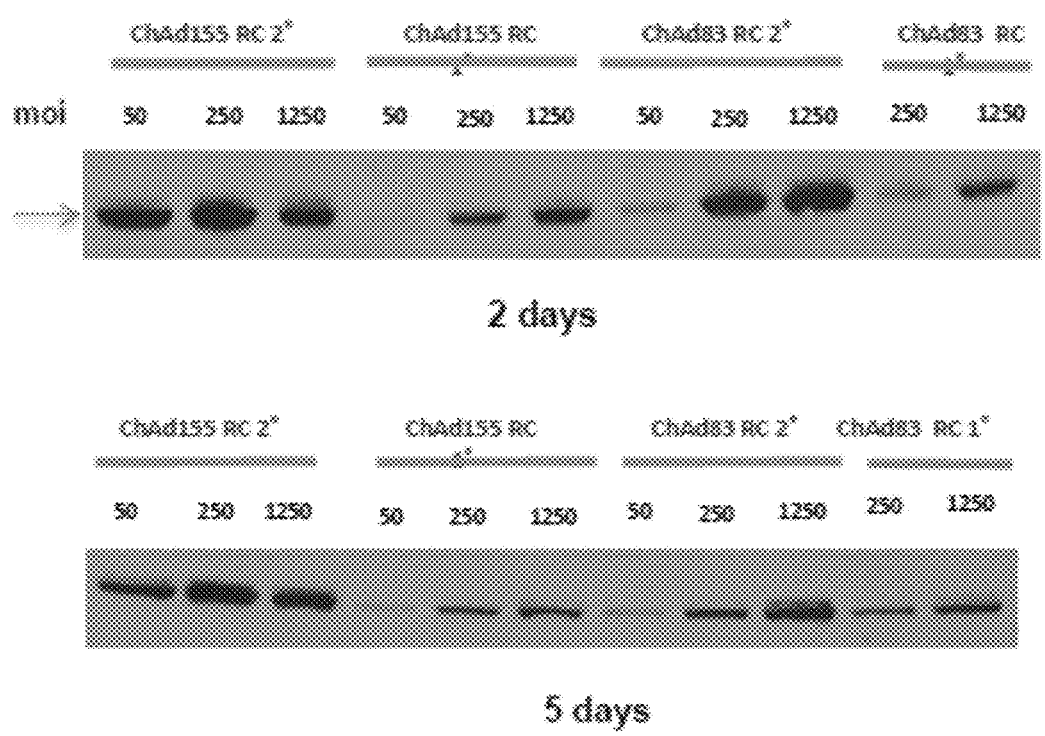

FIG. 5: Comparison of the expression levels of ChAd155 RC1 and RC2 vectors expressing a model rabies glycoprotein (RG) transgene in a murine cell line, demonstrated by western blot at two and five days post-infection FIG. 5(A), top panel). Comparison of the expression levels of ChAd155 RC1 and RC2 vectors with ChAd83 RC1 and RC2 vectors expressing a model rabies glycoprotein (RG) transgene in a murine cell line, demonstrated by western blot at two and five days post-infection FIG. 5(B), bottom panel). Cells were infected at multiplicities of infection of 50, 250 and 1250.

Figure 5C:
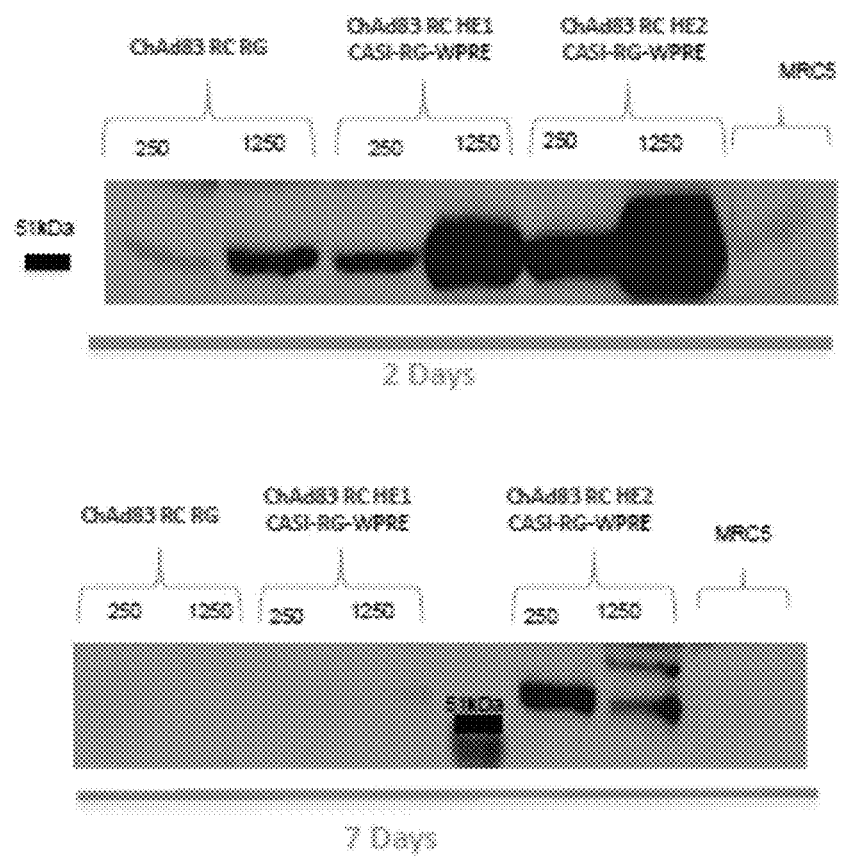

FIG. 5(C): Comparison of the expression levels of ChAd83 RC1, RC2 and RC3 vectors expressing a model rabies glycoprotein (RG) transgene in a human MRC5 cell line, demonstrated by western blot at two and seven days post-infection. Cells were infected at multiplicities of infection of 250 and 1250.

Figure 6:
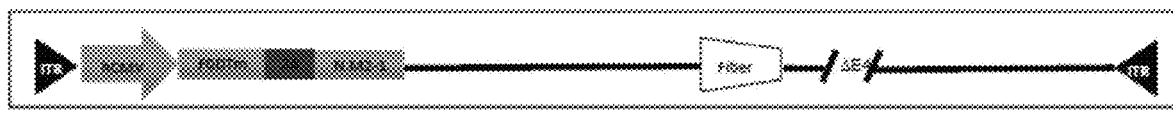

FIG. 6: Another simian adenoviral construct of with a single expression cassette. Inverted terminal repeats (ITR) flank the 3' and 5' ends; human CMV (hCMV) is the cytomegalovirus promoter; FΔTM (F0DTM) and N.M2-1 are RSV antigens; 2A is a self-cleaving linking sequence; ΔE4 denotes that the early gene 4 is deleted; fiber denotes the adenoviral gene encoding the fiber protein. In the vector of FIG. 6, the transgene expression cassette is inserted in place of the E1 region of the adenoviral genome.

Figure 7:
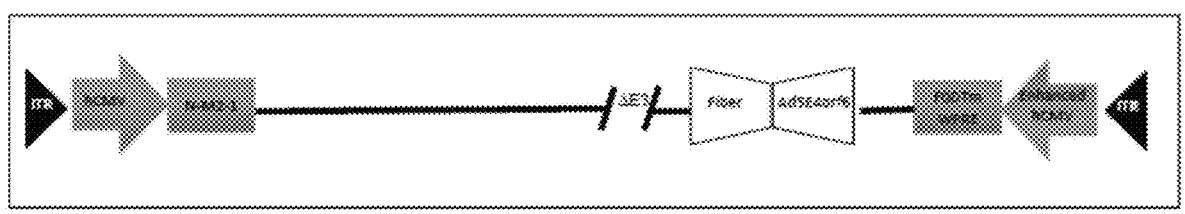

FIG. 7: A simian adenoviral construct according to the invention with a dual expression cassette. Inverted terminal repeats (ITR) flank the 3' and 5' ends; human CMV (hCMV) is the cytomegalovirus promoter; Enhanced hCMV is the enhanced cytomegalovirus promoter; N-M2-1 and FΔTM (F0DTM) are the RSV antigens; WPRE is the Woodchuck Hepatitis Posttranscriptional Regulatory Element; ΔE3 denotes that the early gene 3 is deleted; fiber denotes the adenoviral gene encoding the fiber protein; and Ad5E4orf6 in a substitute in the early gene 4 (E4) region.

The vector of FIG. 7 was constructed by inserting a first transgene expression cassette in place of the E1 region of the adenoviral genome, and a second transgene expression cassette in the HE2 region, i.e., downstream of the right ITR.

Figure 8:
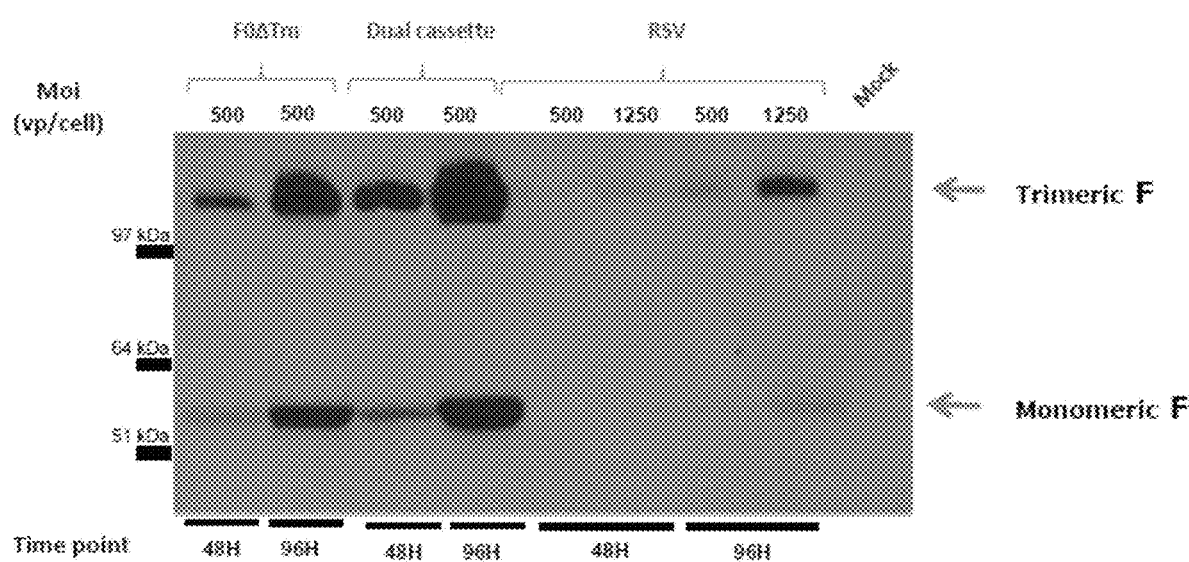

FIG. 8: Comparison of the expression levels of vectors expressing F0ΔTM transgene in a MRC5 cell line, demonstrated by western blot at 48 hours and 96 hours post-infection under non-reducing conditions. Cells were infected at multiplicities of infection of 500 and 1250.

Figure 9:
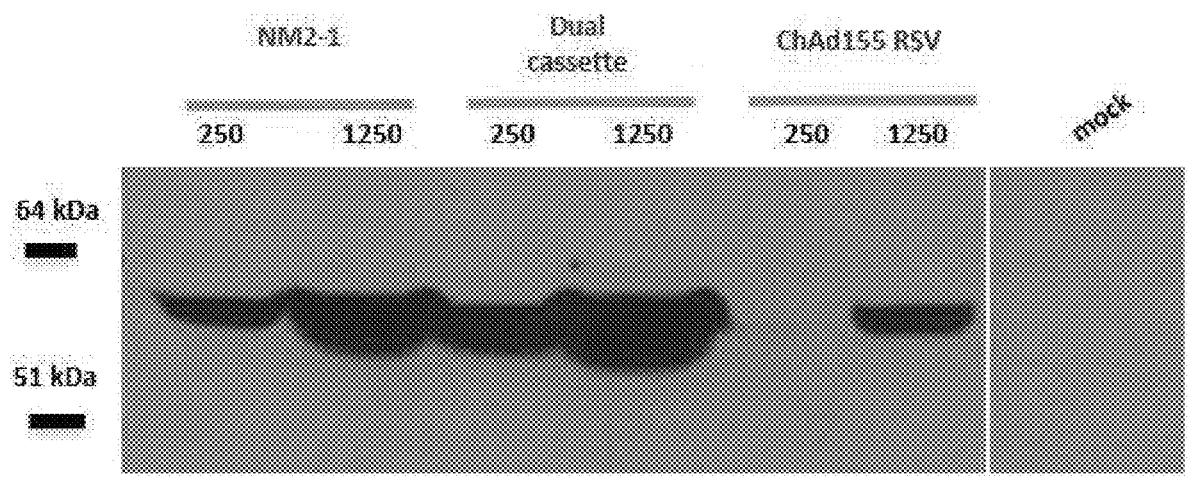

FIG. 9: Comparison of the expression levels of vectors expressing NM2-1 transgene in a MRC5 cell line, demonstrated by western blot at 48 hours post-infection under reducing conditions. Cells were infected at multiplicities of infection of 250 and 1250.

Figure 10:
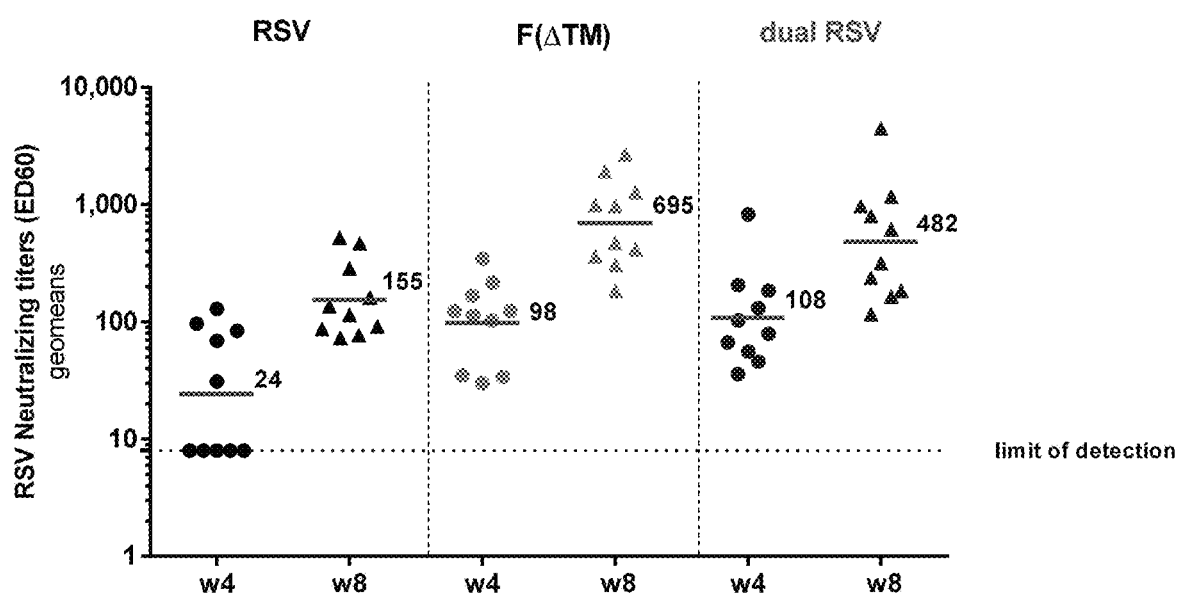

FIG. 10: Comparison of the immunogenicity from ChAd155 vectors expressing the RSV antigen F0ΔTM (FΔTm). The data was collected at 4 weeks and 8 weeks after vaccination with a dose of 5×10$^8$ virus particles.

Figure 11:
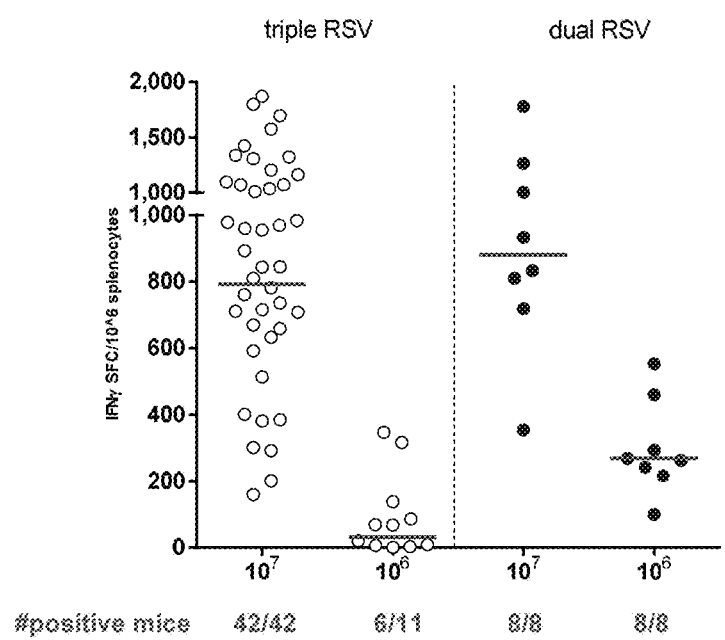

FIG. 11: Comparison of the immunogenicity from ChAd155 vectors expressing the M2 RSV antigen. The data was collected at 3 weeks after vaccination with a dose of either 10$^7$ or 10$^6$ virus particles.

Figure 12A:
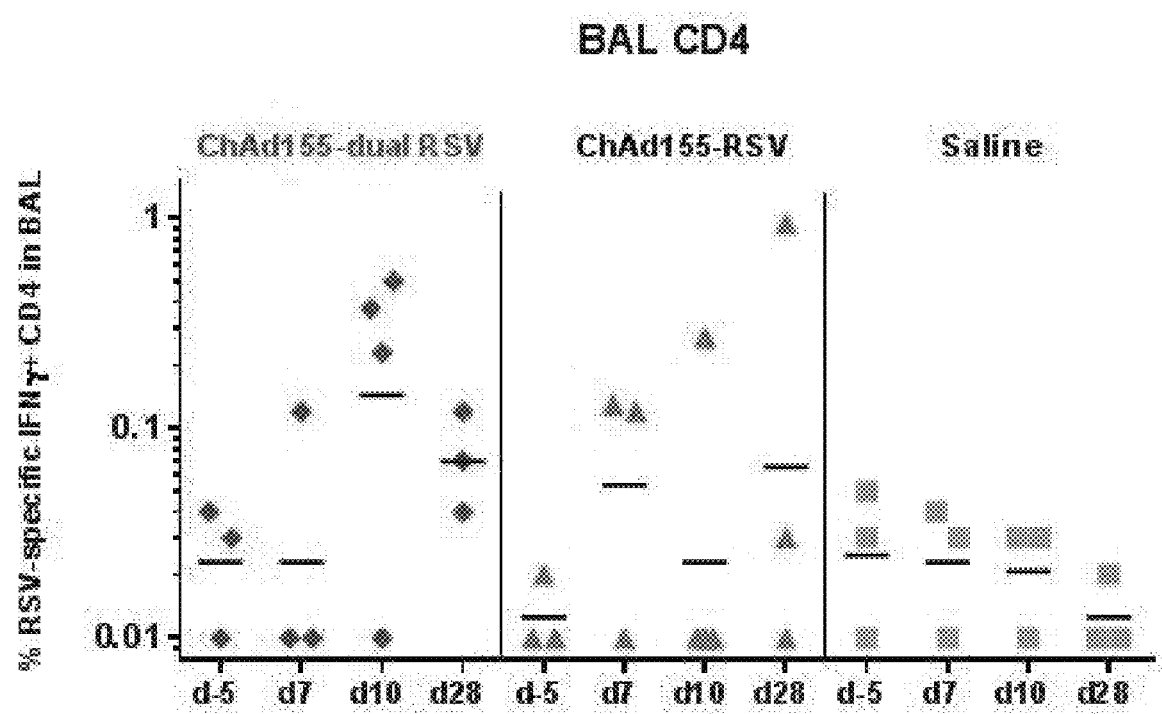
Figure 12B:
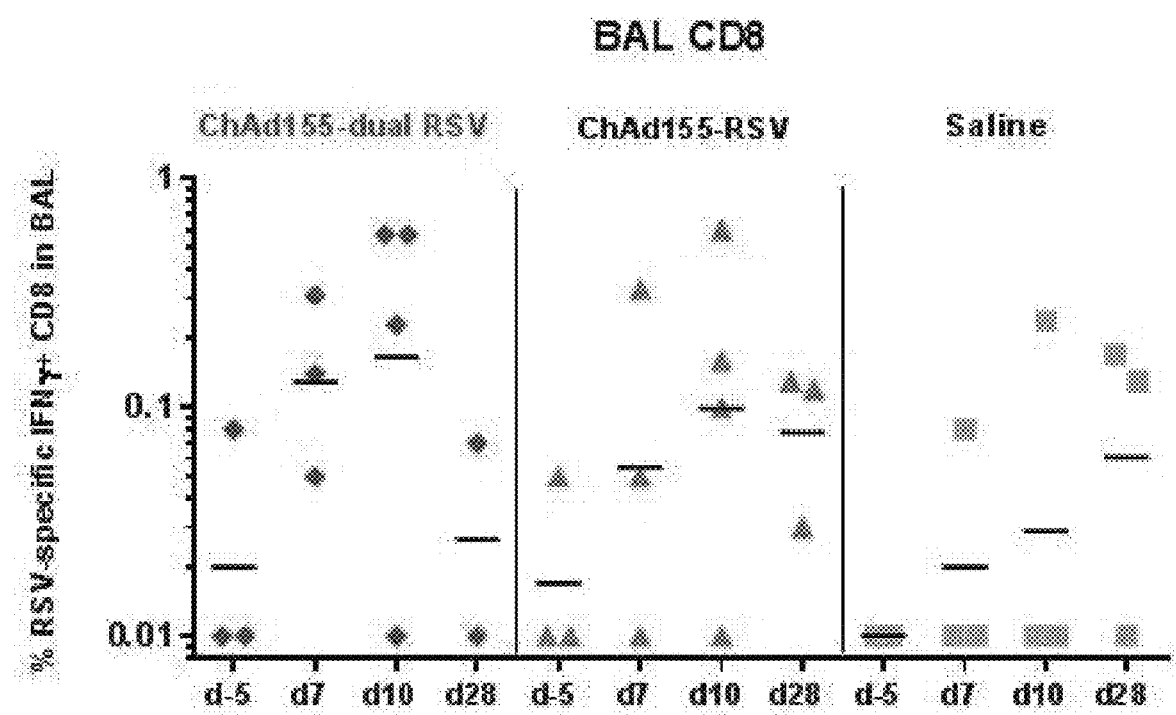

FIGS. 12A and 12B: Illustrate the results from the experiment of Example 9 to investigate the lung T cell responses from ChAd155 vectors. FIG. 12A shows the CD4+ response, and FIG. 12B shows the CD8+ response.

Figure 13A:
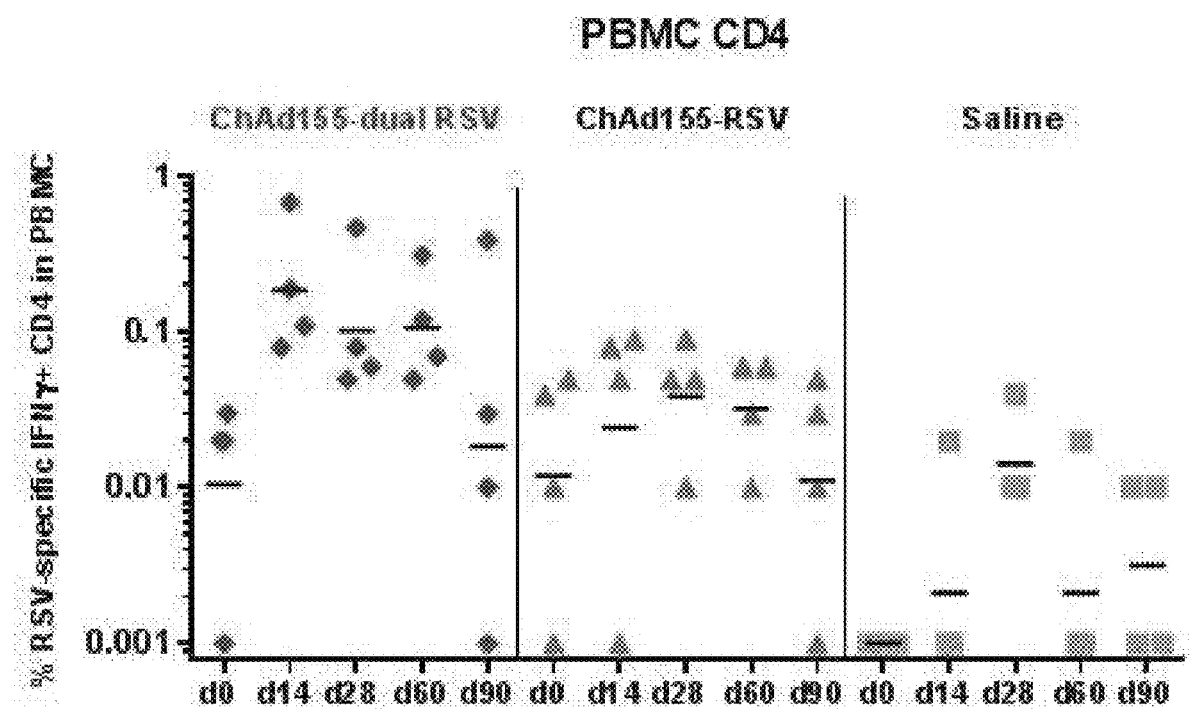
Figure 13B:
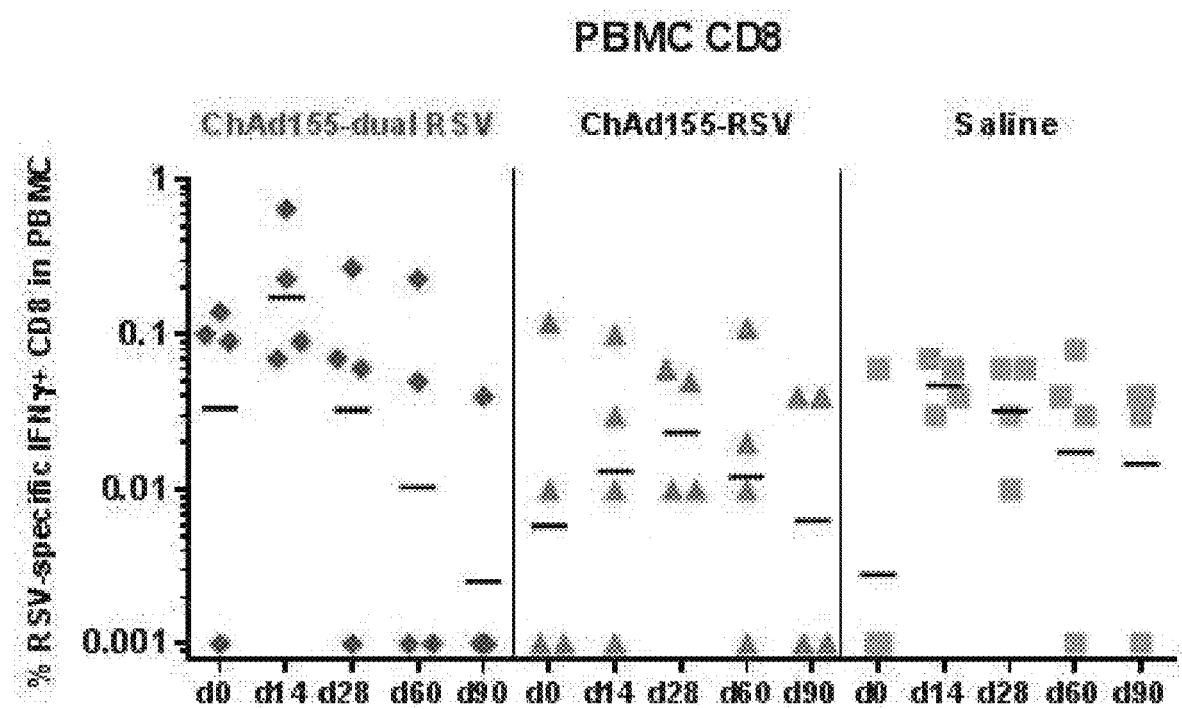

FIGS. 13A and 13B: Show the results from the experiment of Example 9 to investigate the peripheral T cell responses from ChAd155 vectors. FIG. 13A shows the PBMC CD4+ response, and FIG. 13B shows the PBMC CD8+ response.

Figure 14A:
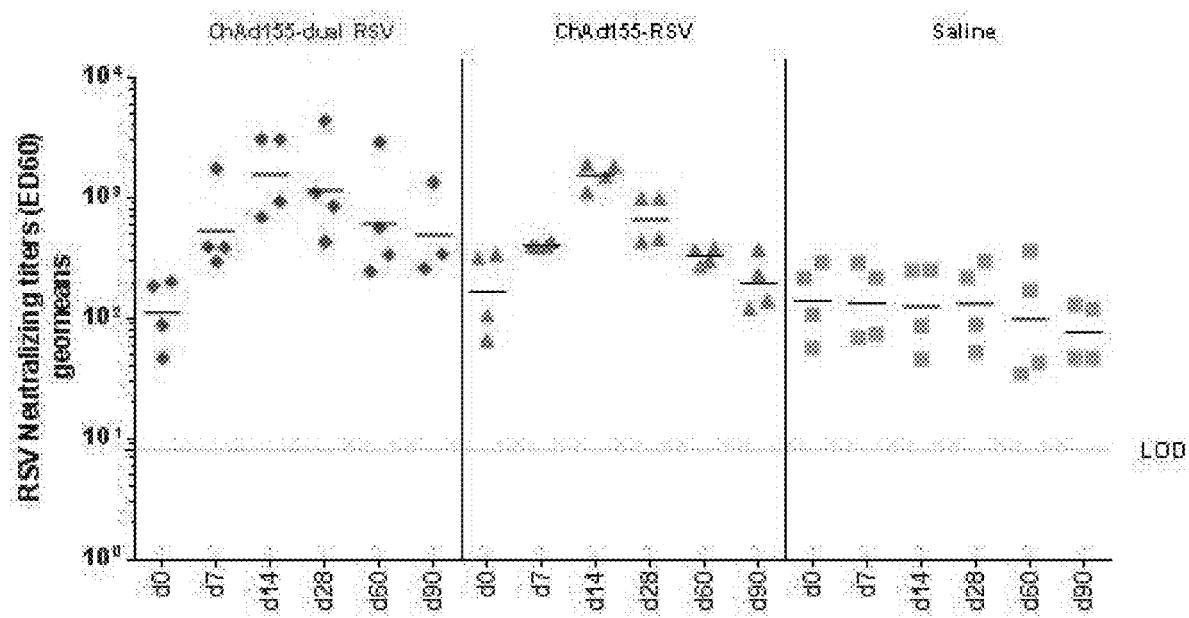
Figure 14B:
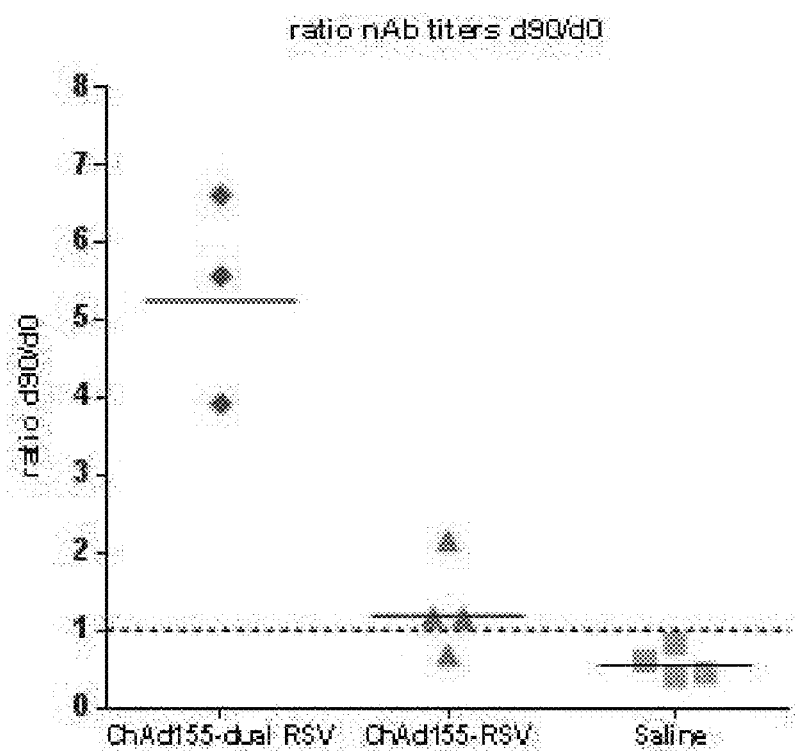

FIGS. 14A and 14B: Also show results from Example 9. FIG. 14A shows the RSV neutralising Ab titres, and FIG. 14B illustrates the ratio of the nAb from day D90 to D0.

Figure 15A:
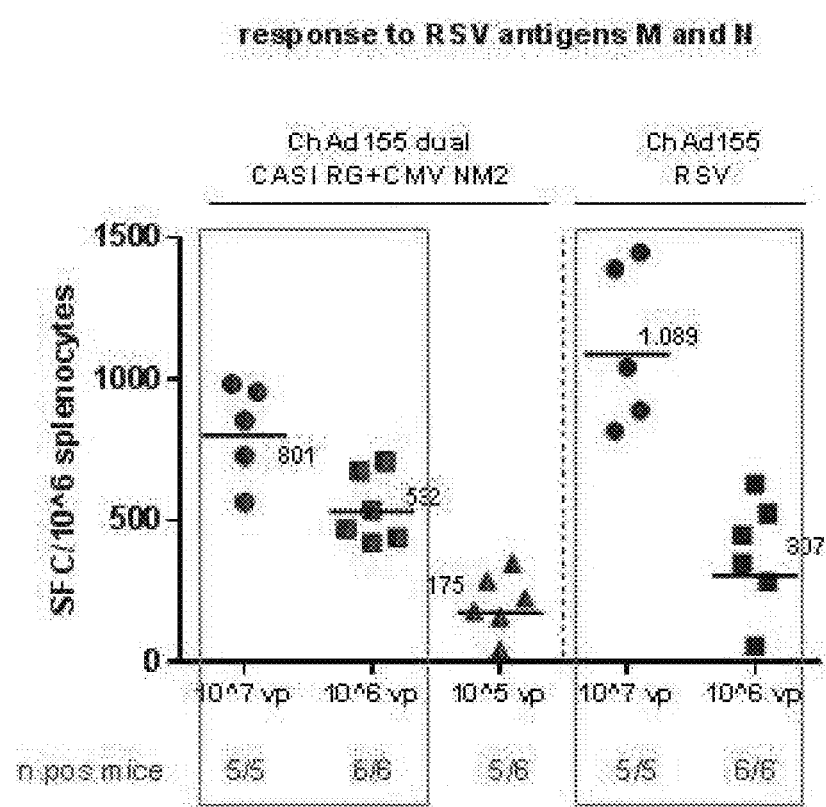

FIGS. 15A. 15B and 15C: Show the results of the immunogenicity experiment of Example 10.

Figure 16A:
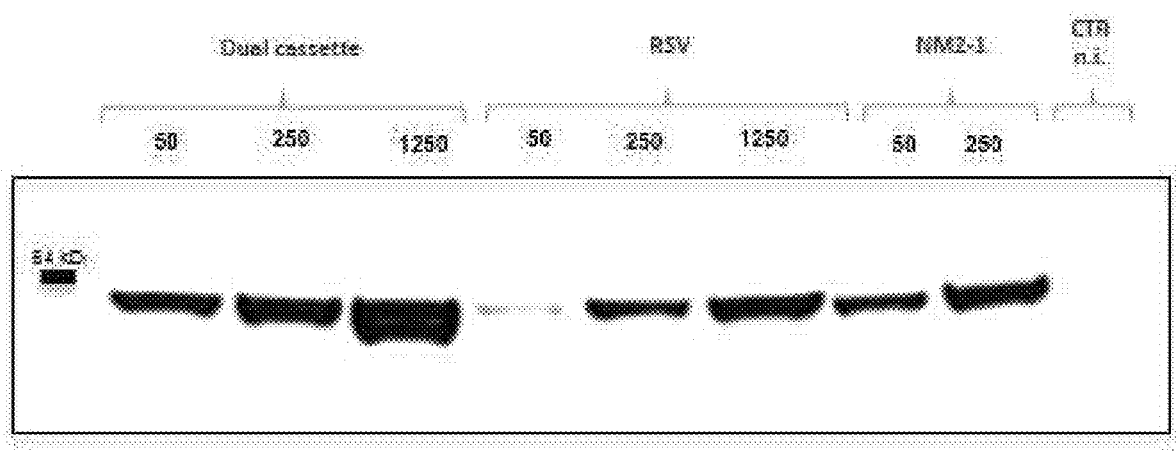
Figure 16B:
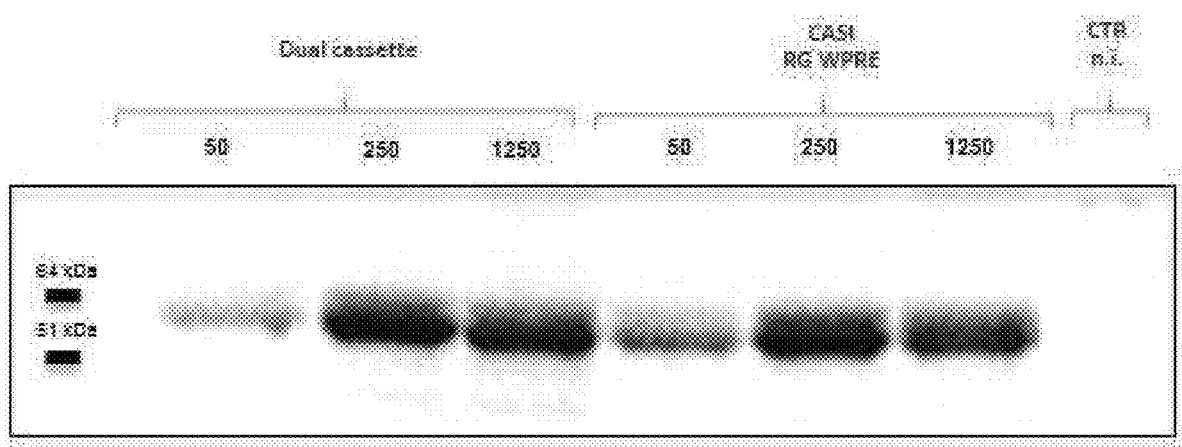

FIGS. 16A and 16B: Western blots obtained using the expression in Hela cells of the vectors in Example 11.

Figure 17:
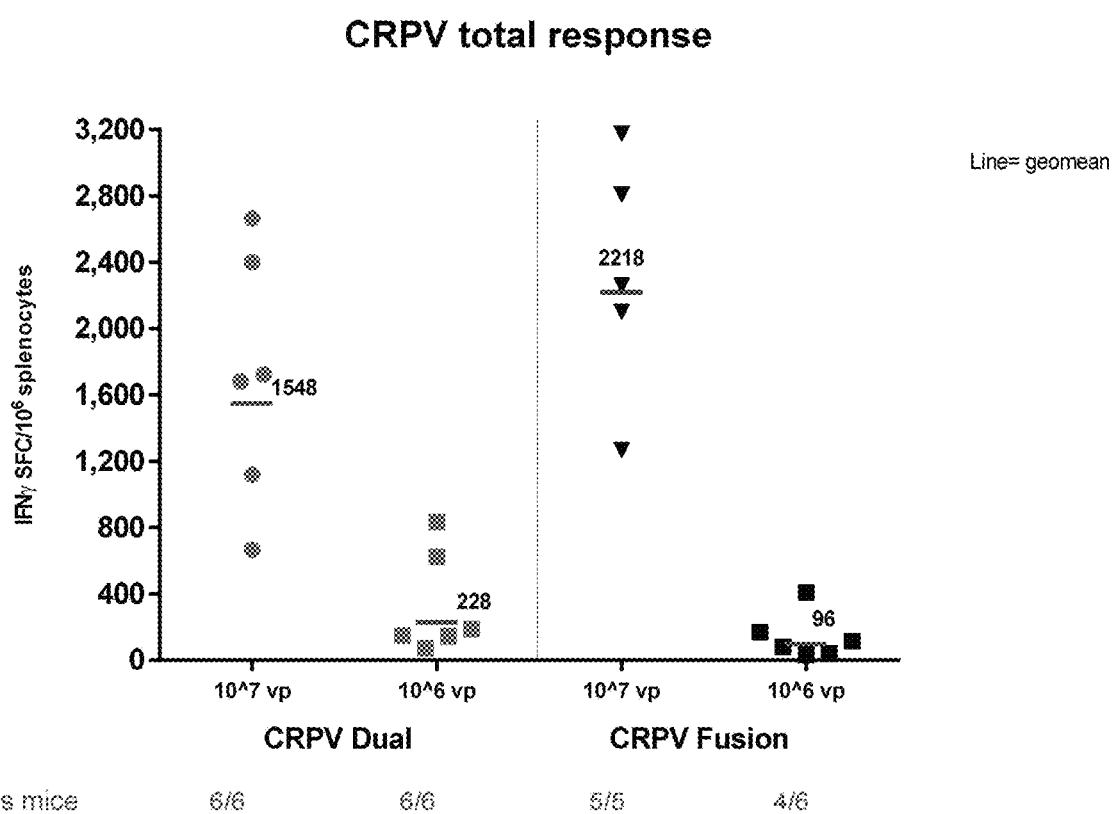

FIG. 17: Illustrates the results of the CRPV experiment of Example 12.

Figure 18:
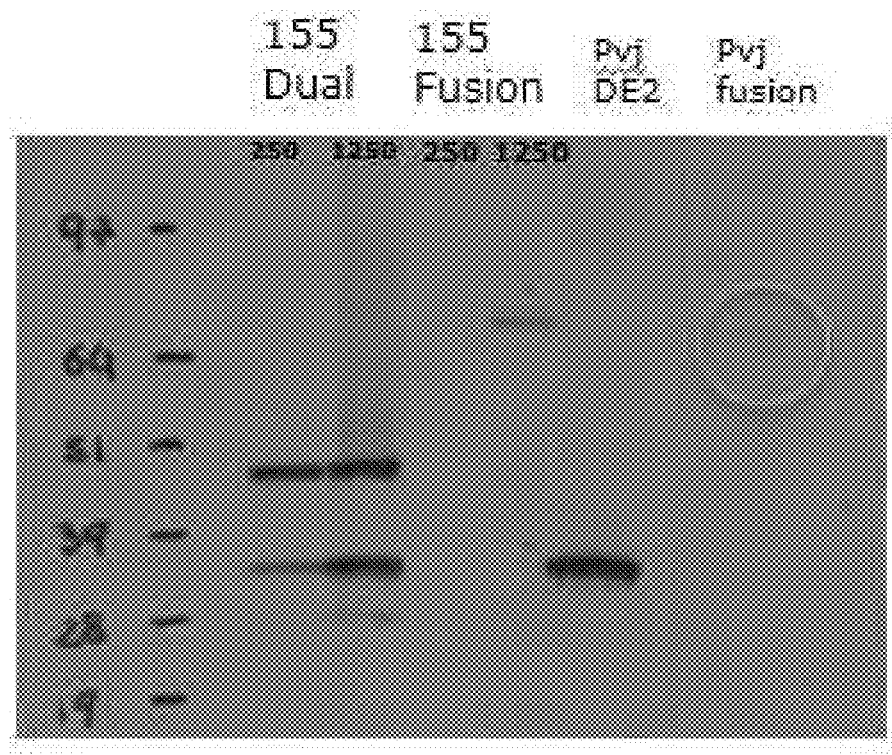

FIG. 18: Shows the results of the HPV dual cassette vector characterisation of Example 13.

ANNOTATION OF THE SEQUENCES

SEQ ID NO: 1—Polynucleotide sequence encoding wild type ChAd155

SEQ ID NO: 2—Polynucleotide sequence encoding wild type ChAd83

SEQ ID NO: 3—Polynucleotide sequence encoding the CASI promoter

SEQ ID NO: 4—Polynucleotide sequence encoding ChAd155/RSV

SEQ ID NO: 5—RSV F0ΔTM-N-M2-1 amino acid sequence

SEQ ID NO: 6—Polynucleotide sequence encoding the enhanced hCMV promoter

SEQ ID NO: 7—Polynucleotide sequence encoding the hCMV NM2 bghpolyA cassette

SEQ ID NO: 8—NM2 amino acid (protein) sequence

SEQ ID NO: 9—Polynucleotide sequence encoding the hCMV F0 WPRE bghpolyA cassette SEQ ID NO: 10—F0 amino acid (protein) sequence SEQ ID NO: 11—Amino acid sequence of a flexible linker SEQ ID NO: 12—Amino acid sequence of a flexible linker

DETAILED DESCRIPTION OF THE INVENTION

Adenoviruses

Adenoviruses are nonenveloped icosahedral viruses with a linear double stranded DNA genome of approximately 36 kb. Adenoviruses can transduce numerous cell types of several mammalian species, including both dividing and nondividing cells, without integrating into the genome of the host cell. They have been widely used for gene transfer applications due to their proven safety, ability to achieve highly efficient gene transfer in a variety of target tissues, and large transgene capacity. Human adenoviral vectors are currently used in gene therapy and vaccines but have the drawback of a high worldwide prevalence of pre-existing immunity, following previous exposure to common human adenoviruses.

Adenoviruses have a characteristic morphology with an icosahedral capsid comprising three major proteins, hexon (II), penton base (III) and a knobbed fiber (IV), along with a number of other minor proteins, VI, VIII, IX, IIIa and IVa2. The hexon accounts for the majority of the structural components of the capsid, which consists of 240 trimeric hexon capsomeres and 12 penton bases. The hexon has three conserved double barrels and the top has three towers, each tower containing a loop from each subunit that forms most of the capsid. The base of the hexon is highly conserved between adenoviral serotypes, while the surface loops are variable. The penton is another adenoviral capsid protein; it forms a pentameric base to which the fiber attaches. The trimeric fiber protein protrudes from the penton base at each of the 12 vertices of the capsid and is a knobbed rod-like structure. The primary role of the fiber protein is to tether the viral capsid to the cell surface via the interaction of the knob region with a cellular receptor. Variations in the flexible shaft, as well as knob regions of fiber, are characteristic of the different adenoviral serotypes.

The adenoviral genome has been well characterized. The linear, double-stranded DNA is associated with the highly basic protein VII and a small peptide pX (also termed mu). Another protein, V, is packaged with this DNA-protein complex and provides a structural link to the capsid via protein VI. There is general conservation in the overall organization of the adenoviral genome with respect to specific open reading frames being similarly positioned, e.g. the location of the E1A, E1B, E2A, E2B, E3, E4, L1, L2, L3, L4 and L5 genes of each virus. Each extremity of the adenoviral genome comprises a sequence known as an inverted terminal repeat (ITR), which is necessary for viral replication. The 5' end of the adenoviral genome contains the 5' cis-elements necessary for packaging and replication; i.e., the 5' ITR sequences (which can function as origins of replication) and the native 5' packaging enhancer domains, which contain sequences necessary for packaging linear adenoviral genomes and enhancer elements for the E1 promoter. The 3' end of the adenoviral genome includes 3' cis-elements, including the ITRs, necessary for packaging and encapsidation. The virus also comprises a virus-encoded protease, which is necessary for processing some of the structural proteins required to produce infectious virions.

The structure of the adenoviral genome is described on the basis of the order in which the viral genes are expressed following host cell transduction. More specifically, the viral genes are referred to as early (E) or late (L) genes according to whether transcription occurs prior to or after onset of DNA replication. In the early phase of transduction, the E1A, E1B, E2A, E2B, E3 and E4 genes of adenovirus are expressed to prepare the host cell for viral replication. The E1 gene is considered a master switch, it acts as a transcription activator and is involved in both early and late gene transcription. E2 is involved in DNA replication; E3 is involved in immune modulation and E4 regulates viral mRNA metabolism. During the late phase of infection, expression of the late genes L1-L5, which encode the structural components of the viral particles, is activated. Late genes are transcribed from the Major Late Promoter (MLP) with alternative splicing.

HE1 and HE2 sites were identified as potential insertion sites for a transgene since the insertion in these specific points does not interrupt the coding sequences or important regulatory sequences of a chimp adenovirus, such as a Type C or E chimp adenovirus, for example, ChAd155 and ChAd83. The HE1 and HE2 sites can be identified by sequence alignment in any chimp adenovirus. Therefore, cloning of expression cassettes in the HE1 and HE2 sites of the ChAd genomes doesn't impact the virus replication cycle.

Adenoviral Replication

Historically, adenovirus vaccine development has focused on defective, non-replicating vectors. They are rendered replication defective by deletion of the E1 region genes, which are essential for replication. Typically, non-essential E3 region genes are also deleted to make room for exogenous transgenes. An expression cassette comprising the transgene under the control of an exogenous promoter is then inserted. These replication-defective viruses are then produced in E1-complementing cells.

The term "replication-defective" or "replication-incompetent" adenovirus refers to an adenovirus that is incapable of replication because it has been engineered to comprise at least a functional deletion (or "loss-of-function" mutation), i.e. a deletion or mutation which impairs the function of a gene without removing it entirely, e.g. introduction of artificial stop codons, deletion or mutation of active sites or interaction domains, mutation or deletion of a regulatory sequence of a gene etc, or a complete removal of a gene encoding a gene product that is essential for viral replication, such as one or more of the adenoviral genes selected from E1A, E1B, E2A, E2B, E3 and E4 (such as E3 ORF1, E3 ORF2, E3 ORF3, E3 ORF4, E3 ORF5, E3 ORF6, E3 ORF7, E3 ORF8, E3 ORF9, E4 ORF7, E4 ORF6, E4 ORF4, E4 ORF3, E4 ORF2 and/or E4 ORF1). Suitably, E1 and optionally E3 and/or E4 are deleted. If deleted, the aforementioned deleted gene region will suitably not be considered in the alignment when determining percent identity with respect to another sequence.

Vectors of the Invention

Viral vectors based on non-human simian adenovirus represent an alternative to the use of human derived vectors for gene therapy and genetic vaccines. Certain adenoviruses isolated from non-human simians are closely related to adenoviruses isolated from humans, as demonstrated by their efficient propagation in cells of human origin. As humans develop little or no immunity to simian adenoviruses, they promise to provide an improved alternative to human adenoviral uses.

"Low seroprevalence" may mean having a reduced pre-existing neutralizing antibody level as compared to human adenovirus 5 (Ad5). Similarly or alternatively, "low seroprevalence" may mean less than about 30% seroprevalence, less than about 20% seroprevalence, less than about 15% seroprevalence, less than about 10% seroprevalence, less than about 5% seroprevalence, less than about 4% seroprevalence, less than about 3% seroprevalence, less than about 2% seroprevalence, less than about 1% seroprevalence or no detectable seroprevalence. Seroprevalence can be measured as the percentage of individuals having a clinically relevant neutralizing titer (defined as a 50% neutralisation titer >200) using methods as described in Hum. Gene Ther. (2004) 15:293.

The adenoviral vector of the present invention is derived from a nonhuman simian adenovirus, also referred to as a "simian adenovirus." Numerous adenoviruses have been isolated from nonhuman simians such as chimpanzees, bonobos, rhesus macaques, orangutans and gorillas. Vectors derived from these adenoviruses can induce strong immune responses to transgenes encoded by these vectors. Certain advantages of vectors based on nonhuman simian adenoviruses include a relative lack of cross-neutralizing antibodies to these adenoviruses in the human target population, thus their use overcomes the pre-existing immunity to human adenoviruses. For example, some simian adenoviruses have no cross reactivity with preexisting human neutralizing antibodies and cross-reaction of certain chimpanzee adenoviruses with pre-existing human neutralizing antibodies is only present in 2% of the target population, compared with 35% in the case of certain candidate human adenovirus vectors (Sci. Transl. Med. (2012) 4:1).

Adenoviral vectors of the invention are derived from a simian adenovirus, e.g., from chimpanzees (*Pan troglodytes*), bonobos (*Pan paniscus*), gorillas (*Gorilla gorilla*) and orangutans (*Pongo abelii* and *Pongo pygmaeus*). They include adenoviruses from Group B, Group C, Group D, Group E and Group G. Chimpanzee adenoviruses include, but are not limited to AdY25, ChAd3, ChAd19, ChAd25.2, ChAd26, ChAd27, ChAd29, ChAd30, ChAd31, ChAd32, ChAd33, ChAd34, ChAd35, ChAd37, ChAd38, ChAd39, ChAd40, ChAd63, ChAd83, ChAd155, ChAd15, SadV41 and ChAd157 ChAd3, ChAd19, ChAd25.2, ChAd26, ChAd27, ChAd29, ChAd30, ChAd31, ChAd32, ChAd33, ChAd34, ChAd35, ChAd37, ChAd38, ChAd39, ChAd40, ChAd63, ChAd83, ChAd155, ChAd15, SadV41, sAd4310A, sAd4312, SAdV31, SAdV-A1337, ChAdOx1, ChAdOx2 and ChAd157. Alternatively, adenoviral vectors may be derived from nonhuman simian adenoviruses isolated from bonobos, such as PanAd1, PanAd2, PanAd3, Pan 5, Pan 6, Pan 7 (also referred to as C7) and Pan 9. Vectors may include, in whole or in part, a nucleotide encoding the fiber, penton or hexon of a non-human adenovirus.

In an embodiment of the adenoviral vectors of the invention, the adenoviral vector has a seroprevalence of less than 30%, less than 20%, less than 10% or less than 5% in human subjects, preferably no seroprevalence in human subjects and more preferably no seroprevalence in human subjects that have not previously been in contact with a chimpanzee adenoviral vector.

In embodiments of the adenoviral vectors of the invention, the adenoviral DNA is capable of entering a mammalian target cell, i.e. it is infectious. An infectious recombinant adenoviral vector of the invention can be used as a prophylactic or therapeutic vaccine and for gene therapy. Thus, in an embodiment, the recombinant adenoviral vector comprises an endogenous molecule for delivery into a target cell. The target cell is a mammalian cell, e.g. a bovine cell, a canine cell, a caprine cell, a cervine cell, a chimpanzee cell, a chiroptera cell, an equine cell, a feline cell, a human cell, a lupine cell, an ovine cell, a porcine cell, a rodent cell, an ursine cell or a vulpine cell. The endogenous molecule for delivery into a target cell is an expression cassette.

In an embodiment of the invention, the vector comprises a left ITR region, a deleted E1 region, then a deleted E3 region, and, optionally, additional enhancer elements; these are followed by a fiber region, an E4 region and a right ITR. Translation occurs in the rightward and leftward directions. In this embodiment, the first expression cassette is inserted in the deleted E1 region, and the second expression cassette is insertion in the deleted E3 region. In a further embodiment, the promoters of the two expression cassettes are CMV promoters. In a yet further embodiment, the enhancer element is the Hepatitis B Posttranslational Regulatory Element (HPRE) or the Woodchuck Hepatitis Posttranslational Regulatory Element (WPRE).

In one embodiment of the invention, the vector comprises left and right ITR regions; a deleted E1 region; at least a partially deleted E3 region; a fiber region; an E4 region; two expression cassettes, each comprising: a promoter and at least one an antigen of interest and, optionally, one or more enhancer elements. The first expression cassette is inserted in the deleted E1 region, and the second expression cassette is inserted at the HE1 site, i.e., between the stop codons of the fiber gene and an E4 region ("the HE1 site"). The ChAd155 HE1 insertion site is between bp 34611 and 34612 of the wild type ChAd155 sequence. The ChAd83 HE1 insertion site is between bp 33535 and 33536 of the wild type ChAd83 sequence. Translation occurs in the rightward and leftward directions. In a further embodiment, the promoters are CMV promoters. In a preferred embodiment, one promoter is a CMV promoter and the other is a eCMV promoter. In a yet further embodiment, the enhancer element is HPRE or WPRE.

In a further embodiment, the vector comprises left and right ITR regions; a deleted E1 region; at least a partially deleted E3 region; a fiber region; an E4 region; two expression cassettes, each comprising: a promoter, at least one antigen of interest and, optionally, one or more enhancer elements. The first expression cassette is inserted in the deleted E1 region, and the second expression cassette is inserted at the HE2 site, i.e., between the end of the left ITR and the cap site of the E4 mRNA ("the HE2 site"). The ChAd155 HE2 insertion site is between bp 37662 and 37663 of the wild type ChAd155 sequence. The ChAd83 HE2 insertion site is between bp 36387 and 36388 of the wild type ChAd83 sequence. Translation occurs in the rightward and leftward directions. In a further embodiment, the promoters are CMV promoters. In a preferred embodiment, one promoter is a CMV promoter and the other is a eCMV promoter. In a yet further embodiment, the enhancer element is HPRE or WPRE (the enhancer element increases expression of the transgene).

The HE1 and HE2 sites were identified as insertion sites for a transgene, as the insertion in these specific points does not interrupt the coding sequences or regulatory sequences of ChAd155 and ChAd83. Therefore, inserting expression cassettes in the HE1 or HE2 sites of the ChAd genome does not affect the viral replication cycle.

In an embodiment of the invention, the vector is a functional or an immunogenic derivative of an adenoviral vector. By "derivative of an adenoviral vector" is meant a modified version of the vector, e.g., one or more nucleotides of the vector are deleted, inserted, modified or substituted.

Regulatory Elements

Regulatory elements, i.e., expression control sequences, include appropriate transcription initiation, termination, promoter and enhancer sequences; efficient RNA processing signals such as splicing and polyadenylation (polyA) signals including rabbit beta-globin polyA; tetracycline regulatable systems, microRNAs, posttranscriptional regulatory elements (e.g., WPRE, posttranscriptional regulatory element of woodchuck hepatitis virus); sequences that stabilize cytoplasmic mRNA; sequences that enhance translation efficiency (e.g., Kozak consensus sequence); sequences that enhance protein stability; and when desired, sequences that enhance secretion of an encoded product.

A "promoter" is a nucleotide sequence that permits the binding of RNA polymerase and directs the transcription of a gene. Typically, a promoter is located in a non-coding region of a gene, proximal to the transcriptional start site. Sequence elements within promoters that function in the initiation of transcription are often characterized by consensus nucleotide sequences. Examples of promoters include, but are not limited to, promoters from bacteria, yeast, plants, viruses, and mammals, including simians and humans. A great number of expression control sequences, including promoters which are internal, native, constitutive, inducible and/or tissue-specific, are known in the art and may be utilized.

Promoters of the invention will typically be heterologous promoters. Promoters of the invention can be constitutive.

Examples of promoters include, but are not limited to, promoters from bacteria, yeast, plants, viruses, and mammals (including humans).

Examples of promoters include, without limitation, the TBG promoter, the retroviral Rous sarcoma virus LTR promoter (optionally with the enhancer), the cytomegalovirus (CMV) promoter (optionally with the CMV enhancer, see, e.g., Boshart et al, Cell, 41: 521-530 (1985)), the CASI promoter, the SV40 promoter, the dihydrofolate reductase promoter, the β-actin promoter, the phosphoglycerol kinase (PGK) promoter, and the EF1a promoter (Invitrogen).

Suitable promoters include the cytomegalovirus (CMV) promoter and the CASI promoter. The CMV promoter is strong and ubiquitously active. It has the ability to drive high levels of transgene expression in many tissue types and is well known in the art. The CMV promoter can be used in vectors of the invention, either with or without a CMV enhancer.

The CASI promoter is a synthetic promoter described as a combination of the CMV enhancer, the chicken beta-actin promoter, and a splice donor and splice acceptor flanking the ubiquitin (UBC) enhancer (U.S. Pat. No. 8,865,881).

In some embodiments, the CASI promoter can include a nucleic acid sequence having at least about 90%, at least about 95%, at least about 96%, at least about 97%, at least about 98%, at least about 99%, or more, sequence identity to SEQ ID NO: 3. In some embodiments, the promoter comprises or consists of a nucleic acid sequence of SEQ ID NO: 3.

In some embodiments, the enhanced hCMV promoter can include a nucleic acid sequence having at least about 90%, at least about 95%, at least about 96%, at least about 97%, at least about 98%, at least about 99%, or more, sequence identity to SEQ ID NO: 6. In some embodiments, the promoter comprises or consists of a nucleic acid sequence of SEQ ID NO: 6.

Optionally, vectors carrying transgenes encoding therapeutically useful or immunogenic products may also include selectable markers or reporter genes. The reporter gene may be chosen from those known in the art. Suitable reporter genes include, but are not limited to enhanced green fluorescent protein, red fluorescent protein, luciferase and secreted embryonic alkaline phosphatase (seAP), which may include sequences encoding geneticin, hygromycin or puromycin resistance, among others. Such selectable reporters or marker genes (which may or may not be located outside the viral genome to be packaged into a viral particle) can be used to signal the presence of the plasmids in bacterial cells, such as ampicillin resistance. Other components of the vector may include an origin of replication.

A "posttranscriptional regulatory element," as used herein, is a DNA sequence that, when transcribed, enhances the expression of the transgene(s) or fragments thereof that are delivered by viral vectors of the invention. Posttranscriptional regulatory elements include, but are not limited to the Hepatitis B Virus Posttranscriptional Regulatory Element (HPRE) and the Woodchuck Hepatitis Posttranscriptional Regulatory Element (WPRE). The WPRE is a tripartite cis-acting element that has been demonstrated to enhance transgene expression driven by certain, but not all promoters.

In embodiments of the invention, a ChAd155 vector may comprise one or more of a promoter, an enhancer, and a reporter gene. For example, vectors of the invention may comprise ChAd155-enhanced hCMV-SeAP, ChAd155-CASI-seAP and ChAd155-hCMV-seAP, optionally with a tetracycline on/off transcriptional control and ChAd155-CMV-hFerL-chEF1-seAP with a tetracycline on/off transcriptional control.

In embodiments of the invention, a ChAd83 vector may comprise one or more of a promoter, an enhancer, and a reporter gene. For example, vectors of the invention may comprise ChAd155-enhanced hCMV-SeAP, ChAd83-enhanced hCMV-SeAP, ChAd155-CASI-seAP and ChAd83-hCMV-seAP, optionally with a tetracycline on/off transcriptional control and ChAd83-CMV-hFerL-chEF1-seAP with a tetracycline on/off transcriptional control.

Vectors of the invention are generated using techniques provided herein, in conjunction with techniques known to those of skill in the art. Such techniques include conventional cloning techniques of cDNA such as those described in texts, use of overlapping oligonucleotide sequences of the adenovirus genomes, polymerase chain reaction, and any suitable method which provides the desired nucleotide sequence.

Transgenes

A "transgene" is a nucleic acid sequence, heterologous to the vector sequences flanking the transgene, which encodes a polypeptide of interest. The nucleic acid coding sequence is operatively linked to regulatory components in a manner which permits transgene transcription, translation, and/or expression in a host cell. In embodiments of the invention, the vectors express transgenes at a therapeutic or a prophylactic level. A "functional derivative" of a transgenic polypeptide is a modified version of a polypeptide, e.g., wherein one or more amino acids are deleted, inserted, modified or substituted.

The transgene may be used for prophylaxis or treatment, e.g., as a vaccine for inducing an immune response, to correct genetic deficiencies by correcting or replacing a defective or missing gene, or as a cancer therapeutic. As used herein, induction of an immune response refers to the ability of a protein to induce a T cell and/or a humoral antibody immune response to the protein.

The immune response elicited by the transgene may be an antigen specific B cell response, which produces neutralizing antibodies. The elicited immune response may be an antigen specific T cell response, which may be a systemic and/or a local response. The antigen specific T cell response may comprise a CD4+ T cell response, such as a response involving CD4+ T cells expressing cytokines, e.g. interferon gamma (IFN gamma), tumor necrosis factor alpha (TNF alpha) and/or interleukin 2 (IL2). Alternatively, or additionally, the antigen specific T cell response comprises a CD8+ T cell response, such as a response involving CD8+ T cells expressing cytokines, e.g., IFN gamma, TNF alpha and/or IL2.

The composition of the transgene sequence will depend upon the use to which the resulting vector will be put. In an embodiment, the transgene is a sequence encoding a product which is useful in biology and medicine, such as a prophylactic transgene, a therapeutic transgene or an immunogenic transgene, e.g., protein or RNA. Protein transgenes include antigens. Antigenic transgenes of the invention induce an immunogenic response to a disease causing organism.

Transgenes of the invention include, but are not limited to, rabies virus antigens, e.g., rabies glycoprotein (RG), respiratory syncytial virus (RSV) antigens, human immunodeficiency virus (HIV) antigens, or fragments thereof.

As a result of the redundancy in the genetic code, a polypeptide can be encoded by a variety of different nucleic acid sequences. Coding is biased to use some synonymous codons, i.e., codons that encode the same amino acid, more than others. By "codon optimized," it is meant that modifications in the codon composition of a recombinant nucleic acid are made without altering the amino acid sequence. Codon optimization has been used to improve mRNA expression in different organisms by using organism-specific codon-usage frequencies.

In addition to, and independently from, codon bias, some synonymous codon pairs are used more frequently than others. This codon pair bias means that some codon pairs are overrepresented and others are underrepresented. Codon pair deoptimization has been used to reduce viral virulence. For example, it has been reported that polioviruses modified to contain underrepresented codon pairs demonstrated decreased translation efficiency and were attenuated compared to wild type poliovirus (Science (2008) 320:1784). Engineering a synthetic attenuated virus by codon pair deoptimization can produce viruses that encode the same amino acid sequences as wild type but use different pairwise arrangements of synonymous codons. Viruses attenuated by codon pair deoptimization generated up to 1000-fold fewer plaques compared to wild type, produced fewer viral particles and required about 100 times as many viral particles to form a plaque.

In contrast, polioviruses modified to contain codon pairs that are overrepresented in the human genome acted in a manner similar to wild type RNA and generated plaques identical in size to wild type RNA (Coleman et al. (2008) Science 320:1784). This occurred despite the fact that the virus with overrepresented codon pairs contained a similar number of mutations as the virus with underrepresented codon pairs and demonstrated enhanced translation compared to wild type. This observation suggests that codon pair optimized constructs would be expected to act in a manner similar to their non-codon pair optimized counterparts and would not be expected to provide a functional advantage. Without wishing to be constrained by theory, this may be because natural evolution has optimized codon pairing.

A construct of the invention may comprise a codon optimized nucleic acid sequence. Alternatively or additionally, a vector of the invention comprises a codon optimized sequence of a transgene or an immunogenic derivative or fragment thereof. A construct of the invention may comprise a codon pair optimized nucleic acid sequence. Alternatively or additionally, a vector of the invention comprises or consists of a codon pair optimized sequence of a transgene or an immunogenic derivative or fragment thereof.

Respiratory Syncytial Virus (RSV) Transgenes

In one embodiment, the present invention provides the use of a recombinant simian-derived adenoviral vector comprising two expression cassettes, wherein each expression cassette comprises an immunogenic transgene derived from human respiratory syncytial virus (RSV), in the treatment or prophylaxis of RSV infection. In one embodiment, the recombinant simian-derived adenoviral vector of the present invention comprises an RSV F antigen in one of the expression cassettes, and another RSV viral antigen in the other expression cassette. Suitable antigens are discussed further below. In one embodiment, the recombinant simian-derived adenoviral vector comprises RSV M and N antigens in the second expression cassette. In such embodiments, the vector preferably encodes an RSV F0ΔTM antigen (fusion (F) protein deleted of the transmembrane and cytoplasmic regions), and RSV M2-1 (transcription anti-termination) and N (nucleocapsid) antigens.

Infection with RSV does not confer full protective immunity. Infection in infancy is followed by symptomatic RSV re-infections which continue throughout adulthood. These re-infections generally go undiagnosed because they usually present as common acute upper respiratory tract infections. In more vulnerable persons (e.g., immunocompromised adults or elderly), re-infections can however also lead to severe disease. Both arms of the immune system (humoral and cellular immunity) are involved in protection from severe disease [Guvenel A K, Chiu C and Openshaw P J. Current concepts and progress in RSV vaccine development. *Expert Rev Vaccines.* 2014; 13(3): 333-44.].

The humoral immune response is capable of neutralizing the virus and inhibiting viral replication, thereby playing a major role in protection against lower respiratory RSV infection and severe disease [Piedra P A, Jewell A M, Cron S G, et al., Correlates of immunity to respiratory syncytial virus (RSV) associated-hospitalization: establishment of minimum protective threshold levels of serum neutralizing antibodies. *Vaccine.* 2003; 21(24): 3479-82.]. Passive immunization, in the form of Immunoglobulin G (IgG) RSV-neutralizing monoclonal antibodies (Synagis) given prophylactically, has been shown to prevent RSV disease to some extent in premature infants and newborns with bronchopulmonary dysplasia or underlying cardiopulmonary disease [Cardenas S, Auais A and Piedimonte G. Palivizumab in the prophylaxis of respiratory syncytial virus infection. *Expert Rev Anti Infect Ther.* 2005; 3(5): 719-26].

T cells are also involved in the control of RSV disease. Lethal RSV infections have been described in patients with low CD8 T cells counts, as in the case of severe combined immunodeficiency, bone marrow and lung transplant recipients [Hertz, 1989]. The histopathology of fatal cases of RSV infection of newborns shows that there is a relative paucity of CD8 T cells in the lung infiltrate [Welliver T P, Garofalo R P, Hosakote Y, et al., Severe human lower respiratory tract illness caused by respiratory syncytial virus and influenza virus is characterized by the absence of pulmonary cytotoxic lymphocyte responses. *J Infect Dis.* 2007. 195(8): 1126-36.]. Moreover, the presence of CD8 T cells producing Interferon-gamma (IFN-γ) has been associated with diminished Th2 responses and reduced eosinophilia in animal models of RSV [Castilow E M and Varga S M. Overcoming T cell-mediated immunopathology to achieve safe RSV vaccination. *Future Virol.* 2008; 3(5): 445-454; Stevens W W, Sun J, Castillo J P, et al., Pulmonary eosinophilia is attenuated by early responding CD8(+) memory T cells in a murine model of RSV vaccine-enhanced disease. *Viral Immunol.* 2009; 22(4): 243-51].

Suitable antigens of RSV which are useful as immunogens to immunize a human or non-human animal can be selected from: the fusion protein (F), the attachment protein (G), the matrix protein (M2) and the nucleoprotein (N). The term "F protein" or "fusion protein" or "F protein polypeptide" or "fusion protein polypeptide" refers to a polypeptide or protein having all or part of an amino acid sequence of an RSV Fusion protein polypeptide. Similarly, the term "G protein" or "G protein polypeptide" refers to a polypeptide or protein having all or part of an amino acid sequence of an RSV Attachment protein polypeptide. The term "M protein" or "matrix protein" or "M protein polypeptide" refers to a polypeptide or protein having all or part of an amino acid sequence of an RSV Matrix protein and may include either or both of the M2-1 (which may be written herein as M2.1) and M2-2 gene products. Likewise, the term "N protein" or "Nucleocapsid protein" or "N protein polypeptide" refers to a polypeptide or protein having all or part of an amino acid sequence of an RSV Nucleoprotein.

Two groups of human RSV strains have been described, the A and B groups, based mainly on differences in the antigenicity of the G glycoprotein. Numerous strains of RSV have been isolated to date, any of which are suitable in the context of the antigens of the immunogenic combinations disclosed herein. Exemplary strains indicated by GenBank and/or EMBL Accession number can be found in US published application number 2010/0203071 (WO2008114149), which is incorporated herein by reference for the purpose of disclosing the nucleic acid and polypeptide sequences of RSV F and G proteins suitable for use in present invention. In an embodiment, the RSV F protein can be an ectodomain of an RSV F Protein (F0ΔTM).

Exemplary M and N protein nucleic acids and protein sequences can be found, e.g., in US published application number 2014/0141042 (WO2012/089833), which are incorporated herein for purpose of disclosing the nucleic acid and polypeptide sequences of RSV M and N proteins suitable for use in present invention.

Suitably, for use with in present invention, transgene nucleic acids encode an RSV F antigen and RSV, M and N antigens. More specifically, the nucleic acids encode an RSV F0ΔTM antigen (fusion (F) protein deleted of the transmembrane and cytoplasmic regions), and RSV M2-1 (transcription anti-termination) and N (nucleocapsid) antigens.

Fusion (F) Protein Deleted of the Transmembrane and Cytoplasmic Regions (F0ΔTM)

The RSV F protein is a major surface antigen and mediates viral fusion to target cells. The F protein is an antigen which is highly conserved among RSV subgroups and strains. The F protein is a target for neutralizing antibodies, including the prophylactic RSV-neutralizing monoclonal antibody Synagis. Deletion of the transmembrane region and cytoplasmic tail permits secretion of the F0ΔTM protein. Neutralizing antibodies including Synagis, that recognize this soluble form of the F protein, inhibit RSV infectivity in vitro [Magro M, Andreu D, Gómez-Puertas P, et al., Neutralization of human respiratory syncytial virus infectivity by antibodies and low-molecular-weight compounds targeted against the fusion glycoprotein. *J Virol*. 2010; 84(16): 7970-82].

Nucleocapsid (N) Protein

The N protein is an internal (non-exposed) antigen, highly conserved between RSV strains and known to be a source of many T cell epitopes. The N protein is essential for the replication and transcription of the RSV genome. The primary function of the N protein is to encapsulate the virus genome for the purposes of RNA transcription, replication and packaging and protects it from ribonucleases.

Transcription Anti-Termination (M2-1) Protein

The M2-1 protein is a transcription anti-termination factor that is important for the efficient synthesis of full-length messenger RNAs (mRNAs) as well as for the synthesis of polycistronic readthrough mRNAs, which are characteristic of non-segmented negative-strand RNA viruses. M2-1 is an internal (non-exposed) antigen, which is highly conserved between RSV strains and known to be a source of many T cell epitopes.

N-M2-1 Fusion Protein

A polynucleotide encoding a linker is positioned between the polynucleotide encoding an RSV N antigen, or fragment thereof, and the polynucleotide encoding an RSV M2.1 antigen, or fragment thereof. Thus, in certain preferred examples, an expression cassette contains a transgene which encodes a fused RSV viral protein N-linker-M2.1 It is preferred that the linker is a flexible linker, preferably a flexible linker comprising an amino acid sequence according to SEQ ID NO: 11 (Gly-Gly-Gly-Ser-Gly-Gly-Gly) or SEQ ID NO: 12 (Gly-Gly-Gly-Gly-Ser-Gly-Gly-Gly-Gly).

Papilloma (PV) Transgenes

In one embodiment, the present invention provides the use of a recombinant simian-derived adenoviral vector comprising two expression cassettes, wherein each expression cassette comprises an immunogenic transgene derived from a papilloma virus (PV), in the treatment or prophylaxis of a papilloma virus induced disease. Suitably, the recombinant simian-derived adenoviral vector of the present invention comprises a modified papilloma virus E1 antigen in one of the expression cassettes, and a modified papilloma virus E2 antigen in the other expression cassette.

Human Papillomavirus (HPV) are small DNA viruses that infect mucosal and/or cutaneous skin and cause multiple disease conditions, including cervical neoplasia, cervical cancer, and other anogenital cancers. There are over 40 types of HPV known to infect the anogenital tract of humans and about 15 high-risk HPV genotypes are causally associated with human cervical cancers. A majority of HPV infections of the cervical epithelium are subclinical and self-resolving within a two years period. However, persistent infection with high risk HPV types may cause lesions and progress to invasive cancer.

Suitable antigens of HPV which are useful as immunogens are described in WO2018060288 and include in particular HPV E1 and E2proteins.

Rabies (RG) Transgenes

*Lyssavirus* is an enveloped, single stranded RNA virus in the Rhabdoviridae family. Members of the *Lyssavirus* genus cause rabies and have the highest fatality rate of all known human viral pathogens. Rabies is transmitted via the saliva of infected mammals. A neurotropic virus, it enters the nervous system of its host, causing an encephalomyelitis that is almost invariably fatal. Currently there are about 60,000 rabies deaths worldwide yearly, mostly caused by dog bites in developing countries in Asia and Africa and by wildlife and bats in North America.

Rabies presents either in a furious or a paralytic form. The incubation period varies between about five days and several years but is typically between about 20 and 90 days. Clinical illness most often starts with prodromal complaints of malaise, anorexia, fatigue, headache and fever followed by pain or parasthesia at the site of exposure. Anxiety, agitation or irritability may be prominent during this period, followed by hyperactivity, disorientation, seizures, hydrophobia, hypersalivation and, eventually, paralysis, coma and death.

Rabies antigens may be derived from the rabies viral glycoprotein (RG). For example, rabies glycoprotein may be used as a model antigen.

Delivery of Adenoviral Vectors

In some embodiments, the recombinant adenoviral vector of the invention is administered to a subject by epicutaneous administration, intradermal administration, intramuscular injection, intraperitoneal injection, intravenous injection, nasal administration, oral administration, rectal administration, subcutaneous injection, transdermal administration or intravaginal administration.

In an embodiment of the invention, the vectors can be administered intramuscularly (IM), i.e., injection directly into muscle. Muscles are well vascularized and the uptake is typically rapid.

Adjuvants

Approaches to establishing strong and lasting immunity to specific pathogens include addition of adjuvants to vaccines. By "adjuvant" is meant an agent that augments, stimulates, activates, potentiates or modulates the immune response to an active ingredient of the composition. The adjuvant effect may occur at the cellular or humoral level, or both. Adjuvants stimulate the response of the immune system to the actual antigen but have no immunological effect themselves. Alternatively or additionally, adjuvented compositions of the invention may comprise one or more immunostimulants. By "immunostimulant" it is meant an agent that induces a general, temporary increase in a subject's immune response, whether administered with the antigen or separately.

A composition of the invention may be administered with or without an adjuvant. Alternatively, or additionally, the composition may comprise, or be administered in conjunction with, one or more adjuvants (e.g. vaccine adjuvants), in particular the composition comprises an immunologically effective amount of a vector of the invention encoding a transgene.

Methods of Use/Uses

Methods are provided for inducing an immune response against a disease caused by a pathogen in a subject in need thereof comprising a step of administering an immunologically effective amount of a construct or composition as disclosed herein. In some embodiments are provided the use of the constructs or compositions disclosed herein for inducing an immune response to a transgenic antigen in a subject in need thereof. Vectors of the invention may be applied for the prophylaxis, treatment or amelioration of diseases due to infection.

Methods of the invention include the use of a vector of the invention in medicine. They include the use of a vector of the invention for the treatment of a disease caused by a pathogen. A vector of the invention can be used in the manufacture of a medicament for treating a disease caused by a pathogen. A vector of the invention can be used in the manufacture of a medicament for the prevention or treatment of a disease, for example, a disease caused by respiratory syncytial virus (RSV).

Effective immunization with adenoviral vectors depends on the intrinsic immunomodulatory capability of the adenoviral vector backbone. Immunologically less potent adenoviruses induce less antigen expression. Effective immunization also depends on the ability of the promoter to drive strong and sustained transgene expression. For example, adenoviral vectors driven by the cytomegalovirus immediate-early (CMV-IE) promoter do not sustain long-term transgene expression because they induce cytokines that dampen expression.

By "subject" is intended a vertebrate, such as a mammal e.g. a human or a veterinary mammal. In some embodiments the subject is human.

General

Vectors of the invention are generated using techniques and sequences provided herein, in conjunction with techniques known to those of skill in the art. Such techniques include conventional cloning techniques of cDNA such as those described in texts, use of overlapping oligonucleotide sequences of the adenovirus genomes, polymerase chain reaction, and any suitable method which provides the desired nucleotide sequence.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "plurality" refers to two or more. Additionally, numerical limitations given with respect to concentrations or levels of a substance, such as solution component concentrations or ratios thereof, and reaction conditions such as temperatures, pressures and cycle times are intended to be approximate. The term "about" used herein is intended to mean the amount±10%.

The present invention will now be further described by means of the following non-limiting examples.

EXAMPLES

Example 1: Construction of Chimpanzee Adenoviruses with a Single Expression Cassette Wild type chimpanzee adenoviruses type 155 (ChAd155) (WO 2016/198621) and type 83 (ChAd83) (WO 2010/086189) were isolated from healthy chimpanzees using standard procedures and were constructed as described in Sci Transl Med (2012) 4:1 and WO 2010/086189.

In Example 1, the ChAd155 and ChAd 83 vectors were each constructed by inserting a single transgene expression cassette. The expression cassette components used either the classical human CMV promoter or the CASI promoter, rabies glycoprotein as a model antigen and, optionally, a WPRE enhancer. Three different insertion sites were tested for the transgene cassette:

(i) replacing the E3 region with the transgene cassette,
(ii) inserting the transgene cassette between the fiber and the E4 region (site HE1), and
(iii) inserting the transgene cassette downstream of the right ITR (site HE2).

This numbering of these insertion sites corresponds to the illustrations of FIG. 1 where:

(i) the top panel illustrates the RC1 vector, in which a transgene cassette replaced the E3 region,
(ii) the middle panel illustrates the RC3 vector, in which a transgene cassette is inserted between the stop codons of the fiber gene and the E4 region (site HE1), and
(iii) the bottom panel illustrates the RC2 vector, in which a transgene cassette is inserted downstream of the right ITR (site HE2).

In the vectors shown in Example 1, the E1 region remains intact in all configurations.

The transgene was inserted by homologous recombination techniques in the following positions of the SEQ ID NO: 1 and of the SEQ ID NO: 2:

HE1 ChAd155: insertion site between bp 34611 and 34612 of SEQ ID NO: 1;
HE2 ChAd155: insertion site between bp 37662 and 37663 of SEQ ID NO: 1;
HE1 ChAd83: insertion site between bp 33535 and 33536 of SEQ ID NO: 2;
HE2 ChAd83: insertion site between bp 36387 and 36388 of SEQ ID NO: 2.

When the transgene cassette was inserted in site HE1, ChAd155 failed to replicate. However, insertion of a transgene cassette into the HE1 site of ChAd83 produced a viable vector.

Example 2: Virus Production, Vector Titer and Expression of Vectors of Example 1

To identify an animal model in which to evaluate vector replication, a type C adenovirus ChAd155 RC2 and a type E adenovirus ChAd83 RC2 vectors of Example 1 were assessed for their ability to replicate, measured by vector titer and genome copy number, in cells of various animal origins. The results are shown in Table 1.

TABLE 1

Replication and Expression of RC2 ChAd155 and RC2 ChAd83 of Example 1

| Cell line: | | Vector | Genome | Expression | |
|---|---|---|---|---|---|
| Species | Vector | Titer | Copy | Day 2 | Day 7 |
| MRC5: | ChAd155 | +++ | +++ | ++ | ++++ |
| Human | ChAd83 | +++++ | +++++ | +++ | +++++ |
| PK15: | ChAd155 | +++++ | +++++ | NA | NA |
| Swine | ChAd83 | +++ | ++++ | NA | NA |
| NMuLi: | ChAd155 | ++ | +++ | +++ | +++ |
| Mouse | ChAd83 | ND | + | ++ | ++ |
| Vero: | ChAd155 | ++ | ++++ | +++ | +++ |
| Non-human primate | ChAd83 | ND | + | + | + |

ND = not detected; NA = not available

As shown in Table 1, human MRC5 cells and swine PK15 cells produced high vector titers and high genome copy numbers of both ChAd155 and ChAd83. Murine NMuLi and non-human primate Vero cells also produced RC ChAd155 but to a lesser extent than the human or swine cells. RC ChAd83 failed to grow well in murine NMuLi cells and, surprisingly, in non-human primate Vero cells.

Human MRC5, mouse NMuLi and non-human primate Vero cells supported the expression of RC ChAd155 through day 7. Human MRC5 cells supported the expression of RC ChAd83 through day 7, as did mouse NMuLi and non-human primate Vero cells, but to a lesser extent than the human cells.

Virus Production

FIG. 2A shows the amount of virus produced by human primary MRC5 cells infected with either ChAd155 or ChAd83, each comprising either the RC1 or RC2 vector construction of Example 1. The cells were harvested seven days post-infection and the vector titer was evaluated in cell lysates obtained following three freeze-thaw cycles. Vector titers were measured by quantitative PCR (QPCR) analysis with primers designed for the respective promoter regions. The multiplicity of infection (moi) was 1250 virus particles per cell. The virus production is indicated in the number of virus particles per cell (vp/cell) above the bars.

Human MRC5 cells supported production of ChAd155 comprising either RC1 ($2.17 \times 10^3$ vp/cell) or RC2 ($4.40 \times 10^3$ vp/cell) and also supported production of ChAd83 comprising either RC1 ($1.18 \times 10^4$ vp/cell) or RC2 ($1.06 \times 10^5$ vp/cell). As shown in FIG. 2A, ChAd83 was produced at a higher level than ChAd155; the ChAd83 vector comprising RC2 was the most robust of the four viral/vector combinations.

FIG. 2B shows the amount of virus produced by human primary MRC5 cells infected with ChAd83 comprising the RC1, RC2 or RC3 vector construction of Example 1. The cells were harvested two and seven days post-infection. As with FIG. 2A, vector titers were measured by quantitative PCR (QPCR) analysis with primers designed for the respective promoter regions. The multiplicity of infection (moi) was 250 or 1250 virus particles per cell. The virus production is indicated in the number of virus particles per cell (vp/cell) above the bars.

Human MRC5 cells supported production of ChAd83 comprising RC1, RC2 or RC3. As shown in FIG. 2B, there was higher virus production for the RC2 and RC3 ChAd83 vectors than for the RC1 vector. There was also higher virus production for the ChAd83 RC2 HE2 vector than the RC3 HE1 vector.

Vector Genome Copy Number

After infection, the vector is replicated in the cell and the vector genome copy number can be measured by QPCR. Vector DNA replication can occur even in cells not fully permissive for viral replication and propagation. QPCR of vector DNA provides a measure of vector replication within the infected cell, independently of the ability of the virus to complete the replication cycle and be released as mature viral progeny. Vector replication can thus be quantified in animal species, tissue types and cell types which are not permissive for ChAd virus replication or propagation.

Vector genome copy number was measured in parallel with vector titer and the results shown in FIG. 3A and FIG. 3B.

As with the virus production shown in FIG. 2A, Human MRC5 cells were infected with either ChAd155 or ChAd83, each comprising either the RC1 or RC2 vector construction of Example 1. The cells were harvested seven days post-infection, the total DNA extracted, the viral genome quantified by QPCR and the results expressed as vector genome copy per cell. The multiplicity of infection (moi) was 250 virus particles per cell and the numbers of virus particles per cell are indicated above the bars denoting viral genome copies per cell. The copy number is directly proportional to the level of transgene expression.

As shown in FIG. 3A, the amount of viral DNA replication of RC1 ($6.21 \times 10^3$ vp/cell) and RC2 ($6.71 \times 10^3$ vp/cell) by ChAd155 was similar. ChAd83 produced more RC1 ($2.76 \times 10^4$ vp/cell) and RC2 ($9.19 \times 10^4$ vp/cell) viral DNA than ChAd155. The highest level of viral DNA replication was observed by ChAd83 RC2.

As with the virus production shown in FIG. 2B, Human MRC5 cells were infected with ChAd83, comprising the RC1, RC2 or RC3 vector construction of Example 1. The cells were harvested at two and seven days post-infection, the total DNA extracted, the viral genome quantified by QPCR and the results expressed as vector genome copy per cell. The multiplicity of infection (moi) was 250 or 1250 virus particles per cell and the numbers of virus particles per cell are indicated above the bars denoting viral genome copies per cell. The copy number is directly proportional to the level of transgene expression.

As shown in FIG. 3B, the amount of viral DNA replication was higher for the RC2 and RC3 ChAd83 vectors than for the RC1 vector. There was comparable viral DNA replication between the RC2 and RC3 ChAd83 vectors.

Example 3: Adenoviral Genome Copy Number of Vectors of Example 1

The efficiency of the replication competent adenoviral vectors with the constructs of Example 1, expressed as vector copies per cell, was evaluated in cell cultures derived from both mice and non-human primates.

FIG. 4(A) shows the genome copy number of replication competent vectors grown in murine hepatic NMuLi cells grown in monolayers and infected with ChAd155 RC1, ChAd155 RC2, ChAd83 RC1 or ChAd83 RC2 at a multiplicity of infection of 250 virus particles per cell. Total DNA was extracted at five days post-infection and the vector replication was measured by QPCR using primers annealing to the vector's promoter region.

The results, expressed as vector copies per cell, are shown in FIG. 4(A). ChAd155 amplified both the RC1 and RC2 vector with high efficiency in NMuLi cells. ChAd155 replicated the RC1 ($1.73 \times 10^4$) and RC2 ($1.92 \times 10^4$) vectors to approximately the same degree. ChAd83 was less efficient than ChAd155 in replicating the RC1 and RC2 vectors. ChAd83 replicated the vector DNA only in small amounts in the murine cells. RC1 vector replicated at a level of $5.47 \times 10^2$ copies per cell and the RC2 vector at a level of $6.74 \times 10^2$ copies per cell.

Non-human primate Vero cells were also grown in monolayers and infected with ChAd155 RC1, ChAd155 RC2, ChAd83 RC1 or ChAd83 RC2 (FIG. 4(B)). Two different multiplicities of infection were used: 50 and 250 virus particles per cell. Total DNA was extracted at five days post-infection and the vector replication was measured by QPCR using primers annealing to the vector's promoter region.

The results, expressed as vector copies per cell, are shown in (FIG. 4(B)). The Vero primate cell line was permissive for ChAd155 RC1 ($3.71 \times 10^3$ copies per cell at an moi of 50 and $4.93 \times 10^4$ copies per cell at an moi of 250) and ChAd155 RC2 ($8.15 \times 10^3$ copies per cell at an moi of 50 and $7.05 \times 10^4$ copies per cell at an moi of 250). The Vero primate cell line was poorly, if at all, permissive for ChAd83 RC1 or ChAd83 RC2. No ChAd83 RC1 or ChAd83 RC2 vectors were detected to be expressed from Vero cells at an moi of 50. At an moi of 250, ChAd83 replicated the RC1 vector at a level of $1.13 \times 10^2$ copies per cell and the RC2 vector at a level of $1.29 \times 10^3$ copies per cell.

Example 4: Transgene Expression From Murine and Non-human Primate Cells of Vectors of Example 1

Western blot analysis was performed to compare the level of transgene expression by ChAd155 RC1 and ChAd155 RC2 in murine NMuLi cells (FIG. 5(A)). The cells were infected with ChAd155 RC1 or ChAd155 RC2 at a multiplicity of infection of 50, 250 or 1250 viral particles per cell. The cells were harvested at two and five days post infection, extracts prepared using standard methods and an equivalent amount of total cell extract loaded onto SDS-PAGE gels. Following electrophoretic separation, the proteins were transferred onto nitrocellulose membranes, which were then probed with a commercially available monoclonal antibody to the rabies glycoprotein transgene.

FIG. 5(A) demonstrates that both ChAd155 RC1 and ChAd155 RC2 express a transgene in murine NMuLi cells. Expression was observed at both two and five days post infection, indicated by the band of about 51 kDa, which corresponds to the expected molecular weight of the rabies glycoprotein (RG). The ChAd155 RC2 vector produced a higher level of transgene expression than the ChAd155 RC1 vector at both two and five days post-infection.

Western blot analysis was then performed to compare the level of transgene expression by ChAd155 RC1, ChAd155 RC2, ChAd83 RC1 and ChAd83 RC2 in murine NMuLi cells FIG. 5(B)). The cells were infected with ChAd155 RC1, ChAd155 RC2, ChAd83 RC1 or ChAd83 RC2 at a multiplicity of infection of 50, 250 or 1250 viral particles per cell (250 and 1250 for ChAd83 RC1). The cells were processed for western blot. The cells were harvested at two and seven days post infection, extracts prepared using standard methods and an equivalent amount of extract loaded onto SDS-PAGE gels. Following electrophoretic separation, the proteins were transferred onto nitrocellulose membranes, which were then probed with a commercially available monoclonal antibody to the rabies glycoprotein transgene.

FIG. 5(B) demonstrates that ChAd155 RC1, ChAd155 RC2, ChAd83 RC1 and ChAd83 RC2 express a transgene in murine NMuLi cells. Expression was observed at both two and five days post infection, indicated by the band of about 51 kDa, which corresponds to the expected molecular weight of the rabies glycoprotein (RG). ChAd155 demonstrated more efficient expression of the transgene than ChAd83. At two days post-infection, robust transgene expression by ChAd155 RC2 was observed even at the low multiplicity of 50 vp/cell, whereas robust transgene expression by ChAd155 RC1 was first observed at higher mois. Also, RC2 demonstrated more efficient transgene expression than RC1 in both ChAd155 and ChAd83 viral serotypes. RC2 was more robustly expressed than RC1 in each of the direct comparisons.

Western blot analysis was performed to compare the level of transgene expression by ChAd83 RC1, RC2 and RC3 in MRC5 cells (FIG. 5(C)). The cells were infected with ChAd83 RC1, RC2 or RC3 at a multiplicity of infection of 250 or 1250 viral particles per cell. The cells were harvested at two and seven days post infection, extracts prepared using standard methods and an equivalent amount of total cell extract loaded onto SDS-PAGE gels. Following electrophoretic separation, the proteins were transferred onto nitrocellulose membranes, which were then probed with a commercially available monoclonal antibody to the rabies glycoprotein transgene.

(FIG. 5(C)) demonstrates that all of ChAd83 RC1, RC2 and RC3 express a transgene in MRC5 cells. Expression was observed at both two and seven days post infection, indicated by the band of about 51 kDa, which corresponds to the expected molecular weight of the rabies glycoprotein (RG). The ChAd83 RC2 vector produced a higher level of transgene expression than the ChAd83 RC1 and RC3 vectors at both two and seven days post-infection. There was no rabies glycoprotein detection for the RC1 and RC3 vectors at 7 days.

Example 5: Construction of Alternative Chimpanzee Adenoviruses With a Single Expression Cassette As in Example 1, wild type chimpanzee adenoviruses type 155 (ChAd155) (WO 2016/198621) isolated from healthy chimpanzees using standard procedures were constructed as replication defective viruses as described in Sci Transl Med (2012) 4:1 and WO 2010/086189.

In Example 5, the ChAd155 is constructed by inserting a single transgene expression cassette. This expression cassette comprises the classical human CMV (hCMV) promoter, F0ΔTM, N and M2-1 RSV antigens and, optionally, a WPRE enhancer. This vector is shown in FIG. 6. The expression cassette is inserted into the E1 region of the adeno virus (after the E1 region has been deleted).

The ChAd155 shown in FIG. 6 comprises a transgene encoding all of the RSV F0ΔTM, M2-1 and N antigens, wherein a self-cleavage site ("2A") is included between the RSV F0ΔTM antigen and the composite RSV N.M2-1 antigen, in which a flexible linker is included between the RSV M2-1 and N antigens.

The ChAd155 RSV vector of Example 5 comprises the polynucleotide of SEQ ID NO: 4 and encodes the polypeptide of SEQ ID NO: 5.

Example 6: Construction of a Chimpanzee Adenoviruses with a Dual Expression Cassette Again, wild type chimpanzee adenoviruses type 155 (ChAd155) (WO 2016/198621) isolated from healthy chimpanzees using standard procedures were constructed as replication defective viruses as described in Sci Transl Med (2012) 4:1 and WO 2010/086189.

The ChAd155 of Example 6 is constructed by inserting two transgene expression cassettes into two different locations in the adenovirus:
  (1) The first expression cassette components comprise the classical human CMV (hCMV) promoter and N.M2-1 RSV composite antigen. This first expression cassette is inserted into the E1 region of the adenovirus (after the E1 region has been deleted).
  (2) The second expression cassette comprises an enhanced classical human CMV (enhanced hCMV) promoter, the F0ΔTM RSV antigen and a WPRE enhancer. This first expression cassette is inserted into the HE2 region of the adenovirus (after the HE2 region has been deleted).

This vector comprising a dual expression cassette is shown in FIG. 7.

In the construct of FIG. 7, Ad5E4orf6 has been substituted into the early gene 4 (E4) region. The substitution is necessary to increase the productivity in HEK 293 cells.

Example 7: Transgene Expression from the Dual Expression Cassette of Example 6

Western blot analysis was performed to compare the level of transgene expression in the ChAd155 vector of Example 6 (labelled "Dual" or "Dual cassette" in the figures) in MRC5 cells with:
  (i) a vector comprising a single F expression cassette (ChAd155-F0ΔTM, labelled "F0ΔTm"),
  (ii) a vector comprising a single NM2 expression cassette (ChAd155-NM2, labelled "NM2-1"), and
  (iii) the vector of Example 5 comprising a single expression cassette containing the F and N.M2-1 RSV antigens (ChAd155-F0ΔTM.NM2, also labelled "RSV")

The western blot analysis is shown in FIG. 8 and FIG. 9.
As shown in FIG. 8, the cells were infected with ChAd155-F0ΔTM, ChAd155-F0ΔTM.NM2 ("RSV") or the ChAd155 dual cassette of Example 6 at a multiplicity of infection of 500 viral particles per cell. In addition, cells were infected with ChAd155-F0ΔTM.NM2 ("RSV") at a multiplicity of infection of 500 or 1250 viral particles per cell. The cells were harvested at 48 hours and 96 hours post infection, extracts prepared using standard methods and an equivalent amount of total cell extract loaded onto SDS-PAGE gels.

FIG. 8 shows that the ChAd155 dual cassette provides an expression level of the F antigen which is comparable to ChAd155F0ΔTM and higher than ChAd155-FΔTM.NM2 in MRC5 cells.

As shown in FIG. 9, the cells were infected with ChAd155-NM2, ChAd155-F0ΔTM.NM2 ("RSV") or the ChAd155 dual cassette of Example 6 at a multiplicity of infection of 250 and 1250 viral particles per cell. The cells were harvested at 48 hours post infection, extracts prepared using standard methods and an equivalent amount of total cell extract loaded onto SDS-PAGE gels.

In FIG. 9, the ChAd155 dual cassette provides NM2-1 expression level at least comparable to the ChAd155-NM2 single vector and higher than ChAd155-FΔTM.NM2 ("RSV") in MRC5 cells.

Example 8: Immunogenicity of the Dual Expression Cassette of Example 6

The immunogenicity of the dual expression cassette of Example 6 was evaluated in CD1 outbred mice (10 per group). The experiment was performed by injecting $5 \times 10^8$ viral particles intramuscularly into the mice. The B-cell response was measured at 4 and 8 weeks after the immunization by measuring the RSV neutralising titres. Each dot represents the response in a single mouse, and the line corresponds to the mean for each dose group. The results of this analysis are shown in FIG. 10.

FIG. 10 shows that the ChAd155 dual cassette provides a B-cell response comparable to ChAd155F0ΔTM and higher than that produced by ChAd155-F0ΔTM.NM2 ("RSV").

The immunogenicity of the dual expression cassette of Example 6 was also evaluated in BALB/c inbred mice (48, 11 or 8 per group). The experiment was performed by injecting $10^7$ or $10^6$ viral particles intramuscularly. The T-cell response was measured 3 weeks after the immunization by ex vivo IFN-gamma enzyme-linked immunospot (ELISpot) using a M2 peptide T cell epitope mapped in BALB/c mice. The results are shown in FIG. 11, expressed as IFN-gamma Spot Forming Cells (SFC) per million splenocytes. Each dot represents the response in a single mouse, and the line corresponds to the mean for each dose group. Injected dose in number of virus particles are shown on the x axis. The results are shown in FIG. 11. FIG. 11 shows that the ChAd155 dual cassette provides a T-cell response higher than that produced by the single cassette ChAd155-F0ΔTM.NM2 ("triple RSV", the results for which are obtained from historical data). This difference in response is greater for the $10^6$ vp dose.

FIG. 11 refers to "#positive mice", i.e. the number of mice which responded to the vaccine.

Example 9: Immunogenicity of the Dual Expression Cassette of Example 6 in Cows The study design is detailed in Table 2 below:

| Group | No. Cows | Vaccine | Route | Dose | Immunization | End of Study |
|---|---|---|---|---|---|---|
| Gp1 | 4 | ChAd155 single RSV | Intramuscular (IM) | $1 \times 10^{11}$ | D0 | D90 |
| Gp2 | 4 | ChAd155 dual RSV | Intramuscular (IM) | $1 \times 10^{11}$ | D0 | D90 |
| Gp3 | 4 | Saline | Intramuscular (IM) | N/A | D0 | D90 |

The "ChAd155 single RSV" is the ChAd155 of Example 5, and the "ChAd155 dual RSV" is the ChAd155 of Example 6.

A total of 12 adult cows were enrolled in the study. The cows ranged in age from 2.7 years to 7.8 years and had a mean range of 4.8 years.

Before they were enrolled in the study, the cows were pre-screened for bovine RSV (BRSV) antibodies by ELISA. This allowed study groups to be established that had a similar distribution and mean BRSV Ab titer (so as to not bias any of the groups).

Samples were collected from the cows before vaccination (D-5 or D0) and after vaccination (D7,10,14,28,60,90). In this study, the cows were vaccinated with 1×10^11 viral particles of one of the two vaccines or with saline on day zero (D0).

A Bronchoalveolar lavage (BAL) was performed at day −5, 7, 10 or 28 after vaccination to isolate T cells in the lungs of the cow. Then IFN-gamma cytokine production of the CD4+ and CD8+ T cells upon stimulation with RSV antigens (in the form of peptide pools) encoded in the vaccines was detected using intracellular cytokine staining (ICS) (i.e. IFNγ ICS was used to detect the lung T cell responses in the animals). The results of this experiment are shown in FIGS. 12A and 12B. It can be concluded from this experiment that the ChAd155-dual RSV induces consistent RSV-specific CD4+ and CD8+ responses in Bronchoalveolar lavage (BAL).

Blood samples were also taken from the cows on day 0, 14, 28, 60 and 90 after vaccination in order for IFN-gamma cytokine production of the RSV-specific CD4+ and CD8+ responses of the peripheral blood mononuclear cells (PBMC) to be detected using intracellular cytokine staining (ICS) (i.e. IFNγ ICS was used to detect the peripheral T cell responses). The results of this experiment are shown in FIGS. 13A and 13B. Based on these results, it can be concluded that the ChAd155-dual RSV consistently expand the pre-existing RSV-specific CD4+ and CD8+ responses in PBMC.

The blood samples were also used to detect neutralising antibodies (nAbs) for RSV in the serum (i.e. the peripheral humoral response was detected). The results of this experiment are shown in FIGS. 14A and 14B. These results show that the ChAd155-dual RSV boosts RSV nAbs in serum which are maintained at levels higher than baseline 3 months after vaccination.

Example 10: Immunogenicity of ChAd155 Dual Encoding Rabies G and RSV NM2 Proteins Three different ChAd155 vectors used constructed in this experiment:
ChAd155 encoding both rabies G (RG) and RSV NM2 proteins (called "ChAd155 dual" in this example, and ChAd155 dual hCMV NM 2-1—CASI RG WPRE);
ChAd155 encoding just the rabies G (RG) protein (called "ChAd155 RG" in this example, and ChAd155(ΔE4) CASI RG WPRE); and
The ChAd155 vector shown in FIG. 6, i.e. the vector with transgene encoding all of the RSV F0ΔTM, M2-1 and N antigens (called "ChAd155 RSV").

Three different doses of the ChAd155 dual adenovirus were administered to mice: a highest dose of $10^7$ viral particles, and a middle dose of $10^6$ viral particles, and a lowest dose of $10^5$ viral particles.

Two different doses of the ChAd155 RG and ChAd155 RSV vectors were administered to mice. For the ChAd155 RSV, this was a higher dose of $10^7$ vaccine particles, and a lower dose of $10^6$ vaccine particles. For the ChAd155 RG, this was a higher dose of $10^6$ vaccine particles, and a lower dose of $10^5$ vaccine particles. Mice were sacrificed 3 weeks later and splenocytes tested by IFNγ ELISpot for T cell response to the vaccine encoded antigens.

Figure 15B:
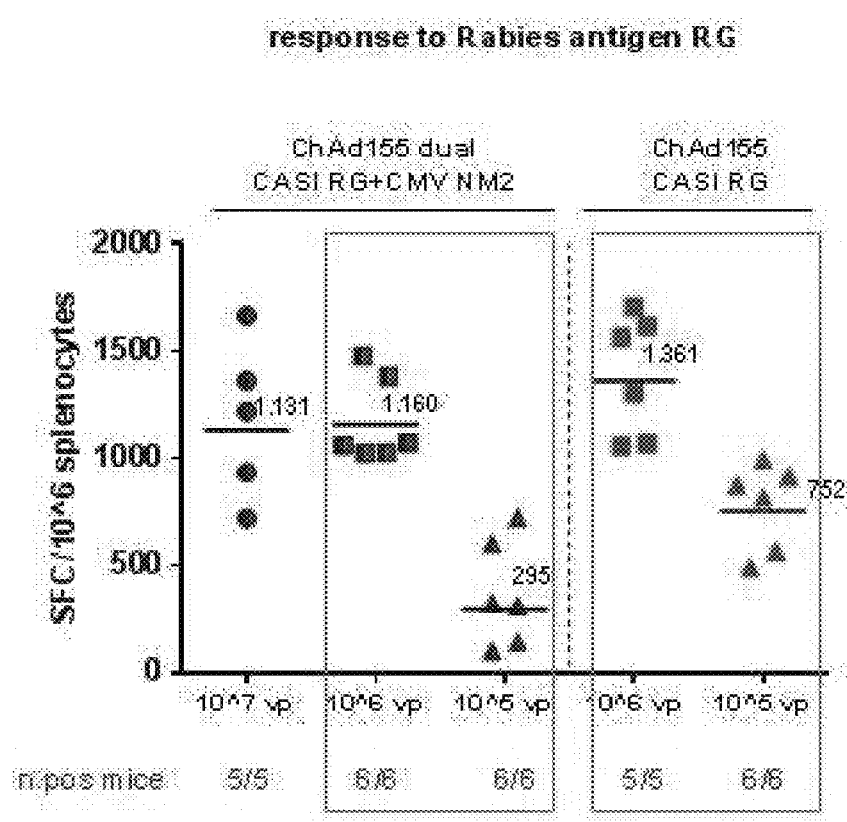
Figure 15C:
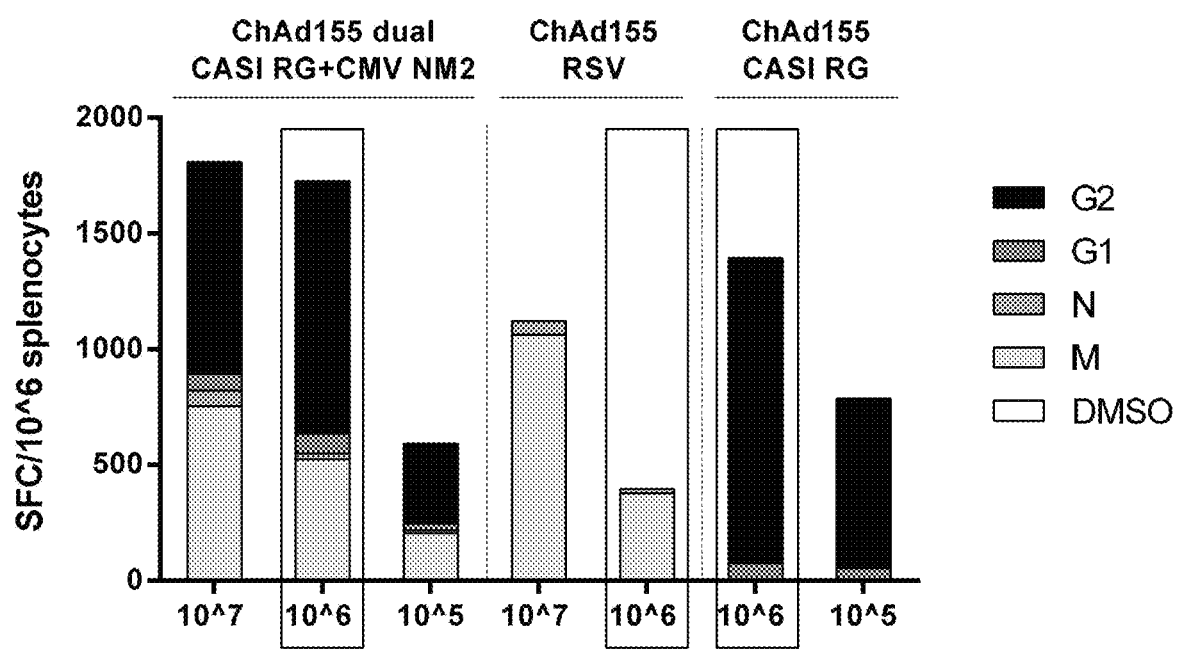

The results of this experiment are shown in FIGS. 15A, 15B and 15C. As can be seen from FIGS. 15A, 15B and 15C, the ChAd155 dual RG-NM2 vector shows overall comparable immune responses to the vectors encoding each of the RG and NM2 antigens alone.

FIG. 15C compares the cumulative response to all encoded antigens at the common $10^6$ vp dosage used for all three different vectors. The rabies G protein is listed twice (G1 and G2) as two pools of overlapping peptides were used to cover the whole sequence of the protein Therefore, placing the two antigens in the same vector still produces a comparable immune response while allowing antigens for different pathogens to be provided in the same vector.

Example 11: Expression of ChAd155 Dual Encoding Rabies G and RSV NM2 Proteins in HeLa Cells In the experiments of Example 11, HeLa cells were infected with the purified "ChAd155 dual", "ChAd155 RG" and "ChAd155 RSV" used in Example 10.

Multiplicities of infection (MOI) of 50, 250 and 1250 were used in this experiment.

In order to obtain the Western Blot shown in FIG. 16A (obtained under reducing conditions), the cell lysate was harvested 48 hours post-infection. The estimated size of the NM2-1 is 65 kDa. FIG. 16A shows a comparable expression level for ChAd155 dual cassette and ChAd155 NM2-1. In addition, the NM2-1 expression level was higher for the ChAd155 dual cassette than the ChAd155 RSV vector.

To obtain the Western Blot shown in FIG. 16B, the supernatant was harvested 48 hours post-infection. The estimated size of the rabies glycoprotein is 57.6 kDa. FIG. 16B shows a comparable expression level for the ChAd155 dual and ChAd155 RG adenoviruses.

In addition, infectivity data was also collected using the four different vectors. The infectivity of purified virus was evaluated in adherent Procell 92 cells by Hexon Immunostaining. The results are given in Table 3 below (vp=virus particle, ifu=infectious unit, and R is the ratio between these two numbers). The infectivity results indicate that all of the vectors have similar infectivity. In addition, as all of the R values were below 300, the infectivity of all vectors was deemed to be within the range of acceptability.

TABLE 3

|  | Vp/ml | Ifu/ml | R (vp/ifu) |
|---|---|---|---|
| ChAd155 hCMV NM 2-1 – CASI RG WPRE | 5.51E+11 | 4.53E+09 | 122 |
| ChAd155(ΔE4)hCMV-RSV | 1.12E+11 | 1.05E+09 | 107 |
| ChAd155(ΔE4)hCMV NM2-1 | 5.68E+11 | 4.26E+09 | 133 |
| ChAd155(ΔE4)CASI RG WPRE | 3.48E+11 | 3.35E+09 | 104 |

Example 12: Immunogenicity of ChAd155 Dual Encoding CRPV E2 and E1 Proteins

Two different ChAd155 vectors were constructed in this experiment:
ChAd155 encoding a modified CRPV E2 protein in a first expression cassette, and a modified CRPV E1 protein in a second expression cassette (called "CRPV Dual"); and
ChAd155 encoding a fusion of the modified CRPV E2 and E1 proteins in a single expression cassette (called "CRPV Fusion")

Two different doses of the two adeno vectors were administered to mice: a higher dose of $10^7$ viral particles, and a lower dose of $10^6$ viral particles. The results of this experiment are shown in FIG. 17. FIG. 17 is a IFNγ ELISpot on splenocytes 3 weeks post vaccination. A statistical analysis was performed on the results and the differences between the response from the different vectors was not deemed to be statistically significant. However, as can be seen from FIG. 17, the ChAd155 CRPV Dual vectors show increased frequency of responding mice at lowest dosage than the CRPV Fusion vectors (6/6 positive responding mice for the $10^6$ dose of the CRPV dual vector, but only 4/6 positive responding mice for the $10^6$ dose of the CRPV fusion vector.

Example 13: Expression of ChAd155 Dual Encoding CRPV E2 and E1 Proteins

The two different ChAd155 vectors used in Example 12 were also used in Example 13.

Multiplicities of infection (MOI) of 250 and 1250 were used in this experiment. The cell lysate was harvested 48 hours post-infection. The estimated size of the modified E1 protein is 48 kDa, the modified E2 protein is 35 kDa, and the fusion protein containing both the modified E1 and E2 proteins is 88 kDa.

FIG. 18 shows a Western blot (obtained under reducing conditions) illustrating that there was better expression of the modified E1 and E2 proteins by the CRPV dual vector than the CRPV fusion vector. The "Pvj" columns shown in FIG. 18 are the controls used.

In addition, infectivity data was collected using the two different vectors. The infectivity of purified virus was evaluated in adherent Procell 92 cells by Hexon Immunostaining. The results are given in Table 4 below (vp=virus particle, ifu=infectious unit, and R is the ratio between these two numbers). The infectivity results indicate that the two vectors have similar infectivity. In addition, as all of the R values were below 300, the infectivity of all vectors was deemed to be within the range of acceptability.

TABLE 4

|  | Vp/ml | Ifu/ml | R (vp/ifu) |
| --- | --- | --- | --- |
| ChAd155 hCMV CRPV DE2DE1 Fusion HA WPRE "CRPV Fusion" | 4.52E+11 | 2.97E+09 | 153 |
| ChAd155 hCMV CRPV DE2 HA WPRE - Enh.CMV CRPV DE1 HA WPRE "CRPV Dual" | 6.20E+11 | 4.39E+09 | 143 |

DESCRIPTION OF THE SEQUENCES

```
DESCRIPTION OF THE SEQUENCES
Polynucleotide sequence encoding wild type ChAd155
                                                                SEQ ID NO: 1
CATCATCAATAATATACCTTATTTTGGATTGAAGCCAATATGATAATGAGATGGGCGGCGCGGGCGGGAG

GCGGGTCCGGGGCGGGCCGGCGGGCGGGGCGGTGTGGCGGAAGTGGACTTTGTAAGTGTGGCGGATGTGACTTGCT

AGTGCCGGGCGCGGTAAAAGTGACGTTTTCCGTGCGCGACAACGCCCACGGGAAGTGACATTTTTCCCGCGGTTTTT

ACCGGATGTTGTAGTGAATTTGGGCGTAACCAAGTAAGATTTGGCCATTTTCGCGGGAAAACTGAAACGGGGAAGTG

AAATCTGATTAATTTCGCGTTAGTCATACCGCGTAATATTTGTCGAGGGCCGAGGGACTTTGGCCGATTACGTGGAG

GACTCGCCCAGGTGTTTTTTGAGGTGAATTTCCGCGTTCCGGGTCAAAGTCTCCGTTTTATTATTATAGTCAGCTGA

CGCGGAGTGTATTTATACCCTCTGATCTCGTCAAGTGGCCACTCTTGAGTGCCAGCGAGTAGAGTTTTCTCCTCTGC

CGCTCTCCGCTCCGCTCCGCTCGGCTCTGACACCGGGGAAAAAATGAGACATTTCACCTACGATGGCGGTGTGCTCA

CCGGCCAGCTGGCTGCTGAAGTCCTGGACACCCTGATCGAGGAGGTATTGGCCGATAATTATCCTCCCTCGACTCCT

TTTGAGCCACCTACACTTCACGAACTCTACGATCTGGATGTGGTGGGGCCCAGCGATCCGAACGAGCAGGCGGTTTC

CAGTTTTTTTCCAGAGTCCATGTTGTTGGCCAGCCAGGAGGGGGTCGAACTTGAGACCCCTCCTCCGATCGTGGATT

CCCCCGATCCGCCGCAGCTGACTAGGCAGCCCGAGCGCTGTGCGGGACCTGAGACTATGCCCCAGCTGCTACCTGAG

GTGATCGATCTCACCTGTAATGAGTCTGGTTTTCCACCCAGCGAGGATGAGGACGAAGAGGGTGAGCAGTTTGTGTT

AGATTCTGTGGAACAACCCGGGCGAGGATGCAGGTCTTGTCAATATCACCGGAAAAACACAGGAGACTCCCAGATTA

TGTGTTCTCTGTGTTATATGAAGATGACCTGTATGTTTATTTACAGTAAGTTTATCATCTGTGGGCAGGTGGGCTAT

AGTGTGGGTGGTGGTCTTTGGGGGGTTTTTTAATATATGTCAGGGGTTATGCTGAAGACTTTTTTATTGTGATTTTT

AAAGGTCCAGTGTCTGAGCCCGAGCAAGAACCTGAACCGGAGCCTGAGCCTTCTCGCCCCAGGAGAAAGCCTGTAAT

CTTAACTAGACCCAGCGCACCGGTAGCGAGAGGCCTCAGCAGCGCGGAGACCACCGACTCCGGTGCTTCCTCATCAC

CCCCGGAGATTCACCCCCTGGTGCCCCTGTGTCCCGTTAAGCCCGTTGCCGTGAGAGTCAGTGGGCGGCGGTCTGCT

GTGGAGTGCATTGAGGACTTGCTTTTTGATTCACAGGAACCTTTGGACTTGAGCTTGAAACGCCCCAGGCATTAAAC

CTGGTCACCTGGACTGAATGAGTTGACGCCTATGTTTGCTTTTGAATGACTTAATGTGTATAGATAATAAAGAGTGA

GATAATGTTTTAATTGCATGGTGTGTTTAACTTGGGCGGAGTCTGCTGGGTATATAAGCTTCCCTGGGCTAAACTTG

GTTACACTTGACCTCATGGAGGCCTGGGAGTGTTTGGAGAACTTTGCCGGAGTTCGTGCCTTGCTGGACGAGAGCTC

TAACAATACCTCTTGGTGGTGGAGGTATTTGTGGGGCTCTCCCCAGGGCAAGTTAGTTTGTAGAATCAAGGAGGATT

ACAAGTGGGAATTTGAAGAGCTTTTGAAATCCTGTGGTGAGCTATTGGATTCTTTGAATCTAGGCCACCAGGCTCTC

TTCCAGGAGAAGGTCATCAGGACTTTGGATTTTTCCACACCGGGGCGCATTGCAGCCGCGGTTGCTTTTCTAGCTTT

TTTGAAGGATAGATGGAGCGAAGAGACCCACTTGAGTTCGGGCTACGTCCTGGATTTTCTGGCCATGCAACTGTGGA

GAGCATGGATCAGACACAAGAACAGGCTGCAACTGTTGTCTTCCGTCCGCCCGTTGCTGATTCCGGCGGAGGAGCAA

CAGGCCGGGTCAGAGGACCGGGCCCGTCGGGATCCGGAGGAGAGGGCACCGAGGCCGGGCGAGAGGAGCGCGCTGAA
```

-continued

```
CCTGGGAACCGGGCTGAGCGGCCATCCACATCGGGAGTGAATGTCGGGCAGGTGGTGGATCTTTTTCCAGAACTGCG
GCGGATTTTGACTATTAGGGAGGATGGGCAATTTGTTAAGGGTCTTAAGAGGGAGAGGGGGGCTTCTGAGCATAACG
AGGAGGCCAGTAATTTAGCTTTTAGCTTGATGACCAGACACCGTCCAGAGTGCATCACTTTTCAGCAGATTAAGGAC
AATTGTGCCAATGAGTTGGATCTGTTGGGTCAGAAGTATAGCATAGAGCAGCTGACCACTTACTGGCTGCAGCCGGG
TGATGATCTGGAGGAAGCTATTAGGGTGTATGCTAAGGTGGCCCTGCGGCCCGATTGCAAGTACAAGCTCAAGGGGC
TGGTGAATATCAGGAATTGTTGCTACATTTCTGGCAACGGGCGGAGGTGGAGATAGAGACCGAAGACAGGGTGGCT
TTCAGATGCAGCATGATGAATATGTGGCCGGGGGTGCTGGGCATGGACGGGGTGGTGATTATGAATGTGAGGTTCAC
GGGGCCCAACTTTAACGGCACGGTGTTTTTGGGGAACACCAACCTGGTCCTGCACGGGGTGAGCTTCTATGGGTTTA
ACAACACCTGTGTGGAGGCCTGGACCGATGTGAAGGTCCGCGGTTGCGCCTTTTATGGATGTTGGAAGGCCATAGTG
AGCCGCCCTAAGAGCAGGAGTTCCATTAAGAAATGCTTGTTTGAGAGGTGCACCTTGGGGATCCTGGCCGAGGGCAA
CTGCAGGGTGCGCCACAATGTGGCCTCCGAGTGCGGTTGCTTCATGCTAGTCAAGAGCGTGGCGGTAATCAAGCATA
ATATGGTGTGCGGCAACAGCGAGGACAAGGCCTCACAGATGCTGACCTGCACGGATGGCAACTGCCACTTGCTGAAG
ACCATCCATGTAACCAGCCACAGCCGGAAGGCCTGGCCCGTGTTCGAGCACAACTTGCTGACCCGCTGCTCCTTGCA
TCTGGGCAACAGGCGGGGGGTGTTCCTGCCCTATCAATGCAACTTTAGTCACACCAAGATCTTGCTAGAGCCCGAGA
GCATGTCCAAGGTGAACTTGAACGGGGTGTTTGACATGACCATGAAGATCTGGAAGGTGCTGAGGTACGACGAGACC
AGGTCCCGGTGCAGACCCTGCGAGTGCGGGGGCAAGCATATGAGGAACCAGCCCGTGATGCTGGATGTGACCGAGGA
GCTGAGGACAGACCACTTGGTTCTGGCCTGCACCAGGGCCGAGTTTGGTTCTAGCGATGAAGACACAGATTGAGGTG
GGTGAGTGGGCGTGGCCTGGGGTGGTCATGAAAATATATAAGTTGGGGGTCTTAGGGTCTCTTTATTTGTGTTGCAG
AGACCGCCGGAGCCATGAGCGGGAGCAGCAGCAGCAGCAGTAGCAGCAGCGCCTTGGATGGCAGCATCGTGAGCCCT
TATTTGACGACGCGGATGCCCCACTGGGCCGGGGTGCGTCAGAATGTGATGGGCTCCAGCATCGACGGCCGACCCGT
CCTGCCCGCAAATTCCGCCACGCTGACCTATGCGACCGTCGCGGGGACGCCGTTGGACGCCACCGCCGCCGCCGCCG
CCACCGCAGCCGCCTCGGCCGTGCGCAGCCTGGCCACGGACTTTGCATTCCTGGGACCACTGGCGACAGGGGCTACT
TCTCGGGCCGCTGCTGCCGCCGTTCGCGATGACAAGCTGACCGCCCTGCTGGCGCAGTTGGATGCGCTTACTCGGGA
ACTGGGTGACCTTTCTCAGCAGGTCATGGCCCTGCGCCAGCAGGTCTCCTCCCTGCAAGCTGGCGGGAATGCTTCTC
CCACAAATGCCGTTTAAGATAAATAAAACCAGACTCTGTTTGGATTAAAGAAAAGTAGCAAGTGCATTGCTCTCTTT
ATTTCATAATTTTCCGCGCGCGATAGGCCCTAGACCAGCGTTCTCGGTCGTTGAGGGTGCGGTGTATCTTCTCCAGG
ACGTGGTAGAGGTGGCTCTGGACGTTGAGATACATGGGCATGAGCCCGTCCCGGGGGTGGAGGTAGCACCACTGCAG
AGCTTCATGCTCCGGGGTGGTGTTGTAGATGATCCAGTCGTAGCAGGAGCGCTGGGCATGGTGCCTAAAAATGTCCT
TCAGCAGCAGGCCGATGGCCAGGGGGAGGCCCTTGGTGTAAGTGTTTACAAAACGGTTAAGTTGGGAAGGGTGCATT
CGGGGAGAGATGATGTGCATCTTGGACTGTATTTTTAGATTGGCGATGTTTCCGCCCAGATCCCTTCTGGGATTCAT
GTTGTGCAGGACCACCAGTACAGTGTATCCGGTGCACTTGGGGAATTTGTCATGCAGCTTAGAGGGAAAAGCGTGGA
AGAACTTGGAGACGCCTTTGTGGCCTCCCAGATTTTCCATGCATTCGTCCATGATGATGGCAATGGGCCCGCGGGAG
GCAGCTTGGGCAAAGATATTTCTGGGGTCGCTGACGTCGTAGTTGTGTTCCAGGGTGAGGTCGTCATAGGCCATTTT
TACAAAGCGCGGGCGGAGGGTGCCCGACTGGGGGATGATGGTCCCCTCTGGCCCTGGGGCGTAGTTGCCCTCGCAGA
TCTGCATTTCCCAGGCCTTAATCTCGGAGGGGGAATCATATCCACCTGCGGGGCGATGAAGAAAACGGTTTCCGGA
GCCGGGGAGATTAACTGGGATGAGAGCAGGTTTCTAAGCAGCTGTGATTTTCCACAACCGGTGGGCCCATAAATAAC
ACCTATAACCGGTTGCAGCTGGTAGTTTAGAGAGCTGCAGCTGCCGTCGTCCCGAGGAGGGGGGCCACCTCGTTGA
GCATGTCCCTGACGCGCATGTTCTCCCCGACCAGATCCGCCAGAAGGCGCTCGCCGCCCAGGGACAGCAGCTCTTGC
AAGGAAGCAAAGTTTTTCAGCGGCTTGAGGCCGTCCGCCGTGGGCATGTTTTTCAGGGTCTGGCTCAGCAGCTCCAG
GCGGTCCCAGAGCTCGGTGACGTGCTCTACGGCATCTCTATCCAGCATATCTCCTCGTTTCGCGGGTTGGGGCGACT
```

-continued

```
TTCGCTGTAGGGCACCAAGCGGTGGTCGTCCAGCGGGGCCAGAGTCATGTCCTTCCATGGGCGCAGGGTCCTCGTCA

GGGTGGTCTGGGTCACGGTGAAGGGGTGCGCTCCGGGCTGAGCGCTTGCCAAGGTGCGCTTGAGGCTGGTTCTGCTG

GTGCTGAAGCGCTGCCGGTCTTCGCCCTGCGCGTCGGCCAGGTAGCATTTGACCATGGTGTCATAGTCCAGCCCCTC

CGCGGCGTGTCCCTTGGCGCGCAGCTTGCCCTTGGAGGTGGCGCCGCACGAGGGGCAGAGCAGGCTCTTGAGCGCGT

AGAGCTTGGGGGCGAGGAAGACCGATTCGGGGGAGTAGGCGTCCGCGCCGCAGACCCCGCACACGGTCTCGCACTCC

ACCAGCCAGGTGAGCTCGGGGCGCGCCGGGTCAAAAACCAGGTTTCCCCCATGCTTTTTGATGCGTTTCTTACCTCG

GGTCTCCATGAGGTGGTGTCCCCGCTCGGTGACGAAGAGGCTGTCCGTGTCTCCGTAGACCGACTTGAGGGGTCTTT

TCTCCAGGGGGGTCCCTCGGTCTTCCTCGTAGAGGAACTCGGACCACTCTGAGACGAAGGCCCGCGTCCAGGCCAGG

ACGAAGGAGGCTATGTGGGAGGGGTAGCGGTCGTTGTCCACTAGGGGGTCCACCTTCTCCAAGGTGTGAAGACACAT

GTCGCCTTCCTCGGCGTCCAGGAAGGTGATTGGCTTGTAGGTGTAGGCCACGTGACCGGGGGTTCCTGACGGGGGGG

TATAAAGGGGGTGGGGGCGCGCTCGTCGTCACTCTCTTCCGCATCGCTGTCTGCGAGGGCCAGCTGCTGGGGTGAG

TATTCCCTCTCGAAGGCGGGCATGACCTCCGCGCTGAGGTTGTCAGTTTCCAAAAACGAGGAGGATTTGATGTTCAC

CTGTCCCGAGGTGATACCTTTGAGGGTACCCGCGTCCATCTGGTCAGAAAACACGATCTTTTTATTGTCCAGCTTGG

TGGCGAACGACCCGTAGAGGGCGTTGGAGAGCAGCTTGGCGATGGAGCGCAGGGTCTGGTTCTTGTCCCTGTCGGCG

CGCTCCTTGGCCGCGATGTTGAGCTGCACGTACTCGCGCGCGACGCAGCGCCACTCGGGGAAGACGGTGGTGCGCTC

GTCGGGCACCAGGCGCACGCGCCAGCCGCGGTTGTGCAGGGTGACCAGGTCCACGCTGGTGGCGACCTCGCCGCGCA

GGCGCTCGTTGGTCCAGCAGAGACGGCCGCCCTTGCGCGAGCAGAAGGGGGGCAGGGGGTCGAGCTGGGTCTCGTCC

GGGGGGTCCGCGTCCACGGTGAAAACCCCGGGGCGCAGGCGCGCGTCGAAGTAGTCTATCTTGCAACCTTGCATGTC

CAGCGCCTGCTGCCAGTCGCGGGCGGCGAGCGCGCGCTCGTAGGGGTTGAGCGGCGGGCCCCAGGGCATGGGGTGGG

TGAGTGCGGAGGCGTACATGCCGCAGATGTCATAGACGTAGAGGGGCTCCCGCAGGACCCCGATGTAGGTGGGGTAG

CAGCGGCCGCCGCGGATGCTGGCGCGCACGTAGTCATACAGCTCGTGCGAGGGGGCGAGGAGGTCGGGGCCCAGGTT

GGTGCGGGCGGGGCGCTCCGCGCGGAAGACGATCTGCCTGAAGATGGCATGCGAGTTGGAAGAGATGGTGGGGCGCT

GGAAGACGTTGAAGCTGGCGTCCTGCAGGCCGACGGCGTCGCGCACGAAGGAGGCGTAGGAGTCGCGCAGCTTGTGT

ACCAGCTCGGCGGTGACCTGCACGTCGAGCGCGCAGTAGTCGAGGGTCTCGCGGATGATGTCATATTTAGCCTGCCC

CTTCTTTTTCCACAGCTCGCGGTTGAGGACAAACTCTTCGCGGTCTTTCCAGTACTCTTGGATCGGGAAACCGTCCG

GTTCCGAACGGTAAGAGCCTAGCATGTAGAACTGGTTGACGGCCTGGTAGGCGCAGCAGCCCTTCTCCACGGGGAGG

GCGTAGGCCTGCGCGGCCTTGCGGAGCGAGGTGTGGGTCAGGGCGAAGGTGTCCCTGACCATGACTTTGAGGTACTG

GTGCTTGAAGTCGGAGTCGTCGCAGCCGCCCCGCTCCCAGAGCGAGAAGTCGGTGCGCTTCTTGGAGCGGGGGTTGG

GCAGAGCGAAGGTGACATCGTTGAAGAGGATTTTGCCCGCGCGGGGCATGAAGTTGCGGGTGATGCGGAAGGGCCCC

GGCACTTCAGAGCGGTTGTTGATGACCTGGGCGGCGAGCACGATCTCGTCGAAGCCGTTGATGTTGTGGCCCACGAT

GTAGAGTTCCAGGAAGCGGGGCCGGCCCTTTACGGTGGGCAGCTTCTTTAGCTCTTCGTAGGTGAGCTCCTCGGGCG

AGGCGAGGCCGTGCTCGGCCAGGGCCCAGTCCGCGAGGTGCGGGTTGTCTCTGAGGAAGGACTTCCAGAGGTCGCGG

GCCAGGAGGGTCTGCAGGCGGTCTCTGAAGGTCCTGAACTGGCGGCCCACGGCCATTTTTTCGGGGGTGATGCAGTA

GAAGGTGAGGGGGTCTTGCTGCCAGCGGTCCCAGTCGAGCTGCAGGGCGAGGTCGCGCGGCGGTGACCAGGCGCT

CGTCGCCCCGAATTTCATGACCAGCATGAAGGGCACGAGCTGCTTTCCGAAGGCCCCCATCCAAGTGTAGGTCTCT

ACATCGTAGGTGACAAAGAGGCGCTCCGTGCGAGGATGCGAGCCGATCGGGAAGAACTGGATCTCCCGCCACCAGTT

GGAGGAGTGGCTGTTGATGTGGTGGAAGTAGAAGTCCCGTCGCCGGGCCGAACACTCGTGCTGGCTTTTGTAAAAGC

GAGCGCAGTACTGGCAGCGCTGCACGGGCTGTACCTCATGCACGAGATGCACCTTTCGCCCGCGCACGAGGAAGCCG

AGGGGAAATCTGAGCCCCCCGCCTGGCTCGCGGCATGGCTGGTTCTCTTCTACTTTGGATGCGTGTCCGTCTCCGTC

TGGCTCCTCGAGGGGTGTTACGGTGGAGCGGACCACCACGCCGCGCGAGCCGCAGGTCCAGATATCGGCGCGCGGCG

GTCGGAGTTTGATGACGACATCGCGCAGCTGGGAGCTGTCCATGGTCTGGAGCTCCCGCGGCGGCGGCAGGTCAGCC
```

-continued

```
GGGAGTTCTTGCAGGTTCACCTCGCAGAGTCGGGCCAGGGCGCGGGGCAGGTCTAGGTGGTACCTGATCTCTAGGGG
CGTGTTGGTGGCGGCGTCGATGGCTTGCAGGAGCCCGCAGCCCCGGGGGGCGACGACGGTGCCCCGCGGGGTGGTGG
TGGTGGTGGCGGTGCAGCTCAGAAGCGGTGCCGCGGGCGGGCCCCCGGAGGTAGGGGGGGCTCCGGTCCCGCGGGCA
GGGGCGGCAGCGGCACGTCGGCGTGGAGCGCGGGCAGGAGTTGGTGCTGTGCCCGGAGGTTGCTGGCGAAGGCGACG
ACGCGGCGGTTGATCTCCTGGATCTGGCGCCTCTGCGTGAAGACGACGGGCCCGGTGAGCTTGAACCTGAAAGAGAG
TTCGACAGAATCAATCTCGGTGTCATTGACCGCGGCCTGGCGCAGGATCTCCTGCACGTCTCCCGAGTTGTCTTGGT
AGGCGATCTCGGCCATGAACTGCTCGATCTCTTCCTCCTGGAGGTCTCCGCGTCCGGCGCGTTCCACGGTGGCCGCC
AGGTCGTTGGAGATGCGCCCCATGAGCTGCGAGAAGGCGTTGAGTCCGCCCTCGTTCCAGACTCGGCTGTAGACCAC
GCCCCCCTGGTCATCGCGGGCGCGCATGACCACCTGCGCGAGGTTGAGCTCCACGTGCCGCGCGAAGACGGCGTAGT
TGCGCAGACGCTGGAAGAGGTAGTTGAGGGTGGTGGCGGTGTGCTCGGCCACGAAGAAGTTCATGACCCAGCGGCGC
AACGTGGATTCGTTGATGTCCCCCAAGGCCTCCAGCCGTTCCATGGCCTCGTAGAAGTCCACGGCGAAGTTGAAAAA
CTGGGAGTTGCGCGCCGACACGGTCAACTCCTCCTCCAGAAGACGGATGAGCTCGGCGACGGTGTCGCGCACCTCGC
GCTCGAAGGCTATGGGGATCTCTTCCTCCGCTAGCATCACCACCTCCTCCTCTTCCTCCTCTTCTGGCACTTCCATG
ATGGCTTCCTCCTCTTCGGGGGGTGGCGGCGGCGGCGGTGGGGAGGGGCGCTCTGCGCCGGCGGCGGCGCACCGG
GAGGCGGTCCACGAAGCGCGCGATCATCTCCCCGCGGCGGCGGCGCATGGTCTCGGTGACGGCGCGGCCGTTCTCCC
GGGGGCGCAGTTGGAAGACGCCGCCGGACATCTGGTGCTGGGGCGGGTGGCCGTGAGGCAGCGAGACGGCGCTGACG
ATGCATCTCAACAATTGCTGCGTAGGTACGCCGCCGAGGGACCTGAGGGAGTCCATATCCACCGGATCCGAAAACCT
TTCGAGGAAGGCGTCTAACCAGTCGCAGTCGCAAGGTAGGCTGAGCACCGTGGCGGGCGGCGGGGGGTGGGGGGAGT
GTCTGGCGGAGGTGCTGCTGATGATGTAATTGAAGTAGGCGGACTTGACACGGCGGATGGTCGACAGGAGCACCATG
TCCTTGGGTCCGGCCTGCTGGATGCGGAGGCGGTCGGCTATGCCCCAGGCTTCGTTCTGGCATCGGCGCAGGTCCTT
GTAGTAGTCTTGCATGAGCCTTTCCACCGGCACCTCTTCTCCTTCCTCTTCTGCTTCTTCCATGTCTGCTTCGGCCC
TGGGGCGGCGCCGCGCCCCCTGCCCCCCATGCGCGTGACCCCGAACCCCCTGAGCGGTTGGAGCAGGGCCAGGTCG
GCGACGACGCGCTCGGCCAGGATGGCCTGCTGCACCTGCGTGAGGGTGGTTTGGAAGTCATCCAAGTCCACGAAGCG
GTGGTAGGCGCCCGTGTTGATGGTGTAGGTGCAGTTGGCCATGACGGACCAGTTGACGGTCTGGTGGCCCGGTTGCG
ACATCTCGGTGTACCTGAGTCGCGAGTAGGCGCGGGAGTCGAAGACGTAGTCGTTGCAAGTCCGCACCAGGTACTGG
TAGCCCACCAGGAAGTGCGGCGGCGGCTGGCGGTAGAGGGGCCAGCGCAGGGTGGCGGGGGCTCCGGGGGCCAGGTC
TTCCAGCATGAGGCGGTGGTAGGCGTAGATGTACCTGGACATCCAGGTGATACCCGCGGCGGTGGTGGAGGCGCGCG
GGAAGTCGCGCACCCGGTTCCAGATGTTGCGCAGGGGCAGAAAGTGCTCCATGGTAGGCGTGCTCTGTCCAGTCAGA
CGCGCGCAGTCGTTGATACTCTAGACCAGGGAAAACGAAAGCCGGTCAGCGGGCACTCTTCCGTGGTCTGGTGAATA
GATCGCAAGGGTATCATGGCGGAGGGCCTCGGTTCGAGCCCCGGGTCCGGGCCGGACGGTCCGCCATGATCCACGCG
GTTACCGCCCGCGTGTCGAACCCAGGTGTGCGACGTCAGACAACGGTGGAGTGTTCCTTTTGGCGTTTTTCTGGCCG
GGCGCCGGCGCCGCGTAAGAGACTAAGCCGCGAAAGCGAAAGCAGTAAGTGGCTCGCTCCCCGTAGCCGGAGGGATC
CTTGCTAAGGGTTGCGTTGCGGCGAACCCCGGTTCGAATCCCGTACTCGGGCCGGCCGGACCCGCGGCTAAGGTGTT
GGATTGGCCTCCCCCTCGTATAAAGACCCCGCTTGCGGATTGACTCCGGACACGGGACGAGCCCCTTTTATTTTTG
CTTTCCCCAGATGCATCCGGTGCTGCGGCAGATGCGCCCCCGCCCCAGCAGCAGCAACAACACCAGCAAGAGCGGC
AGCAACAGCAGCGGGAGTCATGCAGGGCCCCCTCACCCACCCTCGGCGGGCCGGCCACCTCGGCGTCCGCGGCCGTG
TCTGGCGCCTGCGGCGGCGGCGGGGGGCCGGCTGACGACCCCGAGGAGCCCCGCGGCGCAGGGCCAGACACTACCT
GGACCTGGAGGAGGGCGAGGGCCTGGCGCGGCTGGGGGCGCCGTCTCCCGAGCGCCACCCGCGGGTGCAGCTGAAGC
GCGACTCGCGCGAGGCGTACGTGCCTCGGCAGAACCTGTTCAGGGACCGCGCGGGCGAGGAGCCCGAGGAGATGCGG
GACAGGAGGTTCAGCGCAGGGCGGGAGCTGCGGCAGGGGCTGAACCGCGAGCGGCTGCTGCGCGAGGAGGACTTTGA
```

-continued

```
GCCCGACGCGCGGACGGGGATCAGCCCCGCGCGCGCACGTGGCGGCCGCCGACCTGGTGACGGCGTACGAGCAGA
CGGTGAACCAGGAGATCAACTTCCAAAAGAGTTTCAACAACCACGTGCGCACGCTGGTGGCGCGCGAGGAGGTGACC
ATCGGGCTGATGCACCTGTGGGACTTTGTAAGCGCGCTGGTGCAGAACCCCAACAGCAAGCCTCTGACGGCGCAGCT
GTTCCTGATAGTGCAGCACAGCAGGGACAACGAGGCGTTTAGGGACGCGCTGCTGAACATCACCGAGCCCGAGGGTC
GGTGGCTGCTGGACCTGATTAACATCCTGCAGAGCATAGTGGTGCAGGAGCGCAGCCTGAGCCTGGCCGACAAGGTG
GCGGCCATCAACTACTCGATGCTGAGCCTGGGCAAGTTTTACGCGCGCAAGATCTACCAGACGCCGTACGTGCCCAT
AGACAAGGAGGTGAAGATCGACGGTTTTTACATGCGCATGGCGCTGAAGGTGCTCACCCTGAGCGACGACCTGGGCG
TGTACCGCAACGAGCGCATCCACAAGGCCGTGAGCGTGAGCCGGCGGCGCGAGCTGAGCGACCGCGAGCTGATGCAC
AGCCTGCAGCGGGCGCTGGCGGGCGCCGGCAGCGGCGACAGGGAGGCGGAGTCCTACTTCGATGCGGGGCGGACCT
GCGCTGGGCGCCCAGCCGGCGGGCCCTGGAGGCCGCGGGGGTCCGCGAGGACTATGACGAGGACGGCGAGGAGGATG
AGGAGTACGAGCTAGAGGAGGGCGAGTACCTGGACTAAACCGCGGGTGGTGTTTCCGGTAGATGCAAGACCCGAACG
TGGTGGACCCGGCGCTGCGGGCGGCTCTGCAGAGCCAGCCGTCCGGCCTTAACTCCTCAGACGACTGGCGACAGGTC
ATGGACCGCATCATGTCGCTGACGGCGCGTAACCCGGACGCGTTCCGGCAGCAGCCGCAGGCCAACAGGCTCTCCGC
CATCCTGGAGGCGGTGGTGCCTGCGCGCTCGAACCCCACGCACGAGAAGGTGCTGGCCATAGTGAACGCGCTGGCCG
AGAACAGGGCCATCCGCCCGGACGAGGCCGGGCTGGTGTACGACGCGCTGCTGCAGCGCGTGGCCCGCTACAACAGC
GGCAACGTGCAGACCAACCTGGACCGGCTGGTGGGGGACGTGCGCGAGGCGGTGGCGCAGCGCGAGCGCGCGGATCG
GCAGGGCAACCTGGGCTCCATGGTGGCGCTGAATGCCTTCCTGAGCACGCAGCCGGCCAACGTGCCGCGGGGGCAGG
AAGACTACACCAACTTTGTGAGCGCGCTGCGGCTGATGGTGACCGAGACCCCCAGAGCGAGGTGTACCAGTCGGGC
CCGGACTACTTCTTCCAGACCAGCAGACAGGGCCTGCAGACGGTGAACCTGAGCCAGGCTTTCAAGAACCTGCGGGG
GCTGTGGGGCGTGAAGGCGCCCACCGGCGACCGGGCGACGGTGTCCAGCCTGCTGACGCCCAACTCGCGCCTGCTGC
TGCTGCTGATCGCGCCGTTCACGGACAGCGGCAGCGTGTCCCGGGACACCTACCTGGGGCACCTGCTGACCCTGTAC
CGCGAGGCCATCGGGCAGGCGCAGGTGGACGAGCACACCTTCCAGGAGATCACCAGCGTGAGCCGCGCGCTGGGGCA
GGAGGACACGAGCAGCCTGGAGGCGACTCTGAACTACCTGCTGACCAACCGGCGGCAGAAGATTCCCTCGCTGCACA
GCCTGACCTCCGAGGAGGAGCGCATCTTGCGCTACGTGCAGCAGAGCGTGAGCCTGAACCTGATGCGCGACGGGGTG
ACGCCCAGCGTGGCGCTGGACATGACCGCGCGCAACATGGAACCGGGCATGTACGCCGCGCACCGGCCTTACATCAA
CCGCCTGATGGACTACCTGCATCGCGCGGCGGCCGTGAACCCCGAGTACTTTACCAACGCCATCCTGAACCCGCACT
GGCTCCCGCCGCCCGGGTTCTACAGCGGGGGCTTCGAGGTCCCGGAGACCAACGATGGCTTCCTGTGGGACGACATG
GACGACAGCGTGTTCTCCCCGCGGCCGCAGGCGCTGGCGGAAGCGTCCCTGCTGCGTCCCAAGAAGGAGGAGGAGGA
GGAGGCGAGTCGCCGCCGCGGCAGCAGCGGCGTGGCTTCTCTGTCCGAGCTGGGGGCGGCAGCCGCCGCGCGCCCCG
GGTCCCTGGGCGGCAGCCCCTTTCCGAGCCTGGTGGGGTCTCTGCACAGCGAGCGCACCACCCGCCCTCGGCTGCTG
GGCGAGGACGAGTACCTGAATAACTCCCTGCTGCAGCCGGTGCGGGAGAAAAACCTGCCTCCCGCCTTCCCCAACAA
CGGGATAGAGAGCCTGGTGGACAAGATGAGCAGATGGAAGACCTATGCGCAGGAGCACAGGGACGCGCCTGCGCTCC
GGCCGCCCACGCGGCGCCAGCGCCACGACCGGCAGCGGGGCTGGTGTGGGATGACGAGGACTCCGCGGACGATAGC
AGCGTGCTGGACCTGGGAGGGAGCGGCAACCCGTTCGCGCACCTGCGCCCCCGCCTGGGGAGGATGTTTTAAAAAAA
AAAAAAAAAAGCAAGAAGCATGATGCAAAAATTAAATAAAACTCACCAAGGCCATGGCGACCGAGCGTTGGTTTCTT
GTGTTCCCTTCAGTATGCGGCGCGCGGCGATGTACCAGGAGGGACCTCCTCCCTCTTACGAGAGCGTGGTGGGCGCG
GCGGCGGCGGCGCCCTCTTCTCCCTTTGCGTCGCAGCTGCTGGAGCCGCCGTACGTGCCTCCGCGCTACCTGCGGCC
TACGGGGGGGAGAAACAGCATCCGTTACTCGGAGCTGGCGCCCCTGTTCGACACCACCCGGGTGTACCTGGTGGACA
ACAAGTCGGCGGACGTGGCCTCCCTGAACTACCAGAACGACCACAGCAATTTTTTGACCACGGTCATCCAGAACAAT
GACTACAGCCCGAGCGAGGCCAGCACCCAGACCATCAATCTGGATGACCGGTCGCACTGGGGCGGCGACCTGAAAAC
CATCCTGCACACCAACATGCCCAACGTGAACGAGTTCATGTTCACCAATAAGTTCAAGGCGCGGGTGATGGTGTCGC
```

```
GCTCGCACACCAAGGAAGACCGGGTGGAGCTGAAGTACGAGTGGGTGGAGTTCGAGCTGCCAGAGGGCAACTACTCC

GAGACCATGACCATTGACCTGATGAACAACGCGATCGTGGAGCACTATCTGAAAGTGGGCAGGCAGAACGGGGTCCT

GGAGAGCGACATCGGGGTCAAGTTCGACACCAGGAACTTCCGCCTGGGGCTGGACCCCGTGACCGGGCTGGTTATGC

CCGGGGTGTACACCAACGAGGCCTTCCATCCCGACATCATCCTGCTGCCCGGCTGCGGGGTGGACTTCACTTACAGC

CGCCTGAGCAACCTCCTGGGCATCCGCAAGCGGCAGCCCTTCCAGGAGGGCTTCAGGATCACCTACGAGGACCTGGA

GGGGGGCAACATCCCCGCGCTCCTCGATGTGGAGGCCTACCAGGATAGCTTGAAGGAAAATGAGGCGGGACAGGAGG

ATACCGCCCCGCCGCCTCCGCCGCCGCCGAGCAGGGCGAGGATGCTGCTGACACCGCGGCCGCGGACGGGGCAGAG

GCCGACCCCGCTATGGTGGTGGAGGCTCCCGAGCAGGAGGAGGACATGAATGACAGTGCGGTGCGCGGAGACACCTT

CGTCACCCGGGGGAGGAAAAGCAAGCGGAGGCCGAGGCCGCGGCCGAGGAAAAGCAACTGGCGGCAGCAGCGGCGG

CGGCGGCGTTGGCCGCGGCGGAGGCTGAGTCTGAGGGGACCAAGCCCGCCAAGGAGCCCGTGATTAAGCCCCTGACC

GAAGATAGCAAGAAGCGCAGTTACAACCTGCTCAAGGACAGCACCAACACCGCGTACCGCAGCTGGTACCTGGCCTA

CAACTACGGCGACCCGTCGACGGGGGTGCGCTCCTGGACCCTGCTGTGCACGCCGGACGTGACCTGCGGCTCGGAGC

AGGTGTACTGGTCGCTGCCCGACATGATGCAAGACCCCGTGACCTTCCGCTCCACGCGGCAGGTCAGCAACTTCCCG

GTGGTGGGCGCCGAGCTGCTGCCCGTGCACTCCAAGAGCTTCTACAACGACCAGGCCGTCTACTCCCAGCTCATCCG

CCAGTTCACCTCTCTGACCCACGTGTTCAATCGCTTTCCTGAGAACCAGATTCTGGCGCGCCCGCCCGCCCCCACCA

TCACCACCGTCAGTGAAAACGTTCCTGCTCTCACAGATCACGGGACGCTACCGCTGCGCAACAGCATCGGAGGAGTC

CAGCGAGTGACCGTTACTGACGCCAGACGCCGCACCTGCCCCTACGTTTACAAGGCCTTGGGCATAGTCTCGCCGCG

CGTCCTTTCCAGCCGCACTTTTTGAGCAACACCACCATCATGTCCATCCTGATCTCACCCAGCAATAACTCCGGCTG

GGGACTGCTGCGCGCGCCCAGCAAGATGTTCGGAGGGGCGAGGAAGCGTTCCGAGCAGCACCCCGTGCGCGTGCGCG

GGCACTTCCGCGCCCCCTGGGGAGCGCACAAACGCGGCCGCGCGGGGCGCACCACCGTGGACGACGCCATCGACTCG

GTGGTGGAGCAGGCGCGCAACTACAGGCCCGCGGTCTCTACCGTGGACGCGGCCATCCAGACCGTGGTGCGGGCGC

GCGGCGGTACGCCAAGCTGAAGAGCCGCCGGAAGCGCGTGGCCCGCCGCCACCGCCGCCGACCCGGGGCCGCCGCCA

AACGCGCCGCCGCGGCCCTGCTTCGCCGGGCCAAGCGCACGGGCCGCCGCGCCGCCATGAGGGCCGCGCGCCGCTTG

GCCGCCGGCATCACCGCCGCCACCATGGCCCCCCGTACCCGAAGACGCGCGGCCGCCGCCGCCGCCGCCGCCATCAG

TGACATGGCCAGCAGGCGCCGGGGCAACGTGTACTGGGTGCGCGACTCGGTGACCGGCACGCGCGTGCCCGTGCGCT

TCCGCCCCCCGCGGACTTGAGATGATGTGAAAAAACAACACTGAGTCTCCTGCTGTTGTGTGTATCCCAGCGGCGGC

GGCGCGCGCAGCGTCATGTCCAAGCGCAAAATCAAAGAAGAGATGCTCCAGGTCGTCGCGCCGGAGATCTATGGGCC

CCCGAAGAAGGAAGAGCAGGATTCGAAGCCCCGCAAGATAAAGCGGGTCAAAAAGAAAAAGAAAGATGATGACGATG

CCGATGGGGAGGTGGAGTTCCTGCGCGCCACGGCGCCCAGGCGCCCGGTGCAGTGGAAGGGCCGGCGCGTAAAGCGC

GTCCTGCGCCCCGGCACCGCGGTGGTCTTCACGCCCGGCGAGCGCTCCACCCGGACTTTCAAGCGCGTCTATGACGA

GGTGTACGGCGACGAAGACCTGCTGGAGCAGGCCAACGAGCGCTTCGGAGAGTTTGCTTACGGGAAGCGTCAGCGGG

CGCTGGGGAAGGAGGACCTGCTGGCGCTGCCGCTGGACCAGGGCAACCCCACCCCCAGTCTGAAGCCCGTGACCCTG

CAGCAGGTGCTGCCGAGCAGCGCACCCTCCGAGGCGAAGCGGGTCTGAAGCGCGAGGGCGGCGACCTGGCGCCCAC

CGTGCAGCTCATGGTGCCCAAGCGGCAGAGGCTGGAGGATGTGCTGGAGAAAATGAAAGTAGACCCCGGTCTGCAGC

CGGACATCAGGGTCCGCCCCATCAAGCAGGTGGCGCCGGGCCTCGGCGTGCAGACCGTGGACGTGGTCATCCCCACC

GGCAACTCCCCCGCCGCCGCCACCACTACCGCTGCCTCCACGGACATGGAGACACAGACCGATCCCGCCGCAGCCGC

AGCCGCAGCCGCCGCCGCGACCTCCTCGGCGGAGGTGCAGACGGACCCCTGGCTGCCGCCGGCGATGTCAGCTCCCC

GCGCGCGTCGCGGGCGCAGGAAGTACGGCGCCGCCAACGCGCTCCTGCCCGAGTACGCCTTGCATCCTTCCATCGCG

CCCACCCCCGGCTACCGAGGCTATACCTACCGCCCGCGAAGAGCCAAGGGTTCCACCCGCCGTCCCCGCCGACGCGC

CGCCGCCACCACCCGCCGCCGCCGCAGACGCCAGCCCGCACTGGCTCCAGTCTCCGTGAGGAAAGTGGCGCGCG
```

-continued

```
ACGGACACACCCTGGTGCTGCCCAGGGCGCGCTACCACCCCAGCATCGTTTAAAAGCCTGTTGTGGTTCTTGCAGAT
ATGGCCCTCACTTGCCGCCTCCGTTTCCCGGTGCCGGGATACCGAGGAGGAAGATCGCGCCGCAGGAGGGGTCTGGC
CGGCCGCGGCCTGAGCGGAGGCAGCCGCCGCGCACCGGCGGCGACGCGCCACCAGCCGACGCATGCGCGGCGGGG
TGCTGCCCCTGTTAATCCCCCTGATCGCCGCGGCGATCGGCGCCGTGCCCGGATCGCCTCCGTGGCCTTGCAAGCG
TCCCAGAGGCATTGACAGACTTGCAAACTTGCAAATATGGAAAAAAAAACCCCAATAAAAAAGTCTAGACTCTCACG
CTCGCTTGGTCCTGTGACTATTTTGTAGAATGGAAGACATCAACTTTGCGTCGCTGGCCCCGCGTCACGGCTCGCGC
CCGTTCCTGGGACACTGGAACGATATCGGCACCAGCAACATGAGCGGTGGCGCCTTCAGTTGGGGCTCTCTGTGGAG
CGGCATTAAAAGTATCGGGTCTGCCGTTAAAAATTACGGCTCCCGGGCCTGGAACAGCAGCACGGGCCAGATGTTGA
GAGACAAGTTGAAAGAGCAGAACTTCCAGCAGAAGGTGGTGGAGGGCCTGGCCTCCGGCATCAACGGGGTGGTGGAC
CTGGCCAACCAGGCCGTGCAGAATAAGATCAACAGCAGACTGGACCCCCGGCCGCCGGTGGAGGAGGTGCCGCCGGC
GCTGGAGACGGTGTCCCCCGATGGGCGTGGCGAGAAGCGCCCGCGGCCCGATAGGGAAGAGACCACTCTGGTCACGC
AGACCGATGAGCCGCCCCCGTATGAGGAGGCCCTGAAGCAAGGTCTGCCCACCACGCGGCCCATCGCGCCCATGGCC
ACCGGGGTGGTGGGCCGCCACACCCCCGCCACGCTGGACTTGCCTCCGCCCGCCGATGTGCCGCAGCAGCAGAAGGC
GGCACAGCCGGGCCCGCCCGCGACCGCCTCCCGTTCCTCCGCCGGTCCTCTGCGCCGCGCGGCCAGCGGCCCCCGCG
GGGGGGTCGCGAGGCACGGCAACTGGCAGAGCACGCTGAACAGCATCGTGGGTCTGGGGGTGCGGTCCGTGAAGCGC
CGCCGATGCTACTGAATAGCTTAGCTAACGTGTTGTATGTGTATGCGCCCTATGTCGCCGCCAGAGGAGCTGCTG
AGTCGCCGCCGTTCGCGCGCCCACCACCACCGCCACTCCGCCCCTCAAGATGGCGACCCCATCGATGATGCCGCAGT
GGTCGTACATGCACATCTCGGGCCAGGACGCCTCGGAGTACCTGAGCCCCGGGCTGGTGCAGTTCGCCCGCGCCACC
GAGAGCTACTTCAGCCTGAGTAACAAGTTTAGGAACCCCACGGTGGCGCCCACGCACGATGTGACCACCGACCGGTC
TCAGCGCCTGACGCTGCGGTTCATTCCCGTGGACCGCGAGGACACCGCGTACTCGTACAAGGCGCGGTTCACCCTGG
CCGTGGGCGACAACCGCGTGCTGGACATGGCCTCCACCTACTTTGACATCCGCGGGGTGCTGGACCGGGGTCCCACT
TTCAAGCCCTACTCTGGCACCGCCTACAACTCCCTGGCCCCCAAGGGCGCTCCCAACTCCTGCGAGTGGGAGCAAGA
GGAAACTCAGGCAGTTGAAGAAGCAGCAGAAGAGGAAGAAGAAGATGCTGACGGTCAAGCTGAGGAAGAGCAAGCAG
CTACCAAAAAGACTCATGTATATGCTCAGGCTCCCCTTTCTGGCGAAAAAATTAGTAAAGATGGTCTGCAAATAGGA
ACGGACGCTACAGCTACAGAACAAAAACCTATTTATGCAGACCCTACATTCCAGCCCGAACCCCAAATCGGGGAGTC
CCAGTGGAATGAGGCAGATGCTACAGTCGCCGGCGGTAGAGTGCTAAAGAAATCTACTCCCATGAAACCATGCTATG
GTTCCTATGCAAGACCCACAAATGCTAATGGAGGTCAGGGTGTACTAACGGCAAATGCCCAGGGACAGCTAGAATCT
CAGGTTGAAATGCAATTCTTTTCAACTTCTGAAAACGCCCGTAACGAGGCTAACAACATTCAGCCCAAATTGGTGCT
GTATAGTGAGGATGTGCACATGGAGACCCCGGATACGCACCTTTCTTACAAGCCCGCAAAAAGCGATGACAATTCAA
AAATCATGCTGGGTCAGCAGTCCATGCCCAACAGACCTAATTACATCGGCTTCAGAGACAACTTTATCGGCCTCATG
TATTACAATAGCACTGGCAACATGGGAGTGCTTGCAGGTCAGGCCTCTCAGTTGAATGCAGTGGTGGACTTGCAAGA
CAGAAACACAGAACTGTCCTACCAGCTCTTGCTTGATTCCATGGGTGACAGAACCAGATACTTTTCCATGTGGAATC
AGGCAGTGGACAGTTATGACCCAGATGTTAGAATTATTGAAAATCATGGAACTGAAGACGAGCTCCCCAACTATTGT
TTCCCTCTGGGTGGCATAGGGGTAACTGACACTTACCAGGCTGTTAAAACCAACAATGGCAATAACGGGGGCCAGGT
GACTTGGACAAAAGATGAAACTTTTGCAGATCGCAATGAAATAGGGGTGGGAAACAATTTCGCTATGGAGATCAACC
TCAGTGCCAACCTGTGGAGAAACTTCCTGTACTCCAACGTGGCGCTGTACCTACCAGACAAGCTTAAGTACAACCCC
TCCAATGTGGACATCTCTGACAACCCCAACACCTACGATTACATGAACAAGCGAGTGGTGGCCCCGGGGCTGGTGGA
CTGCTACATCAACCTGGGCGCGCGCTGGTCGCTGGACTACATGGACAACGTCAACCCCTTCAACCACCACCGCAATG
CGGGGCCTGCGCTACCGCTCCATGCTCCTGGGCAACGGGCGCTACGTGCCCTTCCACATCCAGGTGCCCCAGAAGTTC
TTTGCCATCAAGAACCTCCTCCTCCTGCCGGGCTCCTACACCTACGAGTGGAACTTCAGGAAGGATGTCAACATGGT
CCTCCAGAGCTCTCTGGGTAACGATCTCAGGGTGGACGGGGCCAGCATCAAGTTCGAGAGCATCTGCCTCTACGCCA
```

-continued

```
CCTTCTTCCCCATGGCCCACAACACGGCCTCCACGCTCGAGGCCATGCTCAGGAACGACACCAACGACCAGTCCTTC
AATGACTACCTCTCCGCCGCCAACATGCTCTACCCCATACCCGCCAACGCCACCAACGTCCCCATCTCCATCCCCTC
GCGCAACTGGGCGGCCTTCCGCGGCTGGGCCTTCACCCGCCTCAAGACCAAGGAGACCCCCTCCCTGGGCTCGGGAT
TCGACCCCTACTACACCTACTCGGGCTCCATTCCCTACCTGGACGGCACCTTCTACCTCAACCACACTTTCAAGAAG
GTCTCGGTCACCTTCGACTCCTCGGTCAGCTGGCCGGGCAACGACCGTCTGCTCACCCCCAACGAGTTCGAGATCAA
GCGCTCGGTCGACGGGGAGGGCTACAACGTGGCCCAGTGCAACATGACCAAGGACTGGTTCCTGGTCCAGATGCTGG
CCAACTACAACATCGGCTACCAGGGCTTCTACATCCCAGAGAGCTACAAGGACAGGATGTACTCCTTCTTCAGGAAC
TTCCAGCCCATGAGCCGGCAGGTGGTGGACCAGACCAAGTACAAGGACTACCAGGAGGTGGGCATCATCCACCAGCA
CAACAACTCGGGCTTCGTGGGCTACCTCGCCCCCACCATGCGCGAGGGACAGGCCTACCCCGCCAACTTCCCCTATC
CGCTCATAGGCAAGACCGCGGTCGACAGCATCACCCAGAAAAAGTTCCTCTGCGACCGCACCCTCTGGCGCATCCCC
TTCTCCAGCAACTTCATGTCCATGGGTGCGCTCTCGGACCTGGGCCAGAACTTGCTCTACGCCAACTCCGCCCACGC
CCTCGACATGACCTTCGAGGTCGACCCCATGGACGAGCCCACCCTTCTCTATGTTCTGTTCGAAGTCTTTGACGTGG
TCCGGGTCCACCAGCCGCACCGCGGCGTCATCGAGACCGTGTACCTGCGTACGCCCTTCTCGGCCGGCAACGCCACC
ACCTAAAGAAGCAAGCCGCAGTCATCGCCGCCTGCATGCCGTCGGGTTCCACCGAGCAAGAGCTCAGGGCCATCGTC
AGAGACCTGGGATGCGGGCCCTATTTTTTGGGCACCTTCGACAAGCGCTTCCCTGGCTTTGTCTCCCCACACAAGCT
GGCCTGCGCCATCGTCAACACGGCCGGCCGCGAGACCGGGGGCGTGCACTGGCTGGCCTTCGCCTGGAACCCGCGCT
CCAAAACATGCTTCCTCTTTGACCCCTTCGGCTTTTCGGACCAGCGGCTCAAGCAAATCTACGAGTTCGAGTACGAG
GGCTTGCTGCGTCGCAGCGCCATCGCCTCCTCGCCCGACCGCTGCGTCACCCTCGAAAAGTCCACCCAGACCGTGCA
GGGGCCCGACTCGGCCGCCTGCGGTCTCTTCTGCTGCATGTTTCTGCACGCCTTTGTGCACTGGCCTCAGAGTCCCA
TGGACCGCAACCCCACCATGAACTTGCTGACGGGGGTGCCCAACTCCATGCTCCAGAGCCCCCAGGTCGAGCCCACC
CTGCGCCGCAACCAGGAGCAGCTCTACAGCTTCCTGGAGCGCCACTCGCCTTACTTCCGCCGCCACAGCGCACAGAT
CAGGAGGGCCACCTCCTTCTGCCACTTGCAAGAGATGCAAGAAGGGTAATAACGATGTACACACTTTTTTTTCTCAAT
AAATGGCATCTTTTTATTTATACAAGCTCTCTGGGGTATTCATTTCCCACCACCACCCGCCGTTGTCGCCATCTGGC
TCTATTTAGAAATCGAAAGGGTTCTGCCGGGAGTCGCCGTGCGCCACGGGCAGGGACACGTTGCGATACTGGTAGCG
GGTGCCCCACTTGAACTCGGGCACCACCAGGCGAGGCAGCTCGGGGAAGTTTTCGCTCCACAGGCTGCGGGTCAGCA
CCAGCGCGTTCATCAGGTCGGGCGCCGAGATCTTGAAGTCGCAGTTGGGGCCGCCGCCCTGCGCGCGCGAGTTGCGG
TACACCGGGTTGCAGCACTGGAACACCAACAGCGCCGGGTGCTTCACGCTGGCCAGCACGCTGCGGTCGGAGATCAG
CTCGGCGTCCAGGTCCTCCGCGTTGCTCAGCGCGAACGGGGTCATCTTGGGCACTTGCCGCCCCAGGAAGGGCGCGT
GCCCCGGTTTCGAGTTGCAGTCGCAGCGCAGCGGGATCAGCAGGTGCCCGTGCCCGGACTCGGCGTTGGGGTACAGC
GCGCGCATGAAGGCCTGCATCTGGCGGAAGGCCATCTGGGCCTTGGCGCCCTCCGAGAAGAACATGCCGCAGGACTT
GCCCGAGAACTGGTTTGCGGGCAGCTGGCGTCGTGCAGGCAGCAGCGCGCGTCGGTGTTGGCGATCTGCACCACGT
TGCGCCCCACCGGTTCTTCACGATCTTGGCCTTGGACGATTGCTCCTTCAGCGCGCGCTGCCCGTTCTCGCTGGTC
ACATCCATCTCGATCACATGTTCCTTGTTCACCATGCTGCTGCCGTGCAGACACTTCAGCTCGCCCTCCGTCTCGGT
GCAGCGGTGCTGCCACAGCGCGCAGCCCGTGGGCTCGAAAGACTTGTAGGTCACCTCCGCGAAGGACTGCAGGTACC
CCTGCAAAAAGCGGCCCATCATGGTCACGAAGGTCTTGTTGCTGCTGAAGGTCAGCTGCAGCCCGCGGTGCTCCTCG
TTCAGCCAGGTCTTGCACACGGCCGCCAGCGCCTCCACCTGGTCGGGCAGCATCTTGAAGTTCACCTTCAGCTCATT
CTCCACGTGGTACTTGTCCATCAGCGTGCGCGCCGCCTCCATGCCCTTCTCCCAGGCCGACACCAGCGGCAGGCTCA
CGGGGTTCTTCACCATCACCGTGGCCGCCGCCTCCGCCGCGCTTTCGCTTTCCGCCCCGCTGTTCTCTTCCTCTTCC
TCCTCTTCCTCGCCGCCGCCCACTCGCAGCCCCCGCACCACGGGGTCGTCTTCCTGCAGGCGCTGCACCTTGCGCTT
GCCGTTGCGCCCCTGCTTGATGCGCACGGGCGGGTTGCTGAAGCCCACCATCACCAGCGCGGCCTCTTCTTGCTCGT
```

-continued

```
CCTCGCTGTCCAGAATGACCTCCGGGGAGGGGGGGTTGGTCATCCTCAGTACCGAGGCACGCTTCTTTTTCTTCCTG
GGGGCGTTCGCCAGCTCCGCGGCTGCGGCCGCTGCCGAGGTCGAAGGCCGAGGGCTGGGCGTGCGCGGCACCAGCGC
GTCCTGCGAGCCGTCCTCGTCCTCCTCGGACTCGAGACGGAGGCGGGCCCGCTTCTTCGGGGGCGCGCGGGGCGGCG
GAGGCGGCGGCGGCGACGGAGACGGGGACGAGACATCGTCCAGGGTGGGTGGACGGCGGGCCGCGCCGCGTCCGCGC
TCGGGGGTGGTCTCGCGCTGGTCCTCTTCCCGACTGGCCATCTCCCACTGCTCCTTCTCCTATAGGCAGAAAGAGAT
CATGGAGTCTCTCATGCGAGTCGAGAAGGAGGAGGACAGCCTAACCGCCCCCTCTGAGCCCTCCACCACCGCCGCCA
CCACCGCCAATGCCGCCGCGGACGACGCGCCCACCGAGACCACCGCCAGTACCACCCTCCCCAGCGACGCACCCCCG
CTCGAGAATGAAGTGCTGATCGAGCAGGACCCGGGTTTTGTGAGCGGAGAGGAGGATGAGGTGGATGAGAAGGAGAA
GGAGGAGGTCGCCGCCTCAGTGCCAAAAGAGGATAAAAAGCAAGACCAGGACGACGCAGATAAGGATGAGACAGCAG
TCGGCGGGGAACGGAAGCCATGATGCTGATGACGGCTACCTAGACGTGGGAGACGACGTGCTGCTTAAGCACCTG
CACCGCCAGTGCGTCATCGTCTGCGACGCGCTGCAGGAGCGCTGCGAAGTGCCCCTGGACGTGGCGGAGGTCAGCCG
CGCCTACGAGCGGCACCTCTTCGCGCCGCACGTGCCCCCCAAGCGCGGGAGAACGGCACCTGCGAGCCCAACCCGC
GTCTCAACTTCTACCCGGTCTTCGCGGTACCCGAGGTGCTGGCCACCTACCACATCTTTTTCCAAAACTGCAAGATC
CCCCTCTCCTGCCGCGCCAACCGCACCCGCGCCGACAAAACCCTGACCCTGCGGCAGGGCGCCCACATACCTGATAT
CGCCTCTCTGGAGGAAGTGCCCAAGATCTTCGAGGGTCTCGGTCGCGACGAGAAACGGGCGGCGAACGCTCTGCACG
GAGACAGCGAAAACGAGAGTCACTCGGGGGTGCTGGTGGAGCTCGAGGGCGACAACGCGCGCCTGGCCGTACTCAAG
CGCAGCATAGAGGTCACCCACTTTGCCTACCCGGCGCTCAACCTGCCCCCCAAGGTCATGAGTGTGGTCATGGGCGA
GCTCATCATGCGCCGCGCCCAGCCCCTGGCCGCGGATGCAAACTTGCAAGAGTCCTCCGAGGAAGGCCTGCCCGCGG
TCAGCGACGAGCAGCTGGCGCGCTGGCTGGAGACCCGCGACCCCGCGCAGCTGGAGGAGCGGCGCAAGCTCATGATG
GCCGCGGTGCTGGTCACCGTGGAGCTCGAGTGTCTGCAGCGCTTCTTCGCGGACCCCGAGATGCAGCGCAAGCTCGA
GGAGACCCTGCACTACACCTTCCGCCAGGGCTACGTGCGCCAGGCCTGCAAGATCTCCAACGTGGAGCTCTGCAACC
TGGTCTCCTACCTGGGCATCCTGCACGAGAACCGCCTCGGGCAGAACGTCCTGCACTCCACCCTCAAAGGGGAGGCG
CGCCGCGACTACATCCGCGACTGCGCCTACCTCTTCCTCTGCTACACCTGGCAGACGGCCATGGGGGTCTGGCAGCA
GTGCCTGGAGGAGCGCAACCTCAAGGAGCTGGAAAAGCTCCTCAAGCGCACCCTCAGGGACCTCTGGACGGGCTTCA
ACGAGCGCTCGGTGGCCGCCGCGCTGGCGGACATCATCTTTCCCGAGCGCCTGCTCAAGACCCTGCAGCAGGGCCTG
CCCGACTTCACCAGCCAGAGCATGCTGCAGAACTTCAGGACTTTCATCCTGGAGCGCTCGGGCATCCTGCCGGCCAC
TTGCTGCGCGCTGCCCAGCGACTTCGTGCCCATCAAGTACAGGGAGTGCCCGCCGCCGCTCTGGGGCCACTGCTACC
TCTTCCAGCTGGCCAACTACCTCGCCTACCACTCGGACCTCATGGAAGACGTGAGCGGCGAGGGCCTGCTCGAGTGC
CACTGCCGCTGCAACCTCTGCACGCCCCACCGCTCTCTAGTCTGCAACCCGCAGCTGCTCAGCGAGAGTCAGATTAT
CGGTACCTTCGAGCTGCAGGGTCCCTCGCCTGACGAGAAGTCCGCGGCTCCAGGGCTGAAACTCACTCCGGGGCTGT
GGACTTCCGCCTACCTACGCAAATTTGTACCTGAGGACTACCACGCCCACGAGATCAGGTTCTACGAAGACCAATCC
CGCCCGCCCAAGGCGGAGCTCACCGCCTGCGTCATCACCCAGGGGCACATCCTGGGCCAATTGCAAGCCATCAACAA
AGCCCGCCGAGAGTTCTTGCTGAAAAAGGGTCGGGGGTGTACCTGGACCCCCAGTCCGGCGAGGAGCTAAACCCGC
TACCCCCGCCGCCGCCCCAGCAGCGGGACCTTGCTTCCCAGGATGGCACCCAGAAAGAAGCAGCAGCCGCCGCCGCC
GCCGCAGCCATACATGCTTCTGGAGGAAGAGGAGGAGGACTGGGACAGTCAGGCAGAGGAGGTTTCGGACGAGGAGC
AGGAGGAGATGATGGAAGACTGGGAGGAGGACAGCAGCCTAGACGAGGAAGCTTCAGAGGCCGAAGAGGTGGCAGAC
GCAACACCATCGCCCTCGGTCGCAGCCCCTCGCCGGGGCCCCTGAAATCCTCCGAACCCAGCACCAGCGCTATAAC
CTCCGCTCCTCCGGCGCCGGCGCCACCCGCCCGCAGACCCAACCGTAGATGGGACACCACAGGAACCGGGGTCGGTA
AGTCCAAGTGCCCGCCGCCGCCACCGCAGCAGCAGCAGCAGCAGCGCCAGGGCTACCGCTCGTGGCGCGGGCACAAG
AACGCCATAGTCGCCTGCTTGCAAGACTGCGGGGGCAACATCTCTTTCGCCCGCCGCTTCCTGCTATTCCACCACGG
GGTCGCCTTTCCCCGCAATGTCCTGCATTACTACCGTCATCTCTACAGCCCCTACTGCAGCGGCGACCCAGAGGCGG
```

-continued

```
CAGCGGCAGCCACAGCGGCGACCACCACCTAGGAAGATATCCTCCGCGGGCAAGACAGCGGCAGCAGCGGCCAGGAG
ACCCGCGGCAGCAGCGGCGGGAGCGGTGGGCGCACTGCGCCTCTCGCCCAACGAACCCCTCTCGACCCGGGAGCTCA
GACACAGGATCTTCCCCACTTTGTATGCCATCTTCCAACAGAGCAGAGGCCAGGAGCAGGAGCTGAAAATAAAAAC
AGATCTCTGCGCTCCCTCACCCGCAGCTGTCTGTATCACAAAAGCGAAGATCAGCTTCGGCGCACGCTGGAGGACGC
GGAGGCACTCTTCAGCAAATACTGCGCGCTCACTCTTAAAGACTAGCTCCGCGCCCTTCTCGAATTTAGGCGGGAGA
AAACTACGTCATCGCCGGCCGCCGCCCAGCCCGCCCAGCCGAGATGAGCAAAGAGATTCCCACGCCATACATGTGGA
GCTACCAGCCGCAGATGGGACTCGCGGCGGGAGCGGCCCAGGACTACTCCACCCGCATGAACTACATGAGCGCGGGA
CCCCACATGATCTCACAGGTCAACGGGATCCGCGCCCAGCGAAACCAAATACTGCTGGAACAGGCGGCCATCACCGC
CACGCCCCGCCATAATCTCAACCCCCGAAATTGGCCCGCCGCCCTCGTGTACCAGGAAACCCCCTCCGCCACCACCG
TACTACTTCCGCGTGACGCCCAGGCCGAAGTCCAGATGACTAACTCAGGGGCGCAGCTCGCGGGCGGCTTTCGTCAC
GGGGCGCGGCCGCTCCGACCAGGTATAAGACACCTGATGATCAGAGGCCGAGGTATCCAGCTCAACGACGAGTCGGT
GAGCTCTTCGCTCGGTCTCCGTCCGGACGGAACTTTCCAGCTCGCCGGATCCGGCCGCTCTTCGTTCACGCCCCGCC
AGGCGTACCTGACTCTGCAGACCTCGTCCTCGGAGCCCCGCTCCGGCGGCATCGGAACCCTCCAGTTCGTGGAGGAG
TTCGTGCCCTCGGTCTACTTCAACCCCTTCTCGGGACCTCCCGGACGCTACCCCGACCAGTTCATTCCGAACTTTGA
CGCGGTGAAGGACTCGGCGGACGGCTACGACTGAATGTCAGGTGTCGAGGCAGAGCAGCTTCGCCTGAGACACCTCG
AGCACTGCCGCCGCCACAAGTGCTTCGCCCGCGGTTCTGGTGAGTTCTGCTACTTTCAGCTACCCGAGGAGCATACC
GAGGGGCCGGCGCACGGCGTCCGCCTGACCACCCAGGGCGAGGTTACCTGTTCCCTCATCGGGAGTTTACCCTCCG
TCCCCTGCTAGTGGAGCGGGAGCGGGGTCCCTGTGTCCTAACTATCGCCTGCAACTGCCCTAACCCTGGATTACATC
AAGATCTTTGCTGTCATCTCTGTGCTGAGTTTAATAAACGCTGAGATCAGAATCTACTGGGGCTCCTGTCGCCATCC
TGTGAACGCCACCGTCTTCACCCACCCCGACCAGGCCCAGGCGAACCTCACCTGCGGTCTGCATCGGAGGGCCAAGA
AGTACCTCACCTGGTACTTCAACGGCACCCCCTTTGTGGTTTACAACAGCTTCGACGGGACGGAGTCTCCCTGAAA
GACCAGCTCTCCGGTCTCAGCTACTCCATCCACAAGAACACCACCCTCCAACTCTTCCCTCCCTACCTGCCGGGAAC
CTACGAGTGCGTCACCGGCCGCTGCACCCACCTCACCCGCCTGATCGTAAACCAGAGCTTTCCGGGAACAGATAACT
CCCTCTTCCCCAGAACAGGAGGTGAGCTCAGGAAACTCCCCGGGGACCAGGGCGGAGACGTACCTTCGACCCTTGTG
GGGTTAGGATTTTTTATTACCGGGTTGCTGGCTCTTTTAATCAAAGTTTCCTTGAGATTTGTTCTTTCCTTCTACGT
GTATGAACACCTCAACCTCCAATAACTCTACCCTTTCTTCGGAATCAGGTGACTTCTCTGAAATCGGGCTTGGTGTG
CTGCTTACTCTGTTGATTTTTTTCCTTATCATACTCAGCCTTCTGTGCCTCAGGCTCGCCGCCTGCTGCGCACACAT
CTATATCTACTGCTGGTTGCTCAAGTGCAGGGGTCGCCACCCAAGATGAACAGGTACATGGTCCTATCGATCCTAGG
CCTGCTGGCCCTGGCGGCCTGCAGCGCCGCCAAAAAAGAGATTACCTTTGAGGAGCCCGCTTGCAATGTAACTTTCA
AGCCCGAGGGTGACCAATGCACCACCCTCGTCAAATGCGTTACCAATCATGAGAGGCTGCGCATCGACTACAAAAAC
AAAACTGGCCAGTTTGCGGTCTATAGTGTGTTTACGCCCGGAGACCCCTCTAACTACTCTGTCACCGTCTTCCAGGG
CGGACAGTCTAAGATATTCAATTACACTTTCCCTTTTTATGAGTTATGCGATGCGGTCATGTACATGTCAAAACAGT
ACAACCTGTGGCCTCCCTCTCCCCAGGCGTGTGTGGAAAATACTGGGTCTTACTGCTGTATGGCTTTCGCAATCACT
ACGCTCGCTCTAATCTGCACGGTGCTATACATAAAATTCAGGCAGAGGCGAATCTTTATCGATGAAAAGAAAATGCC
TTGATCGCTAACACCGGCTTTCTATCTGCAGAATGAATGCAATCACCTCCCTACTAATCACCACCACCCTCCTTGCG
ATTGCCCATGGGTTGACACGAATCGAAGTGCCAGTGGGGTCCAATGTCACCATGGTGGGCCCCGCCGGCAATTCCAC
CCTCATGTGGGAAAAATTTGTCCGCAATCAATGGGTTCATTTCTGCTCTAACCGAATCAGTATCAAGCCCAGAGCCA
TCTGCGATGGGCAAAATCTAACTCTGATCAATGTGCAAATGATGGATGCTGGGTACTATTACGGGCAGCGGGGAGAA
ATCATTAATTACTGGCGACCCCACAAGGACTACATGCTGCATGTAGTCGAGGCACTTCCCACTACCACCCCCACTAC
CACCTCTCCCACCACCACCACCACTACTACTACTACTACTACTACTACTACTACCACTACCGCTGCCCGCCATA
```

-continued
```
CCCGCAAAAGCACCATGATTAGCACAAAGCCCCTCGTGCTCACTCCCACGCCGGCGGGCCCATCGGTGCGACCTCA

GAAACCACCGAGCTTTGCTTCTGCCAATGCACTAACGCCAGCGCTCATGAACTGTTCGACCTGGAGAATGAGGATGT

CCAGCAGAGCTCCGCTTGCCTGACCCAGGAGGCTGTGGAGCCCGTTGCCCTGAAGCAGATCGGTGATTCAATAATTG

ACTCTTCTTCTTTTGCCACTCCCGAATACCCTCCCGATTCTACTTTCCACATCACGGGTACCAAAGACCCTAACCTC

TCTTTCTACCTGATGCTGCTGCTCTGTATCTCTGTGGTCTCTTCCGCGCTGATGTTACTGGGGATGTTCTGCTGCCT

GATCTGCCGCAGAAAGAGAAAAGCTCGCTCTCAGGGCCAACCACTGATGCCCTTCCCCTACCCCCGGATTTTGCAG

ATAACAAGATATGAGCTCGCTGCTGACACTAACCGCTTTACTAGCCTGCGCTCTAACCCTTGTCGCTTGCGACTCGA

GATTCCACAATGTCACAGCTGTGGCAGGAGAAAATGTTACTTTCAACTCCACGGCCGATACCCAGTGGTCGTGGAGT

GGCTCAGGTAGCTACTTAACTATCTGCAATAGCTCCACTTCCCCCGGCATATCCCCAACCAAGTACCAATGCAATGC

CAGCCTGTTCACCCTCATCAACGCTTCCACCCTGGACAATGGACTCTATGTAGGCTATGTACCCTTTGGTGGGCAAG

GAAAGACCCACGCTTACAACCTGGAAGTTCGCCAGCCCAGAACCACTACCCAAGCTTCTCCCACCACCACCACCACC

ACCACCATCACCAGCAGCAGCAGCAGCAGCAGCCACAGCAGCAGCAGCAGATTATTGACTTTGGTTTTGGCCAGCTC

ATCTGCCGCTACCCAGGCCATCTACAGCTCTGTGCCCGAAACCACTCAGATCCACCGCCCAGAAACGACCACCGCCA

CCACCCTACACACCTCCAGCGATCAGATGCCGACCAACATCACCCCCTTGGCTCTTCAAATGGGACTTACAAGCCCC

ACTCCAAAACCAGTGGATGCGGCCGAGGTCTCCGCCCTCGTCAATGACTGGGCGGGGCTGGGAATGTGGTGGTTCGC

CATAGGCATGATGGCGCTCTGCCTGCTTCTGCTCTGGCTCATCTGCTGCCTCCACCGCAGGCGAGCCAGACCCCCCA

TCTATAGACCCATCATTGTCCTGAACCCCGATAATGATGGGATCCATAGATTGGATGGCCTGAAAAACCTACTTTTT

TCTTTTACAGTATGATAAATTGAGACATGCCTCGCATTTTCTTGTACATGTTCCTTCTCCCACCTTTTCTGGGGTGT

TCTACGCTGGCCGCTGTGTCTCACCTGGAGGTAGACTGCCTCTCACCCTTCACTGTCTACCTGCTTTACGGATTGGT

CACCCTCACTCTCATCTGCAGCCTAATCACAGTAATCATCGCCTTCATCCAGTGCATTGATTACATCTGTGTGCGCC

TCGCATACTTCAGACACCACCCGCAGTACCGAGACAGGAACATTGCCCAACTTCTAAGACTGCTCTAATCATGCATA

AGACTGTGATCTGCCTTCTGATCCTCTGCATCCTGCCCACCCTCACCTCCTGCCAGTACACCACAAAATCTCCGCGC

AAAAGACATGCCTCCTGCCGCTTCACCCAACTGTGGAATATACCCAAATGCTACAACGAAAAGAGCGAGCTCTCCGA

AGCTTGGCTGTATGGGGTCATCTGTGTCTTAGTTTTCTGCAGCACTGTCTTTGCCCTCATAATCTACCCCTACTTTG

ATTTGGGATGGAACGCGATCGATGCCATGAATTACCCCACCTTTCCCGCACCCGAGATAATTCCACTGCGACAAGTT

GTACCCGTTGTCGTTAATCAACGCCCCCCATCCCCTACGCCCACTGAAATCAGCTACTTTAACCTAACAGGCGGAGA

TGACTGACGCCCTAGATCTAGAAATGGACGGCATCAGTACCGAGCAGCGTCTCCTAGAGAGGCGCAGGCAGGCGGCT

GAGCAAGAGCGCCTCAATCAGGAGCTCCGAGATCTCGTTAACCTGCACCAGTGCAAAAGAGGCATCTTTTGTCTGGT

AAAGCAGGCCAAAGTCACCTACGAGAAGACCGGCAACAGCCACCGCCTCAGTTACAAATTGCCCACCCAGCGCCAGA

AGCTGGTGCTCATGGTGGGTGAGAATCCCATCACCGTCACCCAGCACTCGGTAGAGACCGAGGGGTGTCTGCACTCC

CCCTGTCGGGGTCCAGAAGACCTCTGCACCCTGGTAAAGACCCTGTGCGGTCTCAGAGATTTAGTCCCCTTTAACTA

ATCAAACACTGGAATCAATAAAAAGAATCACTTACTTAAAATCAGACAGCAGGTCTCTGTCCAGTTTATTCAGCAGC

ACCTCCTTCCCCTCCTCCCAACTCTGGTACTCCAAACGCCTTCTGGCGGCAAACTTCCTCCACACCCTGAAGGGAAT

GTCAGATTCTTGCTCCTGTCCCTCCGCACCCACTATCTTCATGTTGTTGCAGATGAAGCGCACCAAAACGTCTGACG

AGAGCTTCAACCCCGTGTACCCCTATGACACGGAAAGCGGCCCTCCCTCCGTCCCTTTCCTCACCCCTCCCTTCGTG

TCTCCCGATGGATTCCAAGAAAGTCCCCCCGGGGTCCTGTCTCTGAACCTGGCCGAGCCCCTGGTCACTTCCCACGG

CATGCTCGCCCTGAAAATGGGAAGTGGCCTCTCCCTGGACGACGCTGGCAACCTCACCTCTCAAGATATCACCACCG

CTAGCCCTCCCCTCAAAAAAACCAAGACCAACCTCAGCCTAGAAACCTCATCCCCCCTAACTGTGAGCACCTCAGGC

GCCCTCACCGTAGCAGCCGCCGCTCCCCTGGCGGTGGCCGGCACCTCCTCACCATGCAATCAGAGGCCCCCCTGAC

AGTACAGGATGCAAAACTCACCCTGGCCACCAAAGGCCCCCTGACCGTGTCTGAAGGCAAACTGGCCTTGCAAACAT

CGGCCCCGCTGACGGCCGCTGACAGCAGCACCCTCACAGTCAGTGCCACACCACCCCTTAGCACAAGCAATGGCAGC
```

-continued

```
TTGGGTATTGACATGCAAGCCCCCATTTACACCACCAATGGAAAACTAGGACTTAACTTTGGCGCTCCCCTGCATGT

GGTAGACAGCCTAAATGCACTGACTGTAGTTACTGGCCAAGGTCTTACGATAAACGGAACAGCCCTACAAACTAGAG

TCTCAGGTGCCCTCAACTATGACACATCAGGAAACCTAGAATTGAGAGCTGCAGGGGGTATGCGAGTTGATGCAAAT

GGTCAACTTATCCTTGATGTAGCTTACCCATTTGATGCACAAAACAATCTCAGCCTTAGGCTTGGACAGGGACCCCT

GTTTGTTAACTCTGCCCACAACTTGGATGTTAACTACAACAGAGGCCTCTACCTGTTCACATCTGGAAATACCAAAA

AGCTAGAAGTTAATATCAAAACAGCCAAGGGTCTCATTTATGATGACACTGCTATAGCAATCAATGCGGGTGATGGG

CTACAGTTTGACTCAGGCTCAGATACAAATCCATTAAAAACTAAACTTGGATTAGGACTGGATTATGACTCCAGCAG

AGCCATAATTGCTAAACTGGGAACTGGCCTAAGCTTTGACAACACAGGTGCCATCACAGTAGGCAACAAAAATGATG

ACAAGCTTACCTTGTGGACCACACCAGACCCATCCCCTAACTGTAGAATCTATTCAGAGAAAGATGCTAAATTCACA

CTTGTTTTGACTAAATGCGGCAGTCAGGTGTTGGCCAGCGTTTCTGTTTTATCTGTAAAAGGTAGCCTTGCGCCCAT

CAGTGGCACAGTAACTAGTGCTCAGATTGTCCTCAGATTTGATGAAAATGGAGTTCTACTAAGCAATTCTTCCCTTG

ACCCTCAATACTGGAACTACAGAAAAGGTGACCTTACAGAGGGCACTGCATATACCAACGCAGTGGGATTTATGCCC

AACCTCACAGCATACCCAAAAACACAGAGCCAAACTGCTAAAAGCAACATTGTAAGTCAGGTTTACTTGAATGGGGA

CAAATCCAAACCCATGACCCTCACCATTACCCTCAATGGAACTAATGAAACAGGAGATGCCACAGTAAGCACTTACT

CCATGTCATTCTCATGGAACTGGAATGGAAGTAATTACATTAATGAAACGTTCCAAACCAACTCCTTCACCTTCTCC

TACATCGCCCAAGAATAAAAAGCATGACGCTGTTGATTTGATTCAATGTGTTTCTGTTTTATTTTCAAGCACAACAA

AATCATTCAAGTCATTCTTCCATCTTAGCTTAATAGACACAGTAGCTTAATAGACCCAGTAGTGCAAAGCCCCATTC

TAGCTTATAGATCAGACAGTGATAATTAACCACCACCACCACCATACCTTTTGATTCAGGAAATCATGATCATCACA

GGATCCTAGTCTTCAGGCCGCCCCCTCCCTCCCAAGACACAGAATACACAGTCCTCTCCCCCGACTGGCTTTAAAT

AACACCATCTGGTTGGTCACAGACATGTTCTTAGGGGTTATATTCCACACGGTCTCCTGCCGCGCCAGGCGCTCGTC

GGTGATGTTGATAAACTCTCCCGGCAGCTCGCTCAAGTTCACGTCGCTGTCCAGCGGCTGAACCTCCGGCTGACGCG

ATAACTGTGCGACCGGCTGCTGGACGAACGGAGGCCGCGCCTACAAGGGGGTAGAGTCATAATCCTCGGTCAGGATA

GGGCGGTGATGCAGCAGCAGCGAGCGAAACATCTGCTGCCGCCGCCGCTCCGTCCGGCAGGAAAACAACACGCCGGT

GGTCTCCTCCGCGATAATCCGCACCGCCCGCAGCATCAGCTTCCTCGTTCTCCGCGCGCAGCACCTCACCCTTATCT

CGCTCAAATCGGCGCAGTAGGTACAGCACAGCACCACGATGTTATTCATGATCCCACAGTGCAGGGCGCTGTATCCA

AAGCTCATGCCGGGAACCACCGCCCCACGTGGCCATCGTACCACAAGCGCACGTAAATCAAGTGTCGACCCCTCAT

GAACGCGCTGGACACAAACATTACTTCCTTGGGCATGTTGTAATTCACCACCTCCCGGTACCAGATAAACCTCTGGT

TGAACAGGGCACCTTCCACCACCATCCTGAACCAAGAGGCCAGAACCTGCCCACCGGCTATGCACTGCAGGGAACCC

GGGTTGGAACAATGACAATGCAGACTCCAAGGCTCGTAACCGTGGATCATCCGGCTGCTGAAGGCATCGATGTTGGC

ACAACACAGACACACGTGCATGCACTTTCTCATGATTAGCAGCTCTTCCCTCGTCAGGATCATATCCCAAGGAATAA

CCCATTCTTGAATCAACGTAAAACCCACACAGCAGGGAAGGCCTCGCACATAACTCACGTTGTGCATGGTCAGCGTG

TTGCATTCCGGAAACAGCGGATGATCCTCCAGTATCGAGGCGCGGGTCTCCTTCTCACAGGGAGGTAAAGGGTCCCT

GCTGTACGGACTGCGCCGGACGACCGAGATCGTGTTGAGCGTAGTGTCATGGAAAAGGGAACGCCGGACGTGGTCA

TACTTCTTGAAGCAGAACCAGGTTCGCGCGTGGCAGGCCTCCTTGCGTCTGCGGTCTCGCCGTCTAGCTCGCTCCGT

GTGATAGTTGTAGTACAGCCACTCCCGCAGAGCGTCGAGGCGCACCCTGGCTTCCGGATCTATGTAGACTCCGTCTT

GCACCGCGGCCCTGATAATATCCACCACCGTAGAATAAGCAACACCCAGCCAAGCAATACACTCGCTCTGCGAGCGG

CAGACAGGAGGAGCGGGCAGAGATGGGAGAACCATGATAAAAAACTTTTTTTAAAGAATATTTTCCAATTCTTCGAA

AGTAAGATCTATCAAGTGGCAGCGCTCCCCTCCACTGGCGCGGTCAAACTCTACGGCCAAAGCACAGACAACGGCAT

TTCTAAGATGTTCCTTAATGGCGTCCAAAAGACACACCGCTCTCAAGTTGCAGTAAACTATGAATGAAAACCCATCC

GGCTGATTTTCCAATATAGACGCGCCGGCAGCGTCCACCAAACCCAGATAATTTTCTTCTCTCCAGCGGTTTACGAT
```

-continued

```
CTGTCTAAGCAAATCCCTTATATCAAGTCCGACCATGCCAAAAATCTGCTCAAGAGCGCCCTCCACCTTCATGTACA

AGCAGCGCATCATGATTGCAAAAATTCAGGTTCTTCAGAGACCTGTATAAGATTCAAATGGGAACATTAACAAAAA

TTCCTCTGTCGCGCAGATCCCTTCGCAGGGCAAGCTGAACATAATCAGACAGGTCCGAACGGACCAGTGAGGCCAAA

TCCCCACCAGGAACCAGATCCAGAGACCCTATACTGATTATGACGCGCATACTCGGGGCTATGCTGACCAGCGTAGC

GCCGATGTAGGCGTGCTGCATGGGCGGCGAGATAAAATGCAAAGTGCTGGTTAAAAAATCAGGCAAAGCCTCGCGCA

AAAAAGCTAACACATCATAATCATGCTCATGCAGGTAGTTGCAGGTAAGCTCAGGAACCAAAACGGAATAACACACG

ATTTTCCTCTCAAACATGACTTCGCGGATACTGCGTAAAACAAAAAATTATAAATAAAAAATTAATTAAATAACTTA

AACATTGGAAGCCTGTCTCACAACAGGAAAAACCACTTTAATCAACATAAGACGGGCCACGGGCATGCCGGCATAGC

CGTAAAAAAATTGGTCCCCGTGATTAACAAGTACCACAGACAGCTCCCCGGTCATGTCGGGGGTCATCATGTGAGAC

TCTGTATACACGTCTGGATTGTGAACATCAGACAAACAAAGAAATCGAGCCACGTAGCCCGGAGGTATAATCACCCG

CAGGCGGAGGTACAGCAAAACGACCCCCATAGGAGGAATCACAAAATTAGTAGGAGAAAAAAATACATAAACACCAG

AAAAACCCTGTTGCTGAGGCAAAATAGCGCCCTCCCGATCCAAAACAACATAAAGCGCTTCCACAGGAGCAGCCATA

ACAAAGACCCGAGTCTTACCAGTAAAAGAAAAAAGATCTCTCAACGCAGCACCAGCACCAACACTTCGCAGTGTAAA

AGGCCAAGTGCCGAGAGAGTATATATAGGAATAAAAAGTGACGTAAACGGGCAAAGTCCAAAAAACGCCCAGAAAAA

CCGCACGCGAACCTACGCCCCGAAACGAAAGCCAAAAAACACTAGACACTCCCTTCCGGCGTCAACTTCCGCTTTCC

CACGCTACGTCACTTCCCCCGGTCAAACAAACTACATATCCCGAACTTCCAAGTCGCCACGCCCAAAACACCGCCTA

CACCTCCCCGCCCGCCGGCCCGCCCCCGGACCCGCCTCCCGCCCCGCGCCGCCCATCTCATTATCATATTGGCTTCA

ATCCAAAATAAGGTATATTATTGATGATG
```

Polynucleotide sequence encoding wild type ChAd83

SEQ ID NO: 2

```
CATCATCAATAATATACCTCAAACTTTTGGTGCGCGTTAATATGCAAATGAGCTGTTTGAATTTGGGGAT

GCGGGGCGCTGATTGGCTGCGGGAGCGGCGACCGTTAGGGGCGGGGCGGGTGACGTTTTGATGACGTGGC

CGTGAGGCGGAGCCGGTTTGCAAGTTCTCGTGGGAAAAGTGACGTCAAACGAGGTGTGGTTTGAACACGG

AAATACTCAATTTTCCCGCGCTCTCTGACAGGAAATGAGGTGTTTCTGGGCGGATGCAAGTGAAAACGGG

CCATTTTCGCGCGAAAACTGAATGAGGAAGTGAAAATCTGAGTAATTTCGCGTTTATGGCAGGGAGGAGT

ATTTGCCGAGGGCCGAGTAGACTTTGACCGATTACGTGGGGGTTTCGATTACCGTATTTTTCACCTAAAT

TTCCGCGTACGGTGTCAAAGTCCGGTGTTTTTACGTAGGCGTCAGCTGATCGCCAGGGTATTTAAACCTG

CGCTCACTAGTCAAGAGGCCACTCTTGAGTGCCAGCGAGTAGAGTTTTCTCCTCCGCGCCGCGAGTCAGA

TCTACACTTTGAAAGATGAGGCACTTGAGAGACCTGCCCGGTAATGTTTTCCTGGCTACTGGGAACGAGA

TTCTGGAATTGGTGGTGGACGCCATGATGGGTGACGACCCTCCCGAGCCCCCTACCCCATTTGAGGCGCC

TTCGCTGTACGATTTGTATGATCTGGAGGTGGATGTGCCCGAGAACGACCCCAACGAGGAGGCGGTGAAT

GATTTGTTTAGCGATGCCGCGCTGCTGGCTGCCGAGCAGGCTAATACGGACTTTGGCTCAGACAGCGATT

CTTCTCTCCATACCCCGAGACCCGGCAGAGGTGAGAAAAAGATCCCCGAGCTTAAAGGGGAAGAGCTCGA

CCTGCGCTGCTATGAGGAATGCTTGCCTCCGAGCGATGATGAGGAGGACGAGGAGGCGATTCGAGCTGCA

GCGAACCAGGGAGTGAAAGCTGCGGGCGAAAGCTTTAGCCTGGACTGTCCTACTCTGCCCGGACACGGCT

GTAAGTCTTGTGAATTTCATCGCATGAATACTGGAGATAAGAATGTGATGTGTGCCCTGTGCTATATGAG

AGCTTACAACCATTGTGTTTACAGTAAGTGTGATTAACTTTAGTTGGGAAGGCAGAGGGTGACTGGGTGC

TGACTGGTTTATTTATGTATATGTTTTTTATGTGTAGGTCCCGTCTCTGACGCAGATGAGACCCCCACTT

CAGAGTGCATTTCATCACCCCCAGAAATTGGCGAGGAACCGCCCGAAGATATTATTCATAGACCAGTTGC

AGTGAGAGTCACCGGGCGGAGAGCAGCTGTGGAGAGTTTGGATGACTTGCTACAGGGTGGGGATGAACCT

TTGGACTTGTGTACCCGGAAACGCCCCAGGCACTAAGTGCCACACATGTGTGTTTACTTAAGGTGATGTC

AGTATTTATAGGGTGTGGAGTGCAATAAAATCCGTGTTGACTTTAAGTGCGTGGTTTATGACTCAGGGGT
```

-continued

```
GGGGACTGTGGGTATATAAGCAGGTGCAGACCTGTGTGGTCAGTTCAGAGCAGGACTCATGGAGATCTGG
ACGGTCTTGGAAGACTTTCACCAGACTAGACAGCTGCTAGAGAACTCATCGGAGGGAGTCTCTTACCTGT
GGAGATTCTGCTTCGGTGGGCCTCTAGCTAAGCTAGTCTATAGGGCCAAGCAGGATTATAAGGATCAATT
TGAGGATATTTTGAGAGAGTGTCCTGGTATTTTTGACTCTCTCAACTTGGGCCATCAGTCTCACTTTAAC
CAGAGTATTCTGAGAGCCCTTGACTTTTCCACTCCTGGCAGAACTACCGCCGCGGTAGCCTTTTTTGCCT
TTATCCTTGACAAATGGAGTCAAGAAACCCATTTCAGCAGGGATTACCGTCTGGACTGCTTAGCAGTAGC
TTTGTGGAGAACATGGAGGTGCCAGCGCCTGAATGCAATCTCCGGCTACTTGCCAGTACAGCCGGTAGAC
ACGCTGAGGATCCTGAGTCTCCAGTCACCCCAGGAACACCAACGCCGCCAGCAGCCGCAGCAGGAGCAGC
AGCAAGAGGAGGACCGAGAAGAGAACCCGAGAGCCGGTCTGGACCCTCCGGTGGCGGAGGAGGAGGAGTA
GCTGACTTGTTTCCCGAGCTGCGCCGGGTGCTGACTAGGTCTTCCAGTGGACGGGAGAGGGGATTAAGC
GGGAGAGGCATGAGGAGACTAGTCACAGAACTGAACTGACTGTCAGTCTGATGAGCCGCAGGCGCCCAGA
ATCGGTGTGGTGGCATGAGGTGCAGTCGCAGGGGATAGATGAGGTCTCGGTGATGCATGAGAAATATTCC
CTAGAACAAGTCAAGACTTGTTGGTTGGAGCCTGAGGATGATTGGGAGGTAGCCATCAGGAATTATGCCA
AGCTAGCTCTGAAGCCAGACAAGAAGTACAAGATTACCAAACTGATTAATATCAGAAATTCCTGCTACAT
TCAGGGAATGGGGCCGAGGTGGAGATCAGTACCCAGGAGAGGGTGGCCTTCAGATGCTGCATGATGAAT
ATGTACCCGGGGTGGTGGGCATGAGGGAGTCACCTTTATGAACGCGAGGTTCAGGGGCGATGGGTATA
ATGGGGTGGTCTTTATGGCCAACACCAAGCTGACAGTGCACGGATGCTCCTTCTTTGGCTTCAATAACAT
GTGCATCGAGGCCTGGGCAGTGTTTCAGTGAGGGGATGCAGTTTTTCAGCCAACTGGATGGGGGTCGTG
GGCAGAACCAAGAGCAAGGTGTCAGTGAAGAAATGCCTGTTCGAGAGGTGCCACCTGGGGGTGATGAGCG
AGGGCGAAGCCAAAGTCAAACACTGCGCCTCTACTGAGACGGGCTGCTTTGTGCTGATCAAGGGCAATGC
CCAAGTCAAGCATAACATGATCTGTGGGGCCTCGGATGAGCGCGGCTACCAGATGCTGACCTGCGCCGGT
GGGAACAGCCATATGCTGGCCACCGTGCATGTGACCTCGCACCCCCGCAAGACATGGCCCGAGTTCGAGC
ACAACGTCATGACCCGCTGCAATGTGCACCTGGGCTCCCGCCGAGGCATGTTCATGCCCTACCAGTGCAA
CATGCAATTTGTGAAGGTGCTGCTGGAGCCCGATGCCATGTCCAGAGTGAGCCTGACGGGGGTGTTTGAC
ATGAATGTGGAGATGTGGAAAATTCTGAGATATGATGAATCCAAGACCAGGTGCCGGGCCTGCGAATGCG
GAGGCAAGCACGCCAGGCTTCAGCCCGTGTGTGTGGAGGTGACGGAGGACCTGCGACCCGATCATTTGGT
GTTGTCCTGCAACGGGACGGAGTTCGGCTCCAGCGGGGAAGAATCTGACTAGAGTGAGTAGTGTTTGGGG
GAGGTGGAGGGCCTGGATGAGGGGCAGAATGACTAAAATCTGTGTTTTTCTGCGCAGCAGCATGAGCGGA
AGCGCCTCCTTTGAGGGAGGGGTATTCAGCCCTTATCTGACGGGGCGTCTCCCCTCCTGGGCGGAGTGC
GTCAGAATGTGATGGGATCCACGGTGGACGGCCGGCCCGTGCAGCCCGCGAACTCTTCAACCCTGACCTA
CGCGACCCTGAGCTCCTCGTCCGTGGACGCAGCTGCCGCCGCAGCTGCTGCTTCCGCCGCCAGCGCCGTG
CGCGGAATGGCCCTGGGCGCCGGCTACTACAGCTCTCTGGTGGCCAACTCGAGTTCCACCAATAATCCCG
CCAGCCTGAACGAGGAGAAGCTGCTGCTGCTGATGGCCCAGCTCGAGGCCCTGACCCAGCGCCTGGGCGA
GCTGACCCAGCAGGTTGCTCAGCTGCAGGCGGAGACGCGGGCCGCGGTTGCCACGGTGAAAACCAAATAA
AAAATGAATCAATAAATAAACGGAGACGGTTGTTGATTTTAACACAGAGTCTTGAATCTTTATTTGATTT
TTCGCGCGCGGTAGGCCCTGGACCACCGGTCTCGATCATTGAGCACCCGGTGGATCTTTTCCAGGACCCG
GTAGAGGTGGGCTTGGATGTTGAGGTACATGGGCATGAGCCCGTCCCGGGGGTGGAGGTAGCTCCATTGC
AGGGCCTCGTGCTCGGGGGTGGTGTTGTAAATCACCCAGTCATAGCAGGGGCGCAGGGCGTGGTGCTGCA
CGATGTCCTTGAGGAGGAGACTGATGCCACGGGCAGCCCCTTGGTGTAGGTGTTGACGAACCTGTTGAG
CTGGGAGGGATGCATGCGGGGGGAGATGAGATGCATCTTGGCCTGGATCTTGAGATTGGCGATGTTCCCG
```

-continued

```
CCCAGATCCCGCCGGGGGTTCATGTTGTGCAGGACCACCAGCACGGTGTATCCGGTGCACTTGGGGAATT

TGTCATGCAACTTGGAAGGGAAGGCGTGAAAGAATTTGGAGACGCCCTTGTGGCCGCCCAGGTTTTCCAT

GCACTCATCCATGATGATGGCGATGGGCCCGTGGGCGGCGGCCTGGGCAAAGACGTTTCGGGGGTCGGAC

ACATCGTAGTTGTGGTCCTGGGTGAGCTCGTCATAGGCCATTTTAATGAATTTGGGGCGGAGGGTGCCCG

ACTGGGGACGAAGGTGCCCTCGATCCCGGGGGCGTAGTTGCCCTCGCAGATCTGCATCTCCCAGGCCTT

GAGCTCGGAGGGGGGATCATGTCCACCTGCGGGGCGATGAAAAAAACGGTTTCCGGGGCGGGGGAGATG

AGCTGCGCCGAAAGCAGGTTCCGGAGCAGCTGGGACTTGCCGCAGCCGGTGGGGCCGTAGATGACCCCGA

TGACCGGCTGCAGGTGGTAGTTGAGGGAGAGACAGCTGCCGTCCTCGCGGAGGAGGGGGCCACCTCGTT

CATCATCTCGCGCACATGCATGTTCTCGCGCACGAGTTCCGCCAGGAGGCGCTCGCCCCCAGCGAGAGG

AGCTCTTGCAGCGAGGCGAAGTTTTTCAGCGGCTTGAGCCCGTCGGCCATGGGCATTTTGGAGAGGGTCT

GTTGCAAGAGTTCCAGACGGTCCCAGAGCTCGGTGATGTGCTCTAGGGCATCTCGATCCAGCAGACCTCC

TCGTTTCGCGGGTTGGGGCGACTGCGGGAGTAGGGCACCAGGCGATGGGCGTCCAGCGAGGCCAGGGTCC

GGTCCTTCCAGGGTCGCAGGGTCCGCGTCAGCGTGGTCTCCGTCACGGTGAAGGGGTGCGCGCCGGGCTG

GGCGCTTGCGAGGGTGCGCTTCAGGCTCATCCGGCTGGTCGAGAACCGCTCCCGGTCGGCGCCCTGTGCG

TCGGCCAGGTAGCAATTGAGCATGAGTTCGTAGTTGAGCGCCTCGGCCGCGTGGCCCTTGGCGCGGAGCT

TACCTTTGGAAGTGTGTCCGCAGACGGGACAGAGGAGGGACTTGAGGGCGTAGAGCTTGGGGGCGAGGAA

GACGGACTCGGGGCGTAGGCGTCCGCGCCGCAGCTGGCGCAGACGGTCTCGCACTCCACGAGCCAGGTG

AGGTCGGGGCGGTCGGGGTCAAAAACGAGGTTTCCTCCGTGCTTTTTGATGCGTTTCTTACCTCTGGTCT

CCATGAGCTCGTGTCCCCGCTGGGTGACAAAGAGGCTGTCCGTGTCCCCGTAGACCGACTTTATGGGCCG

GTCCTCGAGCGGGGTGCCGCGGTCCTCGTCGTAGAGGAACCCCGCCCACTCCGAGACGAAGGCCCGGGTC

CAGGCCAGCACGAAGGAGGCCACGTGGGAGGGGTAGCGGTCGTTGTCCACCAGCGGGTCCACCTTCTCCA

GGGTATGCAAGCACATGTCCCCCTCGTCCACATCCAGGAAGGTGATTGGCTTGTAAGTGTAGGCCACGTG

ACCGGGGGTCCCGGCCGGGGGGTATAAAAGGGGGCGGGCCCCTGCTCGTCCTCACTGTCTTCCGGATCG

CTGTCCAGGAGCGCCAGCTGTTGGGGTAGGTATTCCCTCTCGAAGGCGGGCATGACCTCGGCACTCAGGT

TGTCAGTTTCTAGAAACGAGGAGGATTTGATATTGACGGTGCCGTTGGAGACGCCTTTCATGAGCCCCTC

GTCCATCTGGTCAGAAAAGACGATCTTTTTGTTGTCGAGCTTGGTGGCGAAGGAGCCGTAGAGGGCGTTG

GAGAGCAGCTTGGCGATGGAGCGCATGGTCTGGTTCTTTTCCTTGTCGGCGCGCTCCTTGGCGGCGATGT

TGAGCTGCACGTACTCGCGCGCCACGCACTTCCATTCGGGGAAGACGGTGGTGAGCTCGTCGGGCACGAT

TCTGACCCGCCAGCCGCGGTTGTGCAGGGTGATGAGGTCCACGCTGGTGGCCACCTCGCCGCGCAGGGGC

TCGTTGGTCCAGCAGAGGCGCCCGCCCTTGCGCGAGCAGAAGGGGGCAGCGGGTCCAGCATGAGCTCGT

CGGGGGGTCGGCGTCCACGGTGAAGATGCCGGGCAGGAGCTCGGGGTCGAAGTAGCTGATGCAGGTGCC

CAGATCGTCCAGCGCCGCTTGCCAGTCGCGCACGGCCAGCGCGCGCTCGTAGGGGCTGAGGGGCGTGCCC

CAGGGCATGGGGTGCGTGAGCGCGGAGGCGTACATGCCGCAGATGTCGTAGACGTAGAGGGGCTCCTCGA

GGACGCCGATGTAGGTGGGGTAGCAGCGCCCCCCGCGGATGCTGGCGCGCACGTAGTCGTACAGCTCGTG

CGAGGGCGCGAGGAGCCCCGTGCCGAGGTTGGAGCGTTGCGGCTTTTCGGCGCGGTAGACGATCTGGCGG

AAGATGGCGTGGGAGTTGGAGGAGATGGTGGGCCTCTGGAAGATGTTGAAGTGGCGTGGGGCAGGCCGA

CCGAGTCCCTGATGAAGTGGGCGTAGGAGTCCTGCAGCTTGGCGACGAGCTCGGCGGTGACGAGGACGTC

CAGGGCGCAGTAGTCGAGGGTCTCTTGGATGATGTCGTACTTGAGCTGGCCCTTCTGCTTCCACAGCTCG

CGGTTGAGAAGGAACTCTTCGCGGTCCTTCCAGTACTCTTCGAGGGGGAACCCGTCCTGATCGGCACGGT

AAGAGCCCACCATGTAGAACTGGTTGACGGCCTTGTAGGCGCAGCAGCCCTTCTCCACGGGGAGGGCGTA

AGCTTGCGCGGCCTTGCGCAGGGAGGTGTGGGTGAGGGCGAAGGTGTCGCGCACCATGACTTTGAGGAAC
```

-continued

```
TGGTGCTTGAAGTCGAGGTCGTCGCAGCCGCCCTGCTCCCAGAGTTGGAAGTCCGTGCGCTTCTTGTAGG
CGGGGTTGGGCAAAGCGAAAGTAACATCGTTGAAGAGGATCTTGCCCGCGCGGGGCATGAAGTTGCGAGT
GATGCGGAAAGGCTGGGGCACCTCGGCCCGGTTGTTGATGACCTGGGCGGCGAGGACGATCTCGTCGAAG
CCGTTGATGTTGTGCCCGACGATGTAGAGTTCCACGAATCGCGGGCAGCCCTTGACGTGGGGCAGCTTCT
TGAGCTCGTCGTAGGTGAGCTCGGCGGGGTCGCTGAGCCCGTGCTGCTCGAGGGCCCAGTCGGCGACGTG
GGGGTTGGCGCTGAGGAAGGAAGTCCAGAGATCCACGGCCAGGGCGGTCTGCAAGCGGTCCCGGTACTGA
CGGAACTGCTGGCCCACGGCCATTTTTTCGGGGGTGACGCAGTAGAAGGTGCGGGGGTCGCCGTGCCAGC
GGTCCCACTTGAGTTGGAGGGCGAGGTCGTGGGCGAGCTCGACGAGCGGCGGGTCCCCGGAGAGTTTCAT
GACCAGCATGAAGGGGACGAGCTGCTTGCCGAAGGACCCCATCCAGGTGTAGGTTTCCACATCGTAGGTG
AGGAAGAGCCTTTCGGTGCGAGGATGCGAGCCGATGGGGAAGAACTGGATCTCCTGCCACCAGTTGGAGG
AATGGCTGTTGATGTGATGGAAGTAGAAATGCCGACGGCGCGCCGAGCACTCGTGCTTGTGTTTATACAA
GCGTCCGCAGTGCTCGCAACGCTGCACGGGATGCACGTGCTGCACGAGCTGTACCTGGGTTCCTTTGACG
AGGAATTTCAGTGGGCAGTGGAGCGCTGGCGGCTGCATCTGGTGCTGTACTACGTCCTGGCCATCGGCGT
GGCCATCGTCTGCCTCGATGGTGGTCATGCTGACGAGCCCGCGCGGGAGGCAGGTCCAGACCTCGGCTCG
GACGGGTCGGAGAGCGAGGACGAGGGCGCGCAGGCCGGAGCTGTCCAGGGTCCTGAGACGCTGCGGAGTC
AGGTCAGTGGGCAGCGGCGGCGCGCGGTTGACTTGCAGGAGCTTTTCCAGGGCGCGCGGGAGGTCCAGAT
GGTACTTGATCTCCACGGCGCCGTTGGTGGCGACGTCCACGGCTTGCAGGGTCCCGTGCCCCTGGGGCGC
CACCACCGTGCCCCGTTTCTTCTTGGGCGGCGGCGGCTCCATGCTTAGAAGCGGCGGCGAGGACGCGCGC
CGGGCGGCAGGGGCGGCTCGGGGCCCGGAGGCAGGGGCGGCAGGGGCACGTCGGCGCCGCGCGCGGGCAG
GTTCTGGTACTGCGCCCGGAGAAGACTGGCGTGAGCGACGACGCGACGGTTGACGTCCTGGATCTGACGC
CTCTGGGTGAAGGCCACGGGACCCGTGAGTTTGAACCTGAAAGAGAGTTCGACAGAATCAATTTCGGTAT
CGTTGACGGCGGCCTGCCGCAGGATCTCTTGCACGTCGCCCGAGTTGTCCTGGTAGGCGATCTCGGTCAT
GAACTGCTCGATCTCCTCCTCCTGAAGGTCTCCGCGGCCGGCGCGCTCGACGGTGGCCGCGAGGTCGTTG
GAGATGCGGCCCATGAGCTGCGAGAAGGCGTTCATGCCGGCCTCGTTCCAGACGCGGCTGTAGACCACGG
CTCCGTTGGGGTCGCGCGCGCGCATGACCACCTGGGCGAGGTTAAGCTCGACGTGGCGCGTGAAGACCGC
GTAGTTGCAGAGGCGCTGGTAGAGGTAGTTGAGCGTGGTGGCGATGTGCTCGGTGACGAAGAAGTACATG
ATCCAGCGGCGGAGCGGCATCTCGCTGACGTCGCCCAGGGCTTCCAAGCGCTCCATGGTCTCGTAGAAGT
CCACGGCGAAGTTGAAAAACTGGGAGTTGCGCGCCGAGACGGTCAACTCCTCCTCCAGAAGACGGATGAG
CTCGGCGATGGTGGCGCGCACCTCGCGCTCGAAGGCCCCGGGGGGCTCCTCTTCTTCCATCTCCTCCTCC
TCTTCCTCCTCCACTAACATCTCTTCTACTTCCTCCTCAGGAGGCGGCGGCGGGGAGGGGCCCTGCGTC
GCCGGCGGCGCACGGGCAGACGGTCGATGAAGCGCTCGATGGTCTCCCCGCGCCGGCGACGCATGGTCTC
GGTGACGGCGCGCCCGTCCTCGCGGGCCGCAGCGTGAAGACGCCGCCGCGCATCTCCAGGTGGCCGCCG
GGGGGTCTCCGTTGGGCAGGGAGAGGGCGCTGACGATGCATCTTATCAATTGGCCCGTAGGGACTCCGC
GCAAGGACCTGAGCGTCTCGAGATCCACGGGATCCGAAAACCGCTGAACGAAGGCTTCGAGCCAGTCGCA
GTCGCAAGGTAGGCTGAGCCCGGTTTCTTGTTCTTCGGGTATTTGGTCGGGAGGCGGCGGGCGATGCTG
CTGGTGATGAAGTTGAAGTAGGCGGTCCTGAGACGGCGGATGGTGGCGAGGAGCACCAGGTCCTTGGGCC
CGGCTTGCTGGATGCGCAGACGGTCGGCCATGCCCCAGGCGTGGTCCTGACACCTGGCGAGGTCCTTGTA
GTAGTCCTGCATGAGCCGCTCTACGGGCACGTCCTCCTCGCCCGCGCGGCCGTGCATGCGCGTGAGCCCG
AACCCGCGCTGCGGCTGGACGAGCGCCAGGTCGGCGACGACGCGCTCGGCGAGGATGGCCTGCTGGATCT
GGGTGAGGGTGGTCTGGAAGTCGTCGAAGTCGACGAAGCGGTGGTAGGCTCCGGTGTTGATGGTGTAGGA
```

-continued

```
GCAGTTGGCCATGACGGACCAGTTGACGGTCTGGTGGCCGGGGCGCACGAGCTCGTGGTACTTGAGGCGC
GAGTAGGCGCGCGTGTCGAAGATGTAGTCGTTGCAGGTGCGCACGAGGTACTGGTATCCGACGAGGAAGT
GCGGCGGCGGCTGGCGGTAGAGCGGCCATCGCTCGGTGGCGGGGCGCCGGGCGCGAGGTCCTCGAGCAT
GAGGCGGTGGTAGCCGTAGATGTACCTGGACATCCAGGTGATGCCGCGGCGGTGGTGGAGGCGCGCGGG
AACTCGCGGACGCGGTTCCAGATGTTGCGCAGCGGCAGGAAGTAGTTCATGGTGGCCGCGGTCTGGCCCG
TGAGGCGCGCGCAGTCGTGGATGCTCTAGACATACGGGCAAAAACGAAAGCGGTCAGCGGCTCGACTCCG
TGGCCTGGAGGCTAAGCGAACGGGTTGGGCTGCGCGTGTACCCCGGTTCGAATCTCGAATCAGGCTGGAG
CCGCAGCTAACGTGGTACTGGCACTCCCGTCTCGACCCAAGCCTGCTAACGAAACCTCCAGGATACGGAG
GCGGGTCGTTTTTTGGCCTTGGTCGCTGGTCATGAAAAACTAGTAAGCGCGGAAAGCGGCCGCCCGCGAT
GGCTCGCTGCCGTAGTCTGGAGAAAGAATCGCCAGGGTTGCGTTGCGGTGTGCCCCGGTTCGAGCCTCAG
CGCTCGGTGCCGGCCGGATTCCGCGGCTAACGTGGGCGTGGCTGCCCCGTCGTTTCCAAGACCCCTTAGC
CAGCCGACTTCTCCAGTTACGGAGCGAGCCCCTCTTTTTCTTGTGTTTTTGCCAGATGCATCCCGTACTG
CGGCAGATGCGCCCCCACCCTCCACCACAACCGCCCCTACCGCAGCAGCAGCAACAGCCGGCGCTTCTGC
CCCCGCCCCAGCAGCAGCAGCCAGCCACTACCGCGGCGGCCGCCGTGAGCGGAGCCGGCGTTCAGTATGA
CCTGGCCTTGGAAGAGGGCGAGGGGCTGGCGCGGCTGGGGGCGTCGTCGCCGGAGCGGCACCCGCGCGTG
CAGATGAAAAGGGACGCTCGCGAGGCCTACGTGCCCAAGCAGAACCTGTTCAGAGACAGGAGCGGCGAGG
AGCCCGAGGAGATGCGCGCCTCCCGCTTCCACGCGGGGCGGGAGCTGCGGCGCGGCCTGGACCGAAAGCG
GGTGCTGAGGGACGAGGATTTCGAGGCGGACGAGCTGACGGGGATCAGCCCCGCGCGCGCACGTGGCC
GCGGCCAACCTGGTCACGGCGTACGAGCAGACCGTGAAGGAGGAGAGCAACTTTCAAAAATCCTTCAACA
ACCACGTGCGCACGCTGATCGCGCGCGAGGAGGTGACCCTGGGCCTGATGCACCTGTGGGACCTGCTGGA
GGCCATCGTGCAGAACCCCACGAGCAAGCCGCTGACGGCGCAGCTGTTTCTGGTGGTGCAGCACAGTCGG
GACAACGAGACGTTCAGGGAGGCGCTGCTGAATATCACCGAGCCCGAGGGCCGCTGGCTCCTGGACCTGG
TGAACATTCTGCAGAGCATCGTGGTGCAGGAGCGCGGGCTGCCGCTGTCCGAGAAGCTGGCGGCCATCAA
CTTCTCGGTGCTGAGCCTGGGCAAGTACTACGCTAGGAAGATCTACAAGACCCCGTACGTGCCCATAGAC
AAGGAGGTGAAGATCGACGGGTTTTACATGCGCATGACCCTGAAAGTGCTGACCCTGAGCGACGATCTGG
GGGTGTACCGCAACGACAGGATGCACCGCGCGGTGAGCGCCAGCCGCCGGCGCGAGCTGAGCGACCAGGA
GCTGATGCACAGCCTGCAGCGGGCCCTGACCGGGGCCGGGACCGAGGGGGAGAGCTACTTTGACATGGGC
GCGGACCTGCGCTGGCAGCCCAGCCGCCGGGCCTTGGAAGCTGCCGGCGGCGTGCCCTACGTGGAGGAGG
TGGACGATGAGGAGGAGGAGGGCGAGTACCTGGAAGACTGATGGCGCGACCGTATTTTTGCTAGATGCAG
CAACAGCCACCGCCGCCTCCTGATCCCGCGATGCGGGCGGCGCTGCAGAGCCAGCCGTCCGGCATTAACT
CCTCGGACGATTGGACCCAGGCCATGCAACGCATCATGGCGCTGACGACCCGCAATCCCGAAGCCTTTAG
ACAGCAGCCTCAGGCCAACCGGCTCTCGGCCATCCTGGAGGCCGTGGTGCCCTCGCGCTCGAACCCCACG
CACGAGAAGGTGCTGGCCATCGTGAACGCGCTGGTGGAGAACAAGGCCATCCGCGGCGACGAGGCCGGGC
TGGTGTACAACGCGCTGCTGGAGCGCGTGGCCCGCTACAACAGCACCAACGTGCAGACGAACCTGGACCG
CATGGTGACCGACGTGCGCGAGGCGGTGTCGCAGCGCGAGCGGTTCCACCGCGAGTCGAACCTGGGCTCC
ATGGTGGCGCTGAACGCCTTCCTGAGCACGCAGCCCGCCAACGTGCCCCGGGGCCAGGAGGACTACACCA
ACTTCATCAGCGCGCTGCGGCTGATGGTGGCCGAGGTGCCCCAGAGCGAGGTGTACCAGTCGGGGCCGGA
CTACTTCTTCCAGACCAGTCGCCAGGGCTTGCAGACCGTGAACCTGAGCCAGGCTTTCAAGAACTTGCAG
GGACTGTGGGGCGTGCAGGCCCCGGTCGGGGACCGCGCGACGGTGTCGAGCCTGCTGACGCCGAACTCGC
GCCTGCTGCTGCTGCTGGTGGCGCCCTTCACGGACAGCGGCAGCGTGAGCCGCGACTCGTACCTGGGCTA
CCTGCTTAACCTGTACCGCGAGGCCATCGGGCAGGCGCACGTGGACGAGCAGACCTACCAGGAGATCACC
```

-continued

```
CACGTGAGCCGCGCGCTGGGCCAGGAGGACCCGGGCAACCTGGAGGCCACCCTGAACTTCCTGCTGACCA
ACCGGTCGCAGAAGATCCCGCCCCAGTACGCGCTGAGCACCGAGGAGGAGCGCATCCTGCGCTACGTGCA
GCAGAGCGTGGGGCTGTTCCTGATGCAGGAGGGGGCCACGCCCAGCGCCGCGCTCGACATGACCGCGCGC
AACATGGAGCCCAGCATGTACGCCCGCAACCGCCCGTTCATCAATAAGCTGATGGACTACTTGCATCGGG
CGGCCGCCATGAACTCGGACTACTTTACCAACGCCATCTTGAACCCGCACTGGCTCCCGCCGCCCGGGTT
CTACACGGGCGAGTACGACATGCCCGACCCCAACGACGGGTTCCTGTGGGATGACGTGGACAGCAGCGTG
TTCTCGCCGCGTCCCACCACCACCGTGTGGAAGAAAGAGGGCGGGGACCGGCGGCCGTCCTCGGCGCTGT
CCGGTCGCGCGGGTGCTGCCGCGGCGGTGCCCGAGGCCGCCAGCCCCTTTCCGAGCCTGCCCTTTTCGCT
GAACAGCGTGCGCAGCAGCGAGCTGGGTCGGCTGACGCGGCCGCGCCTGCTGGGCGAGGAGGAGTACCTG
AACGACTCCTTGTTGAGGCCCGAGCGCGAAAAGAACTTCCCCAATAACGGGATAGAGAGCCTGGTGGACA
AGATGAGCCGCTGGAAGACGTACGCGCACGAGCACAGGGACGAGCCCCGAGCTAGCAGCGCAGGCACCCG
TAGACGCCAGCGGCACGACAGGCAGCGGGGTCTGGTGTGGGACGATGAGGATTCCGCCGACGACAGCAGC
GTGTTGGACTTGGGTGGGAGTGGTGGTGGTAACCCGTTCGCTCACTTGCGCCCCCGTATCGGGCGCCTGA
TGTAAGAATCTGAAAAATAAAAAACGGTACTCACCAAGGCCATGGCGACCAGCGTGCGTTCTTCTCTGTT
GTTTGTAGTAGTATGATGAGGCGCGTGTACCCGGAGGGTCCTCCTCCCTCGTACGAGAGCGTGATGCAGC
AGGCGGTGGCGGCGGCGATGCAGCCCCCGCTGGAGGCGCCTTACGTGCCCCCGCGGTACCTGGCGCCTAC
GGAGGGGCGGAACAGCATTCGTTACTCGGAGCTGGCACCCTTGTACGATACCACCCGGTTGTACCTGGTG
GACAACAAGTCGGCGGACATCGCCTCGCTGAACTACCAGAACGACCACAGCAACTTCCTGACCACCGTGG
TGCAGAACAACGATTTCACCCCCACGGAGGCCAGCACCCAGACCATCAACTTTGACGAGCGCTCGCGGTG
GGGCGGCCAGCTGAAAACCATCATGCACACCAACATGCCCAACGTGAACGAGTTCATGTACAGCAACAAG
TTCAAGGCGCGGGTGATGGTCTCGCGCAAGACCCCCAACGGGGTCACAGTAACAGATGGTAGTCAGGACG
AGCTGACCTACGAGTGGGTGGAGTTTGAGCTGCCCGAGGGCAACTTCTCGGTGACCATGACCATCGATCT
GATGAACAACGCCATCATCGACAACTACTTGGCGGTGGGGCGGCAGAACGGGGTGCTGGAGAGCGACATC
GGCGTGAAGTTCGACACGCGCAACTTCCGGCTGGGCTGGACCCCGTGACCGAGCTGGTGATGCCGGGCG
TGTACACCAACGAGGCCTTCCACCCCGACATCGTCCTGCTGCCCGGCTGCGGCGTGGACTTCACCGAGAG
CCGCCTCAGCAACCTGCTGGGCATCCGCAAGCGGCAGCCCTTCCAGGAGGGCTTCCAGATCCTGTACGAG
GACCTGGAGGGGGGCAACATCCCCGCGCTCTTGGATGTCGAAGCCTACGAGAAAAGCAAGGAGGATAGCA
CCGCCGTGGCTACCGCCGCGACTGTGGCAGATGCCACTGTCACCAGGGGCGATACATTCGCCACCCAGGC
GGAGGAAGCAGCCGCCCTAGCGGCGACCGATGATAGTGAAAGTAAGATAGTTATCAAGCCGGTGGAGAAG
GACAGCAAGGACAGGAGCTACAACGTTCTATCGGATGGAAAGAACACCGCCTACCGCAGCTGGTACCTGG
CCTACAACTACGGCGACCCCGAGAAGGGCGTGCGCTCCTGGACGCTGCTCACCACCTCGGACGTCACCTG
CGGCGTGGAGCAAGTCTACTGGTCGCTGCCCGACATGATGCAAGACCCGGTCACCTTCCGCTCCACGCGT
CAAGTTAGCAACTACCCGGTGGTGGGCGCCGAGCTCCTGCCCGTCTACTCCAAGAGCTTCTTCAACGAGC
AGGCCGTCTACTCGCAGCAGCTGCGCGCCTTCACCTCGCTCACGCACGTCTTCAACCGCTTCCCCGAGAA
CCAGATCCTCGTCCGCCCGCCCGCGCCCACCATTACCACCGTCAGTGAAAACGTTCCTGCTCTCACAGAT
CACGGGACCCTGCCGCTGCGCAGCAGTATCCGGGGAGTCCAGCGCGTGACCGTCACTGACGCCAGACGCC
GCACCTGCCCCTACGTCTACAAGGCCCTGGGCGTAGTCGCGCCGCGCGTCCTCTCGAGCCGCACCTTCTA
AAAAAATGTCCATTCTCATCTCGCCCAGTAATAACACCGGTTGGGGCCTGCGCGCGCCCAGCAAGATGTAC
GGAGGCGCTCGCCAACGCTCCACGCAACACCCCGTGCGCGTGCGCGGGCACTTCCGCGCTCCCTGGGGCG
CCCTCAAGGGTCGCGTGCGCTCGCGCACCACCGTCGACGACGTGATCGACCAGGTGGTGGCCGACGCGCG
```

-continued
```
CAACTACACGCCCGCCGCCGCGCCCGCCTCCACCGTGGACGCCGTCATCGACAGCGTGGTGGCCGACGCG

CGCCGGTACGCCCGCGCCAAGAGCCGGCGGCGGCGCATCGCCCGGCGGCACCGGAGCACCCCCGCCATGC

GCGCGGCGCGAGCCTTGCTGCGCAGGGCCAGGCGCACGGGACGCAGGGCCATGCTCAGGGCGGCCAGACG

CGCGGCCTCCGGCAGCAGCAGCGCCGGCAGGACCCGCAGACGCGCGGCCACGGCGGCGGCGGCGGCCATC

GCCAGCATGTCCCGCCCGCGGCGCGGCAACGTGTACTGGGTGCGCGACGCCGCCACCGGTGTGCGCGTGC

CCGTGCGCACCCGCCCCCCTCGCACTTGAAGATGCTGACTTCGCGATGTTGATGTGTCCCAGCGGCGAGG

AGGATGTCCAAGCGCAAATACAAGGAAGAGATGCTCCAGGTCATCGCGCCTGAGATCTACGGCCCCGCGG

CGGCGGTGAAGGAGGAAAGAAAGCCCCGCAAACTGAAGCGGGTCAAAAAGGACAAAAAGGAGGAGGAAGA

TGTGGACGGACTGGTGGAGTTTGTGCGCGAGTTCGCCCCCCGGCGGCGCGTGCAGTGGCGCGGGCGGAAA

GTGAAACCGGTGCTGCGGCCCGGCACCACGGTGGTCTTCACGCCCGGCGAGCGTTCCGGCTCCGCCTCCA

AGCGCTCCTACGACGAGGTGTACGGGACGAGGACATCCTCGAGCAGGCGGCCGAGCGTCTGGGCGAGTT

TGCTTACGGCAAGCGCAGCCGCCCCGCGCCCTTGAAAGAGGAGGCGGTGTCCATCCCGCTGGACCACGGC

AACCCCACGCCGAGCCTGAAGCCGGTGACCCTGCAGCAGGTGCTGCCGAGCGCGGCGCCGCGCCGGGGCT

TCAAGCGCGAGGGCGGCGAGGATCTGTACCCGACCATGCAGCTGATGGTGCCCAAGCGCCAGAAGCTGGA

GGACGTGCTGGAGCACATGAAGGTGGACCCCGAGGTGCAGCCCGAGGTCAAGGTGCGGCCCATCAAGCAG

GTGGCCCCGGGCCTGGGCGTGCAGACCGTGGACATCAAGATCCCCACGGAGCCCATGGAAACGCAGACCG

AGCCCGTGAAGCCCAGCACCAGCACCATGGAGGTGCAGACGGATCCCTGGATGCCGGCGCCGGCTTCCAC

CACCACTCGCCGAAGACGCAAGTACGGCGCGGCCAGCCTGCTGATGCCCAACTACGCGCTGCATCCTTCC

ATCATCCCCACGCCGGGCTACCGCGGCACGCGCTTCTACCGCGGCTACAGCAGCCGCCGCAAGACCACCA

CCCGCCGCCGCCGTCGCCGCACCCGCCGCAGCACCACCGCGACTTCCGCCGCCGCCTTGGTGCGGAGAGT

GTACCGCAGCGGGCGTGAGCCTCTGACCCTGCCGCGCGCGCGCTACCACCCGAGCATCGCCATTTAACTC

TGCCGTCGCCTCCTTGCAGATATGGCCCTCACATGCCGCCTCCGCGTCCCCATTACGGGCTACCGAGGAA

GAAAGCCGCGCCGTAGAAGGCTGACGGGAACGGGCTGCGTCGCCATCACCACCGGCGGCGGCGCGCCAT

CAGCAAGCGGTTGGGGGAGGCTTCCTGCCCGCGCTGATCCCCATCATCGCCGCGGCGATCGGGGCGATC

CCCGGCATAGCTTCCGTGGCGGTGCAGGCCTCTCAGCGCCACTGAGACACAGCTTGGAAAATTTGTAATA

AAAAAATGGACTGACGCTCCTGGTCCTGTGATGTGTGTTTTTAGATGGAAGACATCAATTTTTCGTCCCT

GGCACCGCGACACGGCACGCGGCCGTTTATGGGCACCTGGAGCGACATCGGCAACAGCCAACTGAACGGG

GGCGCCTTCAATTGGAGCAGTCTCTGGAGCGGGCTTAAGAATTTCGGGTCCACGCTCAAAACCTATGGCA

ACAAGGCGTGGAACAGCAGCACAGGGCAGGCGCTGAGGGAAAAGCTGAAAGAGCAGAACTTCCAGCAGAA

GGTGGTCGATGGCCTGGCCTCGGGCATCAACGGGGTGGTGGACCTGGCCAACCAGGCCGTGCAGAAACAG

ATCAACAGCCGCCTGGACGCGGTCCCGCCCGCGGGGTCCGTGGAGATGCCCCAGGTGGAGGAGGAGCTGC

CTCCCCTGGACAAGCGCGGCGACAAGCGACCGCGTCCCGACGCGGAGGAGACGCTGCTGACGCACACGGA

CGAGCCGCCCCCGTACGAGGAGGCGGTGAAACTGGGTCTGCCCACCACGCGGCCCGTGGCGCCTCTGGCC

ACCGGGGTGCTGAAACCCAGCAGCAGCAGCAGCCAGCCCGCGACCCTGGACTTGCCTCCACCTCGCCCCT

CCACAGTGGCTAAGCCCCTGCCGCCGGTGGCCGTCGCGTCGCGCGCCCCCGAGGCCGCCCCCAGGCGAA

CTGGCAGAGCACTCTGAACAGCATCGTGGGTCTGGGAGTGCAGAGTGTGAAGCGCCGCCGCTGCTATTAA

AAGACACTGTAGCGCTTAACTTGCTTGTCTGTGTGTATATGTATGTCCGCCGACCAGAAGGAGGAGGAAG

AGGCGCGTCGCCGAGTTGCAAGATGGCCACCCCATCGATGCTGCCCCAGTGGGCGTACATGCACATCGCC

GGACAGGACGCTTCGGAGTACCTGAGTCCGGGTCTGGTGCAGTTCGCCCGCGCCACAGACACCTACTTCA

GTCTGGGGAACAAGTTTAGGAACCCCACGGTGGCACCCACGCACGATGTGACCACCGACCGCAGCCAGCG

GCTGACGCTGCGCTTCGTGCCCGTGGACCGCGAGGACAACACCTACTCGTACAAAGTGCGCTACACGCTG
```

-continued

```
GCCGTGGGCGACAACCGCGTGCTGGACATGGCCAGCACCTACTTTGACATCCGCGGCGTGCTGGATCGGG

GCCCCAGCTTCAAACCCTACTCCGGCACCGCCTACAACAGCCTGGCTCCCAAGGGAGCGCCCAACACCTC

ACAGTGGATAACCAAAGACAATGGAACTGATAAGACATACAGTTTTGGAAATGCTCCAGTCAGAGGATTG

GACATTACAGAAGAGGGTCTCCAAATAGGAACCGATGAGTCAGGGGGTGAAAGCAAGAAAATTTTTGCAG

ACAAAACCTATCAGCCTGAACCTCAGCTTGGAGATGAGGAATGGCATGATACTATTGGAGCTGAAGACAA

GTATGGAGGCAGAGCGCTTAAACCTGCCACCAACATGAAACCCTGCTATGGGTCTTTCGCCAAGCCAACT

AATGCTAAGGGAGGTCAGGCTAAAAGCAGAACCAAGGACGATGGCACTACTGAGCCTGATATTGACATGG

CCTTCTTTGACGATCGCAGTCAGCAAGCTAGTTTCAGTCCAGAACTTGTTTTGTATACTGAGAATGTCGA

TCTGGACACCCCGGATACCCACATTATTTACAAACCTGGCACTGATGAAACAAGTTCTTCTTTCAACTTG

GGTCAGCAGTCCATGCCCAACAGACCCAACTACATTGGCTTCAGAGACAACTTTATCGGGCTCATGTACT

ACAACAGCACTGGCAATATGGGTGTACTGGCCGGTCAGGCCTCCCAGCTGAATGCTGTGGTGGACTTGCA

GGACAGAAACACTGAACTGTCCTACCAGCTCTTGCTTGACTCTCTGGGTGACAGAACCAGGTATTTCAGT

ATGTGGAATCAGGCGGTGGACAGCTATGACCCCGATGTGCGCATTATTGAAAATCACGGTGTGGAGGATG

AACTCCCCAACTATTGCTTCCCTTTGAATGGTGTGGGCTTTACAGATACATTCCAGGGAATTAAGGTTAA

AACTACAAATAACGGAACAGCAAATGCTACAGAGTGGGAATCTGATACCTCTGTCAATAATGCTAATGAG

ATTGCCAAGGGCAATCCTTTCGCCATGGAGATCAACATCCAGGCCAACCTGTGGCGGAACTTCCTCTACG

CGAACGTGGCGCTGTACCTGCCCGACTCCTACAAGTACACGCCGGCCAACATCACGCTGCCCACCAACAC

CAACACCTACGATTACATGAACGGCCGCGTGGTGGCGCCCTCGCTGGTGGACGCCTACATCAACATCGGG

GCGCGCTGGTCGCTGGACCCCATGGACAACGTCAACCCCTTCAACCACCACCGCAACGCGGGCCTGCGCT

ACCGCTCCATGCTCCTGGGCAACGGGCGCTACGTGCCCTTCCACATCCAGGTGCCCCAAAAGTTTTTCGC

CATCAAGAGCCTCCTGCTCCTGCCCGGGTCCTACACCTACGAGTGGAACTTCCGCAAGGACGTCAACATG

ATCCTGCAGAGCTCCCTCGGCAACGACCTGCGCACGGACGGGGCCTCCATCGCCTTCACCAGCATCAACC

TCTACGCCACCTTCTTCCCCATGGCGCACAACACCGCCTCCACGCTCGAGGCCATGCTGCGCAACGACAC

CAACGACCAGTCCTTCAACGACTACCTCTCGGCGGCCAACATGCTCTACCCCATCCCGGCCAACGCCACC

AACGTGCCCATCTCCATCCCCTCGCGCAACTGGGCCGCCTTCCGCGGATGGTCCTTCACGCGCCTCAAGA

CCCGCGAGACGCCCTCGCTCGGCTCCGGGTTCGACCCCTACTTCGTCTACTCGGGCTCCATCCCCCTACCT

CGACGGCACCTTCTACCTCAACCACACCTTCAAGAAGGTCTCCATCACCTTCGACTCCTCCGTCAGCTGG

CCCGGCAACGACCGCCTCCTGACGCCCAACGAGTTCGAAATCAAGCGCACCGTCGACGGAGAGGGGTACA

ACGTGGCCCAGTGCAACATGACCAAGGACTGGTTCCTGGTCCAGATGCTGGCCCACTACAACATCGGCTA

CCAGGGCTTCTACGTGCCCGAGGGCTACAAGGACCGCATGTACTCCTTCTTCCGCAACTTCCAGCCCATG

AGCCGCCAGGTCGTGGACGAGGTCAACTACAAGGACTACCAGGCCGTCACCCTGGCCTACCAGCACAACA

ACTCGGGCTTCGTCGGCTACCTCGCGCCCACCATGCGCCAGGGCCAGCCCTACCCCGCCAACTACCCCTA

CCCGCTCATCGGCAAGAGCGCCGTCGCCAGCGTCACCCAGAAAAAGTTCCTCTGCGACCGGGTCATGTGG

CGCATCCCCTTCTCCAGCAACTTCATGTCCATGGGCGCGCTCACCGACCTCGGCCAGAACATGCTCTACG

CCAACTCCGCCCACGCGCTAGACATGAATTTCGAAGTCGACCCCATGGATGAGTCCACCCTTCTCTATGT

TGTCTTCGAAGTCTTCGACGTCGTCCGAGTGCACCAGCCCCACCGCGGCGTCATCGAGGCCGTCTACCTG

CGCACGCCCTTCTCGGCCGGCAACGCCACCACCTAAGCCTCTTGCTTCTTGCAAGATGACGGCCTGTGGC

TCCGGCGAGCAGGAGCTCAGGGCCATCCTCCGCGACCTGGGCTGCGGGCCCTACTTCCTGGGCACCTTCG

ACAAGCGCTTCCCGGGATTCATGGCCCCGCACAAGCTGGCCTGCGCCATCGTCAACACGGCCGGCCGCGA

GACCGGGGGCGAGCACTGGCTGGCCTTCGCCTGGAACCCGCGCACCCACACCTGCTACCTCTTCGACCCC
```

-continued

```
TTCGGGTTCTCGGACGAGCGCCTCAAGCAGATCTACCAGTTCGAGTACGAGGGCCTGCTGCGCCGCAGCG
CCCTGGCCACCGAGGACCGCTGCGTCACCCTGGAAAAGTCCACCCAGACCGTGCAGGGTCCGCGCTCGGC
CGCCTGCGGGCTCTTCTGCTGCATGTTCCTGCACGCCTTCGTGCACTGGCCCGACCGCCCCATGGACAAG
AACCCCACCATGAACTTGCTGACGGGGGTGCCCAACGGCATGCTCCAGTCGCCCCAGGTGGAACCCACCC
TGCGCCGCAACCAGGAGGCGCTCTACCGCTTCCTCAACGCCCACTCCGCCTACTTTCGCTCCCACCGCGC
GCGCATCGAGAAGGCCACCGCCTTCGACCGCATGAATCAAGACATGTAAACTGTGTGTATGTGAATGCTT
TATTCATAATAAACAGCACATGTTTATGCCACCTTCTCTGAGGCTCTGACTTTATTTAGAAATCGAAGGG
GTTCTGCCGGCTCTCGGCGTGCCCCGCGGGCAGGGATACGTTGCGGAACTGGTACTTGGGCAGCCACTTG
AACTCGGGGATCAGCAGCTTCGGCACGGGGAGGTCGGGGAACGAGTCGCTCCACAGCTTGCGCGTGAGTT
GCAGGGCGCCCAGCAGGTCGGGCGCGGATATCTTGAAATCACAGTTGGGACCCGCGTTCTGCGCGCGAGA
GTTGCGGTACACGGGGTTGCAGCACTGGAACACCATCAGGGCCGGGTGCTTCACGCTCGCCAGCACCGTC
GCGTCGGTGATGCCCTCCACGTCCAGATCCTCGGCGTTGGCCATCCCGAAGGGGGTCATCTTGCAGGTCT
GCCGCCCATGCTGGGCACGCAGCCGGGCTTGTGGTTGCAATCGCAGTGCAGGGGGATCAGCATCATCTG
GGCCTGCTCGGAGCTCATGCCCGGGTACATGGCCTTCATGAAAGCCTCCAGCTGGCGGAAGGCCTGCTGC
GCCTTGCCGCCCTCGGTGAAGAAGACCCCGCAGGACTTGCTAGAGAACTGGTTGGTGGCGCAGCCGGCGT
CGTGCACGCAGCAGCGCGCGTCGTTGTTGGCCAGCTGCACCACGCTGCGCCCCCAGCGGTTCTGGGTGAT
CTTGGCCCGGTCGGGGTTCTCCTTCAGCGCGCGCTGCCCGTTCTCGCTCGCCACATCCATCTCGATCGTG
TGCTCCTTCTGGATCATCACGGTCCCGTGCAGGCACCGCAGCTTGCCCTCGGCTTCGGTGCATCCGTGCA
GCCACAGCGCGCAGCCGGTGCACTCCCAGTTCTTGTGGGCGATCTGGGAGTGCGAGTGCACGAAGCCCTG
CAGGAAGCGGCCCATCATCGCGGTCAGGGTCTTGTTGCTGGTGAAGGTCAGCGGGATGCCGCGGTGCTCC
TCGTTCACATACAGGTGGCAGATGCGGCGGTACACCTCGCCCTGCTCGGGCATCAGCTGGAAGGCGGACT
TCAGGTCGCTCTCCACGCGGTACCGCTCCATCAGCAGCGTCATGACTTCCATGCCCTTCTCCCAGGCCGA
AACGATCGGCAGGCTCAGGGGGTTCTTCACCGTTGTCATCTTAGTCGCCGCCGCCGAGGTCAGGGGGTCG
TTCTCGTCCAGGGTCTCAAACACTCGCTTGCCGTCCTTCTCGGTGATGCGCACGGGGGGAAAGCTGAAGC
CCACGGCCGCCAGCTCCTCCTCGGCCTGCCTTTCGTCCTCGCTGTCCTGGCTGATGTCTTGCAAAGGCAC
ATGCTTGGTCTTGCGGGGTTTCTTTTTGGGCGGCAGAGGCGGCGGCGGAGACGTGCTGGGCGAGCGCGAG
TTCTCGCTCACCACGACTATTTCTTCTTCTTGGCCGTCGTCCGAGACCACGCGGCGGTAGGCATGCCTCT
TCTGGGGCAGAGGCGGAGGCGACGGGCTCTCGCGGTTCGGCGGGCGGCTGGCAGAGCCCCTTCCGCGTTC
GGGGGTGCGCTCCTGGCGGCGCTGCTCTGACTGACTTCCTCCGCGGCCGGCCATTGTGTTCTCCTAGGGA
GCAAGCATGGAGACTCAGCCATCGTCGCCAACATCGCCATCTGCCCCCGCCGCCGCCGACGAGAACCAGC
AGCAGCAGAATGAAAGCTTAACCGCCCCGCCGCCCAGCCCCACCTCCGACGCCGCGGCCCCAGACATGCA
AGAGATGGAGGAATCCATCGAGATTGACCTGGGCTACGTGACGCCCGCGGAGCACGAGGAGGAGCTGGCA
GCGCGCTTTTCAGCCCCGGAAGAGAACCACCAAGAGCAGCCAGAGCAGGAAGCAGAGAGCGAGCAGAGCC
AGGCTGGGCTCGAGCATGGCGACTACCTGAGCGGGGCAGAGGACGTGCTCATCAAGCATCTGGCCCGCCA
ATGCATCATCGTCAAGGATGCGCTGCTCGACCGCGCCGAGGTGCCCCTCAGCGTGGCGGAGCTCAGCCGC
GCCTACGAGCGCAACCTCTTCTCGCCGCGCGTGCCCCCCAAGCGCCAGCCCAACGGCACCTGCGAGCCCA
ACCCGCGCCTCAACTTCTACCCGGTCTTCGCGGTGCCCGAGGCCCTGGCCACCTACCACCTCTTTTTCAA
GAACCAAAGGATCCCCGTCTCCTGCCGCGCCAACCGCACCCGCGCCGACGCCCTGCTCAACCTGGGCCCC
GGCGCCCGCCTACCTGATATCGCCTCCTTGGAAGAGGTTCCCAAGATCTTCGAGGGTCTGGGCAGCGACG
AGACTCGGGCCGCGAACGCTCTGCAAGGAAGCGGAGAGGAGCATGAGCACCACAGCGCCCTGGTGGAGTT
GGAAGGCGACAACGCGCGCCTGGCGGTCCTCAAGCGCACGGTCGAGCTGACCCACTTCGCCTACCCGGCG
```

```
CTCAACCTGCCCCCCAAGGTCATGAGCGCCGTCATGGACCAGGTGCTCATCAAGCGCGCCTCGCCCCTCT

CGGAGGAGGAGATGCAGGACCCCGAGAGCTCGGACGAGGGCAAGCCCGTGGTCAGCGACGAGCAGCTGGC

GCGCTGGCTGGGAGCGAGTAGCACCCCCAGAGCCTGGAAGAGCGGCGCAAGCTCATGATGGCCGTGGTC

CTGGTGACCGTGGAGCTGGAGTGTCTGCGCCGCTTCTTCGCCGACGCGGAGACCCTGCGCAAGGTCGAGG

AGAACCTGCACTACCTCTTCAGGCACGGGTTCGTGCGCCAGGCCTGCAAGATCTCCAACGTGGAGCTGAC

CAACCTGGTCTCCTACATGGGCATCCTGCACGAGAACCGCCTGGGGCAGAACGTGCTGCACACCACCCTG

CGCGGGGAGGCCCGCCGCGACTACATCCGCGACTGCGTCTACCTGTACCTCTGCCACACCTGGCAGACGG

GCATGGGCGTGTGGCAGCAGTGCCTGGAGGAGCAGAACCTGAAAGAGCTCTGCAAGCTCCTGCAGAAGAA

CCTGAAGGCCCTGTGGACCGGGTTCGACGAGCGCACCACCGCCTCGGACCTGGCCGACCTCATCTTCCCC

GAGCGCCTGCGGCTGACGCTGCGCAACGGGCTGCCCGACTTTATGAGCCAAAGCATGTTGCAAAACTTTC

GCTCTTTCATCCTCGAACGCTCCGGGATCCTGCCCGCCACCTGCTCCGCGCTGCCCTCGGACTTCGTGCC

GCTGACCTTCCGCGAGTGCCCCCCGCCGCTCTGGAGCCACTGCTACCTGCTGCGTCTGGCCAACTACCTG

GCCTACCACTCGGACGTGATCGAGGACGTCAGCGGCGAGGGTCTGCTCGAGTGCCACTGCCGCTGCAACC

TCTGCACGCCGCACCGCTCCCTGGCCTGCAACCCCCAGCTGCTGAGCGAGACCCAGATCATCGGCACCTT

CGAGTTGCAAGGCCCCGGCGAGGAGGGCAAGGGGGGTCTGAAACTCACCCCGGGGCTGTGGACCTCGGCC

TACTTGCGCAAGTTCGTGCCCGAGGACTACCATCCCTTCGAGATCAGGTTCTACGAGGACCAATCCCAGC

CGCCCAAGGCCGAGCTGTCGGCCTGCGTCATCACCCAGGGGGCCATCCTGGCCCAATTGCAAGCCATCCA

GAAATCCCGCCAAGAATTTCTGCTGAAAAAGGGCCACGGGGTCTACTTGGACCCCCAGACCGGAGAGGAG

CTCAACCCCAGCTTCCCCCAGGATGCCCAGAGGAAGCAGCAAGAAGCTGAAAGTGGAGCTGCCGCTGCCG

CCGGAGGATTTGGAGGAAGACTGGGAGAGCAGTCAGGCAGAGGAGGAGGAGATGGAAGACTGGGACAGCA

CTCAGGCAGAGGAGGACAGCCTGCAAGACAGTCTGGAAGACGAGGTGGAGGAGGAGGCAGAGGAAGAAGC

AGCCGCCGCCAGACCGTCGTCCTCGGCGGAGAAAGCAAGCAGCACGGATACCATCTCCGCTCCGGGTCGG

GGTCTCGGCGGCCGGGCCCACAGTAGGTGGGACGAGACCGGGCGCTTCCCGAACCCCACCACCCAGACCG

GTAAGAAGGAGCGGCAGGGATACAAGTCCTGGCGGGGGCACAAAAACGCCATCGTCTCCTGCTTGCAAGC

CTGCGGGGGCAACATCTCCTTCACCCGGCGCTACCTGCTCTTCCACCGCGGGGTGAACTTCCCCCGCAAC

ATCTTGCATTACTACCGTCACCTCCACAGCCCCTACTACTGTTTCCAAGAAGAGGCAGAAACCCAGCAGC

AGCAGAAAACCAGCAGCAGCTAGAAAATCCACAGCGGCGGCGGCGGCAGGTGGACTGAGGATCGCGGCGA

ACGAGCCGGCGCAGACCCGGGAGCTGAGGAACCGGATCTTTCCCACCCTCTATGCCATCTTCCAGCAGAG

TCGGGGGCAGGAGCAGGAACTGAAAGTCAAGAACCGTTCTCTGCGCTCGCTCACCCGCAGTTGTCTGTAT

CACAAGAGCGAAGACCAACTTCAGCGCACTCTCGAGGACGCCGAGGCTCTCTTCAACAAGTACTGCGCGC

TCACTCTTAAAGAGTAGCCCGCGCCCGCCCACACACGGAAAAAGGCGGGAATTACGTCACCACCTGCGCC

CTTCGCCCGACCATCATCATGAGCAAAGAGATTCCCACGCCTTACATGTGGAGCTACCAGCCCCAGATGG

GCCTGGCCGCCGGCGCCGCCCAGGACTACTCCACCCGCATGAACTGGCTCAGTGCCGGGCCCGCGATGAT

CTCACGGGTGAATGACATCCGCGCCCGCCGAAACCAGATACTCCTAGAACAGTCAGCGATCACCGCCACG

CCCCGCCATCACCTTAATCCGCGTAATTGGCCCGCCGCCCTGGTGTACCAGGAAATTCCCCAGCCCACGA

CCGTACTACTTCCGCGAGACGCCCAGGCCGAAGTCCAGCTGACTAACTCAGGTGTCCAGCTGGCCGGCGG

CGCCGCCCTGTGTCGTCACCGCCCCGCTCAGGGTATAAAGCGGCTGGTGATCCGAGGCAGAGGCACACAG

CTCAACGACGAGGTGGTGAGCTCTTCGCTGGGTCTGCGACCTGACGGAGTCTTCCAACTCGCCGGATCGG

GGAGATCTTCCTTCACGCCTCGTCAGGCCGTCCTGACTTTGGAGAGTTCGTCCTCGCAGCCCCGCTCGGG

TGGCATCGGCACTCTCCAGTTCGTGGAGGAGTTCACTCCCTCGGTCTACTTCAACCCCTTCTCCGGCTCC
```

-continued

```
CCCGGCCACTACCCGGACGAGTTCATCCCGAACTTCGACGCCATCAGCGAGTCGGTGGACGGCTACGATT
GAATGTCCCATGGTGGCGCGGCTGACCTAGCTCGGCTTCGACACCTGGACCACTGCCGCCGCTTCCGCTG
CTTCGCTCGGGATCTCGCCGAGTTTGCCTACTTTGAGCTGCCCGAGGAGCACCCTCAGGGCCCGGCCCAC
GGAGTGCGGATCATCGTCGAAGGGGGCCTCGACTCCCACCTGCTTCGGATCTTCAGCCAGCGTCCGATCC
TGGTCGAGCGCGAGCAAGGACAGACCCGTCTGACCCTGTACTGCATCTGCAACCACCCCGGCCTGCATGA
AAGTCTTTGTTGTCTGCTGTGTACTGAGTATAATAAAAGCTGAGATCAGCGACTACTCCGGACTTCCGTG
TGTTCCTGAATCCATCAACCAGTCCCTGTTCTTCACCGGGAACGAGACCGAGCTCCAGCTCCAGTGTAAG
CCCCACAAGAAGTACCTCACCTGGCTGTTCCAGGGCTCCCCGATCGCCGTTGTCAACCACTGCGACAACG
ACGGAGTCCTGCTGAGCGGCCCTGCCAACCTTACTTTTTCCACCCGCAGAAGCAAGCTCCAGCTCTTCCA
ACCCTTCCTCCCCGGGACCTATCAGTGCGTCTCGGGACCCTGCCATCACACCTTCCACCTGATCCCGAAT
ACCACAGCGTCGCTCCCCGCTACTAACAACCAAACTACCCACCAACGCCACCGTCGCGACCTTTCCTCTG
AATCTAATACCACTACCGGAGGTGAGCTCCGAGGTCGACCAACCTCTGGGATTTACTACGGCCCCTGGGA
GGTGGTGGGGTTAATAGCGCTAGGCCTAGTTGTGGGTGGGCTTTTGGCTCTCTGCTACCTATACCTCCCT
TGCTGTTCGTACTTAGTGGTGCTGTGTTGCTGGTTTAAGAAATGGGGCAGATCACCCTAGTGAGCTGCGG
TGTGCTGGTGGCGGTGGTGCTTTCGATTGTGGGACTGGGCGGCGGGCTGTAGTGAAGGAGAAGGCCGAT
CCCTGCTTGCATTTCAATCCCGACAAATGCCAGCTGAGTTTTCAGCCCGATGGCAATCGGTGCGCGGTGC
TGATCAAGTGCGGATGGGAATGCGAGAACGTGAGAATCGAGTACAATAACAAGACTCGGAACAATACTCT
CGCGTCCGTGTGGCAGCCCGGGGACCCCGAGTGGTACACCGTCTCTGTCCCCGGTGCTGACGGCTCCCCG
CGCACCGTGAATAATACTTTCATTTTTGCGCACATGTGCGACACGGTCATGTGGATGAGCAAGCAGTACG
ATATGTGGCCCCCCACGAAGGAGAACATCGTGGTCTTCTCCATCGCTTACAGCCTGTGCACGGTGCTAAT
CACCGCTATCGTGTGCCTGAGCATTCACATGCTCATCGCTATTCGCCCCAGAAATAATGCCGAAAAAGAG
AAACAGCCATAACACGTTTTTTCACACACCTTGTTTTTACAGACAATGCGTCTGTTAAATTTTTTAAACA
TTGTGCTCAGTATTGCTTATGCCTCTGGCTATGCAAACATACAGAAAACCCTCTATGTAGGATCTGATGA
TACACTAGAGGGTACCCAATCACAAGCTAGGGTTTCATGGTATTTTTATAAAAGCTCAGATAATCCTATT
ACTCTTTGCAAAGGTGATCAGGGGCGGACAACAAAGCCGCCTATCACATTTAGCTGTACCAGAACAAATC
TCACGCTTTTCTCAATTACAAAACAATATGCTGGTATTTATTACAGTACAAACTTTCATAGTGGGCAAGA
TAAATATTATACTGTTAAGGTAGAAAATCCTACCACTCCTAGAACTACCACCACCACCACCACCACCACC
ACTACTGCGAAGCCCACTAAACCTAAAACTACCAAGAAAACCACTGTGAAAACTACAACTAGAACCACCA
CAACTACAGAAACCACCACCAGCACAACACTTGCTGCAACTACACACACACACTGAGCTAACCTTACA
GACCACTAATGATTTGATAGCCCTGTTGCAAAAGGGGGATAACAGCACCACTTCCAATGAGGAGATACCC
AAATCCATGATTGGCATTATTGTTGCTGTAGTGGTGTGCATGTTGATCATCGCCTTGTGCATGGTGTACT
ATGCCTTCTGCTACAGAAAGCACAGACTGAACGACAAGCTGGAACACTTACTAAGTGTTGAATTTTAATT
TTTTAGAACCATGAAGATCCTAGGCCTTTTAGTTTTTTCTATCATTACCTCTGCTCTATGCAATTCTGAC
AATGAGGACGTTACTGTCGTTGTCGGATCAAATTATACACTGAAAGGTCCAGCGAAGGGTATGCTTTCGT
GGTATTGCTGGTTTGGAACTGACACTGATCAAACTGAGCTTTGCAATGCAATGAAAGGTCAAATACCAAC
CTCAAAAATTAAACATAAATGCAATGGTACTGACTTAGTACTACTCAATATCACGAAATCATATGCTGGC
AGCTATTCATGCCCTGGAGATGATGCTGAGAACATGATTTTTTACAAAGTAACTGTTGTTGATCCCACTA
CTCCACCACCCACCACCACAACTACTCACACCACACACACAGAACAAACACCAGAGGCAGCAGAAGCAGA
GTTGGCCTTCCAGGTTCACGGAGATTCCTTTGCTGTCAATACCCCTACACCCGATCATCGGTGTCCGGGG
CTGCTAGTCAGCGGCATTGTCGGTGTGCTTTCGGATTAGCAGTCATAATCATCTGCATGTTCATTTTTG
CTTGCTGCTATAGAAGGCTTTACCGACAAAAATCAGACCCACTGCTGAACCTCTATGTTAATTTTTTCC
```

-continued

```
AGAGCCATGAAGGCAGTTAGCGCTCTAGTTTTTTGTTCTTTGATTGGCATTGTTTTTTGCAATCCTATTA
CTAGAGTTAGCTTTATTAAAGATGTGAATGTTACTGAGGGGGGCAATGTGACACTGGTAGGTGTAGAGGG
TGCTAAAAACACCACCTGGACAAAATACCACCTTGGGTGGAAAGATATTTGCAATTGGAGTGTCACTGTG
TACACATGTGAGGGAGTTAATCTTACCATTGTCAATGCCACCTCAGCTCAAAATGGTAGAATTCAAGGAC
AAAGTGTTAGTGTGACCAGTGATGGGTATTTTACCCAACATACTTTTATCTATGACGTTAAAGTCATACC
ACTGCCTACGCCTAGCCCACCTAGCACCACTACACAAACAACCCACACTACACAGACAACCACATACAGT
ACATCAAATCAGCCTACCACCACTACAGCAGCAGAGGTTGCCAGCTCGTCTGGAGTTCAAGTGGCATTTT
TGTTGTTGCCCCCATCTAGCAGTCCCACTGCTATTACCAATGAGCAGACTACTGCATTTTTGTCCACTGT
CGAGAGCCACACCACAGCTACCTCCAGTGCCTTCTCTAGCACCGCCAATCTCTCCTCGCTTTCCTCTACA
CCAATCAGTCCCGCTACTACTACTACCCCCGCTATTCTTCCCACTCCCCTGAAGCAAACAGACGGCGGCA
TGCAATGGCAGATCACCCTGCTCATTGTGATCGGGTTGGTCATCCTAGCCGTGTTGCTCTACTACATCTT
CTGCCGCCGCATTCCCAACGCGCACCGCAAGCCGGTCTACAAGCCCATCATTGTCGGGCAGCCGGAGCCG
CTTCAGGTGGAAGGGGGTCTAAGGAATCTTCTCTTCTCTTTTACAGTATGGTGATTGAACTATGATTCCT
AGACAATTCTTGATCACTATTCTTATCTGCCTCCTCCAAGTCTGTGCCACCCTCGCTCTGGTGGCCAACG
CCAGTCCAGACTGTATTGGGCCCTTCGCCTCCTACGTGCTCTTTGCCTTCATCACCTGCATCTGCTGCTG
TAGCATAGTCTGCCTGCTTATCACCTTCTTCCAGTTCATTGACTGGATCTTTGTGCGCATCGCCTACCTG
CGCCACCACCCCCAGTACCGCGACCAGCGAGTGGCGCAGCTGCTCAGGCTCCTCTGATAAGCATGCGGGC
TCTGCTACTTCTCGCGCTTCTGCTGTTAGTGCTCCCCCGTCCCGTTGACCCCCGGCCCCCCACTCAGTCC
CCCGAGGAGGTCCGCAAATGCAAATTCCAAGAACCCTGGAAATTCCTCAAATGCTACCGCCAAAAATCAG
ACATGCATCCCAGCTGGATCATGATCATTGGGATCGTGAACATTCTGGCCTGCACCCTCATCTCCTTTGT
GATTTACCCCTGCTTTGACTTTGGTTGGAACTCGCCAGAGGCGCTCTATCTCCCGCCTGAACCTGACACA
CCACCACAGCAACCTCAGGCACACGCACTACCACCACCACAGCCTAGGCCACAATACATGCCCATATTAG
ACTATGAGGCCGAGCCACAGCGACCCATGCTCCCCGCTATTAGTTACTTCAATCTAACCGGCGGAGATGA
CTGACCCACTGGCCAACAACAACGTCAACGACCTTCTCCTGGACATGGACGGCCGCGCCTCGGAGCAGCG
ACTCGCCCAACTTCGCATTCGCCAGCAGCAGGAGAGAGCCGTCAAGGAGCTGCAGGACGGCATAGCCATC
CACCAGTGCAAGAAAGGCATCTTCTGCCTGGTGAAACAGGCCAAGATCTCCTACGAGGTCACCCAGACCG
ACCATCGCCTCTCCTACGAGCTCCTGCAGCAGCGCCAGAAGTTCACCTGCCTGGTCGGAGTCAACCCCAT
CGTCATCACCCAGCAGTCGGGCGATACCAAGGGGTGCATCCACTGCTCCTGCGACTCCCCCGACTGCGTC
CACACTCTGATCAAGACCCTCTGCGGCCTCCGCGACCTCCTCCCCATGAACTAATCACCCACTTATCCAG
TGAAATAAAAAAATAATCATTTGATTTGAAATAAAGATACAATCATATTGATGATTTGAGTTTAACAAAA
ATAAAGAATCACTTACTTGAAATCTGATACCAGGTCTCTGTCCATATTTTCTGCCAACACCACCTCACTC
CCCTCTTCCCAGCTCTGGTACTGCAGGCCCCGGCGGGCTGCAAACTTCCTCCACACGCTGAAGGGGATGT
CAAATTCCTCCTGCCCCTCAATCTTCATTTTATCTTCTATCAGATGTCCAAAAAGCGCGTCCGGGTGGAT
GATGACTTCGACCCCGTCTACCCCTACGATGCAGACAACGCACCGACCGTGCCCTTCATCAACCCCCCCT
TCGTCTCTTCAGATGGATTCCAAGAGAAGCCCCTGGGGGTGTTGTCCCTGCGACTGGCCGACCCCGTCAC
CACCAAGAACGGGGAAATCACCCTCAAGCTGGGAGAGGGGTGGACCTCGACTCCTCGGGAAAACTCATC
TCCAACACGGCCACCAAGGCCGCTGCCCCTCTCAGTTTTTCCAACAACACCATTTCCCTTAACATGGATC
ACCCCTTTTACACTAAAGATGGAAAATTAGCCTTACAAGTTTCTCCACCATTAAATATACTGAGAACAAG
CATTCTAAACACACTAGCTTTAGGTTTTGGATCAGGTTTAGGACTCCGTGGCTCTGCCTTGGCAGTACAG
TTAGTCTCTCCACTTACATTTGATACTGATGGAAACATAAAGCTTACCTTAGACAGAGGTTTGCATGTTA
```

-continued

```
CAACAGGAGATGCAATTGAAAGCAACATAAGCTGGGCTAAAGGTTTAAAATTTGAAGATGGAGCCATAGC

AACCAACATTGGAAATGGGTTAGAGTTTGGAAGCAGTAGTACAGAAACAGGTGTCGATGATGCTTACCCA

ATCCAAGTTAAACTTGGATCTGGCCTTAGCTTTGACAGTACAGGAGCCATAATGGCTGGTAACAAAGAAG

ACGATAAACTCACTTTGTGGACAACACCTGATCCATCACCAAACTGTCAAATACTCGCAGAAAATGATGC

AAAACTAACACTTTGCTTGACTAAATGTGGTAGTCAAATACTGGCCACTGTGTCAGTCTTAGTTGTAGGA

AGTGGAAACCTAAACCCCATTACTGGCACCGTAAGCAGTGCTCAGGTGTTTCTACGTTTTGATGCAAACG

GTGTTCTTTTAACAGAACATTCTACACTAAAAAAATACTGGGGGTATAGGCAGGGAGATAGCATAGATGG

CACTCCATATGTCAATGCTGTAGGATTCATGCCCAATTTAAAAGCTTATCCAAAGTCACAAAGTTCTACT

ACTAAAAATAATATAGTAGGGCAAGTATACATGAATGGAGATGTTTCAAAACCTATGCTTCTCACTATAA

CCCTCAATGGTACTGATGACAGCAACAGTACATATTCAATGTCATTTTCATACACCTGGACTAATGGAAG

CTATGTTGGAGCAACATTTGGAGCTAACTCTTATACCTTCTCCTACATCGCCCAAGAATGAATACTGTAT

CCCACCCTGCATGCCCAACCCTCCCCCACCTCTGTCTATATGGAAAACTCTGAAACACAAAATAAAATAA

AGTTCAAGTGTTTTATTGATTCAACAGTTTTACAGGATTCGAGCAGTTATTTTTCCTCCACCCTCCCAGG

ACATGGAATACACCACCCTCTCCCCCCGCACAGCCTTGAACATCTGAATGCCATTGGTGATGGACATGCT

TTTGGTCTCCACGTTCCACACAGTTTCAGAGCGAGCCAGTCTCGGGTCGGTCAGGGAGATGAAACCCTCC

GGGCACTCCCGCATCTGCACCTCACAGCTCAACAGCTGAGGATTGTCCTCGGTGGTCGGGATCACGGTTA

TCTGGAAGAAGCAGAAGAGCGGCGGTGGGAATCATAGTCCGCGAACGGGATCGGCCGGTGGTGTCGCATC

AGGCCCCGCAGCAGTCGCTGCCGCCGCCGCTCCGTCAAGCTGCTGCTCAGGGGGTCCGGGTCCAGGGACT

CCCTCAGCATGATGCCCACGGCCCTCAGCATCAGTCGTCTGGTGCGGCGGGCGCAGCAGCGCATGCGGAT

CTCGCTCAGGTCGCTGCAGTACGTGCAACACAGGACCACCAGGTTGTTCAACAGTCCATAGTTCAACACG

CTCCAGCCGAAACTCATCGCGGGAAGGATGCTACCCACGTGGCCGTCGTACCAGATCCTCAGGTAAATCA

AGTGGCGCCCCCTCCAGAACACGCTGCCCATGTACATGATCTCCTTGGGCATGTGGCGGTTCACCACCTC

CCGGTACCACATCACCCTCTGGTTGAACATGCAGCCCCGGATGATCCTGCGGAACCACAGGGCCAGCACC

GCCCCGCCCGCCATGCAGCGAAGAGACCCCGGGTCCCGGCAATGGCAATGGAGGACCCACCGCTCGTACC

CGTGGATCATCTGGGAGCTGAACAAGTCTATGTTGGCACAGCACAGGCACACGCTCATGCATCTCTTCAG

CACTCTCAGCTCCTCGGGGGTCAAAACCATATCCCAGGGCACGGGAAACTCTTGCAGGACAGCGAAGCCC

GCAGAACAGGGCAATCCTCGCACATAACTTACATTGTGCATGGACAGGGTATCGCAATCAGGCAGCACCG

GGTGATCCTCCACCAGAGAAGCGCGGGTCTCGGTCTCCTCACAGCGTGGTAAGGGGCCGGCCGATACGG

GTGATGGCGGGACGCGGCTGATCGTGTTCGCGACCGTGTCATGATGCAGTTGCTTTCGGACATTTTCGTA

CTTGCTGAAGCAGAACCTGGTCCGGGCGCTGCACACCGATCGCCGGCGGCGGTCTCGGCGCTTGGAACGC

TCGGTGTTGAAGTTGTAAAACAGCCACTCTCTCAGACCGTGCAGCAGATCTAGGGCCTCAGGAGTGATGA

AGATCCCATCATGCCTGATGGCTCTGATCACATCGACCACCGTGGAATGGGCCAGACCCAGCCAGATGAT

GCAATTTTGTTGGGTTTCGGTGACGGCGGGGGAGGGAAGAACAGGAAGAACCATGATTAACTTTTAATCC

AAACGGTCTCGGAGCACTTCAAAATGAAGGTCGCGGAGATGGCACCTCTCGCCCCCGCTGTGTTGGTGGA

AAATAACAGCCAGGTCAAAGGTGATACGGTTCTCGAGATGTTCCACGGTGGCTTCCAGCAAAGCCTCCAC

GCGCACATCCAGAAACAAGACAATAGCGAAAGCGGGAGGGTTCTCTAATTCCTCAATCATCATGTTACAC

TCCTGCACCATCCCCAGATAATTTTCATTTTTCCAGCCTTGAATGATTCGAACTAGTTCCTGAGGTAAAT

CCAAGCCAGCCATGATAAAGAGCTCGCGCAGAGCGCCCTCCACCGGCATTCTTAAGCACACCCTCATAAT

TCCAAGATATTCTGCTCCTGGTTCACCTGCAGCAGATTGACAAGCGGGATATCAAAATCTCTGCCGCGAT

CCCTGAGCTCCTCCCTCAGCAATAACTGTAAGTACTCTTTCATATCCTCTCCGAAATTTTTAGCCATAGG

ACCCCCAGGAATAAGAGAAGGGCAAGCCACATTACAGATAAACCGAAGTCCCCCCCAGTGAGCATTGCCA
```

-continued

```
AATGTAAGATTGAAATAAGCATGCTGGCTAGACCCGGTGATATCTTCCAGATAACTGGACAGAAAATCGG

GCAAGCAATTTTTAAGAAAATCAACAAAAGAAAAATCTTCCAGGTGCACGTTTAGGGCCTCGGGAACAAC

GATGGAGTAAGTGCAAGGGGTGCGTTCCAGCATGGTTAGTTAGCTGATCTGTAAAAAAACAAAAAATAAA

ACATTAAACCATGCTAGCCTGGCGAACAGGTGGGTAAATCGTTCTCTCCAGCACCAGGCAGGCCACGGGG

TCTCCGGCGCGACCCTCGTAAAAATTGTCGCTATGATTGAAAACCATCACAGAGAGACGTTCCCGGTGGC

CGGCGTGAATGATTCGAGAAGAAGCATACACCCCCGGAACATTGGAGTCCGTGAGTGAAAAAAGCGGCC

GAGGAAGCAATGAGGCACTACAACGCTCACTCTCAAGTCCAGCAAAGCGATGCCATGCGGATGAAGCACA

AAATTTTCAGGTGCGTAAAAAATGTAATTACTCCCCTCCTGCACAGGCAGCGAAGCTCCCGATCCCTCCA

GATACACATACAAAGCCTCAGCGTCCATAGCTTACCGAGCGGCAGCAGCAGCGGCACACAACAGGCGCAA

GAGTCAGAGAAAAGACTGAGCTCTAACCTGTCCGCCCGCTCTCTGCTCAATATATAGCCCCAGATCTACA

CTGACGTAAAGGCCAAAGTCTAAAAATACCCGCCAAATAATCACACACGCCCAGCACACGCCCAGAAACC

GGTGACACACTCAAAAAAATACGCGCACTTCCTCAAACGCCCAAACTGCCGTCATTTCCGGGTTCCCACG

CTACGTCATCAAAACACGACTTTCAAATTCCGTCGACCGTTAAAAACGTCACCCGCCCCGCCCCTAACGG

TCGCCGCTCCCGCAGCCAATCAGCGCCCCGCATCCCCAAATTCAAACAGCTCATTTGCATATTAACGCGC

ACCAAAAGTTTGAGGTATATTATTGATGATG
```

Polynucleotide sequence encoding the CASI promoter

SEQ ID NO: 3

```
GGAGTTCCGCGTTACATAACTTACGGTAAATGGCCCGCCTGGCTGACCGCCCAACGACCCCCGCCCATTGACGTCAA

TAATGACGTATGTTCCCATAGTAACGCCAATAGGGACTTTCCATTGACGTCAATGGGTGGAGTATTTACGGTAAACT

GCCCACTTGGCAGTACATCAAGTGTATCATATGCCAAGTACGCCCCCTATTGACGTCAATGACGGTAAATGGCCCGC

CTGGCATTATGCCCAGTACATGACCTTATGGGACTTTCCTACTTGGCAGTACATCTACGTATTAGTCATCGCTATTA

CCATGGTCGAGGTGAGCCCCACGTTCTGCTTCACTCTCCCCATCTCCCCCCCCTCCCCACCCCCAATTTTGTATTTA

TTTATTTTTAATTATTTTGTGCAGCGATGGGGGCGGGGGGGGGGGGGCGCGCGCCAGGCGGGGCGGGGCGGGGC

GAGGGGCGGGGCGGGCGAGGCGGAGAGGTGCGGCGGCAGCCAATCAGAGCGGCGCGCTCCGAAAGTTTCCTTTTAT

GGCGAGGCGGCGGCGGCGGCCCTATAAAAAGCGAAGCGCTCCCTATCAGTGATAGAGATCTCCCTATCAGTGAT

AGAGATCGTCGACGAGCTCGCGGCGGGCGGGAGTCGCTGCGCGCTGCCTTCGCCCCGTGCCCGCTCCGCCGCCGCC

TCGCGCCGCCCGCCCCGGCTCTGACTGACCGCGTTACTAAAACAGGTAAGTCCGGCCTCCGCGCCGGGTTTTGGCGC

CTCCCGCGGGCGCCCCCCTCCTCACGGCGAGCGCTGCCACGTCAGACGAAGGGCGCAGCGAGCGTCCTGATCCTTCC

GCCCGGACGCTCAGGACAGCGGCCCGCTGCTCATAAGACTCGGCCTTAGAACCCCAGTATCAGCAGAAGGACATTTT

AGGACGGGACTTGGGTGACTCTAGGGCACTGGTTTTCTTTCCAGAGAGCGGAACAGGCGAGGAAAAGTAGTCCCTTC

TCGGCGATTCTGCGGAGGGATCTCCGTGGGGCGGTGAACGCCGATGATGCCTCTACTAACCATGTTCATGTTTTCTT

TTTTTTTCTACAGGTCCTGGGTGACGAACAG
```

Polynucleotide sequence encoding ChAd155/RSV

SEQ ID NO: 4

```
CATCATCAATAATATACCTTATTTTGGATTGAAGCCAATATGATAATGAGATGGGCGGCGCGGGGCGG

GGCGCGGGGCGGGAGGCGGGTTTGGGGGCGGGCCGGCGGGCGGGCGGTGTGGCGGAAGTGGACTTT

GTAAGTGTGGCGGATGTGACTTGCTAGTGCCGGGCGCGGTAAAAGTGACGTTTTCCGTGCGCGACAAC

GCCCCCGGGAAGTGACATTTTTCCCGCGGTTTTTACCGGATGTTGTAGTGAATTTGGGCGTAACCAAGT

AAGATTTGGCCATTTTCGCGGGAAAACTGAAACGGGGAAGTGAAATCTGATTAATTTTGCGTTAGTCA

TACCGCGTAATATTTGTCTAGGGCCGAGGGACTTTGGCCGATTACGTGGAGGACTCGCCCAGGTGTTTT

TTGAGGTGAATTTCCGCGTTCCGGGTCAAAGTCTGCGTTTTATTATTATAGGATATCCCATTGCATACG

TTGTATCCATATCATAATATGTACATTTATATTGGCTCATGTCCAACATTACCGCCATGTTGACATTGAT
```

-continued

```
TATTGACTAGTTATTAATAGTAATCAATTACGGGGTCATTAGTTCATAGCCCATATATGGAGTTCCGCG
TTACATAACTTACGGTAAATGGCCCGCCTGGCTGACCGCCCAACGACCCCCGCCCATTGACGTCAATA
ATGACGTATGTTCCCATAGTAACGCCAATAGGGACTTTCCATTGACGTCAATGGGTGGAGTATTTACG
GTAAACTGCCCACTTGGCAGTACATCAAGTGTATCATATGCCAAGTACGCCCCCTATTGACGTCAATG
ACGGTAAATGGCCCGCCTGGCATTATGCCCAGTACATGACCTTATGGGACTTTCCTACTTGGCAGTACA
TCTACGTATTAGTCATCGCTATTACCATGGTGATGCGGTTTTGGCAGTACATCAATGGGCGTGGATAGC
GGTTTGACTCACGGGGATTTCCAAGTCTCCACCCCATTGACGTCAATGGGAGTTTGTTTTGGCACCAAA
ATCAACGGGACTTTCCAAAATGTCGTAACAACTCCGCCCCATTGACGCAAATGGGCGGTAGGCGTGTA
CGGTGGGAGGTCTATATAAGCAGAGCTCTCCCTATCAGTGATAGAGATCTCCCTATCAGTGATAGAGA
TCGTCGACGAGCTCGTTTAGTGAACCGTCAGATCGCCTGGAGACGCCATCCACGCTGTTTTGACCTCCA
TAGAAGACACCGGGACCGATCCAGCCTCCGCGGCCGGGAACGGTGCATTGGAACGCGGATTCCCCGT
GCCAAGAGTGAGATCTTCCGTTTATCTAGGTACCAGATATCGCCACCATGGAACTGCTGATCCTGAAG
GCCAACGCCATCACCACCATCCTGACCGCCGTGACCTTCTGCTTCGCCAGCGGCCAGAACATCACCGA
GGAATTCTACCAGAGCACCTGTAGCGCCGTGAGCAAGGGCTACCTGAGCGCCCTGAGAACCGGCTGGT
ACACCAGCGTGATCACCATCGAGCTGAGCAACATCAAAGAAAACAAGTGCAACGGCACCGACGCCAA
AGTGAAGCTGATCAAGCAGGAACTGGACAAGTACAAGAACGCCGTGACCGAGCTGCAGCTGCTGATG
CAGAGCACCCCCGCCACCAACAACGGGCCAGACGGGAGCTGCCCCGGTTCATGAACTACACCCTGA
ACAACGCCAAAAAGACCAACGTGACCCTGAGCAAGAAGCGGAAGCGGCGGTTCCTGGGCTTTCTGCT
GGGCGTGGGCAGCGCCATTGCCAGCGGCGTGGCCGTGTCTAAGGTGCTGCACCTGGAAGGCGAAGTG
AACAAGATCAAGAGCGCCCTGCTGAGCACCAACAAGGCCGTGGTGTCCCTGAGCAACGGCGTGAGCG
TGCTGACCAGCAAGGTGCTGGATCTGAAGAACTACATCGACAAGCAGCTGCTGCCCATCGTGAACAAG
CAGAGCTGCAGCATCAGCAACATCGAGACAGTGATCGAGTTCCAGCAGAAGAACAACCGGCTGCTGG
AAATCACCCGGGAGTTCAGCGTGAACGCCGGCGTGACCACCCCTGTGTCCACCTACATGCTGACCAAC
AGCGAGCTGCTGAGCCTGATCAACGACATGCCCATCACCAACGACCAGAAAAAGCTGATGAGCAACA
ACGTGCAGATCGTGCGGCAGCAGAGCTACTCCATCATGTCCATCATCAAAGAAGAGGTGCTGGCCTAC
GTGGTGCAGCTGCCCCTGTACGGCGTGATCGACACCCCCTGCTGGAAGCTGCACACCAGCCCCCTGTG
CACCACCAACACCAAAGAGGGCAGCAACATCTGCCTGACCCGGACCGACAGAGGCTGGTACTGCGAC
AACGCCGGCAGCGTGTCATTCTTTCCACAGGCCGAGACATGCAAGGTGCAGAGCAACCGGGTGTTCTG
CGACACCATGAACAGCCTGACCCTGCCCTCCGAAGTGAACCTGTGCAACGTGGACATCTTCAACCCCA
AGTACGACTGCAAGATCATGACCTCCAAGACCGACGTGTCCAGCTCCGTGATCACCTCCCTGGGCGCC
ATCGTGTCCTGCTACGGCAAGACCAAGTGCACCGCCAGCAACAAGAACCGGGGCATCATCAAGACCTT
CAGCAACGGCTGCGACTACGTGTCCAACAAGGGGGTGGACACCGTGTCCGTGGGCAACACCCTGTACT
ACGTGAACAAACAGGAAGGCAAGAGCCTGTACGTGAAGGGCGAGCCCATCATCAACTTCTACGACCC
CCTGGTGTTCCCCAGCGACGAGTTCGACGCCAGCATCAGCCAGGTGAACGAGAAGATCAACCAGAGC
CTGGCCTTCATCCGGAAGTCCGACGAGCTGCTGCACAATGTGAATGCCGGCAAGTCCACCACCAACCG
GAAGCGGAGAGCCCCTGTGAAGCAGACCCTGAACTTCGACCTGCTGAAGCTGGCCGGCGACGTGGAG
AGCAATCCCGGCCCTATGGCCCTGAGCAAAGTGAAACTGAACGATACACTGAACAAGGACCAGCTGC
TGTCCAGCAGCAAGTACACCATCCAGCGGAGCACCGGCGACAGCATCGATACCCCCAACTACGACGT
GCAGAAGCACATCAACAAGCTGTGCGGCATGCTGCTGATCACAGAGGACGCCAACCACAAGTTCACC
GGCCTGATCGGCATGCTGTACGCCATGAGCCGGCTGGGCCGGGAGGACACCATCAAGATCCTGCGGG
ACGCCGGCTACCACGTGAAGGCCAATGGCGTGGACGTGACCACACACCGGCAGGACATCAACGGCAA
```

-continued

```
AGAAATGAAGTTCGAGGTGCTGACCCTGGCCAGCCTGACCACCGAGATCCAGATCAATATCGAGATCG

AGAGCCGGAAGTCCTACAAGAAAATGCTGAAAGAAATGGGCGAGGTGGCCCCCGAGTACAGACACGA

CAGCCCCGACTGCGGCATGATCATCCTGTGTATCGCCGCCCTGGTGATCACAAAGCTGGCCGCTGGCG

ACAGATCTGGCCTGACAGCCGTGATCAGACGGGCCAACAATGTGCTGAAGAACGAGATGAAGCGGTA

CAAGGGCCTGCTGCCCAAGGACATTGCCAACAGCTTCTACGAGGTGTTCGAGAAGTACCCCCACTTCA

TCGACGTGTTCGTGCACTTCGGCATTGCCCAGAGCAGCACCAGAGGCGGCTCCAGAGTGGAGGGCATC

TTCGCCGGCCTGTTCATGAACGCCTACGGCGCTGGCCAGGTGATGCTGAGATGGGGCGTGCTGGCCAA

GAGCGTGAAGAACATCATGCTGGGCCACGCCAGCGTGCAGGCCGAGATGGAACAGGTGGTGGAGGTG

TACGAGTACGCCCAGAAGCTGGGCGGAGAGGCCGGCTTCTACCACATCCTGAACAACCCTAAGGCCTC

CCTGCTGTCCCTGACCCAGTTCCCCCACTTCTCCAGCGTGGTGCTGGGAAATGCCGCCGGACTGGGCAT

CATGGGCGAGTACCGGGGCACCCCCAGAAACCAGGACCTGTACGACGCCGCCAAGGCCTACGCCGAG

CAGCTGAAAGAAAACGGCGTGATCAACTACAGCGTGCTGGACCTGACCGCTGAGGAACTGGAAGCCA

TCAAGCACCAGCTGAACCCCAAGGACAACGACGTGGAGCTGGGAGGCGGAGGATCTGGCGGCGGAGG

CATGAGCAGACGGAACCCCTGCAAGTTCGAGATCCGGGGCCACTGCCTGAACGGCAAGCGGTGCCAC

TTCAGCCACAACTACTTCGAGTGGCCCCCTCATGCTCTGCTGGTGCGGCAGAACTTCATGCTGAACCGG

ATCCTGAAGTCCATGGACAAGAGCATCGACACCCTGAGCGAGATCAGCGGAGCCGCCGAGCTGGACA

GAACCGAGGAATATGCCCTGGGCGTGGTGGGAGTGCTGGAAAGCTACATCGGCTCCATCAACAACAT

CACAAAGCAGAGCGCCTGCGTGGCCATGAGCAAGCTGCTGACAGAGCTGAACAGCGACGACATCAAG

AAGCTGAGGGACAACGAGGAACTGAACAGCCCCAAGATCCGGGTGTACAACACCGTGATCAGCTACA

TTGAGAGCAACCGCAAGAACAACAAGCAGACCATCCATCTGCTGAAGCGGCTGCCCGCCGACGTGCT

GAAAAAGACCATCAAGAACACCCTGGACATCCACAAGTCCATCACCATCAACAATCCCAAAGAAAGC

ACCGTGTCTGACACCAACGATCACGCCAAGAACAACGACACCACCTGATGAGCGGCCGCGATCTGCTG

TGCCTTCTAGTTGCCAGCCATCTGTTGTTTGCCCCTCCCCCGTGCCTTCCTTGACCCTGGAAGGTGCCAC

TCCCACTGTCCTTTCCTAATAAAATGAGGAAATTGCATCGCATTGTCTGAGTAGGTGTCATTCTATTCT

GGGGGGTGGGGTGGGGCAGGACAGCAAGGGGGAGGATTGGGAAGACAATAGCAGGCATGCTGGGGA

TGCGGTGGGCTCTATGGCCGATCAGCGATCGCTGAGGTGGGTGAGTGGGCGTGGCCTGGGGTGGTCAT

GAAAATATATAAGTTGGGGGTCTTAGGGTCTCTTTATTTGTGTTGCAGAGACCGCCGGAGCCATGAGC

GGGAGCAGCAGCAGCAGCAGTAGCAGCAGCGCCTTGGATGGCAGCATCGTGAGCCCTTATTTGACGA

CGCGGATGCCCCACTGGGCCGGGGTGCGTCAGAATGTGATGGGCTCCAGCATCGACGGCCGACCCGTC

CTGCCCGCAAATTCCGCCACGCTGACCTATGCGACCGTCGCGGGACGCCGTTGGACGCCACCGCCGC

CGCCGCCGCCACCGCAGCCGCCTCGGCCGTGCGCAGCCTGGCCACGGACTTTGCATTCCTGGGACCAC

TGGCGACAGGGGCTACTTCTCGGGCCGCTGCTGCCGCCGTTCGCGATGACAAGCTGACCGCCCTGCTG

GCGCAGTTGGATGCGCTTACTCGGGAACTGGGTGACCTTTCTCAGCAGGTCATGGCCCTGCGCCAGCA

GGTCTCCTCCCTGCAAGCTGGCGGGAATGCTTCTCCCACAAATGCCGTTTAAGATAAATAAAACCAGA

CTCTGTTTGGATTAAAGAAAAGTAGCAAGTGCATTGCTCTCTTTATTTCATAATTTTCCGCGCGCGATA

GGCCCTAGACCAGCGTTCTCGGTCGTTGAGGGTGCGGTGTATCTTCTCCAGGACGTGGTAGAGGTGGC

TCTGGACGTTGAGATACATGGGCATGAGCCCGTCCCGGGGGTGGAGGTAGCACCACTGCAGAGCTTCA

TGCTCCGGGGTGGTGTTGTAGATGATCCAGTCGTAGCAGGAGCGCTGGGCATGGTGCCTAAAAATGTC

CTTCAGCAGCAGGCCGATGGCCAGGGGGAGGCCCTTGGTGTAAGTGTTTACAAAACGGTTAAGTTGGG

AAGGGTGCATTCGGGGAGAGATGATGTGCATCTTGGACTGTATTTTTAGATTGGCGATGTTTCCGCCCA
```

-continued

```
GATCCCTTCTGGGATTCATGTTGTGCAGGACCACCAGTACAGTGTATCCGGTGCACTTGGGGAATTTGT

CATGCAGCTTAGAGGGAAAAGCGTGGAAGAACTTGGAGACGCCTTTGTGGCCTCCCAGATTTTCCATG

CATTCGTCCATGATGATGGCAATGGGCCCGCGGGAGGCAGCTTGGGCAAAGATATTTCTGGGGTCGCT

GACGTCGTAGTTGTGTTCCAGGGTGAGGTCGTCATAGGCCATTTTTACAAAGCGCGGGCGGAGGGTGC

CCGACTGGGGATGATGGTCCCCTCTGGCCCTGGGGCGTAGTTGCCCTCGCAGATCTGCATTTCCCAG

GCCTTAATCTCGGAGGGGGGAATCATATCCACCTGCGGGGCGATGAAGAAAACGGTTTCCGGAGCCG

GGGAGATTAACTGGGATGAGAGCAGGTTTCTAAGCAGCTGTGATTTTCCACAACCGGTGGGCCCATAA

ATAACACCTATAACCGGTTGCAGCTGGTAGTTTAGAGAGCTGCAGCTGCCGTCGTCCCGGAGGAGGGG

GGCCACCTCGTTGAGCATGTCCCTGACGCGCATGTTCTCCCCGACCAGATCCGCCAGAAGGCGCTCGC

CGCCCAGGGACAGCAGCTCTTGCAAGGAAGCAAAGTTTTTCAGCGGCTTGAGGCCGTCCGCCGTGGGC

ATGTTTTTCAGGGTCTGGCTCAGCAGCTCCAGGCGGTCCCAGAGCTCGGTGACGTGCTCTACGGCATCT

CTATCCAGCATATCTCCTCGTTTCGCGGGTTGGGGCGACTTTCGCTGTAGGGCACCAAGCGGTGGTCGT

CCAGCGGGGCCAGAGTCATGTCCTTCCATGGGCGCAGGGTCCTCGTCAGGGTGGTCTGGGTCACGGTG

AAGGGGTGCGCTCCGGGCTGAGCGCTTGCCAAGGTGCGCTTGAGGCTGGTTCTGCTGGTGCTGAAGCG

CTGCCGGTCTTCGCCCTGCGCGTCGGCCAGGTAGCATTTGACCATGGTGTCATAGTCCAGCCCCTCCGC

GGCGTGTCCCTTGGCGCGCAGCTTGCCCTTGGAGGTGGCGCCGCACGAGGGGCAGAGCAGGCTCTTGA

GCGCGTAGAGCTTGGGGGCGAGGAAGACCGATTCGGGGGAGTAGGCGTCCGCGCCGCAGACCCCGCA

CACGGTCTCGCACTCCACCAGCCAGGTGAGCTCGGGGCGCGCCGGGTCAAAAACCAGGTTTCCCCCAT

GCTTTTTGATGCGTTTCTTACCTCGGGTCTCCATGAGGTGGTGTCCCCGCTCGGTGACGAAGAGGCTGT

CCGTGTCTCCGTAGACCGACTTGAGGGGTCTTTTCTCCAGGGGGGTCCCTCGGTCTTCCTCGTAGAGGA

ACTCGGACCACTCTGAGACGAAGGCCCGCGTCCAGGCCAGGACGAAGGAGGCTATGTGGGAGGGGTA

GCGGTCGTTGTCCACTAGGGGGTCCACCTTCTCCAAGGTGTGAAGACACATGTCGCCTTCCTCGGCGTC

CAGGAAGGTGATTGGCTTGTAGGTGTAGGCCACGTGACCGGGGGTTCCTGACGGGGGGGTATAAAAG

GGGGTGGGGCGCGCTCGTCGTCACTCTCTTCCGCATCGCTGTCTGCGAGGGCCAGCTGCTGGGGTGA

GTATTCCCTCTCGAAGGCGGGCATGACCTCCGCGCTGAGGTTGTCAGTTTCCAAAAACGAGGAGGATT

TGATGTTCACCTGTCCCGAGGTGATACCTTTGAGGGTACCCGCGTCCATCTGGTCAGAAAACACGATCT

TTTTATTGTCCAGCTTGGTGGCGAACGACCCGTAGAGGGCGTTGGAGAGCAGCTTGGCGATGGAGCGC

AGGGTCTGGTTCTTGTCCCTGTCGGCGCGCTCCTTGGCCGCGATGTTGAGCTGCACGTACTCGCGCGCG

ACGCAGCGCCACTCGGGGAAGACGGTGGTGCGCTCGTCGGGCACCAGGCGCACGCGCCAGCCGCGGT

TGTGCAGGGTGACCAGGTCCACGCTGGTGGCGACCTCGCCGCGCAGGCGCTCGTTGGTCCAGCAGAGA

CGGCCGCCCTTGCGCGAGCAGAAGGGGGGCAGGGGGTCGAGCTGGGTCTCGTCCGGGGGGTCCGCGT

CCACGGTGAAAACCCCGGGGCGCAGGCGCGCGTCGAAGTAGTCTATCTTGCAACCTTGCATGTCCAGC

GCCTGCTGCCAGTCGCGGGCGGCGAGCGCGCGCTCGTAGGGGTTGAGCGGCGGGCCCCAGGGCATGG

GGTGGGTGAGTGCGGAGGCGTACATGCCGCAGATGTCATAGACGTAGAGGGGCTCCCGCAGGACCCC

GATGTAGGTGGGGTAGCAGCGGCCGCCGCGGATGCTGGCGCGCACGTAGTCATACAGCTCGTGCGAG

GGGGCGAGGAGGTCGGGGCCCAGGTTGGTGCGGGCGGGGCGCTCCGCGCGGAAGACGATCTGCCTGA

AGATGGCATGCGAGTTGGAAGAGATGGTGGGGCGCTGGAAGACGTTGAAGCTGGCGTCCTGCAGGCC

GACGGCGTCGCGCACGAAGGAGGCGTAGGAGTCGCGCAGCTTGTGTACCAGCTCGGCGGTGACCTGC

ACGTCGAGCGCGCAGTAGTCGAGGGTCTCGCGGATGATGTCATATTTAGCCTGCCCCTTCTTTTTCCAC

AGCTCGCGGTTGAGGACAAACTCTTCGCGGTCTTTCCAGTACTCTTGGATCGGGAAACCGTCCGGTTCC

GAACGGTAAGAGCCTAGCATGTAGAACTGGTTGACGGCCTGGTAGGCGCAGCAGCCCTTCTCCACGGG
```

```
GAGGGCGTAGGCCTGCGCGGCCTTGCGGAGCGAGGTGTGGGTCAGGGCGAAGGTGTCCCTGACCATG
ACTTTGAGGTACTGGTGCTTGAAGTCGGAGTCGTCGCAGCCGCCCCGCTCCCAGAGCGAGAAGTCGGT
GCGCTTCTTGGAGCGGGGGTTGGGCAGAGCGAAGGTGACATCGTTGAAGAGGATTTTGCCCGCGCGG
GGCATGAAGTTGCGGGTGATGCGGAAGGGCCCCGGCACTTCAGAGCGGTTGTTGATGACCTGGGCGG
CGAGCACGATCTCGTCGAAGCCGTTGATGTTGTGGCCCACGATGTAGAGTTCCAGGAAGCGGGGCCGG
CCCTTTACGGTGGGCAGCTTCTTTAGCTCTTCGTAGGTGAGCTCCTCGGGCGAGGCGAGGCCGTGCTCG
GCCAGGGCCCAGTCCGCGAGGTGCGGGTTGTCTCTGAGGAAGGACTTCCAGAGGTCGCGGGCCAGGA
GGGTCTGCAGGCGGTCTCTGAAGGTCCTGAACTGGCGGCCCACGGCCATTTTTTCGGGGGTGATGCAG
TAGAAGGTGAGGGGGTCTTGCTGCCAGCGGTCCCAGTCGAGCTGCAGGGCGAGGTCGCGCGCGGCGG
TGACCAGGCGCTCGTCGCCCCCGAATTTCATGACCAGCATGAAGGGCACGAGCTGCTTTCCGAAGGCC
CCCATCCAAGTGTAGGTCTCTACATCGTAGGTGACAAAGAGGCGCTCCGTGCGAGGATGCGAGCCGAT
CGGGAAGAACTGGATCTCCCGCCACCAGTTGGAGGAGTGGCTGTTGATGTGGTGGAAGTAGAAGTCCC
GTCGCCGGGCCGAACACTCGTGCTGGCTTTTGTAAAAGCGAGCGCAGTACTGGCAGCGCTGCACGGGC
TGTACCTCATGCACGAGATGCACCTTTCGCCCGCGCACGAGGAAGCCGAGGGGAAATCTGAGCCCCCC
GCCTGGCTCGCGGCATGGCTGGTTCTCTTCTACTTTGGATGCGTGTCCGTCTCCGTCTGGCTCCTCGAG
GGGTGTTACGGTGGAGCGGACCACCACGCCGCGCGAGCCGCAGGTCCAGATATCGGCGCGCGGCGGT
CGGAGTTTGATGACGACATCGCGCAGCTGGGAGCTGTCCATGGTCTGGAGCTCCCGCGGCGGCGGCAG
GTCAGCCGGGAGTTCTTGCAGGTTCACCTCGCAGAGTCGGGCCAGGGCGCGGGGCAGGTCTAGGTGGT
ACCTGATCTCTAGGGGCGTGTTGGTGGCGGCGTCGATGGCTTGCAGGAGCCCGCAGCCCCGGGGGGCG
ACGACGGTGCCCCGCGGGGTGGTGGTGGTGGTGGCGGTGCAGCTCAGAAGCGGTGCCGCGGGCGGGC
CCCCGGAGGTAGGGGGGGCTCCGGTCCCGCGGGCAGGGGCGGCAGCGGCACGTCGGCGTGGAGCGCG
GGCAGGAGTTGGTGCTGTGCCCGGAGGTTGCTGGCGAAGGCGACGACGCGGCGGTTGATCTCCTGGAT
CTGGCGCCTCTGCGTGAAGACGACGGGCCCGGTGAGCTTGAACCTGAAAGAGAGTTCGACAGAATCA
ATCTCGGTGTCATTGACCGCGGCCTGGCGCAGGATCTCCTGCACGTCTCCCGAGTTGTCTTGGTAGGCG
ATCTCGGCCATGAACTGCTCGATCTCTTCCTCCTGGAGGTCTCCGCGTCCGGCGCGTTCCACGGTGGCC
GCCAGGTCGTTGGAGATGCGCCCCATGAGCTGCGAGAAGGCGTTGAGTCCGCCCTCGTTCCAGACTCG
GCTGTAGACCACGCCCCCCTGGTCATCGCGGGCGCGCATGACCACCTGCGCGAGGTTGAGCTCCACGT
GCCGCGCGAAGACGGCGTAGTTGCGCAGACGCTGGAAGAGGTAGTTGAGGGTGGTGGCGGTGTGCTC
GGCCACGAAGAAGTTCATGACCCAGCGGCGCAACGTGGATTCGTTGATGTCCCCAAGGCCTCCAGCC
GTTCCATGGCCTCGTAGAAGTCCACGGCGAAGTTGAAAAACTGGGAGTTGCGCGCCGACACGGTCAAC
TCCTCCTCCAGAAGACGGATGAGCTCGGCGACGGTGTCGCGCACCTCGCGCTCGAAGGCTATGGGGAT
CTCTTCCTCCGCTAGCATCACCACCTCCTCCTCTTCCTCCTCTTCTGGCACTTCCATGATGGCTTCCTCCT
CTTCGGGGGTGGCGGCGGCGGCGGTGGGGAGGGGCGCTCTGCGCCGGCGGCGGCGCACCGGGAG
GCGGTCCACGAAGCGCGCGATCATCTCCCCGCGGCGGCGGCGCATGGTCTCGGTGACGGCGCGGCCGT
TCTCCCGGGGGCGCAGTTGGAAGACGCCGCCGGACATCTGGTGCTGGGGCGGGTGGCCGTGAGGCAG
CGAGACGGCGCTGACGATGCATCTCAACAATTGCTGCGTAGGTACGCCGCCGAGGGACCTGAGGGAG
TCCATATCCACCGGATCCGAAAACCTTTCGAGGAAGGCGTCTAACCAGTCGCAGTCGCAAGGTAGGCT
GAGCACCGTGGCGGGCGGCGGGGGGTGGGGGAGTGTCTGGCGGAGGTGCTGCTGATGATGTAATTG
AAGTAGGCGGACTTGACACGGCGGATGGTCGACAGGAGCACCATGTCCTTGGGTCCGGCCTGCTGGAT
GCGGAGGCGGTCGGCTATGCCCCAGGCTTCGTTCTGGCATCGGCGCAGGTCCTTGTAGTAGTCTTGCAT
```

-continued

```
GAGCCTTTCCACCGGCACCTCTTCTCCTTCCTCTTCTGCTTCTTCCATGTCTGCTTCGGCCCTGGGCGG
CGCCGCGCCCCCTGCCCCCCATGCGCGTGACCCCGAACCCCCTGAGCGGTTGGAGCAGGGCCAGGTC
GGCGACGACGCGCTCGGCCAGGATGGCCTGCTGCACCTGCGTGAGGGTGGTTTGGAAGTCATCCAAGT
CCACGAAGCGGTGGTAGGCGCCCGTGTTGATGGTGTAGGTGCAGTTGGCCATGACGGACCAGTTGACG
GTCTGGTGGCCCGGTTGCGACATCTCGGTGTACCTGAGTCGCGAGTAGGCGCGGGAGTCGAAGACGTA
GTCGTTGCAAGTCCGCACCAGGTACTGGTAGCCCACCAGGAAGTGCGGCGGCGGCTGGCGGTAGAGG
GGCCAGCGCAGGGTGGCGGGGGCTCCGGGGGCCAGGTCTTCCAGCATGAGGCGGTGGTAGGCGTAGA
TGTACCTGGACATCCAGGTGATACCCGCGGCGGTGGTGGAGGCGCGCGGGAAGTCGCGCACCCGGTTC
CAGATGTTGCGCAGGGGCAGAAAGTGCTCCATGGTAGGCGTGCTCTGTCCAGTCAGACGCGCGCAGTC
GTTGATACTCTAGACCAGGGAAAACGAAAGCCGGTCAGCGGGCACTCTTCCGTGGTCTGGTGAATAGA
TCGCAAGGGTATCATGGCGGAGGGCCTCGGTTCGAGCCCCGGGTCCGGGCCGGACGGTCCGCCATGAT
CCACGCGGTTACCGCCCGCGTGTCGAACCCAGGTGTGCGACGTCAGACAACGGTGGAGTGTTCCTTTT
GGCGTTTTTCTGGCCGGGCGCCGGCGCCGCGTAAGAGACTAAGCCGCGAAAGCGAAAGCAGTAAGTG
GCTCGCTCCCCGTAGCCGGAGGGATCCTTGCTAAGGGTTGCGTTGCGGCGAACCCCGGTTCGAATCCC
GTACTCGGGCCGGCCGGACCCCGCGGCTAAGGTGTTGGATTGGCCTCCCCCTCGTATAAAGACCCCGCT
TGCGGATTGACTCCGGACACGGGACGAGCCCCTTTTATTTTTGCTTTCCCCAGATGCATCCGGTGCTG
CGGCAGATGCGCCCCCCGCCCCAGCAGCAGCAACAACACCAGCAAGAGCGGCAGCAACAGCAGCGGG
AGTCATGCAGGGCCCCTCACCCACCCTCGGCGGGCCGGCCACCTCGGCGTCCGCGGCCGTGTCTGGC
GCCTGCGGCGGCGGCGGGGGGCCGGCTGACGACCCCGAGGAGCCCCCGCGGCGCAGGGCCAGACACT
ACCTGGACCTGGAGGAGGGCGAGGGCCTGGCGCGGCTGGGGGCGCCGTCTCCCGAGCGCCACCCGCG
GGTGCAGCTGAAGCGCGACTCGCGCGAGGCGTACGTGCCTCGGCAGAACCTGTTCAGGGACCGCGCG
GGCGAGGAGCCCGAGGAGATGCGGGACAGGAGGTTCAGCGCAGGGCGGGAGCTGCGGCAGGGGCTG
AACCGCGAGCGGCTGCTGCGCGAGGAGGACTTTGAGCCCGACGCGCGGACGGGGATCAGCCCCGCGC
GCGCGCACGTGGCGGCCGCCGACCTGGTGACGGCGTACGAGCAGACGGTGAACCAGGAGATCAACTT
CCAAAAGAGTTTCAACAACCACGTGCGCACGCTGGTGGCGCGCGAGGAGGTGACCATCGGGCTGATG
CACCTGTGGGACTTTGTAAGCGCGCTGGTGCAGAACCCCAACAGCAAGCCTCTGACGGCGCAGCTGTT
CCTGATAGTGCAGCACAGCAGGGACAACGAGGCGTTTAGGGACGCGCTGCTGAACATCACCGAGCCC
GAGGGTCGGTGGCTGCTGGACCTGATTAACATCCTGCAGAGCATAGTGGTGCAGGAGCGCAGCCTGA
GCCTGGCCGACAAGGTGGCGGCCATCAACTACTCGATGCTGAGCCTGGGCAAGTTTTACGCGCGCAAG
ATCTACCAGACGCCGTACGTGCCCATAGACAAGGAGGTGAAGATCGACGGTTTTTACATGCGCATGGC
GCTGAAGGTGCTCACCCTGAGCGACGACCTGGGCGTGTACCGCAACGAGCGCATCCACAAGGCCGTG
AGCGTGAGCCGGCGGCGCGAGCTGAGCGACCGCGAGCTGATGCACAGCCTGCAGCGGGCGCTGGCGG
GCGCCGGCAGCGGCGACAGGGAGGCGGAGTCCTACTTCGATGCGGGGCGGACCTGCGCTGGGCGCC
CAGCCGGCGGGCCCTGGAGGCCGCGGGGGTCCGCGAGGACTATGACGAGGACGGCGAGGAGGATGA
GGAGTACGAGCTAGAGGAGGGCGAGTACCTGGACTAAACCGCGGGTGGTGTTTCCGGTAGATGCAAG
ACCCGAACGTGGTGGACCCGGCGCTGCGGGCGGCTCTGCAGAGCCAGCCGTCCGGCCTTAACTCCTCA
GACGACTGGCGACAGGTCATGGACCGCATCATGTCGCTGACGGCGCGTAACCCGGACGCGTTCCGGCA
GCAGCCGCAGGCCAACAGGCTCTCCGCCATCCTGGAGGCGGTGGTGCCTGCGCGCTCGAACCCCACGC
ACGAGAAGGTGCTGGCCATAGTGAACGCGCTGGCCGAGAACAGGGCCATCCGCCCGGACGAGGCCGG
GCTGGTGTACGACGCGCTGCTGCAGCGCGTGGCCCGCTACAACAGCGGCAACGTGCAGACCAACCTG
GACCGGCTGGTGGGGGACGTGCGCGAGGCGGTGGCGCAGCGCGAGCGCGCGGATCGGCAGGGCAACC
```

-continued

```
TGGGCTCCATGGTGGCGCTGAATGCCTTCCTGAGCACGCAGCCGGCCAACGTGCCGCGGGGCAGGA

AGACTACACCAACTTTGTGAGCGCGCTGCGGCTGATGGTGACCGAGACCCCCAGAGCGAGGTGTACC

AGTCGGGCCCGGACTACTTCTTCCAGACCAGCAGACAGGGCCTGCAGACGGTGAACCTGAGCCAGGCT

TTCAAGAACCTGCGGGGGCTGTGGGCGTGAAGGCGCCCACCGGCGACCGGGCGACGGTGTCCAGCC

TGCTGACGCCCAACTCGCGCCTGCTGCTGCTGCTGATCGCGCCGTTCACGGACAGCGGCAGCGTGTCC

CGGGACACCTACCTGGGGCACCTGCTGACCCTGTACCGCGAGGCCATCGGGCAGGCGCAGGTGGACG

AGCACACCTTCCAGGAGATCACCAGCGTGAGCCGCGCGCTGGGGCAGGAGGACACGAGCAGCCTGGA

GGCGACTCTGAACTACCTGCTGACCAACCGGCGGCAGAAGATTCCCTCGCTGCACAGCCTGACCTCCG

AGGAGGAGCGCATCTTGCGCTACGTGCAGCAGAGCGTGAGCCTGAACCTGATGCGCGACGGGGTGAC

GCCCAGCGTGGCGCTGGACATGACCGCGCGCAACATGGAACCGGGCATGTACGCCGCGCACCGGCCT

TACATCAACCGCCTGATGGACTACCTGCATCGCGCGGCGGCCGTGAACCCCGAGTACTTTACCAACGC

CATCCTGAACCCGCACTGGCTCCCGCCGCCCGGGTTCTACAGCGGGGGCTTCGAGGTCCCGGAGACCA

ACGATGGCTTCCTGTGGGACGACATGGACGACAGCGTGTTCTCCCCGCGGCCGCAGGCGCTGGCGGAA

GCGTCCCTGCTGCGTCCCAAGAAGGAGGAGGAGGAGGAGGCGAGTCGCCGCCGCGGCAGCAGCGGCG

TGGCTTCTCTGTCCGAGCTGGGGGCGGCAGCCGCCGCGCGCCCCGGGTCCCTGGGCGGCAGCCCCTTT

CCGAGCCTGGTGGGGTCTCTGCACAGCGAGCGCACCACCCGCCCTCGGCTGCTGGGCGAGGACGAGTA

CCTGAATAACTCCCTGCTGCAGCCGGTGCGGGAGAAAAACCTGCCTCCCGCCTTCCCCAACAACGGGA

TAGAGAGCCTGGTGGACAAGATGAGCAGATGGAAGACCTATGCGCAGGAGCACAGGGACGCGCCTGC

GCTCCGGCCGCCCACGCGGCGCCAGCGCCACGACCGGCAGCGGGGCTGGTGTGGGATGACGAGGAC

TCCGCGGACGATAGCAGCGTGCTGGACCTGGGAGGGAGCGGCAACCCGTTCGCGCACCTGCGCCCCC

GCCTGGGGAGGATGTTTTAAAAAAAAAAAAAAAAAAGCAAGAAGCATGATGCAAAAATTAAATAAAA

CTCACCAAGGCCATGGCGACCGAGCGTTGGTTTCTTGTGTTCCCTTCAGTATGCGGCGCGCGGCGATGT

ACCAGGAGGGACCTCCTCCCTCTTACGAGAGCGTGGTGGGCGCGGCGGCGGCGGCGCCCTCTTCTCCC

TTTGCGTCGCAGCTGCTGGAGCCGCCGTACGTGCCTCCGCGCTACCTGCGGCCTACGGGGGGGAGAAA

CAGCATCCGTTACTCGGAGCTGGCGCCCCTGTTCGACACCACCCGGGTGTACCTGGTGGACAACAAGT

CGGCGGACGTGGCCTCCCTGAACTACCAGAACGACCACAGCAATTTTTTGACCACGGTCATCCAGAAC

AATGACTACAGCCCGAGCGAGGCCAGCACCCAGACCATCAATCTGGATGACCGGTCGCACTGGGGCG

GCGACCTGAAAACCATCCTGCACACCAACATGCCCAACGTGAACGAGTTCATGTTCACCAATAAGTTC

AAGGCGCGGGTGATGGTGTCGCGCTCGCACACCAAGGAAGACCGGGTGGAGCTGAAGTACGAGTGGG

TGGAGTTCGAGCTGCCAGAGGGCAACTACTCCGAGACCATGACCATTGACCTGATGAACAACGCGATC

GTGGAGCACTATCTGAAAGTGGGCAGGCAGAACGGGGTCCTGGAGAGCGACATCGGGGTCAAGTTCG

ACACCAGGAACTTCCGCCTGGGGCTGGACCCCGTGACCGGGCTGGTTATGCCCGGGGTGTACACCAAC

GAGGCCTTCCATCCCGACATCATCCTGCTGCCCGGCTGCGGGGTGGACTTCACTTACAGCCGCCTGAG

CAACCTCCTGGGCATCCGCAAGCGGCAGCCCTTCCAGGAGGGCTTCAGGATCACCTACGAGGACCTGG

AGGGGGGCAACATCCCCGCGCTCCTCGATGTGGAGGCCTACCAGGATAGCTTGAAGGAAAATGAGGC

GGGACAGGAGGATACCGCCCCCGCCGCCTCCGCCGCCGCCGAGCAGGGCGAGGATGCTGCTGACACC

GCGGCCGCGGACGGGGCAGAGGCCGACCCCGCTATGGTGGTGGAGGCTCCCGAGCAGGAGGAGGACA

TGAATGACAGTGCGGTGCGCGGAGACACCTTCGTCACCCGGGGGGAGGAAAAGCAAGCGGAGGCCGA

GGCCGCGGCCGAGGAAAAGCAACTGGCGGCAGCAGCGGCGGCGGCGGCGTTGGCCGCGGCGGAGGC

TGAGTCTGAGGGGACCAAGCCCGCCAAGGAGCCCGTGATTAAGCCCCTGACCGAAGATAGCAAGAAG
```

-continued

```
CGCAGTTACAACCTGCTCAAGGACAGCACCAACACCGCGTACCGCAGCTGGTACCTGGCCTACAACTA
CGGCGACCCGTCGACGGGGGTGCGCTCCTGGACCCTGCTGTGCACGCCGGACGTGACCTGCGGCTCGG
AGCAGGTGTACTGGTCGCTGCCCGACATGATGCAAGACCCCGTGACCTTCCGCTCCACGCGGCAGGTC
AGCAACTTCCCGGTGGTGGGCGCCGAGCTGCTGCCCGTGCACTCCAAGAGCTTCTACAACGACCAGGC
CGTCTACTCCCAGCTCATCCGCCAGTTCACCTCTCTGACCCACGTGTTCAATCGCTTTCCTGAGAACCA
GATTCTGGCGCGCCCGCCCGCCCCACCATCACCACCGTCAGTGAAAACGTTCCTGCTCTCACAGATC
ACGGGACGCTACCGCTGCGCAACAGCATCGGAGGAGTCCAGCGAGTGACCGTTACTGACGCCAGACG
CCGCACCTGCCCCTACGTTTACAAGGCCTTGGGCATAGTCTCGCCGCGCGTCCTTTCCAGCCGCACTTT
TTGAGCAACACCACCATCATGTCCATCCTGATCTCACCCAGCAATAACTCCGGCTGGGGACTGCTGCG
CGCGCCCAGCAAGATGTTCGGAGGGGCGAGGAAGCGTTCCGAGCAGCACCCCGTGCGCGTGCGCGGG
CACTTCCGCGCCCCCTGGGGAGCGCACAAACGCGGCCGCGCGGGGCGCACCACCGTGGACGACGCCA
TCGACTCGGTGGTGGAGCAGGCGCGCAACTACAGGCCCGCGGTCTCTACCGTGGACGCGGCCATCCAG
ACCGTGGTGCGGGGCGCGCGGCGGTACGCCAAGCTGAAGAGCCGCCGGAAGCGCGTGGCCCGCCGCC
ACCGCCGCCGACCCGGGGCCGCCGCCAAACGCGCCGCCGCGGCCCTGCTTCGCCGGGCCAAGCGCAC
GGGCCGCCGCGCCGCCATGAGGGCCGCGCGCCGCTTGGCCGCCGGCATCACCGCCGCCACCATGGCCC
CCCGTACCCGAAGACGCGCGGCCGCCGCCGCCGCCGCCGCCATCAGTGACATGGCCAGCAGGCGCCG
GGGCAACGTGTACTGGGTGCGCGACTCGGTGACCGGCACGCGCGTGCCCGTGCGCTTCCGCCCCCCGC
GGACTTGAGATGATGTGAAAAAACAACACTGAGTCTCCTGCTGTTGTGTATCCCAGCGGCGGCGGC
GCGCGCAGCGTCATGTCCAAGCGCAAAATCAAAGAAGAGATGCTCCAGGTCGTCGCGCCGGAGATCT
ATGGGCCCCCGAAGAAGGAAGAGCAGGATTCGAAGCCCCGCAAGATAAAGCGGGTCAAAAAGAAAA
AGAAAGATGATGACGATGCCGATGGGGAGGTGGAGTTCCTGCGCGCCACGGCGCCCAGGCGCCCGGT
GCAGTGGAAGGGCCGGCGCGTAAAGCGCGTCCTGCGCCCCGGCACCGCGGTGGTCTTCACGCCCGGC
GAGCGCTCCACCCGGACTTTCAAGCGCGTCTATGACGAGGTGTACGGCGACGAAGACCTGCTGGAGCA
GGCCAACGAGCGCTTCGGAGAGTTTGCTTACGGGAAGCGTCAGCGGGCGCTGGGGAAGGAGGACCTG
CTGGCGCTGCCGCTGGACCAGGGCAACCCCACCCCCAGTCTGAAGCCCGTGACCCTGCAGCAGGTGCT
GCCGAGCAGCGCACCCTCCGAGGCGAAGCGGGGTCTGAAGCGCGAGGGCGGCGACCTGGCGCCCACC
GTGCAGCTCATGGTGCCCAAGCGGCAGAGGCTGGAGGATGTGCTGGAGAAAATGAAAGTAGACCCCG
GTCTGCAGCCGGACATCAGGGTCCGCCCCATCAAGCAGGTGGCGCCGGGCCTCGGCGTGCAGACCGTG
GACGTGGTCATCCCCACCGGCAACTCCCCCGCCGCCGCCACCACTACCGCTGCCTCCACGGACATGGA
GACACAGACCGATCCCGCCGCAGCCGCAGCCGCAGCCGCCGCCGCGACCTCCTCGGCGGAGGTGCAG
ACGGACCCCTGGCTGCCGCCGGCGATGTCAGCTCCCCGCGCGCGTCGCGGGCGCAGGAAGTACGGCG
CCGCCAACGCGCTCCTGCCCGAGTACGCCTTGCATCCTTCCATCGCGCCCACCCCCGGCTACCGAGGCT
ATACCTACCGCCCGCGAAGAGCCAAGGGTTCCACCCGCCGTCCCCGCCGACGCGCCGCCGCCACCACC
CGCCGCCGCCGCCGCAGACGCCAGCCCGCACTGGCTCCAGTCTCCGTGAGGAAAGTGGCGCGCGACG
GACACACCCTGGTGCTGCCCAGGGCGCGCTACCACCCCAGCATCGTTTAAAAGCCTGTTGTGGTTCTTG
CAGATATGGCCCTCACTTGCCGCCTCCGTTTCCCGGTGCCGGGATACCGAGGAGGAAGATCGCGCCGC
AGGAGGGGTCTGGCCGGCCGCGGCCTGAGCGGAGGCAGCCGCCGCGCGCACCGGCGGCGACGCGCCA
CCAGCCGACGCATGCGCGGCGGGTGCTGCCCCTGTTAATCCCCCTGATCGCCGCGGCGATCGGCGCC
GTGCCCGGGATCGCCTCCGTGGCCTTGCAAGCGTCCCAGAGGCATTGACAGACTTGCAAACTTGCAAA
TATGGAAAAAAAACCCCAATAAAAAAGTCTAGACTCTCACGCTCGCTTGGTCCTGTGACTATTTTGT
AGAATGGAAGACATCAACTTTGCGTCGCTGGCCCCGCGTCACGGCTCGCGCCCGTTCCTGGGACACTG
```

-continued

```
GAACGATATCGGCACCAGCAACATGAGCGGTGGCGCCTTCAGTTGGGGCTCTCTGTGGAGCGGCATTA

AAAGTATCGGGTCTGCCGTTAAAAATTACGGCTCCCGGGCCTGGAACAGCAGCACGGGCCAGATGTTG

AGAGACAAGTTGAAAGAGCAGAACTTCCAGCAGAAGGTGGTGGAGGGCCTGGCCTCCGGCATCAACG

GGGTGGTGGACCTGGCCAACCAGGCCGTGCAGAATAAGATCAACAGCAGACTGGACCCCCGGCCGCC

GGTGGAGGAGGTGCCGCCGGCGCTGGAGACGGTGTCCCCCGATGGGCGTGGCGAGAAGCGCCCGCGG

CCCGATAGGGAAGAGACCACTCTGGTCACGCAGACCGATGAGCCGCCCCCGTATGAGGAGGCCCTGA

AGCAAGGTCTGCCCACCACGCGGCCCATCGCGCCCATGGCCACCGGGGTGGTGGGCCGCCACACCCCC

GCCACGCTGGACTTGCCTCCGCCCGCCGATGTGCCGCAGCAGCAGAAGGCGGCACAGCCGGGCCCGC

CCGCGACCGCCTCCCGTTCCTCCGCCGGTCCTCTGCGCCGCGCGGCCAGCGGCCCCCGCGGGGGGTC

GCGAGGCACGGCAACTGGCAGAGCACGCTGAACAGCATCGTGGGTCTGGGGGTGCGGTCCGTGAAGC

GCCGCCGATGCTACTGAATAGCTTAGCTAACGTGTTGTATGTGTGTATGCGCCCTATGTCGCCGCCAGA

GGAGCTGCTGAGTCGCCGCCGTTCGCGCGCCCACCACCACCGCCACTCCGCCCCTCAAGATGGCGACC

CCATCGATGATGCCGCAGTGGTCGTACATGCACATCTCGGGCCAGGACGCCTCGGAGTACCTGAGCCC

CGGGCTGGTGCAGTTCGCCCGCGCCACCGAGAGCTACTTCAGCCTGAGTAACAAGTTTAGGAACCCCA

CGGTGGCGCCCACGCACGATGTGACCACCGACCGGTCTCAGCGCCTGACGCTGCGGTTCATTCCCGTG

GACCGCGAGGACACCGCGTACTCGTACAAGGCGCGGTTCACCCTGGCCGTGGGCGACAACCGCGTGCT

GGACATGGCCTCCACCTACTTTGACATCCGCGGGGTGCTGGACCGGGGTCCCACTTTCAAGCCCTACTC

TGGCACCGCCTACAACTCCCTGGCCCCCAAGGGCGCTCCCAACTCCTGCGAGTGGGAGCAAGAGGAA

ACTCAGGCAGTTGAAGAAGCAGCAGAAGAGGAAGAAGAAGATGCTGACGGTCAAGCTGAGGAAGAG

CAAGCAGCTACCAAAAAGACTCATGTATATGCTCAGGCTCCCCTTTCTGGCGAAAAAATTAGTAAAGA

TGGTCTGCAAATAGGAACGGACGCTACAGCTACAGAACAAAAACCTATTTATGCAGACCCTACATTCC

AGCCCGAACCCCAAATCGGGGAGTCCCAGTGGAATGAGGCAGATGCTACAGTCGCCGGCGGTAGAGT

GCTAAAGAAATCTACTCCCATGAAACCATGCTATGGTTCCTATGCAAGACCCACAAATGCTAATGGAG

GTCAGGGTGTACTAACGGCAAATGCCCAGGGACAGCTAGAATCTCAGGTTGAAATGCAATTCTTTTCA

ACTTCTGAAAACGCCCGTAACGAGGCTAACAACATTCAGCCCAAATTGGTGCTGTATAGTGAGGATGT

GCACATGGAGACCCCGGATACGCACCTTTCTTACAAGCCCGCAAAAAGCGATGACAATTCAAAAATCA

TGCTGGGTCAGCAGTCCATGCCCAACAGACCTAATTACATCGGCTTCAGAGACAACTTTATCGGCCTC

ATGTATTACAATAGCACTGGCAACATGGGAGTGCTTGCAGGTCAGGCCTCTCAGTTGAATGCAGTGGT

GGACTTGCAAGACAGAAACACAGAACTGTCCTACCAGCTCTTGCTTGATTCCATGGGTGACAGAACCA

GATACTTTTCCATGTGGAATCAGGCAGTGGACAGTTATGACCCAGATGTTAGAATTATTGAAAATCAT

GGAACTGAAGACGAGCTCCCCAACTATTGTTTCCCTCTGGGTGGCATAGGGGTAACTGACACTTACCA

GGCTGTTAAAACCAACAATGGCAATAACGGGGGCCAGGTGACTTGGACAAAAGATGAAACTTTTGCA

GATCGCAATGAAATAGGGGTGGGAAACAATTTCGCTATGGAGATCAACCTCAGTGCCAACCTGTGGA

GAAACTTCCTGTACTCCAACGTGGCGCTGTACCTACCAGACAAGCTTAAGTACAACCCCTCCAATGTG

GACATCTCTGACAACCCCAACACCTACGATTACATGAACAAGCGAGTGGTGGCCCCGGGGCTGGTGGA

CTGCTACATCAACCTGGGCGCGCGCTGGTCGCTGGACTACATGGACAACGTCAACCCCTTCAACCACC

ACCGCAATGCGGGCCTGCGCTACCGCTCCATGCTCCTGGGCAACGGGCGCTACGTGCCCTTCCACATC

CAGGTGCCCCAGAAGTTCTTTGCCATCAAGAACCTCCTCCTCCTGCCGGGCTCCTACACCTACGAGTGG

AACTTCAGGAAGGATGTCAACATGGTCCTCCAGAGCTCTCTGGGTAACGATCTCAGGGTGGACGGGGC

CAGCATCAAGTTCGAGAGCATCTGCCTCTACGCCACCTTCTTCCCCATGGCCCACAACACGGCCTCCAC
```

-continued

```
GCTCGAGGCCATGCTCAGGAACGACACCAACGACCAGTCCTTCAATGACTACCTCTCCGCCGCCAACA
TGCTCTACCCCATACCCGCCAACGCCACCAACGTCCCCATCTCCATCCCCTCGCGCAACTGGGCGGCCT
TCCGCGGCTGGGCCTTCACCCGCCTCAAGACCAAGGAGACCCCCTCCCTGGGCTCGGGATTCGACCCC
TACTACACCTACTCGGGCTCCATTCCCTACCTGGACGGCACCTTCTACCTCAACCACACTTTCAAGAAG
GTCTCGGTCACCTTCGACTCCTCGGTCAGCTGGCCGGGCAACGACCGTCTGCTCACCCCCAACGAGTTC
GAGATCAAGCGCTCGGTCGACGGGGAGGGCTACAACGTGGCCCAGTGCAACATGACCAAGGACTGGT
TCCTGGTCCAGATGCTGGCCAACTACAACATCGGCTACCAGGGCTTCTACATCCCAGAGAGCTACAAG
GACAGGATGTACTCCTTCTTCAGGAACTTCCAGCCCATGAGCCGGCAGGTGGTGGACCAGACCAAGTA
CAAGGACTACCAGGAGGTGGGCATCATCCACCAGCACAACAACTCGGGCTTCGTGGGCTACCTCGCCC
CCACCATGCGCGAGGGACAGGCCTACCCCGCCAACTTCCCCTATCCGCTCATAGGCAAGACCGCGGTC
GACAGCATCACCCAGAAAAAGTTCCTCTGCGACCGCACCCTCTGGCGCATCCCCTTCTCCAGCAACTTC
ATGTCCATGGGTGCGCTCTCGGACCTGGGCCAGAACTTGCTCTACGCCAACTCCGCCCACGCCCTCGA
CATGACCTTCGAGGTCGACCCCATGGACGAGCCCACCCTTCTCTATGTTCTGTTCGAAGTCTTTGACGT
GGTCCGGGTCCACCAGCCGCACCGCGGCGTCATCGAGACCGTGTACCTGCGTACGCCCTTCTCGGCCG
GCAACGCCACCACCTAAAGAAGCAAGCCGCAGTCATCGCCGCCTGCATGCCGTCGGGTTCCACCGAGC
AAGAGCTCAGGGCCATCGTCAGAGACCTGGGATGCGGGCCCTATTTTTTGGGCACCTTCGACAAGCGC
TTCCCTGGCTTTGTCTCCCCACACAAGCTGGCCTGCGCCATCGTCAACACGGCCGGCCGCGAGACCGG
GGGCGTGCACTGGCTGGCCTTCGCCTGGAACCCGCGCTCCAAAACATGCTTCCTCTTTGACCCCTTCGG
CTTTTCGGACCAGCGGCTCAAGCAAATCTACGAGTTCGAGTACGAGGGCTTGCTGCGTCGCAGCGCCA
TCGCCTCCTCGCCCGACCGCTGCGTCACCCTCGAAAAGTCCACCCAGACCGTGCAGGGGCCCGACTCG
GCCGCCTGCGGTCTCTTCTGCTGCATGTTTCTGCACGCCTTTGTGCACTGGCCTCAGAGTCCCATGGAC
CGCAACCCCACCATGAACTTGCTGACGGGGGTGCCCAACTCCATGCTCCAGAGCCCCCAGGTCGAGCC
CACCCTGCGCCGCAACCAGGAGCAGCTCTACAGCTTCCTGGAGCGCCACTCGCCTTACTTCCGCCGCC
ACAGCGCACAGATCAGGAGGGCCACCTCCTTCTGCCACTTGCAAGAGATGCAAGAAGGGTAATAACG
ATGTACACACTTTTTTTCTCAATAAATGGCATCTTTTTATTTATACAAGCTCTCTGGGGTATTCATTTCC
CACCACCACCCGCCGTTGTCGCCATCTGGCTCTATTTAGAAATCGAAAGGGTTCTGCCGGGAGTCGCC
GTGCGCCACGGGCAGGGACACGTTGCGATACTGGTAGCGGGTGCCCCACTTGAACTCGGGCACCACCA
GGCGAGGCAGCTCGGGGAAGTTTTCGCTCCACAGGCTGCGGGTCAGCACCAGCGCGTTCATCAGGTCG
GGCGCCGAGATCTTGAAGTCGCAGTTGGGGCCGCCGCCCTGCGCGCGCGAGTTGCGGTACACCGGGTT
GCAGCACTGGAACACCAACAGCGCCGGGTGCTTCACGCTGGCCAGCACGCTGCGGTCGGAGATCAGC
TCGGCGTCCAGGTCCTCCGCGTTGCTCAGCGCGAACGGGGTCATCTTGGGCACTTGCCGCCCCAGGAA
GGGCGCGTGCCCCGGTTTCGAGTTGCAGTCGCAGCGCAGCGGGATCAGCAGGTGCCCGTGCCCGGACT
CGGCGTTGGGGTACAGCGCGCGCATGAAGGCCTGCATCTGGCGGAAGGCCATCTGGGCCTTGGCGCCC
TCCGAGAAGAACATGCCGCAGGACTTGCCCGAGAACTGGTTTGCGGGGCAGCTGGCGTCGTGCAGGC
AGCAGCGCGCGTCGGTGTTGGCGATCTGCACCACGTTGCGCCCCACCGGTTCTTCACGATCTTGGCCT
TGGACGATTGCTCCTTCAGCGCGCGCTGCCCGTTCTCGCTGGTCACATCCATCTCGATCACATGTTCCT
TGTTCACCATGCTGCTGCCGTGCAGACACTTCAGCTCGCCCTCCGTCTCGGTGCAGCGGTGCTGCCACA
GCGCGCAGCCCGTGGGCTCGAAAGACTTGTAGGTCACCTCCGCGAAGGACTGCAGGTACCCCTGCAAA
AAGCGGCCCATCATGGTCACGAAGGTCTTGTTGCTGCTGAAGGTCAGCTGCAGCCCGCGGTGCTCCTC
GTTCAGCCAGGTCTTGCACACGGCCGCCAGCGCCTCCACCTGGTCGGGCAGCATCTTGAAGTTCACCTT
CAGCTCATTCTCCACGTGGTACTTGTCCATCAGCGTGCGCGCCGCCTCCATGCCCTTCTCCCAGGCCGA
```

-continued

```
CACCAGCGGCAGGCTCACGGGGTTCTTCACCATCACCGTGGCCGCCGCCTCCGCCGCGCTTTCGCTTTC

CGCCCCGCTGTTCTCTTCCTCTTCCTCCTCTTCCTCGCCGCCGCCCACTCGCAGCCCCCGCACCACGGGG

TCGTCTTCCTGCAGGCGCTGCACCTTGCGCTTGCCGTTGCGCCCCTGCTTGATGCGCACGGGCGGGTTG

CTGAAGCCCACCATCACCAGCGCGGCCTCTTCTTGCTCGTCCTCGCTGTCCAGAATGACCTCCGGGGAG

GGGGGGTTGGTCATCCTCAGTACCGAGGCACGCTTCTTTTTCTTCCTGGGGGCGTTCGCCAGCTCCGCG

GCTGCGGCCGCTGCCGAGGTCGAAGGCCGAGGGCTGGGCGTGCGCGGCACCAGCGCGTCCTGCGAGC

CGTCCTCGTCCTCCTCGGACTCGAGACGGAGGCGGGCCCGCTTCTTCGGGGGCGCGCGGGGCGGCGGA

GGCGGCGGCGGCGACGGAGACGGGGACGAGACATCGTCCAGGGTGGGTGGACGGCGGGCCGCGCCG

CGTCCGCGCTCGGGGGTGGTCTCGCGCTGGTCCTCTTCCCGACTGGCCATCTCCCACTGCTCCTTCTCCT

ATAGGCAGAAAGAGATCATGGAGTCTCTCATGCGAGTCGAGAAGGAGGAGGACAGCCTAACCGCCCC

CTCTGAGCCCTCCACCACCGCCGCCACCACCGCCAATGCCGCCGCGGACGACGCGCCCACCGAGACCA

CCGCCAGTACCACCCTCCCCAGCGACGCACCCCCGCTCGAGAATGAAGTGCTGATCGAGCAGGACCCG

GGTTTTGTGAGCGGAGAGGAGGATGAGGTGGATGAGAAGGAGAAGGAGGAGGTCGCCGCCTCAGTGC

CAAAAGAGGATAAAAAGCAAGACCAGGACGACGCAGATAAGGATGAGACAGCAGTCGGGCGGGGA

ACGGAAGCCATGATGCTGATGACGGCTACCTAGACGTGGGAGACGACGTGCTGCTTAAGCACCTGCAC

CGCCAGTGCGTCATCGTCTGCGACGCGCTGCAGGAGCGCTGCGAAGTGCCCCTGGACGTGGCGGAGGT

CAGCCGCGCCTACGAGCGGCACCTCTTCGCGCCGCACGTGCCCCCCAAGCGCCGGGAGAACGGCACCT

GCGAGCCCAACCCGCGTCTCAACTTCTACCCGGTCTTCGCGGTACCCGAGGTGCTGGCCACCTACCAC

ATCTTTTTCCAAAACTGCAAGATCCCCCTCTCCTGCCGCGCCAACCGCACCCGCGCCGACAAAACCCTG

ACCCTGCGGCAGGGCGCCCACATACCTGATATCGCCTCTCTGGAGGAAGTGCCCAAGATCTTCGAGGG

TCTCGGTCGCGACGAGAAACGGGCGGCGAACGCTCTGCACGGAGACAGCGAAAACGAGAGTCACTCG

GGGGTGCTGGTGGAGCTCGAGGGCGACAACGCGCGCCTGGCCGTACTCAAGCGCAGCATAGAGGTCA

CCCACTTTGCCTACCCGGCGCTCAACCTGCCCCCCAAGGTCATGAGTGTGGTCATGGGCGAGCTCATC

ATGCGCCGCGCCCAGCCCCTGGCCGCGGATGCAAACTTGCAAGAGTCCTCCGAGGAAGGCCTGCCCGC

GGTCAGCGACGAGCAGCTGGCGCGCTGGCTGGAGACCCGCGACCCCGCGCAGCTGGAGGAGCGGCGC

AAGCTCATGATGGCCGCGGTGCTGGTCACCGTGGAGCTCGAGTGTCTGCAGCGCTTCTTCGCGGACCC

CGAGATGCAGCGCAAGCTCGAGGAGACCCTGCACTACACCTTCCGCCAGGGCTACGTGCGCCAGGCCT

GCAAGATCTCCAACGTGGAGCTCTGCAACCTGGTCTCCTACCTGGGCATCCTGCACGAGAACCGCCTC

GGGCAGAACGTCCTGCACTCCACCCTCAAAGGGGAGGCGCGCCGCGACTACATCCGCGACTGCGCCTA

CCTCTTCCTCTGCTACACCTGGCAGACGGCCATGGGGGTCTGGCAGCAGTGCCTGGAGGAGCGCAACC

TCAAGGAGCTGGAAAAGCTCCTCAAGCGCACCCTCAGGGACCTCTGGACGGGCTTCAACGAGCGCTCG

GTGGCCGCCGCGCTGGCGGACATCATCTTTCCCGAGCGCCTGCTCAAGACCCTGCAGCAGGGCCTGCC

CGACTTCACCGCCAGAGCATGCTGCAGAACTTCAGGACTTTCATCCTGGAGCGCTCGGGCATCCTGC

CGGCCACTTGCTGCGCGCTGCCCAGCGACTTCGTGCCCATCAAGTACAGGGAGTGCCCGCCGCCGCTC

TGGGGCCACTGCTACCTCTTCCAGCTGGCCAACTACCTCGCCTACCACTCGGACCTCATGGAAGACGT

GAGCGGCGAGGGCCTGCTCGAGTGCCACTGCCGCTGCAACCTCTGCACGCCCCACCGCTCTCTAGTCT

GCAACCCGCAGCTGCTCAGCGAGAGTCAGATTATCGGTACCTTCGAGCTGCAGGGTCCCTCGCCTGAC

GAGAAGTCCGCGGCTCCAGGGCTGAAACTCACTCCGGGGCTGTGGACTTCCGCCTACCTACGCAAATT

TGTACCTGAGGACTACCACGCCCACGAGATCAGGTTCTACGAAGACCAATCCCGCCCGCCCAAGGCGG

AGCTCACCGCCTGCGTCATCACCCAGGGGCACATCCTGGGCCAATTGCAAGCCATCAACAAAGCCCGC
```

-continued

```
CGAGAGTTCTTGCTGAAAAAGGGTCGGGGGGTGTACCTGGACCCCCAGTCCGGCGAGGAGCTAAACC

CGCTACCCCCGCCGCCGCCCCAGCAGCGGGACCTTGCTTCCCAGGATGGCACCCAGAAAGAAGCAGC

AGCCGCCGCCGCCGCAGCCATACATGCTTCTGGAGGAAGAGGAGGAGGACTGGGACAGTCAGGC

AGAGGAGGTTTCGGACGAGGAGCAGGAGGAGATGATGGAAGACTGGGAGGAGGACAGCAGCCTAGA

CGAGGAAGCTTCAGAGGCCGAAGAGGTGGCAGACGCAACACCATCGCCCTCGGTCGCAGCCCCCTCG

CCGGGGCCCCTGAAATCCTCCGAACCCAGCACCAGCGCTATAACCTCCGCTCCTCCGGCGCCGGCGCC

ACCCGCCCGCAGACCCAACCGTAGATGGGACACCACAGGAACCGGGGTCGGTAAGTCCAAGTGCCCG

CCGCCGCCACCGCAGCAGCAGCAGCAGCAGCGCCAGGGCTACCGCTCGTGGCGCGGGCACAAGAACG

CCATAGTCGCCTGCTTGCAAGACTGCGGGGGCAACATCTCTTTCGCCCGCCGCTTCCTGCTATTCCACC

ACGGGGTCGCCTTTCCCCGCAATGTCCTGCATTACTACCGTCATCTCTACAGCCCCTACTGCAGCGGCG

ACCCAGAGGCGGCAGCGGCAGCCACAGCGGCGACCACCACCTAGGAAGATATCCTCCGCGGGCAAGA

CAGCGGCAGCAGCGGCCAGGAGACCCGCGGCAGCAGCGGCGGGAGCGGTGGGCGCACTGCGCCTCTC

GCCCAACGAACCCCTCTCGACCCGGGAGCTCAGACACAGGATCTTCCCCACTTTGTATGCCATCTTCCA

ACAGAGCAGAGGCCAGGAGCAGGAGCTGAAAATAAAAAACAGATCTCTGCGCTCCCTCACCCGCAGC

TGTCTGTATCACAAAAGCGAAGATCAGCTTCGGCGCACGCTGGAGGACGCGGAGGCACTCTTCAGCAA

ATACTGCGCGCTCACTCTTAAAGACTAGCTCCGCGCCCTTCTCGAATTTAGGCGGGAGAAAACTACGT

CATCGCCGGCCGCCGCCCAGCCCGCCCAGCCGAGATGAGCAAAGAGATTCCCACGCCATACATGTGG

AGCTACCAGCCGCAGATGGGACTCGCGGCGGGAGCGGCCCAGGACTACTCCACCCGCATGAACTACA

TGAGCGCGGGACCCCACATGATCTCACAGGTCAACGGGATCCGCGCCCAGCGAAACCAAATACTGCT

GGAACAGGCGGCCATCACCGCCACGCCCCGCCATAATCTCAACCCCCGAAATTGGCCCGCCGCCCTCG

TGTACCAGGAAACCCCCTCCGCCACCACCGTACTACTTCCGCGTGACGCCCAGGCCGAAGTCCAGATG

ACTAACTCAGGGGCGCAGCTCGCGGGCGGCTTTCGTCACGGGGCGCGGCCGCTCCGACCAGGTATAAG

ACACCTGATGATCAGAGGCCGAGGTATCCAGCTCAACGACGAGTCGGTGAGCTCTTCGCTCGGTCTCC

GTCCGGACGGAACTTTCCAGCTCGCCGGATCCGGCCGCTCTTCGTTCACGCCCCGCCAGGCGTACCTG

ACTCTGCAGACCTCGTCCTCGGAGCCCCGCTCCGGCGGCATCGGAACCCTCCAGTTCGTGGAGGAGTT

CGTGCCCTCGGTCTACTTCAACCCCTTCTCGGGACCTCCCGGACGCTACCCCGACCAGTTCATTCCGAA

CTTTGACGCGGTGAAGGACTCGGCGGACGGCTACGACTGAATGTCAGGTGTCGAGGCAGAGCAGCTTC

GCCTGAGACACCTCGAGCACTGCCGCCGCCACAAGTGCTTCGCCCGCGGTTCTGGTGAGTTCTGCTACT

TTCAGCTACCCGAGGAGCATACCGAGGGGCCGGCGCACGGCGTCCGCCTGACCACCCAGGGCGAGGT

TACCTGTTCCCTCATCCGGGAGTTTACCCTCCGTCCCCTGCTAGTGGAGCGGGAGCGGGTCCCTGTGT

CCTAACTATCGCCTGCAACTGCCCTAACCCTGGATTACATCAAGATCTTTGCTGTCATCTCTGTGCTGA

GTTTAATAAACGCTGAGATCAGAATCTACTGGGGCTCCTGTCGCCATCCTGTGAACGCCACCGTCTTCA

CCCACCCCGACCAGGCCCAGGCGAACCTCACCTGCGGTCTGCATCGGAGGGCCAAGAAGTACCTCACC

TGGTACTTCAACGGCACCCCCTTTGTGGTTTACAACAGCTTCGACGGGGACGGAGTCTCCCTGAAAGA

CCAGCTCTCCGGTCTCAGCTACTCCATCCACAAGAACACCACCCTCCAACTCTTCCCTCCCTACCTGCC

GGGAACCTACGAGTGCGTCACCGGCCGCTGCACCCACCTCACCCGCCTGATCGTAAACCAGAGCTTTC

CGGGAACAGATAACTCCCTCTTCCCCAGAACAGGAGGTGAGCTCAGGAAACTCCCCGGGGACCAGGG

CGGAGACGTACCTTCGACCCTTGTGGGGTTAGGATTTTTTATTACCGGGTTGCTGGCTCTTTTAATCAA

AGTTTCCTTGAGATTTGTTCTTTCCTTCTACGTGTATGAACACCTCAACCTCCAATAACTCTACCCTTTC

TTCGGAATCAGGTGACTTCTCTGAAATCGGGCTTGGTGTGCTGCTTACTCTGTTGATTTTTTCCTTATC

ATACTCAGCCTTCTGTGCCTCAGGCTCGCCGCCTGCTGCGCACACATCTATATCTACTGCTGGTTGCTC
```

-continued

```
AAGTGCAGGGGTCGCCACCCAAGATGAACAGGTACATGGTCCTATCGATCCTAGGCCTGCTGGCCCTG
GCGGCCTGCAGCGCCGCCAAAAAAGAGATTACCTTTGAGGAGCCCGCTTGCAATGTAACTTTCAAGCC
CGAGGGTGACCAATGCACCACCCTCGTCAAATGCGTTACCAATCATGAGAGGCTGCGCATCGACTACA
AAAACAAAACTGGCCAGTTTGCGGTCTATAGTGTGTTTACGCCCGGAGACCCCTCTAACTACTCTGTCA
CCGTCTTCCAGGGCGGACAGTCTAAGATATTCAATTACACTTTCCCTTTTTATGAGTTATGCGATGCGG
TCATGTACATGTCAAAACAGTACAACCTGTGGCCTCCCTCTCCCAGGCGTGTGTGGAAAATACTGGG
TCTTACTGCTGTATGGCTTTCGCAATCACTACGCTCGCTCTAATCTGCACGGTGCTATACATAAAATTC
AGGCAGAGGCGAATCTTTATCGATGAAAAGAAAATGCCTTGATCGCTAACACCGGCTTTCTATCTGCA
GAATGAATGCAATCACCTCCCTACTAATCACCACCACCCTCCTTGCGATTGCCCATGGGTTGACACGA
ATCGAAGTGCCAGTGGGGTCCAATGTCACCATGGTGGGCCCCGCCGGCAATTCCACCCTCATGTGGGA
AAAATTTGTCCGCAATCAATGGGTTCATTTCTGCTCTAACCGAATCAGTATCAAGCCCAGAGCCATCTG
CGATGGGCAAAATCTAACTCTGATCAATGTGCAAATGATGGATGCTGGGTACTATTACGGGCAGCGGG
GAGAAATCATTAATTACTGGCGACCCCACAAGGACTACATGCTGCATGTAGTCGAGGCACTTCCCACT
ACCACCCCCACTACCACCTCTCCCACCACCACCACCACTACTACTACTACTACTACTACTACTACTACT
ACCACTACCGCTGCCCGCCATACCCGCAAAAGCACCATGATTAGCACAAAGCCCCTCGTGCTCACTC
CCACGCCGGCGGGCCCATCGGTGCGACCTCAGAAACCACCGAGCTTTGCTTCTGCCAATGCACTAACG
CCAGCGCTCATGAACTGTTCGACCTGGAGAATGAGGATGTCCAGCAGAGCTCCGCTTGCCTGACCCAG
GAGGCTGTGGAGCCCGTTGCCCTGAAGCAGATCGGTGATTCAATAATTGACTCTTCTTCTTTTGCCACT
CCCGAATACCCTCCCGATTCTACTTTCCACATCACGGGTACCAAAGACCCTAACCTCTCTTTCTACCTG
ATGCTGCTGCTCTGTATCTCTGTGGTCTCTTCCGCGCTGATGTTACTGGGGATGTTCTGCTGCCTGATCT
GCCGCAGAAAGAGAAAAGCTCGCTCTCAGGGCCAACCACTGATGCCCTTCCCCTACCCCCCGGATTTT
GCAGATAACAAGATATGAGCTCGCTGCTGACACTAACCGCTTTACTAGCCTGCGCTCTAACCCTTGTCG
CTTGCGACTCGAGATTCCACAATGTCACAGCTGTGGCAGGAGAAAATGTTACTTTCAACTCCACGGCC
GATACCCAGTGGTCGTGGAGTGGCTCAGGTAGCTACTTAACTATCTGCAATAGCTCCACTTCCCCCGGC
ATATCCCCAACCAAGTACCAATGCAATGCCAGCCTGTTCACCCTCATCAACGCTTCCACCCTGGACAAT
GGACTCTATGTAGGCTATGTACCCTTTGGTGGGCAAGGAAAGACCCACGCTTACAACCTGGAAGTTCG
CCAGCCCAGAACCACTACCCAAGCTTCTCCCACCACCACCACCACCACCACCATCACCAGCAGCAGCA
GCAGCAGCAGCCACAGCAGCAGCAGCAGATTATTGACTTTGGTTTTGGCCAGCTCATCTGCCGCTACC
CAGGCCATCTACAGCTCTGTGCCCGAAACCACTCAGATCCACCGCCCAGAAACGACCACCGCCACCAC
CCTACACACCTCCAGCGATCAGATGCCGACCAACATCACCCCCTTGGCTCTTCAAATGGGACTTACAA
GCCCCACTCCAAAACCAGTGGATGCGGCCGAGGTCTCCGCCCTCGTCAATGACTGGGCGGGGCTGGGA
ATGTGGTGGTTCGCCATAGGCATGATGGCGCTCTGCCTGCTTCTGCTCTGGCTCATCTGCTGCCTCCAC
CGCAGGCGAGCCAGACCCCCCATCTATAGACCCCATCATTGTCCTGAACCCCGATAATGATGGGATCCA
TAGATTGGATGGCCTGAAAAACCTACTTTTTTCTTTTACAGTATGATAAATTGAGACATGCCTCGCATT
TTCTTGTACATGTTCCTTCTCCCACCTTTTCTGGGGTGTTCTACGCTGGCCGCTGTGTCTCACCTGGAGG
TAGACTGCCTCTCACCCTTCACTGTCTACCTGCTTTACGGATTGGTCACCCTCACTCTCATCTGCAGCCT
AATCACAGTAATCATCGCCTTCATCCAGTGCATTGATTACATCTGTGTGCGCCTCGCATACTTCAGACA
CCACCCGCAGTACCGAGACAGGAACATTGCCCAACTTCTAAGACTGCTCTAATCATGCATAAGACTGT
GATCTGCCTTCTGATCCTCTGCATCCTGCCCACCCTCACCTCCTGCCAGTACACCACAAAATCTCCGCG
CAAAAGACATGCCTCCTGCCGCTTCACCCAACTGTGGAATATACCCAAATGCTACAACGAAAAGAGCG
```

-continued

```
AGCTCTCCGAAGCTTGGCTGTATGGGGTCATCTGTGTCTTAGTTTTCTGCAGCACTGTCTTTGCCCTCAT
AATCTACCCCTACTTTGATTTGGGATGGAACGCGATCGATGCCATGAATTACCCCACCTTTCCCGCACC
CGAGATAATTCCACTGCGACAAGTTGTACCCGTTGTCGTTAATCAACGCCCCCCATCCCCTACGCCCAC
TGAAATCAGCTACTTTAACCTAACAGGCGGAGATGACTGACGCCCTAGATCTAGAAATGGACGGCATC
AGTACCGAGCAGCGTCTCCTAGAGAGGCGCAGGCAGGCGGCTGAGCAAGAGCGCCTCAATCAGGAGC
TCCGAGATCTCGTTAACCTGCACCAGTGCAAAAGAGGCATCTTTTGTCTGGTAAAGCAGGCCAAAGTC
ACCTACGAGAAGACCGGCAACAGCCACCGCCTCAGTTACAAATTGCCCACCCAGCGCCAGAAGCTGG
TGCTCATGGTGGGTGAGAATCCCATCACCGTCACCCAGCACTCGGTAGAGACCGAGGGGTGTCTGCAC
TCCCCCTGTCGGGGTCCAGAAGACCTCTGCACCCTGGTAAAGACCCTGTGCGGTCTCAGAGATTTAGT
CCCCTTTAACTAATCAAACACTGGAATCAATAAAAAGAATCACTTACTTAAAATCAGACAGCAGGTCT
CTGTCCAGTTTATTCAGCAGCACCTCCTTCCCCTCCTCCCAACTCTGGTACTCCAAACGCCTTCTGGCG
GCAAACTTCCTCCACACCCTGAAGGGAATGTCAGATTCTTGCTCCTGTCCCTCCGCACCCACTATCTTC
ATGTTGTTGCAGATGAAGCGCACCAAAACGTCTGACGAGAGCTTCAACCCCGTGTACCCCTATGACAC
GGAAAGCGGCCCTCCCTCCGTCCCTTTCCTCACCCCTCCCTTCGTGTCTCCCGATGGATTCCAAGAAAG
TCCCCCCGGGGTCCTGTCTCTGAACCTGGCCGAGCCCCTGGTCACTTCCCACGGCATGCTCGCCCTGAA
AATGGGAAGTGGCCTCTCCCTGGACGACGCTGGCAACCTCACCTCTCAAGATATCACCACCGCTAGCC
CTCCCCTCAAAAAAACCAAGACCAACCTCAGCCTAGAAACCTCATCCCCCCTAACTGTGAGCACCTCA
GGCGCCCTCACCGTAGCAGCCGCCGCTCCCCTGGCGGTGGCCGGCACCTCCCTCACCATGCAATCAGA
GGCCCCCCTGACAGTACAGGATGCAAAACTCACCCTGGCCACCAAAGGCCCCCTGACCGTGTCTGAAG
GCAAACTGGCCTTGCAAACATCGGCCCCGCTGACGGCCGCTGACAGCAGCACCCTCACAGTCAGTGCC
ACACCACCCCTTAGCACAAGCAATGGCAGCTTGGGTATTGACATGCAAGCCCCCATTTACACCACCAA
TGGAAAACTAGGACTTAACTTTGGCGCTCCCCTGCATGTGGTAGACAGCCTAAATGCACTGACTGTAG
TTACTGGCCAAGGTCTTACGATAAACGGAACAGCCCTACAAACTAGAGTCTCAGGTGCCCTCAACTAT
GACACATCAGGAAACCTAGAATTGAGAGCTGCAGGGGGTATGCGAGTTGATGCAAATGGTCAACTTA
TCCTTGATGTAGCTTACCCATTTGATGCACAAAACAATCTCAGCCTTAGGCTTGGACAGGGACCCCTGT
TTGTTAACTCTGCCCACAACTTGGATGTTAACTACAACAGAGGCCTCTACCTGTTCACATCTGGAAATA
CCAAAAAGCTAGAAGTTAATATCAAAACAGCCAAGGGTCTCATTTATGATGACACTGCTATAGCAATC
AATGCGGGTGATGGGCTACAGTTTGACTCAGGCTCAGATACAAATCCATTAAAAACTAAACTTGGATT
AGGACTGGATTATGACTCCAGCAGAGCCATAATTGCTAAACTGGGAACTGGCCTAAGCTTTGACAACA
CAGGTGCCATCACAGTAGGCAACAAAAATGATGACAAGCTTACCTTGTGGACCACACCAGACCCATCC
CCTAACTGTAGAATCTATTCAGAGAAAGATGCTAAATTCACACTTGTTTTGACTAAATGCGGCAGTCA
GGTGTTGGCCAGCGTTTCTGTTTTATCTGTAAAAGGTAGCCTTGCGCCCATCAGTGGCACAGTAACTAG
TGCTCAGATTGTCCTCAGATTTGATGAAAATGGAGTTCTACTAAGCAATTCTTCCCTTGACCCTCAATA
CTGGAACTACAGAAAAGGTGACCTTACAGAGGGCACTGCATATACCAACGCAGTGGGATTTATGCCCA
ACCTCACAGCATACCCAAAAACACAGAGCCAAACTGCTAAAAGCAACATTGTAAGTCAGGTTTACTTG
AATGGGGACAAATCCAAACCCATGACCCTCACCATTACCCTCAATGGAACTAATGAAACAGGAGATG
CCACAGTAAGCACTTACTCCATGTCATTCTCATGGAACTGGAATGGAAGTAATTACATTAATGAAACG
TTCCAAACCAACTCCTTCACCTTCTCCTACATCGCCCAAGAATAAAAAGCATGACGCTGTTGATTTGAT
TCAATGTGTTTCTGTTTTATTTTCAAGCACAACAAAATCATTCAAGTCATTCTTCCATCTTAGCTTAATA
GACACAGTAGCTTAATAGACCCAGTAGTGCAAAGCCCCATTCTAGCTTATAACTAGTGGAGAAGTACT
CGCCTACATGGGGGTAGAGTCATAATCGTGCATCAGGATAGGGCGGTGGTGCTGCAGCAGCGCGCGA
```

```
ATAAACTGCTGCCGCCGCCGCTCCGTCCTGCAGGAATACAACATGGCAGTGGTCTCCTCAGCGATGAT
TCGCACCGCCCGCAGCATAAGGCGCCTTGTCCTCCGGGCACAGCAGCGCACCCTGATCTCACTTAAAT
CAGCACAGTAACTGCAGCACAGCACCACAATATTGTTCAAAATCCCACAGTGCAAGGCGCTGTATCCA
AAGCTCATGGCGGGGACCACAGAACCCACGTGGCCATCATACCACAAGCGCAGGTAGATTAAGTGGC
GACCCCTCATAAACACGCTGGACATAAACATTACCTCTTTTGGCATGTTGTAATTCACCACCTCCCGGT
ACCATATAAACCTCTGATTAAACATGGCGCCATCCACCACCATCCTAAACCAGCTGGCCAAAACCTGC
CCGCCGGCTATACACTGCAGGGAACCGGGACTGGAACAATGACAGTGGAGAGCCCAGGACTCGTAAC
CATGGATCATCATGCTCGTCATGATATCAATGTTGGCACAACACAGGCACACGTGCATACACTTCCTC
AGGATTACAAGCTCCTCCCGCGTTAGAACCATATCCCAGGGAACAACCCATTCCTGAATCAGCGTAAA
TCCCACACTGCAGGGAAGACCTCGCACGTAACTCACGTTGTGCATTGTCAAAGTGTTACATTCGGGCA
GCAGCGGATGATCCTCCAGTATGGTAGCGCGGGTTTCTGTCTCAAAAGGAGGTAGACGATCCCTACTG
TACGGAGTGCGCCGAGACAACCGAGATCGTGTTGGTCGTAGTGTCATGCCAAATGGAACGCCGGACGT
AGTCATATTTCCTGAAGTCTTAGATCTCTCAACGCAGCACCAGCACCAACACTTCGCAGTGTAAAAGG
CCAAGTGCCGAGAGAGTATATATAGGAATAAAAAGTGACGTAAACGGGCAAAGTCCAAAAAACGCCC
AGAAAAACCGCACGCGAACCTACGCCCCGAAACGAAAGCCAAAAAACACTAGACACTCCCTTCCGGC
GTCAACTTCCGCTTTCCCACGCTACGTCACTTGCCCCAGTCAAACAAACTACATATCCCGAACTTCCAA
GTCGCCACGCCCAAAACACCGCCTACACCTCCCCGCCCGCCGGCCCGCCCCAAACCCGCCTCCCGCC
CCGCGCCCCGCCCCGCGCCGCCCATCTCATTATCATATTGGCTTCAATCCAAAATAAGGTATATTATTG
ATGATG
```

RSV F0ΔTM-N-M2-1 amino acid sequence
SEQ ID NO: 5

MELLILKANAITTILTAVTFCFASGQNITEEFYQSTCSAVSKGYLSALRTGWYTSVITIELSNIKENKCNGTDA
KVKLIKQELDKYKNAVTELQLLMQSTPATNNRARRELPRFMNYTLNNAKKTNVTLSKKRKRRFLGFLLGV
GSAIASGVAVSKVLHLEGEVNKIKSALLSTNKAVVSLSNGVSVLTSKVLDLKNYIDKQLLPIVNKQSCSISNI
ETVIEFQQKNNRLLEITREFSVNAGVTTPVSTYMLTNSELLSLNDMPITNDQKKLMSNNVQIVRQQSYSIMSI
IKEEVLAYVVQLPLYGVIDTPCWKLHTSPLCTTNTKEGSNICLTRTDRGWYCDNAGSVSFFPQAETCKVQS
NRVECDTMNSLTLPSEVNLCNVDIFNPKYDCKIMTSKTDVSSSVITSLGAIVSCYGKTKCTASNKNRGIIKTF
SNGCDYVSNKGVDTVSVGNTLYYVNKQEGKSLYVKGEPIINFYDPLVFPSDEFDASISQVNEKINQSLAFIR
KSDELLHNVNAGKSTTNRKRRAPVKQTLNFDLLKLAGDVESNPGPMALSKVKLNDTLNKDQLLSSSKYTI
QRSTGDSIDTPNYDVQKHINKLCGMLLITEDANHKFTGLIGMLYAMSRLGREDTIKILRDAGYHVKANGVD
VTTHRQDINGKEMKFEVLTLASLTTEIQINIEIESRKSYKKMLKEMGEVAPEYRHDSPDCGMIILCIAALVIT
KLAAGDRSGLTAVIRRANNVLKNEMKRYKGLLPKDIANS
FYEVFEKYPHFIDVFVHFGIAQSSTRGGSRVEGIFAGLEMNAYGAGQVMLRWGVLAKSVKNIMLGHASVQ
AEMEQVVEVYLYAQKLGGEAGFYHILNNPKASLLSLTQFPHFSSVVLGNAAGLGIMGEYRGTPRNQDLYD
AAKAYAEQLKENGVINYSVLDLTAEELEAIKHQLNPKDNDVELGGGGSGGGGMSRRNPCKFEIRGHCLNG
KRCHFSHNYFEWPPHALLVRQNFMLNRILKSMDKSIDTLSEISGAAELDRTEEYALGVVGVLESYIGSINNIT
KQSACVAMSKLLTELNSDDIKKLRDNEELNSPKIRVYNTVISYIESNRKNNKQTIHLLKRLPADVLKKTIKN
TLDIHKSITINNPKESTVSDTNDHAKNNDTT

Polynucleotide sequence encoding the enhanced hCMV promoter
SEQ ID NO: 6

```
CCATTGCATACGTTGTATCCATATCATAATATGTACATTTATATTGGCTCATGTCCAACATTACCGCCATGTTG
ACATTGATTATTGACTAGTTATTAATAGTAATCAATTACGGGGTCATTAGTTCATAGCCCATATATGGAGTTCC
```

-continued

```
GCGTTACATAACTTACGGTAAATGGCCCGCCTGGCTGACCGCCCAACGACCCCCGCCCATTGACGTCAATAATG

ACGTATGTTCCCATAGTAACGCCAATAGGGACTTTCCATTGACGTCAATGGGTGGAGTATTTACGGTAAACTGC

CCACTTGGCAGTACATCAAGTGTATCATATGCCAAGTACGCCCCCTATTGACGTCAATGACGGTAAATGGCCCG

CCTGGCATTATGCCCAGTACATGACCTTATGGGACTTTCCTACTTGGCAGTACATCTACGTATTAGTCATCGCT

ATTACCATGGTGATGCGGTTTTGGCAGTACATCAATGGGCGTGGATAGCGGTTTGACTCACGGGGATTTCCAAG

TCTCCACCCCATTGACGTCAATGGGAGTTTGTTTTGGCACCAAAATCAACGGGACTTTCCAAATGTCGTAACA

ACTCCGCCCCATTGACGCAAATGGGCGGTAGGCGTGTACGGTGGGAGGTCTATATAAGGCGAAGCGCTCCCTAT

CAGTGATAGAGATCTCCCTATCAGTGATAGAGATCGTCGACGAGCTCGCGGCGGGCGGGAGTCGCTGCGCGCTG

CCTTCGCCCCGTGCCCCGCTCCGCCGCCGCCTCGCGCCGCCCGCCCCGGCTCTGACTGACCGCGTTACTAAAAC

AGGTAAGTCCGGCCTCCGCGCCGGGTTTTGGCGCCTCCCGCGGGCGCCCCCTCCTCACGGCGAGCGCTGCCAC

GTCAGACGAAGGGCGCAGCGAGCGTCCTGATCCTTCCGCCCGGACGCTCAGGACAGCGGCCCGCTGCTCATAAG

ACTCGGCCTTAGAACCCCAGTATCAGCAGAAGGACATTTTAGGACGGGACTTGGGTGACTCTAGGGCACTGGTT

TTCTTTCCAGAGAGCGGAACAGGCGAGGAAAAGTAGTCCCTTCTCGGCGATTCTGCGGAGGGATCTCCGTGGGG

CGGTGAACGCCGATGATGCCTCTACTAACCATGTTCATGTTTTCTTTTTTTTCTACAGGTCCTGGGTGACGAA

CAG
```

Polynucleotide sequence encoding the hCMV NM2 bghpolyA cassette
SEQ ID NO: 7

```
CCATTGCATACGTTGTATCCATATCATAATATGTACATTTATATTGGCTCATGTCCAACATTACCGCCATGTTG

ACATTGATTATTGACTAGTTATTAATAGTAATCAATTACGGGGTCATTAGTTCATAGCCCATATATGGAGTTCC

GCGTTACATAACTTACGGTAAATGGCCCGCCTGGCTGACCGCCCAACGACCCCCGCCCATTGACGTCAATAATG

ACGTATGTTCCCATAGTAACGCCAATAGGGACTTTCCATTGACGTCAATGGGTGGAGTATTTACGGTAAACTGC

CCACTTGGCAGTACATCAAGTGTATCATATGCCAAGTACGCCCCCTATTGACGTCAATGACGGTAAATGGCCCG

CCTGGCATTATGCCCAGTACATGACCTTATGGGACTTTCCTACTTGGCAGTACATCTACGTATTAGTCATCGCT

ATTACCATGGTGATGCGGTTTTGGCAGTACATCAATGGGCGTGGATAGCGGTTTGACTCACGGGGATTTCCAAG

TCTCCACCCCATTGACGTCAATGGGAGTTTGTTTTGGCACCAAAATCAACGGGACTTTCCAAATGTCGTAACA

ACTCCGCCCCATTGACGCAAATGGGCGGTAGGCGTGTACGGTGGGAGGTCTATATAAGCAGAGCTCTCCCTATC

AGTGATAGAGATCTCCCTATCAGTGATAGAGATCGTCGACGAGCTCGTTTAGTGAACCGTCAGATCGCCTGGAG

ACGCCATCCACGCTGTTTTGACCTCCATAGAAGACACCGGGACCGATCCAGCCTCCGCGGCCGGGAACGGTGCA

TTGGAACGCGGATTCCCCGTGCCAAGAGTGAGATCTTCCGTTTATCTAGGTACCAGATATCGCCACCATGGCCC

TGAGCAAAGTGAAACTGAACGATACACTGAACAAGGACCAGCTGCTGTCCAGCAGCAAGTACACCATCCAGCGG

AGCACCGGCGACAGCATCGATACCCCCAACTACGACGTGCAGAAGCACATCAACAAGCTGTGCGGCATGCTGCT

GATCACAGAGGACGCCAACCACAAGTTCACCGGCCTGATCGGCATGCTGTACGCCATGAGCCGGCTGGGCCGGG

AGGACACCATCAAGATCCTGCGGGACGCCGGCTACCACGTGAAGGCCAATGGCGTGGACGTGACCACACACCGG

CAGGACATCAACGGCAAAGAAATGAAGTTCGAGGTGCTGACCCTGGCCAGCCTGACCACCGAGATCCAGATCAA

TATCGAGATCGAGAGCCGGAAGTCCTACAAGAAAATGCTGAAAGAAATGGGCGAGGTGGCCCCCGAGTACAGAC

ACGACAGCCCCGACTGCGGCATGATCATCCTGTGTATCGCCGCCCTGGTGATCACAAAGCTGGCCGCTGGCGAC

AGATCTGGCCTGACAGCCGTGATCAGACGGGCCAACAATGTGCTGAAGAACGAGATGAAGCGGTACAAGGGCCT

GCTGCCCAAGGACATTGCCAACAGCTTCTACGAGGTGTTCGAGAAGTACCCCCACTTCATCGACGTGTTCGTGC

ACTTCGGCATTGCCCAGAGCAGCACCAGAGGCGGCTCCAGAGTGGAGGGCATCTTCGCCGGCCTGTTCATGAAC

GCCTACGGCGCTGGCCAGGTGATGCTGAGATGGGGCGTGCTGGCCAAGAGCGTGAAGAACATCATGCTGGGCCA

CGCCAGCGTGCAGGCCGAGATGGAACAGGTGGTGGAGGTGTACGAGTACGCCCAGAAGCTGGGCGGAGAGGCCG

GCTTCTACCACATCCTGAACAACCCTAAGGCCTCCCTGCTGTCCCTGACCCAGTTCCCCCACTTCTCCAGCGTG
```

-continued

```
GTGCTGGGAAATGCCGCCGGACTGGGCATCATGGGCGAGTACCGGGCACCCCCAGAAACCAGGACCTGTACGA
CGCCGCCAAGGCCTACGCCGAGCAGCTGAAAGAAAACGGCGTGATCAACTACAGCGTGCTGGACCTGACCGCTG
AGGAACTGGAAGCCATCAAGCACCAGCTGAACCCCAAGGACAACGACGTGGAGCTGGGAGGCGGAGGATCTGGC
GGCGGAGGCATGAGCAGACGGAACCCCTGCAAGTTCGAGATCCGGGGCCACTGCCTGAACGGCAAGCGGTGCCA
CTTCAGCCACAACTACTTCGAGTGGCCCCCTCATGCTCTGCTGGTGCGGCAGAACTTCATGCTGAACCGGATCC
TGAAGTCCATGGACAAGAGCATCGACACCCTGAGCGAGATCAGCGGAGCCGCCGAGCTGGACAGAACCGAGGAA
TATGCCCTGGGCGTGGTGGGAGTGCTGGAAAGCTACATCGGCTCCATCAACAACATCACAAAGCAGAGCGCCTG
CGTGGCCATGAGCAAGCTGCTGACAGAGCTGAACAGCGACGACATCAAGAAGCTGAGGGACAACGAGGAACTGA
ACAGCCCCAAGATCCGGGTGTACAACACCGTGATCAGCTACATTGAGAGCAACCGCAAGAACAACAAGCAGACC
ATCCATCTGCTGAAGCGGCTGCCCGCCGACGTGCTGAAAAAGACCATCAAGAACACCCTGGACATCCACAAGTC
CATCACCATCAACAATCCCAAAGAAAGCACCGTGTCTGACACCAACGATCACGCCAAGAACAACGACACCACCT
GATGAGCGGCCGCGATCTGCTGTGCCTTCTAGTTGCCAGCCATCTGTTGTTTGCCCCTCCCCCGTGCCTTCCTT
GACCCTGGAAGGTGCCACTCCCACTGTCCTTTCCTAATAAAATGAGGAAATTGCATCGCATTGTCTGAGTAGGT
GTCATTCTATTCTGGGGGGTGGGGTGGGGCAGGACAGCAAGGGGGAGGATTGGGAAGACAATAGCAGGCATGCT
GGGGATGCGGTGGGCTCTATGG
```

CMV Promoter sequence: bold
Transgene sequence NM2: Italic
bghpolyA PolyA signal: italic + underline NM2 protein sequence
SEQ ID NO: 8

MALSKVKLNDTLNKDQLLSSSKYTIQRSTGDSIDTPNYDVQKHINKLCGMLLITEDANHKFTGLIGMLYAMSRL
GREDTIKILRDAGYHVKANGVDVTTHRQDINGKEMKFEVLTLASLTTEIQINIEIESRKSYKKMLKEMGEVAPE
YRHDSPDCGMIILCIAALVITKLAAGDRSGLTAVIRRANNVLKNEMKRYKGLLPKDIANSFYEVFEKYPHFIDV
FVHFGIAQSSTRGGSRVEGIFAGLFMNAYGAGQVMLRWGVLAKSVKNIMLGHASVQAEMEQVVEVYEYAQKLGG
EAGFYHILNNPKASLLSLTQFPHFSSVVLGNAAGLGIMGEYRGTPRNQDLYDAAKAYAEQLKENGVINYSVLDL
TAEELEAIKHQLNPKDNDVELGGGGSGGGGMSRRNPCKFEIRGHCLNGKRCHFSHNYFEWPPHALLVRQNFMLN
RILKSMDKSIDTLSEISGAAELDRTEEYALGVVGVLESYIGSINNITKQSACVAMSKLLTELNSDDIKKLRDNE
ELNSPKIRVYNTVISYIESNRKNNKQTIHLLKRLPADVLKKTIKNTLDIHKSITINNPKESTVSDTNDHAKNND
TT

Polynucleotide sequence encoding the hCMV F0 WPRE bghpolyA cassette
SEQ ID NO: 9

```
CCATTGCATACGTTGTATCCATATCATAATATGTACATTTATATTGGCTCATGTCCAACATTACCGCCATGTTG
ACATTGATTATTGACTAGTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCCGCCCATTGACGTCAATAATG
ACGTATGTTCCCATAGTAACGCCAATAGGGACTTTCCATTGACGTCAATGGGTGGAGTATTTACGGTAAACTGC
CCACTTGGCAGTACATCAAGTGTATCATATGCCAAGTACGCCCCCTATTGACGTCAATGACGGTAAATGGCCCG
CCTGGCATTATGCCCAGTACATGACCTTATGGGACTTTCCTACTTGGCAGTACATCTACGTATTAGTCATCGCT
ATTACCATGGTGATGCGGTTTTGGCAGTACATCAATGGGCGTGGATAGCGGTTTGACTCACGGGGATTTCCAAG
TCTCCACCCCATTGACGTCAATGGGAGTTTGTTTTGGCACCAAAATCAACGGGACTTTCCAAAATGTCGTAACA
ACTCCGCCCCATTGACGCAAATGGGCGGTAGGCGTGTACGGTGGAGGTCTATATAAGCAGAGCGCTCCCTAT
CAGTGATAGAGATCTCCCTATCAGTGATAGAGATCGTCGACGAGCTCGCGGCGGGCGGGAGTCGCTGCGCGCTG
CCTTCGCCCCGTGCCCCGCTCCGCCGCCGCCTCGCGCCGCCCGCCCCGGCTCTGACTGACCGCGTTACTAAAAC
AGGTAAGTCCGGCCTCCGCGCCGGGTTTTGGCGCCTCCCGCGGGCGCCCCCCTCCTCACGGCGAGCGCTGCCAC
GTCAGACGAAGGGCGCAGCGAGCGTCCTGATCCTTCCGCCCGGACGCTCAGGACAGCGGCCCGCTGCTCATAAG
```

-continued

ACTCGGCCTTAGAACCCCAGTATCAGCAGAAGGACATTTTAGGACGGGACTTGGGTGACTCTAGGGCACTGGTT

TTCTTTCCAGAGAGCGGAACAGGCGAGGAAAAGTAGTCCCTTCTCGGCGATTCTGCGGAGGGATCTCCGTGGGG

CGGTGAACGCCGATGATGCCTCTACTAACCATGTTCATGTTTTCTTTTTTTTTCTACAGGTCCTGGGTGACGAA

CAGGATATCGCCACCATGGAACTGCTGATCCTGAAGGCCAACGCCATCACCACCATCCTGACCGCCGTGACCTT

*CTGCTTCGCCAGCGGCCAGAACATCACCGAGGAATTCTACCAGAGCACCTGTAGCGCCGTGAGCAAGGGCTACC*

*TGAGCGCCCTGAGAACCGGCTGGTACACCAGCGTGATCACCATCGAGCTGAGCAACATCAAAGAAAACAAGTGC*

*AACGGCACCGACGCCAAAGTGAAGCTGATCAAGCAGGAACTGGACAAGTACAAGAACGCCGTGACCGAGCTGCA*

*GCTGCTGATGCAGAGCACCCCCGCCACCAACAACCGGGCCAGACGGGAGCTGCCCCGGTTCATGAACTACACCC*

*TGAACAACGCCAAAAAGACCAACGTGACCCTGAGCAAGAAGCGGAAGCGGCGGTTCCTGGGCTTTCTGCTGGGC*

*GTGGGCAGCGCCATTGCCAGCGGCGTGGCCGTGTCTAAGGTGCTGCACCTGGAAGGCGAAGTGAACAAGATCAA*

*GAGCGCCCTGCTGAGCACCAACAAGGCCGTGGTGTCCCTGAGCAACGGCGTGAGCGTGCTGACCAGCAAGGTGC*

*TGGATCTGAAGAACTACATCGACAAGCAGCTGCTGCCCATCGTGAACAAGCAGAGCTGCAGCATCAGCAACATC*

GAGACAGTGATCGAGTTCCAGCAGAAGAACAACCGGCTGCTGGAAATCACCCGGGAGTTCAGCGTGAACGCCGG

*CGTGACCACCCCTGTGTCCACCTACATGCTGACCAACAGCGAGCTGCTGAGCCTGATCAACGACATGCCCATCA*

*CCAACGACCAGAAAAAGCTGATGAGCAACAACGTGCAGATCGTGCGGCAGCAGAGCTACTCCATCATGTCCATC*

*ATCAAAGAAGAGGTGCTGGCCTACGTGGTGCAGCTGCCCCTGTACGCGTGATCGACACCCCTGCTGGAAGCT*

*GCACACCAGCCCCCTGTGCACCACCAACACCAAAGAGGGCAGCAACATCTGCCTGACCCGGACCGACAGAGGCT*

*GGTACTGCGACAACGCCGGCAGCGTGTCATTCTTTCCACAGGCCGAGACATGCAAGGTGCAGAGCAACCGGGTG*

*TTCTGCGACACCATGAACAGCCTGACCCTGCCCTCCGAAGTGAACCTGTGCAACGTGGACATCTTCAACCCCAA*

*GTACGACTGCAAGATCATGACCTCCAAGACCGACGTGTCCAGCTCCGTGATCACCTCCCTGGGCGCCATCGTGT*

*CCTGCTACGGCAAGACCAAGTGCACCGCCAGCAACAAGAACCGGGGCATCATCAAGACCTTCAGCAACGGCTGC*

*GACTACGTGTCCAACAAGGGGGTGGACACCGTGTCCGTGGGCAACACCCTGTACTACGTGAACAAACAGGAAGG*

*CAAGAGCCTGTACGTGAAGGGCGAGCCCATCATCAACTTCTACGACCCCCTGGTGTTCCCCAGCGACGAGTTCG*

*ACGCCAGCATCAGCCAGGTGAACGAGAAGATCAACCAGAGCCTGGCCTTCATCCGGAAGTCCGACGAGCTGCTG*

*CACAATGTGAATGCCGGCAAGTCCACCACCAACTGATGAGCGGCCATCTAA*<u>TCAACCTCTGGATTACAAAATTT</u>

<u>GTGAAAGATTGACTGGTATTCTTAACTATGTTGCTCCTTTTACGCTATGTGGATACGCTGCTTTAATGCCTTTG</u>

<u>TATCATGCTATTGCTTCCCGTATGGCTTTCATTTTCTCCTCCTTGTATAAATCCTGGTTGCTGTCTCTTTATGA</u>

<u>GGAGTTGTGGCCCGTTGTCAGGCAACGTGGCGTGGTGTGCACTGTGTTTGCTGACGCAACCCCCACTGGTTGGG</u>

<u>GCATTGCCACCACCTGTCAGCTCCTTTCCGGGACTTTCGCTTTCCCCCTCCCTATTGCCACGGCGGAACTCATC</u>

<u>GCCGCCTGCCTTGCCCGCTGCTGGACAGGGGCTCGGCTGTTGGGCACTGACAATTCCGTGGTGTTGTCGGGGAA</u>

<u>ATCATCGTCCTTTCCTTGGCTGCTCGCCTGTGTTGCCACCTGGATTCTGCGCGGGACGTCCTTCTGCTACGTCC</u>

<u>CTTCGGCCCTCAATCCAGCGGACCTTCCTTCCCGCGGCCTGCTGCCGGCTCTGCGGCCTCTTCCGCGTCTTCGC</u>

<u>CTTCGCCCTCAGACGAGTCGGATCTCCCTTTGGGCCGCCTCCCCGCCT</u>GCGGCCGCGATCTG<u>CTGTGCCTTCTA</u>

<u>GTTGCCAGCCATCTGTTGTTTGCCCCTCCCCCGTGCCTTCCTTGACCCTGGAAGGTGCCACTCCCACTGTCCTT</u>

<u>TCCTAATAAAATGAGGAAATTGCATCGCATTGTCTGAGTAGGTGTCATTCTATTCTGGGGGGTGGGGTGGGGCA</u>

<u>GGACAGCAAGGGGGAGGATTGGGAAGACAATAGCAGGCATGCTGGGGATGCGGTGGGCTCTATGG</u>

Enhanced CMV Promoter sequence: bold
Transgene sequence F0: Italic
WPRE sequence: underlined bold
bghpolyA PolyA signal: italic + underline F0 protein sequence
SEQ ID NO: 10

MELLILKANAITTILTAVTFCFASGQNITEEFYQSTCSAVSKGYLSALRTGWYTSVITIELSNIKENKCNGTDA

KVKLIKQELDKYKNAVTELQLLMQSTPATNNRARRELPRFMNYTLNNAKKTNVTLSKKRKRRFLGFLLGVGSAI

ASGVAVSKVLHLEGEVNKIKSALLSTNKAVVSLSNGVSVLTSKVLDLKNYIDKQLLPIVNKQSCSISNIETVIE

FQQKNNRLLEITREFSVNAGVTTPVSTYMLTNSELLSLINDMPITNDQKKLMSNNVQIVRQQSYSIMSIIKEEV

LAYVVQLPLYGVIDTPCWKLHTSPLCTTNTKEGSNICLTRTDRGWYCDNAGSVSFFPQAETCKVQSNRVFCDTM

NSLTLPSEVNLCNVDIFNPKYDCKIMTSKTDVSSSVITSLGAIVSCYGKTKCTASNKNRGIIKTFSNGCDYVSN

KGVDTVSVGNTLYYVNKQEGKSLYVKGEPIINFYDPLVFPSDEFDASISQVNEKINQSLAFIRKSDELLHNVNA

GKSTTN

Amino acid sequence of a flexible linker
SEQ ID NO: 11

Gly-Gly-Gly-Ser-Gly-Gly-Gly

Amino acid sequence of a flexible linker
SEQ ID NO: 12

Gly-Gly-Gly-Gly-Ser-Gly-Gly-Gly-Gly

---

SEQUENCE LISTING

Sequence total quantity: 12
SEQ ID NO: 1    moltype = DNA   length = 37830
FEATURE          Location/Qualifiers
source           1..37830
                  mol_type = unassigned DNA
                  organism = unidentified
                  note = Chimpanzee adenovirus
SEQUENCE: 1
catcatcaat aatataccct attttggatt gaagccaata tgataatgag atgggcggcg 60
cggggcggga ggcgggtccg ggggcgggcc ggcgggcggg gcggtgtggc ggaagtggac 120
tttgtaagtg tggcggatgt gacttgctag tgccgggcag cgtaaaagtg acgttttccg 180
tgcgcgacaa cgcccacggg aagtgacatt tttcccgcgg ttttttaccgg atgttgtagt 240
gaatttgggc gtaaccaagt aagatttggc cattttcgcg ggaaaactga aacgggaag 300
tgaaatctga ttaatttcgc gttagtcata ccgcgtaata tttgtcgagg gccgagggac 360
tttggccgat tacgtggagg actcgcccag gtgtttttg aggtgaattt ccgcgttccg 420
ggtcaaagtc tccgttttat tattatagtc agctgacgcg gagtgtattt ataccctctg 480
atctcgtcaa gtgccactc ttgagtgcca gcgagtagag ttttctcctc tgccgctctc 540
cgctccgctc cgctcggctc tgacaccggg gaaaaatga acatttcac ctacgatggc 600
ggtgtgctca ccggcagct ggctgctgaa gtcctgaca ccctgatcga ggaggtattg 660
gccgataatt atcctccctc gactccttt gagccaccta cacttcacga actctacgat 720
ctggatgtgg tggggcccag cgatccgaac gagcaggcgg tttccagttt tttccagag 780
tccatgttgt tggccagcca ggaggggtc gaacttgaga cccctcctcc gatcgtggat 840
tcccccgatc cgccgcagct gactaggcag cccgagcgct gtgcgggacc tgagactatg 900
ccccagctgc tacctgaggt gatcgatctc acctgtaatg agtctggttt tccacccagc 960
gaggatgagg acgaagaggg tgagcagttt gtgttagatt ctgtgaaaca acccgggcga 1020
ggatgcaggt cttgtcaata tcaccggaaa acacaggag actcccagat tatgtgttct 1080
ctgtgttata tgaagatgac ctgtatgttt atttacagta agttatcat ctgtgggcag 1140
gtgggctata tgtgtggtgg tggtcttttgg ggggttttt aatatatgtc aggggtatg 1200
ctgaagactt ttttattgtg attttttaaag gtccagtgtc tgagcccgag caagaacctg 1260
aaccggagcc tgagccttct cgccccagga gaaagcctgt aatcttaact agacccagcg 1320
caccggtagc gagaggcctc agcagcgcgg agaccaccga ctccggtgct tcctcatcac 1380
ccccggagat tcaccccctg gtgccccctgt gtcccgttaa gcccgttgcc gtgagagtca 1440
gtgggcggcg gtctgctgtg gagtgcattg aggacttgct ttttgattca caggaacctt 1500
tggacttgag cttgaaacgc cccaggcatt aaacctggtc acctgactg aatgagttga 1560
cgcctatgtt tgcttttgaa tgacttaatg tgtatagata ataaagagtg agataatgtt 1620
ttaattgcat ggtgtgttta acttgggcgg agtctgctgg tataataagc ttccctgcgt 1680
taaacttggt tacacttgac ctcatggagg cctgggagtg tttggagaac tttgccggag 1740
ttcgtgcctt gctggacgag agctctaaca atacctcttg gtggtggagg tatttgtggg 1800
gctctcccca gggcaagtta gttttgtgaa tcaaggagga ttacaagtgg gaatttgaag 1860
agcttttgaa atccgtggt gagctattgg attcttttaa tctaggccgac caggctctct 1920
tccaggagaa ggtcatcagg actttggatt tttccacacc ggggcgcatt gcagccgcgg 1980
ttgctttct agcttttttg aaggatagat ggagcgaaga gacccacttg agttcgggct 2040
acgtcctgga ttttctggcc atgcaactgt ggagagcatg gatcagacac aagaacaggc 2100
tgcaactgtt gtcttccgtc cgcccgttgc tgattccggc ggaggagcaa caggccgggt 2160

```
cagaggaccg ggcccgtcgg gatccggagg agagggcacc gaggccgggc gagaggagcg   2220
cgctgaacct gggaaccggg ctgagcggcc atccacatcg ggagtgaatg tcgggcaggt   2280
ggtggatctt tttccagaac tgcggcggat tttgactatt agggaggatg ggcaatttgt   2340
taagggtctt aagagggaga gggggggcttc tgagcataac gaggaggcca gtaatttagc  2400
ttttagcttg atgaccagac accgtccaga gtgcatcact tttcagcaga ttaaggacaa   2460
ttgtgccaat gagttggatc tgttgggtca gaagtatagc atagagcagc tgaccactta   2520
ctggctgcag ccgggtgatg atctggagga agctattagg gtgtatgcta aggtggccct   2580
gcggcccgat tgcaagtaca agctcaaggg gctggtgaat atcaggaatt gttgctacat   2640
ttctggcaac ggggcggagg tggagataga gaccgaagac agggtggctt tcagatgcag   2700
catgatgaat atgtggccgg gggtgctggg catggacggg ggtgtgatta tgaatgtgaa   2760
gttcacgggg cccaactttta acggcacggt gttttttgggg aacaccaacc tggtcctgca  2820
cggggtgagc ttctatgggt ttaacaacac ctgtgtggag gcctggaccg atgtgaaggt   2880
ccgcggttgc gccttttatg gatgttgaaa ggccatagtg agccgcccta agagcaggag   2940
ttccattaag aaatgcttgt ttgagaggtg cacctttgggg atcctggccg agggcaactg  3000
cagggtgcgc cacaatgtgg cctccgagtg cggttgcttc atgctagtca agagcgtggc   3060
ggtaatcaag cataatatgg tgtgcggcaa cagcgaggac aaggcctcac agatgctgac   3120
ctgcacggat ggcaactgcc acttgctgaa gaccatccat gtaaccagcc acagccggaa   3180
ggcctggccc gtgttcgagc acaacttgct gacccgctgc tccttgcatc tgggcaacag   3240
gcgggggggtg ttcctgccct atcaatgcaa cttttagtcac accaagatct tgctagagcc  3300
cgagagcatg tccaaggtga acttgaacgg ggtgtttgac atgaccatga agatctggaa   3360
ggtgctgagg tacgacgaga ccaggtcccg gtgcagaccc tgcgagtgcg ggggcaagca   3420
tatggaaac cagcccgtga tgctggatgt gaccgaggag ctgaccgacag accacttgt   3480
tctggcctgc accagggccg agtttggttc tagcgatgaa gacacagatt gaggtgggtg   3540
agtgggcgtg gcctggggtg gtcatgaaaa tatataagtt gggggtctta gggtctcttt   3600
atttgtgttg cagagaccgc cggagccatg agcgggagca gcagcagcag cagtagcagc   3660
agcgccttgg atggcagcat cgtgagccct tatttgacga gggcgatgcc ccactgggcc   3720
ggggtgcgtc agaatgtgat gggctccagc atcgacgccc gacccgtcct gcccgcaaat   3780
tccgccacgc tgacctatgc gaccgtcgcg gggacgccgt tggacgccac cgccgccgcc   3840
gccgccaccg cagccgcctc ggccgtgcgc agcctggcca cggactttgc attcctggga   3900
ccactggcga caggggctac ttctcgggcc gctgctgccg ccgttcgcga tgacaagctg   3960
accgccctgc tggcgcagtt ggatgcgctt actcggggaac tgggtgacct ttctcagcag   4020
gtcatgcccc tgcgccagca ggtctcctcc ctgcaagctg gcgggaatgc ttctcccaca   4080
aatgccgttt aagataaata aaaccagact ctgtttggat taaagaaaag tagcaagtgc   4140
attgctctct ttatttcata attttccgcg cgcgataggc cctagaccag cgttctcggt   4200
cgttgagggt gcggtgtatc ttctccagga cgtggtagag gtggctctgg acgttgagat   4260
acatgggcat gagcccgtcc cgggggtgga ggtagcacca ctgcagagct tcatgctccg   4320
gggtggtgtt gtagatgatc cagtcgtagc aggagcgctg ggcatggtgc ctaaaaatgt   4380
ccttcagcag caggccgatg gccagggggga ggcccttggt gtaagtgttt acaaaaacggt  4440
taagttggga agggtgcatt cgggggagaga tgatgtgcat cttggactgt attttttagat 4500
tggcgatgtt tccgcccaga tcccttctgg gattcatgtt gtgcaggacc accagtacag   4560
tgtatccggt gcacttgggg aatttgtcat gcagcttaga gggaaaagcg tggaagaact   4620
tggagacgcc tttgtggcct cccagatttt ccatgcattc gtccatgatg atggcaatgg   4680
gcccgtggga ggcagcttgg gcaaagatat ttctggggtc gctgacgtcg tagttgtgtt   4740
ccagggtgag gtcgtcatag gccattttta caaagcgcgg gcggagggtg cccgactggg   4800
ggatgatggt cccctctggc cctggggcgt agttgccctc gcagatctgc atttcccagg   4860
ccttaatctc ggaggggggga atcatatcca cctgcgggggc gatgaagaaa acggtttccg  4920
gagccgggga gattaactgg gatgagagca ggtttctaaa cagctgtgat tttccacaac   4980
cggtgggccc ataaataaca cctataaccg gttgcagctg gtagtttaga gagctcagc    5040
tgccgtcgtc ccggaggagg ggggccacct cgttgagcat gtccctgacg cgcatgttct   5100
ccccgaccag atccgccaga aggcgctcgc cgcccaggga cagcagctct tgcaaggaag   5160
caaagttttt cagcggcttg aggccgtccg ccgtggccat gttttttcagg gtctggctca   5220
gcagctccag gcggtcccag agctcggtga cgtgctctac ggcatctcta tccagcatat   5280
ctcctcgttt cgcgggttgg ggcgactttc gctgtagggc accaagcggt ggtcgtccag   5340
cggggccaga gtcatgtcct tccatgggcg cagggtcctc gtcagggtgg tctgggtcac   5400
ggtgaagggg tgcgctccgg gctgaggcct tgccaaggtg gcgcttgagc tggttctgga   5460
ggtgctgaag cgctgccggt cttcgccctg cgcgtcggcc aggtagcatt tgaccatggt   5520
gtcatagtcc agccctccg cggcgtgtcc ctttggcgcgc agcttgccct tggaggtggc   5580
gccgcacgag gggcagagca ggctcttgag cgcgtagagc ttgggggcga ggaagaccga   5640
ttcggggggag taggcgtccg cgccgcagac cccgcacacg gtctcgcact ccaccagcca   5700
ggtgagctcg gggcgcgccg ggtcaaaaac caggtttccc ccatgctttt tgatgcgttt   5760
cttacctcgg gtctccatga ggtggtgtcc ccgctcggtg acgaagaggc tgtccgtgtc   5820
tccgtagacc gacttgaggg gtcttttctc cagggggggtc cctcggtctt cctcgtagag   5880
gaactcggac cactctgaga cgaaggcccg cgtccaggcc aggacgaagg aggctatgtg   5940
ggagggagga cggtcgttgt ccactagggg gtccaccttc tccaaggtgt gaagacactg   6000
gtcgccttcc tcggcgtcca ggaaggtgat tggcttgtag gtgtaggcca cgtgaccggg   6060
ggttcctgac gggggggtat aaaaggggggt ggggggcgcgc tcgtcgtcac tctcttccgc  6120
atcgctgtct gcgagggcca gctgctgggg tgagtattcc ctctcgaagg cgggcatgac   6180
ctccgcgctg aggtgtcag tttccaaaaa cgaggaggat ttgatgttca cctgtcccga   6240
ggtgataccct ttgagggtac ccgcgtccat ctggtcagaa aacacgatct tttttattgtc  6300
cagcttggtg gcgaacgacc cgtagagggc gttggagagc agctggcga tggagcgcag   6360
ggtctggttc ttgtccctgt cggcgcgctc cttggccgcg atgttgagct gcacgtactc   6420
gcgcgcgacg cagcgccact cggggaagac ggtggtgcgc tcgtcgggca ccaggcgcac   6480
gcgcagccg cggttgtgca gggtgaccag gtccacgctg tggcgacct cgccgcgcag    6540
gcgctcgttg gtccagcaga gacgccgcc cttgcgcag cagaaggggg gcaggggcgc     6600
gagctggtc tcgtccgggg ggtccgcgtc cacggtgaaa acccggggc caggcgcgc      6660
gtcgaagtag tctatcttgc aaccttgcat gtccagcgcc tgctgccagt cgcgggcggc   6720
gagcgcgcgc tcgtagggggt tgagcggcgg gccccagggc atgggtggg tgagtgcgga   6780
ggcgtacatg ccgcagatgt catagacgta gaggggctcc cgcaggaccc cgatgtaggt   6840
ggggtagcag cggccgccgc ggatgctggc gcgcacgtag tcatacagct cgtgcgaggg   6900
```

```
ggcgaggagg tcggggccca ggttggtgcg ggcggggcgc tccgcgcgga agacgatctg   6960
cctgaagatg gcatgcgagt tggaagagat ggtggggcgc tggaagacgt tgaagctggc   7020
gtcctgcagg ccgacggcgt cgcgcacgaa ggaggcgtag gagtcgcgca gcttgtgtac   7080
cagctcggcg gtgacctgca cgtcgagcgc gcagtagtcg agggtctcgc ggatgatgtc   7140
atatttagcc tgcccttct tttccacag ctcgcggttg aggacaaact cttcgcggtc    7200
tttccagtac tcttggatcg ggaaaccgtc cggttccgaa cggtaagagc ctagcatgta   7260
gaactggttg acggcctggt aggcgcagca gcccttctcc acggggaggg cgtaggcctg   7320
cgcggccttg cggagcgagg tgtgggtcag ggcgaaggtg tccctgacca tgactttgag   7380
gtactggtgc ttgaagtcgg agtcgtcgca gccgccccgc tcccagagcg agaagtcggt   7440
gcgcttcttg gagcggggt tgggcagagc gaaggtgaca tcgttgaaga ggattttgcc    7500
cgcgcggggc atgaagttgc gggtgatgcg gaagggcccc ggcacttcag agcggttgtt   7560
gatgacctgg gcgcgagca cgatctcgtc gaagccgttg atgttgtggc ccacgatgta    7620
gagttccagg aagcggggcc ggcccttac ggtgggcagc ttctttagct cttcgtaggt    7680
gagctcctcg ggcgaggcga ggccgtgctc ggccagggcc cagtccgcga ggtgcgggtt   7740
gtctctgagg aaggacttcc agaggtcgcg ggccaggagg gtctgcaggc ggtctctgaa   7800
ggtcctgaac tggcggccca cggccatttt tcgggggtg atgcagtaga aggtgagggg    7860
gtcttgctgc cagcggtccc agtcgagctg cagggcgagg tcgcgcgcgg cggtgaccag   7920
gcgctcgtcg cccccgaatt tcatgaccag catgaaggcc acgagctgct ttccgaaggc   7980
ccccatccaa gtgtaggtct ctacatcgta ggtgacaaag aggcgctccg tgcgaggatg   8040
cgagccgatc gggaagaact ggatctcccg ccaccagttg gaggagtggc tgttgatgtg   8100
gtggaagtag aagtcccgtc gccgggccga acactcgtgc tggcttttgt aaaagcgagc   8160
gcagtactgg cagcgctgca cgggcgtac ctcatgcacg agatgcacct ttcgcccgcg   8220
cacgaggaag ccgaggggaa atctgagccc cccgcctggc tcgcggcatg gctggttctc   8280
ttctactttg gatgcgtgtc cgtctccgtc tggctcctcg aggggtgtta cggtggagcg   8340
gaccaccacg ccgcgcgagc cgcaggtcca gatatcggcg cgcggcggtc ggagtttgat   8400
gacgacatcg cgcagctggg agctgtccat ggtctggagc tcccgcgtgg gccaggtc    8460
agccgggagt tcttgcaggt tcacctcgca gagtcgggcc agggcgcggg gcaggctag    8520
gtggtacctg atctctaggg gcgtgttggt ggcggcgtcg atggcttgca ggagcccgca   8580
gccccggggg gcgacgacgg tgccccgcgg ggtggtggtg gtggtggcgg tgcagctcag   8640
aagcggtgcc gcgggcgggc cccggaggt agggggggct ccggtcccgc gggcaggggc   8700
ggcagcggca cgtcggcgtg gagcgcgggc aggagttggt gctgtgcccg gaggttgctg   8760
gcgaaggcga cgacgcggcg gttgatctcc tggatctggc gcctctgcgt gaagacgacg   8820
ggcccggtga gcttgaacct gaaagagagt tcgacagaat caatctcggt gtcattgacc   8880
gcggcctggc gcaggatctc ctgcacgtct cccgagttgt cttggtaggc gatctcggcc   8940
atgaactgct cgatctcttc ctcctgagg tctccgcgtc cggcgcgttc cacggtggcc   9000
gccaggtcgt tggagatgcg cccatgagc tgcgagaagg cgttgagtcc gccctcgttc    9060
cagactcggc tgtagaccac gccccctgg tcatcgcggg cgcgcatgac cacctgcgcg    9120
aggttgagct ccacgtgccg cgcgaagacg gcgtagttgc gcagacgctg gaagaggtag   9180
ttgagggtgg tggcggtgtg ctcggccacg aagaagttca tgacccagcg gcgcaacgtg   9240
gattcgttga tgtcccccaa ggcctccagc cgttccatgg cctcgtagaa gtccacggcg   9300
aagttgaaaa actgggagtt gcgcgccgac acgtcaact cctcctccag aagacggatg    9360
agctcggcga cggtgtcgcg cacctcgcgc tcgaaggcta tggggatctc ttcctccgct   9420
agcatcacca cctcctcctc ttcctcct tctggcactt ccatgatgcc ttcctcctct     9480
tcggggggtg gcgcggcgg cggtggggga ggggcgctc tgccgccgcg gcggcgcacc     9540
gggaggcggt ccacgaagcg cgcgatcatc tccccgcggc ggcggcgcat ggtctcggtg   9600
acggcgcggc cgttctcccg ggggcgcagt tggaagacgc cgccggacat ctggtgctgg   9660
ggcggggtgg ccgtgaggcag cgagacggcg ctgacgatgc atctcaacaa ttgctgcgta   9720
ggtacgccgc cgagggacct gagggagtcc atatccaccg gatccgaaaa cctttcgagg   9780
aaggcgtcta accagtcgca gtcgcaaggt aggctgagca ccgtggcggg cggcggggg    9840
tggggggagt gtctggcgga ggtgctgctg atgatgtaat tgaagtaggc ggacttgaca   9900
cggcggatgg tcgacaggag caccatgtcc ttgggtccgg cctgctggat ggcggaggcgg   9960
tcggctatgc cccaggcttc gttctggcat cggcgcaggg ccttgtagta gtcttgcatg  10020
agcctttcca ccggcacctc ttctccttcc tcttctgctt cttccatgtc tgcttcggcc  10080
ctggggcggg gccgcgcccc cctgccccc atgcgcgtga ccccgaaccc cctgagcggt  10140
tggagcaggg ccaggtcggc gacgacgcgc tcggccagga tggcctgctg cacctgcctg  10200
aggtggttt ggaagtcatc caagtccacg aagcggtggt aggcgccgt gttgatggtg     10260
taggtggcagt tggccatgac ggaccagttg acggtctggt ggcccggttg cgacatctcg  10320
gtgtacctga gtcgcgagta ggcgcgggag tcgaagacgt agtcgttgca agtccgcacc   10380
aggtactggt agcccaccag gaagtgcggc ggcggctggc ggtagagggg ccagcgcagg   10440
gtgcggggga ctccggggcg caggtcttcc agcatgaggc ggtggtaggc gtagatgtac   10500
ctggacatcc aggtgatacc cgcggcggtg gtggaggcg gcgggaagtc gcgcacccgg    10560
ttccagatgt tgcgcagggg cagaaagtgc tccatggtag gcgtgctctg tccagtcaga   10620
cgcgcgcagt cgttgatact ctagaccagg gaaaacgaaa gccggtcagc gggcactctt   10680
ccgtggtctg gtgaatagat cgcaaggta tcatgcgag ggcctcggtt tcgagcccg      10740
ggtccgggcc ggacggtccg ccatgatcca cgcggttacc gcccgcgtgt cgaacccagg   10800
tgtgcgacgt cagacaacgg tggagtgttc cttttggcgt ttttctgcc gggcgccggc    10860
gccgcgtaag agactaagcc gcgaaagcga agcagtaag tggctcgctc cccgtagccg    10920
gagggatcct tgctaagggt tgcgttgcgg cgaacccgtc ttcgaatccc gtactcgggc  10980
cggccgaacc cgcggctaag gtgttggatt ggcctcccc tcgtataaag accccgctg    11040
cggattgact ccggacacgg ggacgagccc cttttatttt tgctttcccc agatgcatcc  11100
ggtgctgcgg cagatgcgcc ccccgcccca gcagcagcaa caacaccagc aagagcggca  11160
gcaacagcag cgggagtcat gcagggcccc ctcacccacc ctcggcgggc cggccacctc  11220
ggcgtccgcg gccgtgtctg gcgcctgcgg cggcggcggg gggccggctg acgaccccga  11280
gggaccccgg cggcgcgggg ccagacacta cctggacctg gagggaggcg agggcctggc  11340
gcggctgggg gcgccgtctc ccgagcgcca cccgcgggtg cagctgaagc gcgactcgcg  11400
cgaggcgtac gtgcctcggc agaacctgtt cagggaccgc gcgggcgagg agcccgagga  11460
gatgcgggac aggaggttca gcgcagggcg ggagctgcgg caggggctga accgcgagcg  11520
gctgctgcgc gaggaggact ttgagcccga cgcgcggacg ggatcagcc ccgcgcgcgc   11580
gcacgtggcg gccgccgacc tggtgacggc gtacgagcag acggtgaacc aggagatcaa  11640
```

```
cttccaaaag agtttcaaca accacgtgcg cacgctggtg gcgcgcgagg aggtgaccat  11700
cgggctgatg cacctgtggg actttgtaag cgcgctggtg cagaacccca acagcaagcc  11760
tctgacggcg cagctgttcc tgatagtgca gcacagcagg gacaacgagg cgtttaggga  11820
cgcgctgctg aacatcaccg agcccgaggg tcggtggctg ctggacctga ttaacatcct  11880
gcagagcata gtggtgcagg agcgcagcct gagcctggcc gacaaggtgg cggccatcaa  11940
ctactcgatg ctgagcctgg gcaagtttta cgcgcgcaag atctaccaga cgccgtacgt  12000
gcccatagac aaggaggtga agatcgacgg ttttacatg cgcatggcgc tgaaggtgct  12060
caccctgagc gacgacctgg gcgtgtaccg caacgagcgc atccacaagg ccgtgagcgt  12120
gagccggcgc cgcgagctga gcgaccgcga gctgatgcac agcctgcagc gggcgctggc  12180
gggcgccggc agcgcgcgaca gggaggcgga gtcctacttc gatgcggggg cggacctgcg  12240
ctgggcgccc agccggcggg ccctggaggc cgcgggggtc cgcgaggact atgacgagga  12300
cggcgaggag gatgaggagt acgagctaga ggagggcgag tacctggact aaaccgcggg  12360
tggtgtttcc ggtagatgca agacccgaac gtggtggacc cggcgctgcg ggcggctctg  12420
cagagccagc cgtccggcct taactcctca gacgactggc gacaggtcat ggaccgcatc  12480
atgtcgctga cggcgcgtaa cccgacgcg ttccggcagc agccgcaggc caacaggctc  12540
tccgccatcc tggaggcggt ggtgcctgcg cgctcgaacc ccacgcacga gaaggtgctg  12600
gccatagtga acgcgctggc cgagaacagg gccatccgcc cggacgaggc cgggctggtg  12660
tacgacgcgc tgctgcagcg cgtggcccgc tacaacagcg gcaacgtgca gccaacctg  12720
gaccggctgg tggggacgt gcgcgaggcg gtgcgcagc gcgagcgcgc ggatcggcag  12780
ggcaacctgg gctccatggt ggcgctgaat gccttcctga gcacgcagcc ggccaacgtg  12840
ccgcgggggc aggaagacta caccaacttt gtgagcgcgc tgcggctgat ggtgaccgag  12900
accccccaga gcgaggtgta ccagtcgggc ccggactact tcttccagac cagcagacag  12960
ggcctgcaga cggtgaacct gagccaggct ttcaagaacc tgcgggggct gtggggcgtg  13020
aaggcgccca ccggcgaccg ggcgacggtg tccagcctgc tgacgcccaa ctcgcgcctg  13080
ctgctgctgc tgatcgcgcc gttcacggac agcggcagcg tgtcccggga cacctacctg  13140
gggcacctgc tgaccctgta ccgcgaggcc atcgggacgg cgcaggtgga cgagcacacc  13200
ttccaggaga tcaccagcgt gagccgcgcg ctggggcagg aggacacgag cagcctggag  13260
gcgactctga actacctgct gaccaaccgg cggcagaaga ttccctcgct gcacagcctg  13320
acctccgagg aggagcgcat cttgcgctac gtgcagcaga gcgtgagcct gaacctgatg  13380
cgcgacgggg tgacgcccag cgtggcgctg gacatgacgg cgcgcaacat ggaaccgggc  13440
atgtacgccg cgcaccggcc ttacatcaac cgcctgatgg actacctgca tcgcgcagg  13500
gccgtgaacc ccgagtactt taccaacgcc atcctgaacc cgcactggct cccgccgccc  13560
gggttctaca gcggggcttc gaggtcccg gagaccaacg atggcttcct gtgggacgac  13620
atggcacgca gcgtgttctc cccgcggccg caggcgctgg cggaagcgtc cctgctgcgt  13680
cccaagaagg aggaggagga ggaggcgagt gcgcgcccgg gcagcagcgg cgtggcttct  13740
ctgtccgagc tgggggcggc agccgccgcg cgccccgggt ccctgggcgg cagcccctt  13800
ccgagcctgc tgggtctct gcacagcgag cgcaccaccc gccctcggct gctgggcgag  13860
gacgagtacc tgaataactc cctgctgcag ccggtgcggg agaaaaacct gcctcccgcc  13920
ttcccaaca acgggatagg agcctggtg gacaagatga gcagatggaa gacctatgcg  13980
caggagcaca gggacgcgcc tgcgctccgg ccgcccacgc ggcgccagcg ccacgaccgg  14040
cagcgggggc tggtgtggga tgacgaggac tccgcggacg atagcagcgt gctgacctgg  14100
ggaggagcgc gcaacccgtt cgcgcacctg cgcccccgcc tggggaggat gttttaaaaa  14160
aaaaaaaaaa aagcaagaag catgatgcaa aaattaaata aaactcacca aggccatggc  14220
gaccgagcgt tggttcttg tgttcccttc agtatgcggc gcgcggcgat gtaccaggag  14280
ggacctcctc cctcttacga gagcgtggtg ggcgcggcgg cggcggcgcc ctcttctccc  14340
tttgcgtcgc agctgctgga gccgccgtac gtgcctccgc gctacctgcg gcctacgggg  14400
gggagaaaca gcatcgtta ctcggacctg gcgccccctgt tcgacaccac ccgggtgtac  14460
ctggtggaca acaagtcggc ggacgtggcc tccctgaact accagaacga ccacagcaat  14520
tttttgacca cggtcatcca gaacaatgac tacagcccga gcgaggccag cacccagacc  14580
atcaatctga tgaccggtc gcactgggc ggcgacctga aaaccatcct gcacaccaac  14640
atgccaacg tgaacgagtt catgttcacc aataagttca aggcgcggt gatggtgtc  14700
cgctcgcaca ccaaggaaga ccgggtggag ctgaagtacg agtgggtgga gttcgagctg  14760
ccagagggca actactccga gaccatgacc attgacctga tgaacaacgc gatcgtggag  14820
cactatctga aagtgggcag gcagaacggg gtcctggaga gcgacatcgg ggtcaagttc  14880
gacaccagga acttccgcct ggggctggc cccgtgaccg gctggttat gccggggtg  14940
tacaccaacg aggccttcca tcccgacatc atcctgctgc ccggctgcgg ggtggacttc  15000
acttacagcc gcctgagcaa cctcctgggc atccgcaagc ggcagccctt ccaggagggc  15060
ttcaggatca cctacgagga cctggagggg ggcaacatcc ccgcgctcct cgatgtggag  15120
gcctaccagg atagcttgaa ggaaaatgag gcggacagg aggataccgc ccccgccgcc  15180
tccgccgccc ccgagcaggg cgaggatgct gctgacaccg cggccg cgcgag cggggcagag  15240
gccgacccg ctatggtggt ggaggctccc gagcagcagg aggacatgaa tgacagtgcg  15300
gtgcgcggag acaccttcgt cacccggggg gaggaaaagc aagcggaggc cgaggccgcg  15360
gccgaggaaa agcaactggc ggcagcagcg gcggcggcgg cgttggccgc ggcggaggct  15420
gagtctgagg ggaccaagcc cgccaaggag ccgtgatta agccctgac agcagatagc  15480
aagaagcgca gttacaacct gctcaaggac agcaccaaca ccgcgtaccg cagctggtac  15540
ctggcctaca actacggcga cccgtcgacg ggggtgcgct cctggaccct gctgtgcacg  15600
ccggacgtga cctgcggctc ggagcaggtg tactggtcgc tgcccgacat gatgcaagac  15660
cccgtgacct tccgctccac gcggcaggtc agcaacttcc cggtggtggg cgccgagctg  15720
ctgcccgtga actccaagag cttctacaac gaccaggcg tctactccca gctcatccgc  15780
cagttcacct ctctgaccca cgtgttcaat cgctttcctg agaaccagat tctggcgcgc  15840
ccgccgccc ccaccatcac caccgtcagt gaaaacgttc ctgctctcac agatcacggg  15900
acgctaccgc tgcgcaacag catcggagga gtccagcgag tgaccgttac tgacgccaga  15960
cgccgcacct gccctacgt ttacaaggcc ttgggcatag tctcgccgcg cgtcctttcc  16020
agcccgcactt ttgagcaac accaccatca tgtccatcct gatctcaccc agcaataact  16080
ccggctgggg actgctgcgc gcgcccagca agatgttcgg aggggcgagg aagcgttccg  16140
agcagcaccc cgtgcgcgtg cgcgggcact tccgcgcccc ctggggagcg cacaaacgcg  16200
gccgcgcggg gcgcaccacc gtggacgacg ccatcgactc ggtggtggag caggcgcgca  16260
actacaggc cgcggtctct accgtggacg cggccatcca gaccgtggtg cggggcgcgc  16320
ggcggtacgc caagctgaag agccgccgga agcgcgtggc ccgccgccac cgccgccgac  16380
```

```
ccggggccgc cgccaaacgc gccgccgcgg ccctgcttcg ccgggccaag cgcacgggcc   16440
gccgcgccgc catgagggcc gcgcgccgct tggccgccgg catcaccgcc gccaccatgg   16500
cccccccgtac ccgaagacgc gcggccgccg ccgccgccgc cgccatcagt gacatggcca  16560
gcaggcgccg gggcaacgtg tactgggtgc gcgactcggt gaccggcacg cgcgtgcccg   16620
tgcgcttccg ccccccgcgg acttgagatg atgtgaaaaa acaacactga gtctcctgct   16680
gttgtgtgta tcccagcggc ggcggcgcgc gcagcgtcat gtccaagcgc aaaatcaaag   16740
aagagatgct ccaggtcgtc gcgccggaga tctatgggcc cccgaagaag gaagagcagg   16800
attcgaagcc ccgcaagata aagcgggtca aaaagaaaaa gaaagatgat gacgatgccg   16860
atggggaggt ggagttcctg cgcgcccacg cgccaggcg ccggtgcag tggaagggcc     16920
ggcgcgtaaa gcgcgtcctg cgccccggca ccgcggtggt cttcacgccc ggcgagcgct   16980
ccacccggac tttcaagcgc gtctatgacg aggtgtacgg cgacgaagac ctgctggagc   17040
aggccaacga gcgcttcgga gagtttgctt acgggaagcg tcagcgggcg ctggggaagg   17100
aggacctgct ggcgctgccg ctggaccagg gcaaccccac ccccagtctg aagcccgtga   17160
ccctgcaagca ggtgctgccg agcagcgcac cctccgaggc gggcgtgcct ctgaagcgcg   17220
agggcggcga cctggcgccc accgtgcagc tcatggtgcc caagcggcag aggctggagg   17280
atgtgctgga gaaaatgaaa gtagacccct gtctgcagcc ggacatcagg gtccgcccca   17340
tcaagcaggt ggcgccgggc ctcggcgtgc agaccgtgga cgtggtcatc cccaccggca   17400
actcccccgc cgccgccacc actaccgctg cctccacgga catggagaca cagaccgatc   17460
ccgccgcagc cgcagccgca ccgccgccg cgacctcctc ggcggaggtg cagacggacc    17520
cctggctgcc gccggcgatg tcagctcccc gcgcgcgtcg cgggcgcagg aagtacggcg   17580
ccgccaacgc gctcctgccc gagtacgcct tgcatccttc catcgcgccc accccggct    17640
accgaggcta tacctaccgc ccgcgaagag ccaagggttc caccgccgt cctgccccgac   17700
gcgccgccgc caccaccccg cgccgccgcc gcagacgcca gcccgcactg gctccagtcct  17760
ccgtgaggaa agtggcgcgc gacggacaca ccctggtgct gccccagggcg cgctaccacc   17820
ccagcatcgt ttaaaagcct gttgtggttc ttgcagatat ggcctcact tgccgcctcc   17880
gtttcccggt gccgggatac cgaggaggaa gatcgccgg caggaggggt ctggccggga     17940
gcggcctgag cggaggcagc cgccgcgcgc accgcggcg acgccacc agccgacga       18000
tgcgcggcgg ggtgctgccc ctgttaatcc ccctgatcgc cgcggcgatc ggccgcgtgc   18060
ccgggatcgc ctccgtggcc ttgcaagcgt cccagaggca ttgacagact tgcaaacttg   18120
caaatatgga aaaaaaaacc ccaataaaaa agtctagatc ctcacgctcg cttggtcctg   18180
tgactatttt gtagaatgga agacatcaac tttgcgtcgc tggccccgcg tcacggctca   18240
cgcccgttcc tgggacactg gaacgatatc ggcaccagca acatgagcgg tggcgccttc   18300
agttgggggct ctctgtggag cggcattaaa agtatcgggt ctgccgttaa aaattacggc   18360
tccgggcct ggaacagcag cacgggccag atgttgagag acaagttgaa agagcagaac   18420
ttccagcaga aggtggtgga gggcctggcc tccggcatca acggggtggt ggacctggcc   18480
aaccaggccc tgcagaataa gatcaacagc agactggacc cccgccgcc ggtgaggag    18540
gtgccgccgc cgctggagac ggtgtccccc gatgggcgtg gcgagaagcg cccgcggccc   18600
gatagggaag agaccactct ggtcacgcag accgatgagc cgcccccgta tgaggaggcc   18660
ctgaagcaag gtctgcccac cacgcgggcc atcgcgccca tggccaccgg ggtggtgggc   18720
cgccacaccc ccgccacgct ggacttgcct ccgcccgccg atgtgccgca gcagcagaag   18780
gcggcacagc cgggccgcc cgcgaccgcc tcccgttcct ccgccggtcc tctgcgccgc    18840
gcggccagcg gcccccgcgg ggggtcgcg aggcacggca actggcagag cacgctgaac    18900
agcatcgtgg gtctggggt gcgtccgtg aagcgccgcc gatgctactg aatagcttag    18960
ctaacgtgtt gtatgtgtgt atgcgcccta tgtcgccgcc agaggagctg ctgagtcgcc   19020
gccgttcgcg cgccaccac caccgccact ccgcccctca agatggcgac cccatcgatg    19080
atgccgcagt ggtcgtacat gcacatctcg ggccaggacg cctcggagta cctgagcccc   19140
gggctgtgc agttcgcccg gccaccgag agctactcca gcctgagtaa caagtttagg    19200
aaccccacgg tggcgcccac gcacgatgtg accaccgacc ggtctcagcg cctgacgctg   19260
cggttcattc ccgtgaccg cgaggacacc gcgtactcgt acaaggcgcg gttcacccctg   19320
gccgtgggcg acaaccgcgt gctggacatg gcctccacct actttgacat ccgcggggtg   19380
ctggaccagg gtcccacttt caagcccctac tctggcacg cctacaactc cctggcccc    19440
aagggcgctc ccaactcctg cgagtgggag caagaggaaa ctcaggcagt gaagaagca    19500
gcagaagagg aagaagaaga tgctgacggt caagctgagg aagagcaagc agctaccaaa   19560
aagactcatg tatatgctca ggctcccctt tctggcaaaa aaattagtaa agatggtctg   19620
caaataggaa cggacgctac agctacagaa caaaaaccta tttatgcga ccctacattc     19680
cagcccgaac cccaaatcgg ggagtccag tggaatgagg cagatgctac agtcgccggc     19740
ggtagagtgc taaagaaatc tactcccatg aaaccatgct atggttccta tgcaagaccc   19800
acaaatgcta atggaggtca gggtgtacta acggcaaatg cccagggaca gctagaatct   19860
caggttgaaa tgcaattctt ttcaacttct gaaaacgccc gtaacgaggc taacaacatt   19920
cagcccaaat tggtgctgta tagtgaggat gtgcacatgg agaccccgga tacgcacctt   19980
tcttacaagc ccgcaaaaag cgatgacaat tcaaaaatca tgctgggtca gcagtccatg   20040
cccaacagac ctaattacat cggcttcaga gacaacttta tcggcctcat gtattacaat   20100
agcactggca acatgggagt gcttgcaggt caggcctctc agttgaatgc agtggtggac   20160
ttgcaagaca gaaacacaga actgtcctac cagctcttgc ttgattccat gggtgacaga   20220
accagatact tttccatgtg gaatcaggca gtgacagtt atgacccaga tgttagaatt   20280
attgaaaatc atgaactga agacgagctc cccaactatt gtttccctct gggtggcata   20340
ggggtaactg acacttacca ggctgttaaa accaacaatg caataacgg ggccaggtg    20400
acttggacaa aagatgaaac ttttgcagat cgcaagtgaa taggggtggg aaacaattttc  20460
gctatggaga tcaacctcag tgccaacctg tggagaaact tcctgtactc caacgtgcg    20520
ctgtacctac cagacaagct taagtacaac ccctccaatg tggacatctc tgacaaccc    20580
aacacctacg attacatgaa caagcgagtg gtggccccgg ggctggtgga ctgctacatc   20640
aacctgggcg cgcgctggtc gctggactac atggacaacg tcaacccctt caaccaccac   20700
cgcaatgcg gcctgcgcta ccgctccatg ctcctgggca cgggcgcta cgtgccccttc   20760
cacatccagg tgcccagaa gttctttgcc atcaagaacc tcctcctcct gccgggctcc   20820
tacacctacg agtggaactt caggaaggat gtcaacatgg tcctccagag ctctctgggt   20880
aacgatctca gggtggacgg ggccagcatc aagttcgaga gcatctgcct ctacgccacc   20940
ttcttcccca tggcccacaa cacggcctcc acgctcgagg ccatgctcag gaacgacacc   21000
aacgaccagt ccttcaatga ctacctctcc gccgccaaca tgctctaccc catacccgcc   21060
aacgccacca acgtccccat ctccatcccc tcgcgcaact gggcggcctt ccgcggctgg   21120
```

```
gccttcaccc gcctcaagac caaggagacc ccctccctgg gctcgggatt cgaccoctac  21180
tacacctact cgggctccat tcctacctg gacggcacct tctacctcaa ccacactttc  21240
aagaaggtct cggtcacctt cgactcctcg gtcagctggc cgggcaacga ccgtctgctc  21300
accccaacg agttcgagat caagcgctcg gtcgacgggg agggctacaa cgtggcccag  21360
tgcaacatga ccaaggactg gttcctggtc cagatgctgg ccaactacaa catcggctac  21420
cagggcttct acatcccaga gagctacaag gacaggatgt actccttctt caggaacttc  21480
cagcccatga gccggcaggt ggtggaccag accaagtaca aggactacca ggaggtgggc  21540
atcatccacc agcacaacaa ctcgggcttc gtgggctacc tcgcccccac catgcgcgag  21600
ggacaggcct accccgccaa cttccctat ccgctcatag gcaagaccgc ggtcgacagc  21660
atcacccaga aaaagttcct ctgcgaccgc accctctggc gcatcccctt ctccagcaac  21720
ttcatgtcca tgggtgcgct ctcggacctg ggcagaact tgctctacgc caactccgcc  21780
cacgccctcg acatgacctt cgaggtcgac cccatggacg agcccaccct tctctatgtt  21840
ctgttcgaag tctttgacgt ggtccgggtc caccagccgc accgcggcgt catcgagacc  21900
gtgtacctgc gtacgccctt ctcggccggc aacgccacca cctaaagaag caagccgcag  21960
tcatcgccgc ctgcatgccg tcgggttcca ccgagcaaga gctcagggcc atcgtcagag  22020
acctgggatg cgggccctat ttttggca ccttcgacaa gcgcttccct ggctttgtct  22080
ccccacacaa gctggcctgc gccatcgtca acacggccgg ccgcgagacc ggggcgtgc  22140
actggctggc cttcgctgg aacccgcgct ccaaaacatg cttcctcttt gacccctcg  22200
gcttttcgga ccagcggctc aagcaaatct acgagttcga gtacgagggc ttgctgcgtc  22260
gcagcgccat cgcctcctcg cccgaccgct cgtcaccct cgaaaagtcc acccagaccg  22320
tgcagggcc cgactcggcc gcctgcgtc tcttctgctg catgtttctg cacgcctttg  22380
tgcactggcc tcagagtccc atggaccgca acccaccat gaacttcgtc acggggtcg  22440
ccaactccat gctccagagc ccccaggtcg agccccacct cgccgcaac caggagcagc  22500
tctacagctt cctggagcgc cactcgcctt acttccgccg ccacagcgca cagatcagga  22560
gggccacctc cttctgccac ttgcaagaga tgcaagaagg gtaataacga tgtacacact  22620
tttttctca ataaatgcca tcttttatt tatacacgct ctctggggta ttcatttccc  22680
accaccaccc gccgttgtcg ccatctggct ctatttagaa atcgaaaggg ttctgccggg  22740
agtcgccgtg cgccacggcc agggacacgt tgcgatactg gtagcgggtg ccccacttga  22800
actcgggcac caccaggcga ggcagctcgg ggaagttttc gctccacagg ctgcgggtca  22860
gcaccagcgc gttcatcagg tcgggcgccg agatcttgaa gtcgcagttg gggccgccg  22920
cctgcgcgcg cgagttgcgg tacaccgggt tgcagcactg gaacaccaac agcgccgggt  22980
gcttcacgct ggccagcacg ctgccggtcgg agatcagctc ggcgtccagg tcctccgcgt  23040
tgctcagcgc gaacgggtc atcttgggca cttgccgccc caggaaggc gcgtgccccg  23100
gtttcgagtt gcagtcgcag cgcagcggga tcagcaggtg cccgtgatccg gactcggcgt  23160
tgggggtacag cgccgccatg aaggcctgca tctgccgaca gccatctgg gccttgccgc  23220
cctccgagaa gaacatgccg caggacttgc ccgagaactg gtttgcgggg cagctggcgt  23280
cgtgcaggca gcagcgcgcg tcggtgttgg cgatctgcac cacgttgcgc ccccaccggt  23340
tcttcacgat cttggccttg gacgattgct ccttcagcgc gcgctgcccg ttctcgctgg  23400
tcacatccat ctcgatcaca tgttccttgt tcaccatgct gctgccgtgc agcacttca  23460
gctcgccctc cgtctcggtg cagcggtgct gccacagcgc gcagcccgtg ggctcgaaag  23520
acttgtaggt cacctccgcg aaggactgca ggtaccctg caaaaagcgg cccatcatgg  23580
tcacgaaggt cttgttgctg ctgaaggtca gctgcagccc gcggtgctcc tcgttcagcc  23640
aggtcttgca caggccgcc agcgcctcca cctggtcggg cagcatcttg aagttcacct  23700
tcagctcatt ctccacgtgg tacttgtcca tcagcgtgcg cgccgcctcc atgcccttct  23760
cccaggccga ccaccagcgg aggctcacgg ggttcttcac catcaccgtg gccgccgcct  23820
ccgccgcgct ttcgctttcc gccccgctgt tctcttcctc ttcctcctct tcctcgccgc  23880
cgcccactcg cagcccccgc accacggggt cgtcttcctg caggcgctgc acctttgcgct  23940
tgccgttgcg ccctgcttg atgcgcacgg gcgggttgct gaagcccacc atcaccagcg  24000
cggcctcttc ttgctcgtcc tcgctgtcca gaatgacctc cggggagggg gggttggtca  24060
tcctcagtac cgaggcacgc ttcttttct tcctgggggc gttcgccagc tccgcggctg  24120
cggccgctgc cgaggtcgaa ggccgagggc tgggcgtgcg cggcaccagc gcgtcctgcg  24180
agccgtcctc gtcctcctcg gactcgagac ggaggcgggc ccgcttcttc ggggcgcgc  24240
ggggcggcgg aggcggcggc ggcgacgag acggggacga gacatcgtcc agggtgggtg  24300
gacggcgggc cgcgccgcgt ccgcgctcgg gggtggtctc gcgctggtcc tcttcccgac  24360
tggccatctc ccactgctcc ttctcctata ggcagaaaga gatcatggag tctctcatgc  24420
gagtcgagaa ggaggaggac agcctaaccg cccccctga gccctccacc accgccgcca  24480
ccaccgccaa tgccgccgcg gacgacgcgc ccaccgagac cacgccagt accaccctcc  24540
ccagcgacgc accccgctc gagaatgaag tgctgatcga gcaggacccg ggttttgtga  24600
gcggagagga ggatgaggtg gatgagaagg agaaggagga ggtcgccgcc tcagtgccaa  24660
aagaggataa aaagcaagac caggacgacg cagataaga tgagacgacg gtcgggcggg  24720
ggaacgaaag ccatgatgct gatgacggct acctagacgt ggggagacgac gtgctgctta  24780
agcacctgca ccgccagtgc gtcatcgtct gcgacgcgct gcaggagcgc tgcgaagtgc  24840
ccctggacgt ggcggaggtc agccgcgcct acgagcggca cctcttcgcg ccgcacgtgc  24900
cccccaagcg ccgggaaac ggtcacctgcg agcccaaccc ggtctcaac ttctacccg  24960
tcttcgcggt acccgaggtg ctggccacct accacatctt tttccaaaac tgcaagatcc  25020
ccctctcctg ccgcgccaac cgcacccgcg ccgacaaaac cctgacccta cggcagggcg  25080
cccacatacc tgtatcgcc tctctggagg aagtgcccaa gatcttcgag ggtctcggtc  25140
gcgacgagaa acgggcggcg aacgctctgc acggagacag cgaaaacgag agtcactcgg  25200
gggtgctggt ggagctcgag ggagacaacg cgcgctggc cgtactcaag cgcagcatag  25260
aggtcaccca ctttgcctac ccggcgctca acctgcccc caaggtcatg agtgtggtca  25320
tgggcgagct catcatgcgc cgccgccagc ccctggccgc ggatgcaaac ttgcaagagt  25380
cctccgagga aggcctgccc gcggtcagcg acagcagct ggcgcgctgg ctggagaccc  25440
gcgacccgc cagctggag gagcggcgca agctcatgat ggccgcggtg ctggtcaccg  25500
tggagctcga gtgtctgcag cgcttcttcg cggaccccgga gaagccggaa agcgctggag  25560
agacctgca ctacaccttc cgccaggct acgtgcgcca ggcctgcaag atctccaacg  25620
tggagctctg caacctggtc tcctacctgg gcatcctgca cgagaaccgc ctcgggcaga  25680
acgtcctgca ctccacccte aaggggagg cgcgcgcga ctacatccgc gactgcgcct  25740
acctcttcct ctgctacacc tggcagacgg ccatggggt ctggcagcag tgcctggagg  25800
agcgcaacct caaggagctg gaaaagctcc tcaagcgcac cctcagggac ctctggacgg  25860
```

```
gcttcaacga gcgctcggtg gccgccgcgc tggcggacat catctttccc gagcgcctgc   25920
tcaagaccct gcagcagggc ctgcccgact tcaccagcca gagcatgctg cagaacttca   25980
ggactttcat cctggagcgc tcgggcatcc tgccggccac ttgctgcgcg ctgcccagcg   26040
acttcgtgcc catcaagtac agggagtgcc cgccgccgct ctggggccac tgctacctct   26100
tccagctggc caactacctc gcctaccact cggacctact ggaagacgtg acgggcgagg   26160
gcctgctcga gtgccactgc cgctgcaacc tctgcacgcc ccaccgctct ctagtctgca   26220
acccgcagct gctcagcgag agtcagatta tcggtacctt cgagctgcag ggtccctcgc   26280
ctgacgagaa gtccgcggct ccagggctga aactcactcc ggggctgtgg acttccgcct   26340
acctacgcaa atttgtacct gaggactacc acgcccacga gatcaggttc tacgaagacc   26400
aatcccgccc gcccaaggcg gagctcaccg cctgcgtcat cacccagggg cacatcctgg   26460
gccaattgca agccatcaac aaagcccgcc gagagttctt gctgaaaaag ggtcgggggg   26520
tgtacctgga ccccccagtcc ggcgaggagc taaacccgct accccgccg ccgcccagc   26580
agcgggacct tgcttcccag gatggcaccc agaaagaagc agcagccgcc gccgccgccg   26640
cagccataca tgcttctgga ggaagaggag gaggactggg acagtcaggc aggcgaggtt   26700
tcggacgagg agcaggagga gatgatgaaa gactgggagg aggacagcag cctagacgag   26760
gaagcttcag aggccgaaga ggtggcagac gcaacaccat cgcccctcggt cgcagccccc   26820
tcgccggggc ccctgaaatc ctccgaaccc agcaccagcg ctataacctc cgctcctccg   26880
gcgccgggcg cacccgcccg cagacccaac cgtagatggg acaccacgga aaccgggggtc   26940
ggtaagtcca agtgcccgcc gccgccaccg cagcagcagc agcagcagcg ccagggctac   27000
cgctcgtggc gcgggcacaa gaacgccata gtcgcctgct tgcaagactg cggggggcaac   27060
atctcttttcg cccgccgctt cctgctattc caccacgggg tcgcctttcc ccgcaatgtc   27120
ctgcattact accgtcatct ctacagcccc tactgcagcg cgacccaga ggcgcgagtc   27180
gcagccacag cggcgaccac cacctaggaa gatatcctcc gcgggcaaga cagcggcagc   27240
agcggccagg agacccgcgg cagcagcggc gggagcggtg ggcgcactgc gcctctcgcc   27300
caacgaaccc ctctcgaccc gggagctcag acacaggatc ttccccactt tgtatgccat   27360
cttcaacacag agcagaggca aggagcagga gctgaaaata aaaaacagat ctctgcagcg   27420
cctcacccgc agctgtctgt atcacaaaag cgaagatcag cttcggcgca cgctggagga   27480
cgcggaggca ctcttcagca aatactgcgc gctcactctt aaagactagc tccgcgccct   27540
tctcgaattt aggcgggaga aaactacgtc atcgccggcc gccgcccagc ccgcccagcc   27600
gagatgagca aagagattcc cacgccatac atgtggagct accagccgca gatgggactc   27660
gcggcgggag cggcccagga ctactccacc cgcatgaact acatgagcgc gggaccccac   27720
atgatctcac aggtcaacgg gatccgcgcc cagcgaaacc aaatactgct ggaacaggcg   27780
gccatcaccg ccacgccccg ccataatctc aaccccgaa attggccgc cgccctcgtg   27840
taccaggaaa ccccctccgc caccaccgta ctacttccgc gtgacgccca ggcgaaagtc   27900
cagatgacta actcagggc gcagctcgcg ggcggctttc gtcacggggc gcggccgctc   27960
cgaccaggta taagcacct gatgatcaga ggccgaggta tccagctcaa cgacgagtcg   28020
gtgagctctt cgctcggtct ccgtccggac ggaactttcc agctcgccgg atccggccgc   28080
tcttcgttca cgccccgcca ggcgtacctg actctgcaga cctcgtcctc ggagcccgc   28140
tccggccgca tcggaaaccct ccagttcgtg gaggagttcg tgccctcggt ctacttcaac   28200
cccttctcgg gacctcccgg acgctacccc gaccagttca ttccgaactt tgacgcggtg   28260
aaggactcgg cggacggcta cgactgaatg tcaggtgtcg aggcagagca gcttcgcctg   28320
agacacctcg agcactgccg ccgccacaag tgcttcgccc gcggttctgg tgagttctgc   28380
tactttcagc tacccgagga gcataccgag gggccgggcc acgcgtccg cctgaccacc   28440
cagggcgagg ttacctgttc cctcatccgg gagtttaccc tccgtcccct gctagtggag   28500
cgggagcggg tccctgtgt cctaactatc gcctgcaact gccctaaccc tggattacat   28560
caagatcttt gctgtcatct ctgtgctgag tttaataaac gctgagatca gaatctactg   28620
gggctcctgt cgccatcctg tgaacgccac cgtcttcacc cacccgacca aggccaggc   28680
gaacctcacc tgcggtctgc atcggaggg caagaagtac ctcacctggt acttcaacgg   28740
caccccctt gtggtttaca acagcttcga cggggacgga gtctccctga agaccagct   28800
ctccggtctc agctactcca tccacaagaa caccaccctc caactcttcc ctccctacct   28860
gccggaacc tacgagtgcg tcaccggccg ctgcacccac ctcaccgcc tgatcgtaa   28920
ccagagcttt ccgggaacag ataactccct cttccccaga acaggaggtg agctcaggaa   28980
actcccggg gaccagggcg gagacgtacc ttcgacccctt gtgggggttag gatttttat   29040
taccggggtg ctggctctt taatcaaagt ttccttgaga tttgttcttt ccttctacgt   29100
gtatgaacac ctcaacctcc aataactcta ccctttcttc ggaatcaggt gacttctctg   29160
aaatcgggct tggtgtgctg cttactctgt tgatttttt ccttatcata ctcagccttc   29220
tgtgcctcag gctcgccgcc tgctgcgcac acatctatat ctactgctgg ttgctcaagt   29280
gcaggggtcg ccaccaaga tgaacaggta catggtccta tcgatcctag gcctgctggc   29340
cctgcggcc tgcagcggcg ccaaaaaaga gattaccttt gaggagcccg cttgcaatgt   29400
aactttcaag cccgagggtg accatgcac cacccctcgtc aaatgcgtta ccaatcatga   29460
gaggctcgcg atcgactaca aaacaaaac tggccagttt gcggtctata gtgtgtttac   29520
gccccggagac ccctctaact actctgtcac cgtcttccag ggcggacagt ctaagatatt   29580
caattacact ttccctttttt atgagttatg cgatgcggtc atgtacatgt caaaacagta   29640
caacctgtgg cctccctctc cccaggcgtg tgtggaaaat actgggtctt actgctgtat   29700
ggctttcgca atcactacgc tcgctctaat ctgcacggtg ctatacataa aattcaggca   29760
gaggcgaatc tttatcgatg aaaagaaaat gccttgatcg ctaacaccgg ctttctatct   29820
gcagaatgaa tgcaatcacc tccctactaa tcaccaccac cctccttgcg attgccatg   29880
ggttgacacg aatcgaagtg ccagtggggt ccaatgtcac catgtgggc cccgccggca   29940
attccacccct catgtgggaa aaatttgtcc gcaatcaatg ggttccattc tgctctaacc   30000
gaatcagtat caagcccaga gccatctgcg atgggcaaaa tctaactctg atcaatgtgc   30060
aaatgatgga tgctgggtac tattacgggc agcggggaga aatcattaat tactggcgac   30120
cccacaagga ctacatgctg catgtagtcg aggcacttcc cactaccacc cccactacca   30180
cctctcccac caccaccacc actactacta ctactactac tactactact actaccacta   30240
ccccatcacg ccatacccgc aaaagcacca tgattagcac aaagcccctc cgtgctcact   30300
cccacgccgg cgggcccatc ggtgcgacct cagaaccac cgagctttgc ttctgccaat   30360
gcactaacgc cagcgctcat gaactgttcg acctggagaa tgaggatgtc cagcagagct   30420
ccgcttgcct gacccaggag gctgtggagc ccgttgccct gaagcagatc ggtgattcaa   30480
taattgactc ttcttctttt gccactcccg aatacctcc cgattctact ttccacatca   30540
cgggtaccaa agaccctaac ctctctttct acctgatgct gctgctctgt atctctgtgg   30600
```

```
tctcttccgc gctgatgtta ctggggatgt tctgctgcct gatctgccgc agaaagagaa   30660
aagctcgctc tcagggccaa ccactgatgc ccttccccta ccccccggat tttgcagata   30720
acaagatatg agctcgctgc tgacactaac cgctttacta gcctgcgctc taacccttgt   30780
cgcttgcgac tcgagattcc acaatgtcac agctgtggca ggagaaaatg ttactttcaa   30840
ctccacggcc gatacccagt ggtcgtggag tggctcaggt agctacttaa ctatctgcaa   30900
tagctccact tcccccggca tatccccaac caagtaccaa tgcaatgcca gcctgttcac   30960
cctcatcaac gcttccaccc tggacaatgg actctatgta ggctatgtac cctttggtgg   31020
gcaaggaaag acccacgctt acaacctgga agttcgccag cccagaacca ctacccaagc   31080
ttctcccacc accaccacca ccaccaccat caccagcagc agcagcagca gcagccacag   31140
cagcagcagc agattattga ctttggtttt ggccagctca tctgccgcta cccaggccat   31200
ctacagctct gtgcccgaaa ccactcagat ccaccgccca gaaacgacca ccgccaccac   31260
cctacacacc tccagcgatc agatgccgac caacatcacc cccttggctc ttcaaatggg   31320
acttacaagc cccactccaa aaccagtgga tgcggccgag gtctccgccc tcgtcaatga   31380
ctgggcgggg ctgggaatgt ggtggttcgc cataggcatg atggcgctct gctgcttct    31440
gctctggctc atctgctgcc tccaccgcag gcgagccaga ccccccatct atagaccat    31500
cattgtcctg aaccccgata atgatgggat ccatagattg gatggcctga aaaacctact   31560
tttttctttt acagtatgat aaattgagac atgcctcgca ttttcttgta catgttcctt   31620
ctcccacctt ttctggggtg ttctacgctg gccgctgtg ctcacctgga ggtagactgc    31680
ctctcaccct tcactgtcta cctgcttttac ggattggtca ccctcactct catctgcagc   31740
ctaatcacag taatcatcgc cttcatccag tgcattgatt acatctgtgt gcgcctcgca   31800
tacttcagac accaccgca gtaccgagac aggaacattg cccaacttct aagactgctc    31860
taatcatgca taagactgtg atctgccttc tgatcctctg catcctgccc acccctcacct   31920
cctgccagta caccacaaaa tctccgcgca aaagacatgc ctcctgccgc ttcacccaac    31980
tgtggaatat acccaaatgc tacaacgaaa agagcgagct ctccgaagct tggctgtatg   32040
gggtcatctg tgtcttagtt ttctgcagca ctgtctttgc cctcataatc taccctact    32100
ttgatttggg atggaacgcg atcgatgcca tgaattaccc cacctttccc gcaccgaga    32160
taattccact gcgacaagtt gtacccgttg tcgttaatca acgccccca tccctacgc     32220
ccactgaaat cagctacttt aacctaacag gcggagatga ctgacgccct agatctagaa   32280
atggacggca tcagtaccga gcagcgtctc ctagagaggc gcaggcaggc ggctgagcaa   32340
gagcgcctca atcaggagct ccgagatctc gttaacctgc accagtgcaa aagaggcatc   32400
ttttgtctgg taaagcaggc caaagtcacc tacgaagaa ccggcaacag ccaccgcctc    32460
agttacaaat tgcccaccca gcgccagaag ctggtgctca tggtgggtga aatccatc     32520
accgtcaccc agcactcggt agagaccgag gggtgtctgc actccccctg tcggggtcca   32580
gaagacctct gcaccctggt aaagaccctg tgcggtctca gagatttagt cccctttaac   32640
taatcaaaca ctggaatcaa taaaagaat cacttactta aaatcagaca gcaggtctct    32700
gtccagttta ttcagcagca cctccttccc ctcctcccaa ctctggtact ccaaacgcct   32760
tctggcggca aacttcctcc acacctgaa gggaatgtca gattcttgct cctgtccctc    32820
cgcacccact atcttcatgt tgttgcagat gaagcgcacc aaaacgtctg acgagagctt   32880
caaccccgtg taccctatg acacggaaag cggccctccc tccgtcctt tcctcaccc     32940
tcccttcgtg tctcccgatg gattccaaga aagtccccc ggggtcctgt ctctgaacct    33000
ggccgagccc ctggtcactt cccacggcat gctcgccctg aaaatgggaa gtggcctctc   33060
cctggacgac gctggcaacc tcacctctca agatatcacc accgctagcc ctccccctcaa  33120
aaaaaccaag accaacctca gcctagaaac ctcatccccc ctaactgtga gacctcagg    33180
cgccctcacc gtagcagccg ccgctcccct ggcggtggcc ggcacctccc tcaccatgca   33240
atcagaggcc cccctgacag tacaggatgc aaaaactcac ctggccacca aggcccct     33300
gaccgtgtctc gaaggcaaac tggccttgca acatcggcc ccgctgacgg ccgctgacag    33360
cagcaccctc acagtcagtg ccacaccacc ccttagcaca agcaatggca gcttgggtat   33420
tgacatgcaa gcccccattt acaccaccaa tggaaaacta ggacttaact ttggcgctcc   33480
cctgcatgtg gtagacagcc taaatgcact gactgtagtt actggccaag gtcttacgat   33540
aaaacggaaca gcccctacaaa ctagagtctc aggtgccctc aactatgaca catcaggaaa   33600
cctagaattg agagctgcag ggggtatgcg agttgatgca aatgctcaac ttatccttga   33660
tgtagcttac ccatttgatg cacaaaaacaa tctcagcctt aggcttggac agggacccct   33720
gtttgttaac tctgcccaca acttggatgt taactacaac agaggcctct acctgttcac    33780
atctggaaat accaaaaagc tagaagttaa tatcaaaaca gccaagggtc tcatttatga   33840
tgacactgct atagcaatca atgcgggtga tgggctaacg tttgactag gctcagatac   33900
aaatccatta aaaactaaac ttggattagg actggattat gactccagca gagccataat   33960
tgctaaactg ggaactggcc taagctttga caacacaggt gccatcacag taggcaacaa   34020
aaatgatgac aagcttacct tgtggaccac accagaccca tccctaact gtagaatcta    34080
ttcagagaaa atgctaaat tcacacttgt tttgactaaa tgcggcagtc aggtgttggc   34140
cagcgtttct gttttatctg taaaggtag ccttgcgccc atcagtggca cagtaactag    34200
tgctcagatt gtcctcagat ttgatgaaaa tggagttcta ctaagcaatt cttcccttga   34260
ccctcaatac tggaactaca gaaaaggtga ccttacagag ggcactgcat ataccaacgc   34320
agtgggattt atgcccaacc tcacagcata cccaaaaaaca cagagccaaa ctgctaaaag    34380
caacattgta agtcaggttt acttgaatgg ggacaaatcc aaacccatga ccctcaccat   34440
taccctcaat ggaactaatg aaacaggaga tgccacagta agcacttact ccatgtcatt   34500
ctcatgaac tggaatggaa gtaattacat taatgaaacg ttccaaacca actccttcac    34560
cttctcctac atcgcccaag aataaaaagc atgacgctgt tgatttgatt caatgtgttt   34620
ctgtttttatt ttcaagcaca acaaaatcat tcaagtcatt cttccatctt agcttaatag   34680
acacagtagc ttaatagacc cagtagtgca aagccccatt ctagcttata gatcagacag   34740
tgataattaa ccaccaccac caccatacct tttgattcag gaaatcatga tcatcacagg   34800
atcctagtct tcaggccgcc ccctccctcc caagacacag aatacacagt cctctcccc    34860
cgactggctt taaataacac catctggttg gtcacagaca tgttcttagg ggttatattc   34920
cacacggtct cctgccgcgc caggcgctcg tcggtgatgt tgataaactc tcccggcagc   34980
tcgctcaagt tcacgtcgcg gtccgggcca tgaactcagg gcagtaactc ggcagcagca  35040
accggctgct ggacgaacgg aggccgcgcc tacaaggggg tagagtcata atcctccggtc   35100
aggatagggc ggtgatcgag cagcagcgag cgaaacatct gctgccgccg ccgctccgtc   35160
cggcaggaaa acaacacgcc ggtggtctcc tccgcgataa tccgcaccgc ccgcagcatc   35220
agcttcctcg ttctccgcgc gcagcacctc acccttatct cgctcaaatc ggcgcagtag   35280
gtacagcaca gcaccacgat gttattcatg atcccacagt gcagggcgct gtatccaaag   35340
```

```
ctcatgccgg gaaccaccgc ccccacgtgg ccatcgtacc caagcgcac gtaaatcaag    35400
tgtcgacccc tcatgaacgc gctgacaca  acattactt  ccttgggcat gttgtaattc   35460
accacctccc ggtaccagat aaacctctgg ttgaacaggg caccttccac caccatcctg   35520
aaccaagagg ccagaacctg cccaccggct atgcactgca gggaacccgg gttggaacaa   35580
tgacaatgca gactccaagg ctcgtaaccg tggatcatcc ggctgctgaa ggcatcgatg   35640
ttggcacaac acagacacac gtgcatgcac ttctcatga  ttagcagctc ttccctcgtc   35700
aggatcatat cccaaggaat aacccattct tgaatcaacg taaacccac  acagcaggga   35760
aggcctcgca cataactcac gttgtgcatg gtcagcgtgt tgcattccgg aaacagcgga   35820
tgatcctcca gtatcgaggc gcgggtctcc ttctcacagg gaggtaaagg gtccctgctg   35880
tacggactgc gccgggacga ccgagatcgt gttgagcgta gtgtcatgga aaagggaacg   35940
ccggacgtgg tcatacttct tgaagcagaa ccaggttcgc gcgtggcagg cctccttgcg   36000
tctgcggtct cgccgtctag ctcgctccgt gtgatagttg tagtacagcc actcccgcag   36060
agcgtcgagg cgcaccctgg cttccggatc tatgtagact ccgtcttgca ccgcggccct   36120
gataatatcc accaccgtag aataagcaac acccagccaa gcaatacact cgctctgcga   36180
gcggcagaca ggaggagcgg gcagagatgg gagaaccatg ataaaaaact ttttttaaag   36240
aatatttttcc aattcttcga aagtaagatc tatcaagtgg cagcgctccc ctccactggc   36300
gcggtcaaac tctacggcca aagcacagac aacggcattt ctaagatgtt ccttaatggc   36360
gtccaaaaga cacaccgctc tcaagttgca gtaaactatg atgaaaacc  catccggctg   36420
attttccaat atagacgcgc cggcagcgtc caccaaaccc agataatttt cttctctcca   36480
gcggtttacg atctgtctaa gcaaatccct tatatcaagt ccgaccatgc caaaaatctg   36540
ctcaagagcg ccctccacct tcatgtacaa gcagcgcatc atgattgcaa aaattcaggt   36600
tcttcagaga cctgtataag attcaaaatg ggaaactaca caaaaattcc tctgtcgcgc   36660
agatcccttc gcagggcaag ctgaacataa tcagacaggt ccgaacggac cagtgaggcc   36720
aaatccccac caggaaccag atccagagac cctatactga ttatgacgcg catactcggg   36780
gctatgctga ccagcgtagc gccgatgtag gcgtgctgca tgggcggcga gataaaatgc   36840
aaagtgctgg ttaaaaaatc aggcaaagcc tcgcgcaaaa aagctaacac atcataatca   36900
tgctcatgca ggtagttgca ggtaagctca ggaaccaaaa cggaataaca cacgattttc   36960
ctctcaaaca tgacttcgcg gatactgcgt aaaacaaaaa attataaata aaaaattaat   37020
taaataactt aaacattgga agcctgtctc acaacaggaa aaaccacttt aatcaacata   37080
agacggccca cgggcatgcc ggcatagccg taaaaaaatt ggtccccgtg attaacaagt   37140
accacagaca gctccccggt catgtcgggg gtcatcatgt gagactctgt atacacgtct   37200
ggattgtgaa catcagacaa acaaagaaat cgaccacgt  agcccggagg tataatcacc   37260
cgcaggcgga ggtacagcaa aacgaccccc ataggaggaa tcacaaaatt agtaggagaa   37320
aaaaatacat aaacaccaga aaaacccctgt tgctgaggca aaatagcgcc ctcccgatcc   37380
aaaacaacat aaagcgcttc cacaggagca gccataacaa agacccgagt cttaccagta   37440
aaagaaaaaa gatctctcaa cgcagcacca gcaccaacac ttcgcagtgt aaaaggccaa   37500
gtgccgagag agtatatata ggaataaaaa gtgacgtaaa cgggcaaagt ccaaaaaacg   37560
cccagaaaaa ccgcacgcga acctacgccc cgaaacgaaa gccaaaaaac actagacact   37620
cccttccggc gtcaacttcc gctttcccac gctacgtcac ttccccggt  caaacaaact   37680
acatatcccg aacttccaag tcgccacgcc caaacaccg  cctacacctc cccgcccgcc   37740
ggcccgcccc cggacccgcc tcccgccccg cgccgcccat ctcattatca tattggcttc   37800
aatccaaaat aaggtatatt attgatgatg                                   37830
```

| | |
|---|---|
| SEQ ID NO: 2 | moltype = DNA length = 36571 |
| FEATURE | Location/Qualifiers |
| source | 1..36571 |
| | mol_type = unassigned DNA |
| | organism = unidentified |
| | note = Chimpanzee adenovirus |

SEQUENCE: 2

```
catcatcaat aatataccte aaacttttgg tgcgcgttaa tatgcaaatg agctgtttga    60
atttggggat gcggggcgct gattggctgc gggagcggcg accgttaggg gcggggcggg   120
tgacgttttg atgacgtggc cgtgaggcgg agccggtttg caagttctcg tgggaaaagt   180
gacgtcaaac gaggtgtggt ttgaacacgg aaatactcaa ttttcccgcg ctctctgaca   240
ggaaatgagg tgtttctggg cggatgcaag tgaaaacggg ccatttttcgc gcgaaaactg   300
aatgaggaag tgaaaatctg agtaatttcg cgtttatggc agggaggagt atttgccgag   360
ggccgagtag actttgaccg attacgtggg ggtttcgatt accgtatttt tcacctaaat   420
ttccgcgtac ggtgtcaaag tccggtgttt ttacgtaggc gtcagctgat cgccagggta   480
tttaaacctg cgctcactga tcaagaggcc actcttgagt gccacgcagt agagtttct    540
cctccgcgcc gcgagtcaga tctacacttt gaaagatgag gcacttgaga gacctgcccg   600
gtaatgtttt cctggctact gggaacgaga ttctggaatt ggtggtggac gccatgatgg   660
gtgacgaccc tcccgagccc cctacccccat ttgaggcgcc ttcgctgtac gatttgtatg   720
atctggaggt ggatgtgccc gagaacgacc caacgaggag ggcggtgaat gatttgttta   780
gcgatgccgc gctgctggct gccgagcagg ctaatacgaa ctttggctca gacagcgatt   840
cttctctcca tacccgaga  cccggcagag gtgagaaaaa gatccccgag cttaaagggg   900
aagagctcga cctgcgctgc tatgaggaat gcttgcctcc gagcgatgat gaggaggacg   960
aggaggcgat tcgagctgca gcgaaccagg gagtgaaagc tgcgggcgaa agctttagcc  1020
tggactgtcc tactctgccc ggacacggct gtaagtcttg tgaatttcat cgcatgaata  1080
ctggagataa gaatgtggga tgtgccctgt gctatatgga agcttacaac cattgtgttt  1140
acagtaagtg tgattaactt tagttgggaa ggcagagggt gactgggtgc tgactggttt  1200
atttatgtat atgtttttta tgtgtaggtc ccgtctctga cgcagatgag accccactt   1260
cagagtgcat ttcatcaccc ccagaaattg gcgaggaacc gcccgaagat attattcata  1320
gaccagttgc agtgagagtc accgggcgga gagcagctgg ggagagtttg gatgacttgc  1380
tacagggtgg ggatgaacct ttggacttgt gtacccggaa acgccccagg cactaagtgc  1440
cacacatgtg tgtttactta aggtgatgtc agtatttata gggtgtggag tgcaataaaa  1500
tccgtgttga ctttaagtgc gtggtttatg actcaggggt ggggactgtg ggtatataag  1560
caggtgcaga cctgtgtggt cagttcagag caggactcat ggagatctgg acggtcttgg  1620
aagactttca ccagactaga cagctgctag agaactcatc ggagggagtc tcttacctgt  1680
ggagattctg cttcggtggg cctctagcta agctagtcta tagggccaag caggattata  1740
```

```
aggatcaatt tgaggatatt ttgagagagt gtcctggtat ttttgactct ctcaacttgg      1800
gccatcagtc tcactttaac cagagtattc tgagagccct tgactttttcc actcctggca    1860
gaactaccgc cgcggtagcc ttttttgcct ttatccttga caaatggagt caagaaaccc     1920
atttcagcag ggattaccgt ctggactgct tagcagtagc tttgtggaga acatggaggt     1980
gccagcgcct gaatgcaatc tccggctact tgccagtaca gccggtagac acgctgagga    2040
tcctgagtct ccagtcaccc caggaacacc aacgccgcca gcagccgcag caggagcagc    2100
agcaagagga ggaccgagaa gagaacccga gagccggtct ggaccctccg gtggcggagg    2160
aggaggagta gctgacttgt ttcccgagct gcgccgggtg ctgactaggt cttccagtgg    2220
acgggagagg gggattaagc gggagaggca tgaggagact agtcacagaa ctgaactgac    2280
tgtcagtctg atgagccgca ggcgcccaga atcggtgtgg tggcatgagg tgcagtcgca    2340
ggggatagat gaggtctcgg tgatgcatga gaaatattcc ctagaacaag tcaagacttg    2400
ttggttggag cctgaggatg attgggaggt agccatcagg aattatgcca agctagctct    2460
gaagccagac aagaagtaca agattaccaa actgattaat atcagaaatt cctgctacat    2520
ttcagggaat ggggccgagg tggagatcag tacccaggag agggtggcct tcagatgctg    2580
catgatgaat atgtacccgg gggtggtggg catggaggga gtcacccttta tgaacgcgag    2640
gttcaggggc gatgggtata atgggtggt ctttatggcc aacaccaagc tgacagtgca     2700
cggatgctcc ttctttggct tcaataacat gtgcatcgag gcctgggca gtgtttcagt     2760
gaggggatgc agttttttcag ccaactggat ggggtcgtg ggcagaacca agcaaggt      2820
gtcagtgaag aaatgcctgt tcgagaggtg ccacctgggg gtgatgagcg agggcgaagc    2880
caaagtcaaa cactgcgcct ctactgagac gggctgcttt gtgctgatca agggcaatgc    2940
ccaagtcaag cataacatga tctgtgggc ctcggatgag cgcggctacc agatgctgac     3000
ctgcgccggt gggaacagcc atatgctggc caccgtgcat tgtgacctcg accccccgcaa   3060
gacatggccc gagttcgagc acaacgtcat gacccgctgc aatgtgcacc tgggctcccg    3120
ccgaggcatg ttcatgccct accagtgcaa catgcaattt gtgaaggtgc tgctggagcc    3180
cgatgccatg tccagagtga gcctgacggg ggtgtttgac atgaatgtgg agatgtgaa     3240
aattctgaga tatgatgaat ccaagaccag gtgccggcc tgcgaatgcc gaggcaagca     3300
cgccaggctt cagcccgtgt gtgtggaggt gacggaggac ctgcgacccg atcatttggt    3360
gttgtcctgc aacgggacgg agttcggctc cagcgggaa gaatctgact agagtgagta     3420
gtgtttgggg gaggtggagg gcctggatga ggggcagaat gactaaatc tgtgtttttc     3480
tgcgcagcag catgagcgga agcgcctcct ttgagggagg ggtattcagc ccttatctga    3540
cggggcgtct cccctcctgg gcgggagtgc gtcagaatgt gatgggatcc acggtggacg    3600
gccgccccgt gcagcccgcg aactcttcaa ccctgaccta cgcgaccctg agctcctcgt    3660
ccgtggacga agctgccgcc gcagctgctg cttccgccgc cagcgccgtg cgcggaatgg    3720
ccctgggcgc cggctactac agctctctgg tggccaactc gagttccacc aataatcccg    3780
ccagcctgaa cgaggagaag ctgctgctgc tgatggccca gctcgaggcc ctgacccagc    3840
gcctgggcga gctgacccag caggttgctc agctgcaggc ggagacgcgg gccgcggttg    3900
ccacggtgaa aaccaaataa aaaatgaatc aataaataaa cggagacggt tgttgatttt    3960
aacacagagt cttgaatctt tatttgattt ttcgcgcgcg gtaggccctg gaccaccggt    4020
ctcgatcatt gagcaccgg tggatctttt ccaggaccg gtagaggtgg gcttggatgt      4080
tgaggtacat gggcatgagc ccgtcccggg ggtggaggta gctccattgc agggcctcgt    4140
gctcggggt ggtgttgtaa atcacccagt catagcaggg gcgcagggcg tggtgctgca     4200
cgatgtcctt gaggaggaga ctgatggcca cgggcagccc cttggtgtag gtgttgacga    4260
acctgtgag ctgggaggga tgcatgcggg gggagatga atgcatcttg gcctggatct      4320
tgagattggc gatgttcccg cccagatccc gccgggggtt catgttgtgc aggaccacca    4380
gcacggtgta tccggtgcac ttggggaatt tgtcatgcaa cttggaaggg aaggcgtgaa    4440
agaatttgga gacgcccttg tggccgccca ggttttccat gcactcatcc atgatgatgg    4500
cgatgggccc gtgggcggcg gcctgggcaa agacgttttcg gggtccggac acatcgtagt   4560
tgtggtcctg ggtgagctcg tcataggcca ttttaatgaa tttggggcgg agggtgcccg    4620
actggggac gaaggtgccc tcgatcccgg gggcgtagtt gccctcgcag atctgcatct     4680
cccaggcctt gagctcggag ggggggatca tgtccacctg cggggcgatg aaaaaaacgg    4740
ttttcggaga ggggagatg agctgcgccg aaagcaggtt ccggagccgc tgggacttgc     4800
cgcagccggt ggggccgtag atgcccccga tgaccggctg caggtggtag ttgagggaga   4860
gacagctgcc gtcctcgcgg aggaggggg ccacctcgtt catcatcctcg cgcacatgca    4920
tgttctcgcg cacgagttcc gccaggaggc gctcgcccc cagcgagagg agctcttgca     4980
gcgagcgaa gttttttcagc ggcttgagcc cgtcggccat gggcattttg gagagggtct    5040
gttgcaagag ttccagacgg tcccagagct cggtgatgtg ctctagggca tctcgatcca    5100
gcagacctcc tcgtttcgcg ggttgggggcg actgcgggag tagggcacca ggcgatgggc   5160
gtccagcgag gccagggtcc ggtccttcca gggtcgcagg gtccgcgtca gcgtggtctc    5220
cgtcacggtg aagggtgcg cgccgggctg ggcgcttgcg agggtgcgct tcaggctcat     5280
ccggctggtc gagaaccgct cccgtctggc gcctgctgcg tcggccaggt agcaattgac    5340
catgagttcg tagttgagcg cctcggccgc gtgcccttg gcgcggagct tacctttgga     5400
agtgtgtccg cagacgggac agaggaggga cttgaggcg tagagcttgg gggcgaggaa     5460
gacggactcg ggggcgtagg cgtccgcgcc gcagctggcg cagacggtct cgcactccac    5520
gagccaggtg aggtcggggc ggtcgggtc aaaaacgagg tttcctccgt gcttttttgat    5580
gcgtttctta cctctggtct ccatgagctc gtgtccccgc tgggtgacaa agaggctgtc    5640
cgtgtccccg tagaccgact ttatgggccg gtcctcgage ggggtgccgc ggtcctcgtc    5700
gtagaggaac cccgcccact ccgagacgaa ggcccgggtc caggccagca cgaaggaggc    5760
cacgtgggag gggtagcgt cgttgtccac cagcgggtcc accttctcca gggtatgcaa    5820
gcacatgtcc ccctcgtcca catccaggaa ggtgattggc ttgtaagtgt aggccacgtg    5880
accggggtc ccggccgggg gggtataaaa ggggcgggc cctgctcgt cctcactgtc       5940
ttccggatcc ctgtccagga gcgccagctg ttggggtagg tattccctct cgaaggcggg    6000
catgacctcg gcactcaggt tgtcagtttc tagaaacgag gaggatttga tattgacggt    6060
gccgttggag acgcctttca tgagccctc gtccatctgg tcagaaaaga cgatcttttt    6120
gttgtcgagc ttggtggcga aggagccgta gagggcgtga tggagtgga                6180
gcgcatggtc tggttctttt ccttgtcgg gcgctccttg gcggcgatgt tgagctgcac    6240
gtactcgcgc gccacgcact tccattcgg gaagacggtg gtgagctcgt cgggcacgat    6300
tctgacccgc cagccgcggt tgtgcaggt gatgaggtcc acgctggtgg ccacctcgcc    6360
gcgcaggggc tcgttggtcc agcagaggcg cccgcccttg cgcgagcaga ggggggcag    6420
cgggtccagc atgagctcgt cgggggggtc ggcgtccacg gtgaagatgc cggcaggag    6480
```

```
ctcggggtcg aagtagctga tgcaggtgcc cagatcgtcc agcgccgctt gccagtcgcg   6540
cacggccagc gcgcgctcgt aggggctgag gggcgtgccc cagggcatgg ggtgcgtgag   6600
cgcggaggcg tacatgccgc agatgtcgta gacgtagagg ggctcctcga ggacgccgat   6660
gtaggtgggg tagcagcgcc ccccgcggat gctggcgcgc acgtagtcgt acagctcgtg   6720
cgagggcgcg aggagcccg tgccgaggtt ggagcgttgc ggcttttcgg cgcggtagac   6780
gatctggccg aagatggcgt gggagttgga ggagatggtg ggcctctgga agatgttgaa   6840
gtgggcgtgg ggcaggccga ccgagtccct gatgaagtgg gcgtaggagt cctgcagctt   6900
ggcgacgagc tcggcggtga cgaggacgtc cagggcgcag tagtcgaggg tctcttggat   6960
gatgtcgtac ttgagctggc ccttctgctt ccacagctcg cggttgagaa ggaactcttc   7020
gcggtccttc cagtactctt cgaggggggaa cccgtcctga tcggcacggt aagagcccac   7080
catgtagaac tggttgacgg ccttgtaggc gcagcagccc ttctccacgg ggagggcgta   7140
agcttgcgcg gccttgcgca gggaggtgtg ggtgagggcg aaggtgtcgc gcaccatgac   7200
tttgaggaac tggtgcttga agtcgaggtc gtcgcagccg ccctgctccc agagttggaa   7260
gtccgtgcgc ttcttgtagg cgggggttggg caaagcgaaa gtaacatcgt tgaagaggat   7320
cttgcccgcg cggggcatga agttgcgagt gatgcggaaa ggctggggca cctcggcccg   7380
gttgttgatg acctgggcgg cgaggacgat ctcgtcgaag ccgttgatgt tgtgcccgac   7440
gatgtagagt tccacgaatc gcgggcagcc cttgacgtgg ggcagcttct tgagctcgtc   7500
gtaggtgagc tcggcggggt cgctgagccc gtgctgctcg agggcccagt cggcgacgtg   7560
ggggttggcg ctgaggaagg aagtccagag atccacggcc agggcggtct gcaagcggtc   7620
ccggtactga cggaactgct ggcccacggg cattttttcg ggggtgacgc agtagaaggt   7680
gcgggggtcg ccgtgccagc ggtcccactt gagttggagg gcgaggtcgt gggcgagctc   7740
gacgagcggc gggtccccgg agagtttcat gaccagcatg aaggggacga gctgcttgcc   7800
gaaggacccc atccaggtgt aggttttcca atcgtaggtg aggaagagcc tttcggtgcg   7860
aggatgcgag ccgatgggga agaactggat ctcctgccac cagttggagg aatggctgtt   7920
gatgtgatgg aagtagaaat gccgacggcg cgccgagcac tcgtgcttgt gtttatacaa   7980
gcgtccgcag tgctccaac gctgcacgtgg atgcacgtgc tgcacgagct gtacctgggt   8040
tcctttgacg aggaatttca gtgggcagtg gagcgctgcg ggctgcatct ggtgctgtac   8100
tacgtcctgg ccatcggcgt ggccatcgtc tgcctcgatg gtggtcatgc tgacgagccc   8160
gcgcggggagg caggtccaga cctcggctcg gacgggtcgg agagcgagga cgagggcgcg   8220
caggccggag ctgtccaggg tcctgagacg ctgcggagtc aggtcagtgg gcagcggcgtg   8280
cgcgcggttg acttgcagga gctttttccaa ggcgcgcggg aggtccagat ggtacttgat   8340
ctccacggcg ccgttggtgg cgacgtccac ggcttgcagg gtcccgtgcc cctggggcgc   8400
caccaccgtg ccccgtttct tcttgggcgg cggcggctcc atgcttagaa gcggcggcga   8460
ggacgcgcgc cgggcggcag gggcggctcg gggcccggag gcaggggcgg caggggcacg   8520
tcggccgccgc gcgcgggcag gttctggtac tgcgccggga gaagactggc gtgagcgacg   8580
acgcgacggt tgacgtcctg gatctgacgc ctctgggtga aggccacggg acccgtgagt   8640
ttgaacctga aagagagttc gacagaatca atttcggtat cgttgacggc ggcctgccgc   8700
aggatctctt gcacgtcgcc cgagttgtcc tggtaggcga tctcggtcat gaactgctcg   8760
atctcctcct cctgaaggtc tccgcggccg gcgcgctcga cggtggccgc gaggtcgttg   8820
gagatgcggc ccatgagctg cgagaaggcg ttcatgccgg cctcgttcca gacgcggctg   8880
tagaccacgg ctccgttggg gtcgcgcgcg cgcatgacca cctgggcgag gttaagctcg   8940
acgtggcgcg tgaagaccgc gtagttcag aggcgctggt agaggtagtt gagcgtggtg   9000
gcgatgtgct cggtgacgaa gaagtacatg atccagcggc gcagcgggct ctcgctgacg   9060
tcgcccaggg cttccaagcg ctccatggtc tcgtagaagt ccacggcgaa gttgaaaaac   9120
tgggagttgc gcgccgagac ggtcaactcc tcctccagaa gacggatgag ctcggcgatg   9180
gtggcgcgca cctcgcgctc gaaggccccg ggggctcct cttcttccat ctcctcctcc   9240
tcttcctcct ccactaacat ctcttctact tcctcctcag gaggcgggcg cgggggaggg   9300
gccctgcgtc gccggcggcg cacgggcaga cggtcgatga agcgctcgat ggtctccccg   9360
cgccggcgac gcatggtctc ggtgacggcg cgcccgtcct cgcggggccg cagcgtgaag   9420
acgccgccgc gcatctccag gtggccgccg gggggtctc cgttgggcag ggagagggcg   9480
ctgacgatgc atcttatcaa ttggcccgta gggactccgg gcaaggacct gagcgtcctg   9540
agatccacgg gatccgaaaa ccgctgaacg aaggcttcga gccagtcgca gtcgcaaggt   9600
aggctgagcc cggtttcttg ttcttcgggt atttggtcgg gaggcgggcg ggcgatgctg   9660
ctggtgatga agttgaagta ggcggtcctg agacggcgga tggtggcgag gagcaccagg   9720
tccttgggcc cggcttgctg gatgcgcaga cggtcggcca tgcccaggc gtggtcctga   9780
cacctggcga ggtccttgta gtagtcctgc atgagccgct ctacgggcac gtcctcctcg   9840
cccgcgcggc cgtgcatgcg cgtgagcccg aacccgcgct gcggctggac gagcgccagg   9900
tcggcgacga cgcgctcggc gaggatggcc tgctggatct gggtgagggt ggtctggaag   9960
tcgtcgaagt cgacgaagcg gtggtaggct ccggtgttga tggtgtagga gcagttggcc  10020
atgacggacc agttgacggt ctggtggccg gggcgacga gctcgtggta cttgaggcgc  10080
gagtaggcgc gcgtgtcgaa gatgtagtcg ttgcaggtgc gcacgaggta ctggtatccg  10140
acgaggaagt gcggcggcgg ctgcggtag agcggccatc gctcggtggc gggggcgccg  10200
ggcgcgaggt cctcgagcat gaggcggtgg tagccgtaga tgtacctgga catccaggtg  10260
atgccggcgg cggttggtgga ggcgcggggg aactcgcgga cgcggttcca gatgttgccg  10320
agcggcagga agtagttcat ggtggccgcg gtctggcccg tgaggcgcgc cagtcgtgg  10380
atgctctaga catacgggca aaaacgaaag cggtcagcgg ctcgactccg tggcctggag  10440
gctaagcgaa cgggttgggc tgcgcgtgta ccccggttcg aatctcgaat caggctggag  10500
ccgcagctaa cgtggtactg gcactcccgt ctcgacccaa gcctgctaac gaaacctcca  10560
ggatacggag gcgggtcgtt ttttggcctt ggtcgctgat catgaaaaac tagtaagcgc  10620
ggaaagcggc cgcccgcgat ggctcgctgc cgtagtctgg agaaagaatc gccagggttg  10680
cgttgcgtg tgcccggtt cgagcctcag cgctcggtgc cggccggatt ccgcggctaa  10740
cgtgggcgtg gctgccccgt cgtttccaag accccttagc cagccgactt ctccagttac  10800
ggagcgagcc cctctttttc ttgtgttttt gccagatgca tccgtactg cggcagatgc  10860
gccccgcacc tccaccacaa ccgccctac cgcacgcaga gcaacagccg gcgcttctgc  10920
ccccgcccca gcagcagcag ccagccacta ccgcggcggc cgccgtgagc ggagccggcg  10980
ttcagtatga cctggccttg gaagagggcg aggggctggc gcgctgggg gcgtcgtcgc  11040
cggagcggca cccgcgcgtg cagatgaaaa gggacgctcg cgaggcctac gtgcccaagc  11100
agaacctgtt cagagacagg agcggcgagg agcccgagga gatgcgcgcc tcccgcttcc  11160
acgcggggcg ggagctgcgg cgcggcctgg accgaaagcg ggtgctgagg gacgaggatt  11220
```

```
tcgaggcgga cgagctgacg gggatcagcc ccgcgcgcgc gcacgtggcc gcggccaacc     11280
tggtcacggc gtacgagcag accgtgaagg aggagagcaa ctttcaaaaa tccttcaaca     11340
accacgtgcg cacgctgatc gcgcgcgagg aggtgaccct gggcctgatg cacctgtggg     11400
acctgctgga ggccatcgtg cagaacccca cgagcaagcc gctgacggcg cagctgtttc     11460
tggtggtgca gcacagtcgg gacaacgaga cgttcaggga ggcgctgctg aatatcaccg     11520
agcccgaggg ccgctggctc ctggacctgg tgaacattct gcagagcatc gtggtgcagg     11580
agcgcgggct gccgctgtcc gagaagctgg cggccatcaa cttctcggtg ctgagcctgg     11640
gcaagtacta cgctaggaag atctacaaga ccccgtacgt gcccatagac aaggaggtga     11700
agatcgaccg gttttacatg cgcatgaccc tgaaagtgct gacccctgag cgacgatctgg    11760
gggtgtaccg caacgacagg atgcaccgcg cggtgagcgc cagccgccgg cgcgagctgg     11820
gcgaccagga gctgatgcac agcctgcagc gggccctgac cggggccggg accgaggggg     11880
agagctactt tgacatgggc gcggacctgc gctggcagcc cagccgccgg gccttggaag     11940
ctgccggcgg cgtgccctac gtggaggagg tggacgatga ggaggaggag ggcgagtacc     12000
tggaagactg atggcgcgac cgtatttttg ctagatgcag caacagccac cgcccgcctcc    12060
tgatcccgcg atgcgggcgg cgctgcagag ccagccgtcc ggcattaact cctcggacga     12120
ttggacccag gccatgcaac gcatcatggc gctgacgacc cgcaatcccg aagcctttag     12180
acagcagcct caggccaacc ggctctcggc catcctggag gccgtggtgc cctcgcgctc     12240
gaaccccacg cacgagaagg tgctggccat cgtgaaccgc ctggtggaga acaaggccat     12300
ccgcggcgac gaggccgggc tggtgtacaa cgcgctgctg gagcgcgtgg cccgctacaa     12360
cagcaccaac gtgcagacga acctggaccg catggtgacc gacgtgcgcg aggcggtgtc     12420
gcagcgcgag cggttccacc gcgagtcgaa cctgggctcc atggtggcgc tgaacgcctt     12480
cctgagcacg cagcccgcca acgtgccccg gggccaggag gactacacca acttcatcag     12540
cgcgctgcgg ctgatggtgg ccgaggtgcc ccagagcgag gtgtaccagt cggggccgga     12600
ctacttcttc cagaccagtc gccagggctt gcagaccgtg aacctgagcc aggctttcaa     12660
gaacttgcag ggactgtggg gcgtgcaggc cccggtcggg gaccgcgcga cggtgtcgag     12720
cctgctgacg ccgaactcgc gcctgctgct gctgctggtg gcgcccttca cggacagcgg     12780
cagcgtgagc cgcgactcgt acctgggcta cctgcttaac ctgtaccgca aggccatcgg     12840
gcaggcgcac gtggacagcg agacctacca ggagatcacc cacgtgagcc gcgcgctggg     12900
ccaggaggac ccgggcaacc tggaggccac cctgaacttc ctgctgacca accggtcgca     12960
gaagatcccg ccccagtacg cgctgagcac cgaggaggag cgcatcctgc gctacgtgca     13020
gcagagcgtg gggctgttcc tgatgcagga gggggccacg cccagcgccg cgctcgacat     13080
gaccgcgcgc aacatggagc ccagcatgta cgcccgcaac cgcccgttca tcaataagct     13140
gatggactac ttgcatcggg cggccgccat gaactcggac tacttaccca acgccatctt     13200
gaacccgcac tggctcccgc cgcccgggtt ctacacgggc gagtacgaca tgcccgaccc     13260
caacgacggg ttcctgtggg atgacgtgga cagcagcgtg ttctcgcgcg gtcccaccac     13320
caccgtgtgg aagaaagagg gcggggaccg gcggccgtcc tcggcgctgt ccggtcgcgc     13380
gggtgctgcc gcggcggtgc ccgaggccgc cagcccctttt ccgagcctgc cctttcgct    13440
gaacagcgtg cgcagcagcg agctgggtcg gctgacgcgg ccgcgcctgc tgggcgagga     13500
ggagtaccgg aacgactcct tgttgaggcc cgagcgcgaa aagaacttcc ccaataacgg     13560
gatagagagc ctggtggaca agatgagccg ctggaagacg tacgcgcacg agcacaggga     13620
cgagccccga gctagcagcg caggcaccccg tagacgccag cggcacgaca ggcagcgggg    13680
tctggtgtgg gacgatgagg attccgccga cgacagcagc gtgttggact tgggtgggag     13740
tggtggtggt aacccgttcg ctcacttgcg ccccgtatc gggggcctga tgtaagaatc      13800
tgaaaaataa aaaacggtac tcaccaaggc catggcgacc agcgtgcgtt cttctctgtt     13860
gtttgtagta gtatgatgag gcgcgtgtac ccggagggtc ctcctccctc gtacgagagc     13920
gtgatgcagc aggcggtggc ggcggcgatg cagccccccgc tggaggcgcc ttacgtgccc   13980
ccgcgtaccc tggcgcctac ggaggggcag aacagcattc gttactcgga tcggcaccc     14040
ttgtacgata ccaccccggtt gtacctggtg gacaacaagt cggcggacat cgcctcgctg    14100
aactaccaga acgaccacag caacttcctg accaccgtgg tgcagaacaa cgatttcacc     14160
cccacgcgagg ccagcaccca gaccatcaac tttgacgagc gctcgcggtg gggcggccag    14220
ctgaaaacca tcatgcacac caacatgccc aacgtgaacg agttcatgta cagcaacaag     14280
ttcaaggcgc gggtgatggt ctcgcgcaag accccaacg gggtcacagt aacagatggt      14340
agtcaggacg agctgaccta cgagtgggtg gagtttgagc tgcccgaggg caacttctcg     14400
gtgaccatga ccatcgatct gatgaacaac gccatcatcg acaactactt ggcggtgggg     14460
cggcagaacg gggtgctgga gagcgacatc ggcgtgaagt tcgacacgcg caacttccgg     14520
ctgggctggg accccgtgac cgagctggtg atgccgaggcg tgtacaccaa cgaggccttc     14580
cacccccgaca tcgtcctgct gcccggctgc ggcgtggact tcaccgagag ccgcctcagc     14640
aacctgctgg gcatccgcaa gcggcagccc ttccaggagg gcttccagat cctgtacgag     14700
gacctggagg ggggcaaacat ccccgcgctc ttggatgtcg aagcctacga gaaaagcaag    14760
gaggatagca ccgccgtggc tacctgtgcag actgtggcag atgcactgt caccagggcg    14820
gatacattcg ccaccaggc ggaggaagca gccgccctag cggcgaccga tgatagtgaa      14880
agtaagatag ttatcaagcc ggtggagaag gacagcaagg acaggagcta caacgttcta     14940
tcggatgaa agaacaccgc ctaccgcagc tggtacctgg cctacaacta cggcgacccc     15000
gagaaggcg tgcgctcctg gacgctgctc accacctcgg acgtcacctg cgcggcggag     15060
caagtctact ggtcgctgcc cgacatgatg caagacccgg tcaccttccg ctccacgcgt     15120
caagttagca actaccggt ggtgggcgcc gagctcctgc ccgtctactc caagagcttc     15180
ttcaacgagc aggccgtcta ctcgcagcag ctgcgcgcct tcacctcgct cacgcacgtc     15240
ttcaaccgct tccccgagaa ccagatcctc gtccccgcgc ccgcgcccac cattaccacc     15300
gtcagtgaaa acgttcctgc tctcacagat cacgggaccc tgcctgacgg cagcagtatc     15360
cggggagtcc agcgcgtgac cgtcactgac gccagacgcc gcacctgccc ctacgtctac     15420
aaggccctgg gcgtagtcgc gccgcgcgtc ctctcgagcc gcaccttcta aaaaatgtcc     15480
attctcatct cgcccagtaa taacaccggt tggggcctgc gcgcgcccag caagatgtac     15540
ggaggcgctc gccaacgctc cacgcaacac cccgtgcgcg tgcgcgggca cttccgcgct     15600
ccctgggca ccctcaaggg tcgctgtcgc tgcgcaccag cgtcgacga cgtgatcgac       15660
caggtggtgg ccgacgcgcg caactacacg cccgccgccg cgcccgcctc caccgtggac     15720
gccgtcatcg acagcgtggt ggccgacgcg cgcggtacg cccgcccaa gagccggcgg      15780
cggcgcatcg cccggcggca ccggagcacc cccgccatgc gcgcggcgcg agccttgctg     15840
cgcagggcca ggcgcacggg acgcagggcc atgctcaggc cggccagacg cgcggcctcc     15900
ggcagcagca gcgccggcag gacccgcaga cgcgcggcca cggcggcggc ggcggccatc     15960
```

```
gccagcatgt cccgcccgcg gcgcggcaac gtgtactggg tgcgcgacgc cgccaccggt   16020
gtgcgcgtgc ccgtgcgcac ccgcccccct cgcacttgaa gatgctgact tcgcgatgtt   16080
gatgtgtccc agcggcgagg aggatgtcca agcgcaaata caaggaagag atgctccagg   16140
tcatcgcgcc tgagatctac ggcccgcgg cggcggtgaa ggaggaaaga aagcccgca    16200
aactgaagcg ggtcaaaaag gacaaaaagg aggaggaaga tgtggacgga ctggtggagt   16260
ttgtgcgcga gttcgccccc cggcggcgcg tgcagtggcg cggcggaaa gtgaaaccgg    16320
tgctgcggcc cggcaccacg gtggtcttca cgcccggcga gcgttccggc tccgcctcca   16380
agcgctccta cgacgaggtg tacgggacg aggacatcct cgagcaggcg ccgagcgtc    16440
tgggcgagtt tgcttacggc aagcgcagcc gccccgcgcc cttgaaagag gaggcggtgt   16500
ccatcccgct ggaccacggc aaccccacgc cgagcctgaa gccggtgacc ctgcagcagg   16560
tgctgccgag cgcggcgccg cgccggggct tcaagcgcga gggcggcgag gatctgtacc   16620
cgaccatgca gctgatggtg cccaagcgcc agaagctgga ggacgtgctg gagcacatga   16680
aggtggaccc cgaggtgcag cccgaggtca aggtgcggcc catcaagcag gtggccccgg   16740
gcctgggcgt gcagaccgtg gacatcaaga tccccacgga gccatggaca acgcagaccg   16800
agcccgtgaa gcccagcacc agcaccatgg aggtgcagac ggatccctgg atgcggcgc    16860
cggcttccac caccactcgc cgaagacgca agtacgcgc ggccagcctg ctgatgccca    16920
actacgcgct gcatccttcc atcatcccca cgccgggcta ccgcggcacg cgcttctacc   16980
gcggctacag cagccgccgc aagaccacca cccgccgacg ccgtcgccgc acccgccgca   17040
gcaccaccgc gacttccgcc gccgccttgg tgcggagagt gtaccgcagc gggcgtgagc   17100
ctctgacccct gccgcgcgcg cgctaccacc cgagcatcgc catttaactc tgccgtcgcc   17160
tccttgcaga tatggccctc acatgccgcc tccgcgtccc cattacgggc taccgaggaa   17220
gaaagccgcg ccgtagaagg ctgacgggga acgggctggg tcgccatcac caccggcggc   17280
ggcgcgccat cagcaagcgg ttggggggag gcttcctgcc cgcgctgatc cccatcatcg   17340
ccgcggcgat cggggcgatc cccggcatag cttccgtggc ggtgcaggcc tctcagcgcc   17400
actgagacac agcttggaaa atttgtaata aaaaaatgga ctgacgctcc tggtcctgtg   17460
atgtgtgttt ttagatggaa gacatcaatt tttcgtccct ggcaccggca cacggcacgc   17520
ggccgtttat gggcacctgg agcgacatcg gcaacagcca actgaacggg ggcgccttca   17580
attggagcag tctctggagc gggcttaaga atttcgggtc cacgctcaaa acctatggca   17640
acaaggcgtg gaacagcagc acagggcagg cgctgaggga aaagctgaaa gagcagaact   17700
tccagcagaa ggtggtcgat ggcctcagcct cgggcatcaa cagggtggtg gacctggcca   17760
accaggccgt gcagaaacag atcaacagcc gcctggacgc ggtcccgcc gcggggtccg    17820
tggagatgcc ccaggtggag gaggagctgc ctccccctgga caagcgcggc gacaagcgac   17880
cgcgtcccga cgcggaggag acgctgctga cgcacacgga cgagccgccc cgtacgagg    17940
aggcggtgaa actgggtctg cccaccacgc ggcccgtggc gcctctggcc accggggtgc   18000
tgaaacccag cagcagcagc agcagcccg cgaccctgga cttgcctcca cctcgcccct    18060
ccacagtggc taagccctg ccgccggtgg ccgtcgcgtc gcgcgccccc cgaggccgcc    18120
cccaggcgaa ctgcagagc actctgaaca gcatcgtggg tctgggagtg cagagtgtga   18180
agcgccgccg ctgctattaa aagacactgt agcgcttaac ttgcttgtct gtgtgtatat    18240
gtatgtccgc cgaccagaag gaggaggaag aggcgcgtcc ccgagttgca agatggccac   18300
cccatcgatg ctgccccagt gggcgtacat gcacatcgcc ggacaggacg cttcggagta   18360
cctgagtccg ggtctggtgc agttcgcccg cgccacagac acctacttca gtctgggaa   18420
caagtttagg aaccccacgg tggcacccac gcacgatgtg accaccgacc gcagccagcg   18480
gctgacgccg cgcttcgtgc ccgtggaccg cgaggacaac acctactcgt acaaagtgcg   18540
ctacacgctg gccgtgggcg acaaccgcgt gctggacatg gccagcacct acttttgacat   18600
ccgcggcgtg ctggatcggg gccccagctt caaacctac tccggcaccg cctacaacag   18660
cctggctccc aagggagcgc ccaacacctc acagtggata accaaagaca atggaactga   18720
taagacatac agttttgaa atgctccagt cagaggattg gacattacag aagagggtct   18780
ccaaatagga accgatgagt caggggggtga agcaagaaaa attttttgcag acaaaaccta   18840
tcagcctgaa cctcagcttg gagatgagga atggcatgat actattggag ctgaagacaa   18900
gtatggaggc agagcgctta aacctgccac caacatgaaa ccctgctatg gtctttcgc    18960
caagccaact aatgctaagg gaggtcaggc taaaagcaag aaccaaggacg atggcactac   19020
tgagcctgat attgacatgg ccttctttga cgatcgcagt cagcaagcta gtttcagtcc   19080
agaacttgtt ttgtatactg agaatgtcga tctggcacc ccggataccc acattattta    19140
caaacctggc actgatgaaa caagttcttc tttcaacttg ggtcagcagt ccatgccaa    19200
cagaccaac tacattggct tcagagacaa ctttatcggg ctcatgtact acaacagcac    19260
tggcaatatg ggtgtactgg ccggtcaggc ctcccagctg aatgctgtgg tggacttgca   19320
ggacagaaac actgaactgt cctaccagct cttgcttgac tctctgggtg acagaaccag   19380
gtatttcagt atgtggaatc aggcggtgga cagctatgac cccgatgtgc gcattattga   19440
aaatcacggt gtgaaggatg aactcccaa ctattgcttc tcctttgaatg gtgtgggcgtt   19500
tacagataca ttccagggaa ttaaggttaa aactacaaat aacgaaacag tgtgggctac   19560
agagtgggaa tctgatacct ctgtcaataa tgcaatgag attgcaaagg gcaatccttt    19620
cgccatggag atcaacatcc aggccaacct gtggcgaaac ttcctctacg caacgtggc    19680
gctgtacctg cccgactcct acaagtacac gccggccaac atcacgctgc ccaccaacac   19740
caacacctac gattacatga acggccgcgt ggtggcgcgc tcgctggtgg acgcctacat   19800
caacatcggg gcgcgctggt gctggaccc catggacaaa gtcaaccct tcaaccacca     19860
ccgcaacgcg ggcctgcgct accgctccat gctcctgggc aacgggcgct acgtgccttt   19920
ccacatccag gtgccccaaa agttttcgc catcaagagc ctcctgctcc tgcccgggtc    19980
ctacacctac gagtggaact tccgcaagga cgtcaacatg atctgcaga gctccctcgg    20040
caacgacctg cgcacggacg gggcctccat cgccttcacc agcatcaacc tctacgccac   20100
cttcttcccc atggcgcaca acaccgcctc cacgctcgag gccatgctgc gcaacgacac   20160
caacgaccag tccttcaacg actacctctc ggcggcaac atgctctacc catccggc     20220
caacgccacc aacgtgccca tctccatccc ctcgcgcaac tgggccgcct ccgcggatg    20280
gtccttcacg cgcctcaaga cccgcgagac gccctcgctc ggctccgggt tcgaccccta   20340
cttcgtctac tcgggcgcacc tccccctacct cgacgcacc tttctacctca accacctt    20400
caagaaggtc tccatcacct tcgactcctc cgtcagctgg cccggcaacg accgcctcct   20460
gacgcccaac gagttcgaaa tcaagcgcac cgtcgacgga gagggtaca acgtggccca   20520
gtgcaacatg accaaggact ggttcctggt ccagatgctg ccccactaca acatcggcta   20580
ccagggcttc tacgtgcccg agggctacaa ggaccgcatg tactccttct tccgcaactt    20640
ccagcccatg agccgccagg tcgtggacga ggtcaactac aaggactacc aggccgtcac   20700
```

```
cctggcctac cagcacaaca actcgggctt cgtcggctac ctcgcgccca ccatgcgcca   20760
gggccagccc taccccgcca actacccta cccgctcatc ggcaagagcg ccgtcgccag    20820
cgtcacccag aaaaagttcc tctgcgaccg ggtcatgtgg cgcatcccct tctccagcaa   20880
cttcatgtcc atgggcgcgc tcaccgacct cggccagaac atgctctacg ccaactccgc   20940
ccacgcgcta gacatgaatt tcgaagtcga ccccatgga gagtccaccc ttctctatgt    21000
tgtcttcgaa gtcttcgacg tcgtccgagt gcaccagccc caccgcggcg tcatcgaggc   21060
cgtctacctg cgcacgccct tctcggccgg caacgccacc acctaagcct cttgcttctt   21120
gcaagatgac ggcctgtggc tccggcgagc aggagctcag ggccatcctc cgcgacctgg   21180
gctgcgggcc ctacttcctg ggcaccttcg acaagcgctt cccgggattc atggcccccgc   21240
acaagctggc ctgcgccatc gtcaacacgg ccggccgcga gaccgggggc gagcactggc   21300
tggccttcgc ctggaacccg cgcacccaca cctgctacct cttcgacccc ttcgggttct   21360
cggacgagcg cctcaagcag atctaccagt tcgagtacga gggcctgctg cgccgcagcg   21420
ccctggccac cgaggaccgc tgcgtcaccc tggaaaagtc cacccagacc gtgcagggtc   21480
cgcgctcggc cgcctgcggg ctcttctgct gcatgttcct gcacgccttc gtgcactggc   21540
ccgaccgccc catggacaag aaccccacca tgaacttgct gacggggtg cccaacggca    21600
tgctccagtc gccccaggtg gaacccaccc tgcgccgcaa ccaggaggcg ctctaccgct   21660
tcctcaacgc ccactccgcc tactttcgct cccaccgcgc gcgcatcgag aaggccaccg   21720
ccttcgaccg catgaatcaa gacatgtaaa ctgtgtgtat gtgaatgctt tattcataat   21780
aaacagcaca tgtttatgcc accttctctg aggctctgac tttatttaga aatcgaaggg   21840
gttctgccgc ctctcggcgt gccccgcggg cagggatacg ttgcggaact ggtacttggg   21900
cagccacttg aactcgggga tcagcagctt cggcacgggg aggtcgggga acgagtcgct   21960
ccacagcttg cgcgtgagtt cggcagcgcc cagcagttcg ggcgcggata tcttgaaatc   22020
acagttggga cccgcgttct gcgcgcgaga gttgcggtac acggggttgc agcactggaa   22080
caccatcagg gccgggtgct tcacgctcgc cagcaccgtc gcgtcggtga tgccctccac   22140
gtccagatcc tcggcgttgg ccatcccgaa ggggtcatc ttgcaggtct gccgccccat    22200
gctgggcagc cagccgggct tgtggttgca atcgcagtgc aggggatca gcatcatctg    22260
ggcctgctcg gagctcatgc ccgggtacat ggccttcatg aaagcctcca gctggcggaa   22320
ggcctgctgc gccttgccgc cctcggttgaa gaagacccccg caggacttgc tagagaactg   22380
gttggtggcg cagccggcgt cgtgcacgca gcagcgcgcg tcgttgttgg ccagctgcac   22440
cacgctgcgc cccagcggt tctggttgat ctttggccgg tcggggttct ccttcagcgc    22500
gcgctgcccg ttctcgctcg ccacatccat ctcgatcgtg tgctccttct ggatcatcac   22560
ggtcccgtgc aggcaccgca gcttgccctc ggcttcggtg catccgtgca gccacagcgc   22620
gcagccggtg cactccagt tcttgtgggc gatctgggag tgcgagtgca cgaagccctg    22680
caggaagcgg cccatcatcg cggtcagggt cttgttgctg gtgaaggtca gcgggatgcc   22740
gcggtgctcc tcgttcacat acaggtggca gatgcggcgg tacacctcgc cctgctcggg   22800
catcagctgg aaggcggact tcaggtcgct ctccacgcgg taccgctcca tcagcagcgt   22860
catgacttcc atgcccttct cccaggccga aacgatcggc aggctcaggg ggttcttcac   22920
cgttgtcatc ttagtcgccg ccgccaggt caggggggtcg ttctcgtcca gggtctcaaa    22980
cactcgcttg ccgtccttct cggtgatgcg cacgggggga aagctgaagc cacggccgc    23040
cagctcctcc tcggcctgcc tttcgtcctc gctgtcctgg ctgatgtctt gcaaaggcac   23100
atgcttggtc ttgcggggtt tctttttggg cggcagaggc ggcggcggag acgtgctggg   23160
cgagcgcgag ttctcgctca ccacgactat ttcttcttct tggccgtcgt ccgagaccac   23220
gcggcggtag gcatgcctct tctggggcag aggcggggc gacgggctct cgccggttcgg    23280
cgggcggctg gcagagcccc ttccgcgttc ggggggtgcgc tcctggcggc gctgctctga   23340
ctgacttcct ccgcggccgg ccattgtgtt ctcctaggga gcaagcatgg agactcagcc   23400
atcgtcgcca acatcgccat ctgcccccgc cgccgccgac gagaaccagc agcagcagaa   23460
tgaaagctta accgccccgc cgcccagccc cacctccgac gccgcggccc cagacatgca   23520
agagatggag gaatccatcg agattgacct gggctacgtg acgcccgcgg agcacgagga   23580
ggagctggca gcgcgctttt cagccccgga agagaaccac caagagcagc cagagcagga   23640
agcagagagc gagcagagcc aggctgggct cgagcatggc gactacctga gcggggcaga   23700
ggacgtgctc atcaagcatc tggcccgcca atgcatcatc gtcaaggatg cgctgctcga   23760
ccgcgccgag gtgcccctca gcgtggcgga gctcagccgc gcctacgagc gcaacctctt   23820
ctcgccgcgc gtgcccccca agcgccagcc aacggcacc tgcgagccca cccgcgcct    23880
caacttctac ccgtcttcg cggtgcccga ggccctggcc acctaccacc tcttttttcaa   23940
gaaccaaagg atccccgtct cctgccgcgc caaccgcacc gccgcgacg ccctgctcaa    24000
cctgggcccc ggcgcccgcc tacctgatat cgcctccttg gaagaggttc ccaagatcct   24060
cgagggtctg ggcagcgacg agactcgggc cgcgaacgct ctgcaaggaa gcggagagga   24120
gcatgagcac cacagcgccc tggtggagtt ggaaggcgac aacgcgcgcc tggcggtcct   24180
caagcgcacg gtcgagctga cccacttcgc ctacccggcg ctcaacctgc ccccaaggt    24240
catgagcgcc gtcatgacc aggtgctcat caagcgcgcc tcgcccctct cggaggagga    24300
gatgcaggac cccgagagct cggacgaggg caagcccgtg gtcagcgacg agcagctggc   24360
gcgctggctg ggagcgagta gcaccccca gagcctggaa gagcggcgca agctcatgat   24420
ggccgtggtc ctggtgaccg tggagctgga gtgtctgcgc cgcttcttcg ccgacgcgga   24480
gacctgccgc aaggtcgagg agaacctgca ctacctcttc aggcacggagt tcgtgcgcca   24540
ggcctgcaag atctccaacg tggagctgac caacctggtc tcctacatgg gcatcctgca   24600
cgagaaccgc ctggggcaga acgtgctgca caccccctg cgcggggagg cccgccgcga    24660
ctacatccgc gactgcgtct acctgtacct ctgccacacc tggcagacgg gcatgggcgt   24720
gtggcagcag tgcctggagg agcagaacct gaaagagctc tgcagctcc tgcagaagaa    24780
cctgaaggcc ctgtggaccg ggttcgacga gcgcaccacc gcctcggacc tgcgccgcaa   24840
catcttcccc gagcgcctgc ggctgacgct cgcaacggg ctgccgact ttatgagcca     24900
aagcatgttg caaactttc gctctttcat cctcgaacgc tccgggatcc tgcccgccac   24960
ctgctccgc ctgccctcgg acttcgtgcc gctgaccttc cgcgagtgcc cccgccgct    25020
ctggagccac tgctacctgc tgcgtctggc caactacctg gctaccact cggacgtgat    25080
cgaggacgtc agcgcggagg gtctgctcga tgccacctgc gtcagcctcc tctgcacgcc   25140
gcaccgctcc ctggcctgca accccagct gctgagcgag acccagatca tcggcaccttc   25200
cgagttgcaa ggccccggcg aggagggcaa gggggggctg aaactcaccc cggggctgtg   25260
gacctcggcc tacttgcgca gttcgtgcc cgaggactac catcccttcg agatcaggtt    25320
ctacgaggac caatcccagc cgcccaaggc cgagctgtcg gcctgcgtca tcacccaggg   25380
ggccatcctg gcccaattgc aagccatcca gaaatccgc caagaatttc tgctgaaaaa    25440
```

```
gggccacggg gtctacttgg accccccagac cggagaggag ctcaacccca gcttccccca   25500
ggatgcccag aggaagcagc aagaagctga aagtggagct gccgctgccg ccggaggatt   25560
tggaggaaga ctgggagagc agtcaggcag aggaggagga gatggaagac tgggacagca   25620
ctcaggcaga ggaggacagc ctgcaagaca gtctggaaga cgaggtggag gaggaggcag   25680
aggaagaagc agccgccgcc agaccgtcgt cctcggcgga gaaagcaagc agcacggata   25740
ccatctccgc tccgggtcgg ggtctcggcg gccgggccca cagtaggtgg gacgagaccg   25800
ggcgcttccc gaaccccacc acccagaccg gtaagaagga gcggcaggga tacaagtcct   25860
ggcggggggca caaaaacgcc atcgtctcct gcttgcaagc ctgcggggggc aacatctcct   25920
tcacccggcg ctacctgctc ttccaccgcg gggtgaactt cccccgcaac atcttgcatt   25980
actaccgtca cctccacagc cctactact gtttccaaga agaggcagaa acccagcagc   26040
agcagaaaac cagcagcagc tagaaaatcc acagcggcgg cggcggcagg tggactgagg   26100
atcgcggcga acgagccggc gcagaccggg gagctgagga accggatctt cccaccctc   26160
tatgccatct tccagcagag tcgggggcag gagcaggaac tgaaagtcaa gaaccgttct   26220
ctgcgctcgc tcacccgcag ttgtctgtat cacaagagcg aagaccaact tcagccgcact   26280
ctcgaggacg ccgaggctct cttcaacaag tactgcgcgc tcactcttaa agagtagccc   26340
gcgcccgccc acacacggaa aaaggcggga attacgtcac cacctgcgcc cttcgcccga   26400
ccatcatcat gagcaaagag attcccacgc cttacatgtg gagctaccag ccccagatgg   26460
gcctggccgc cggcgccgcc caggactact ccacccgcat gaactggctc agtgccgggc   26520
ccgcgatgat ctcacgggtg aatgacatcc gcgcccgccg aaaccagata ctcctagaac   26580
agtcagcgat caccgccacg cccgccatc accttaatcc gcgtaattgg cccgccgccc   26640
tggtgtacca ggaaattccc cagcccacga ccgtactact tccgcgagac gcccaggccg   26700
aagtccagct gactaactca ggtgtccagc tggccggcgg ccgcgccctg tgtcgtcacc   26760
gccccgctca gggtataaag cggctggtga tccgaggcag aggcacacag ctcaacgacg   26820
aggtggtgag ctcttcgctg ggtctgcgac ctgacggagt cttccaactc gccggatcgg   26880
ggagatcttc cttcacgcct cgtcaggccg tcctgacttt ggagagttcg tcctcgcagc   26940
cccgctcggg tggcatcggc actctccagt tcgtggagga gttcactccc tcggtctact   27000
tcaaccccct tctccggctcc cccgccact acccggacga gttcatcccg aacttcgacg   27060
ccatcagcga gtcggtggac ggctacgatt gaatgtccca tggtggcgcg gctgacctag   27120
ctcggcttcg acacctggac cactgccgcc gcttccgctg cttcgctcgg gatctcgccg   27180
agtttgccta ctttgagctg cccgaggagc accctccggg cccggcccac ggagtgcgga   27240
tcatcgtcga aggggggcctc gactccacc tgcttcggat cttcagccag cgtccgatcc   27300
tggtcgagcg cgagcaagga cagaccgtc tgacccgtg ctgcatctgc aaccacccg   27360
gcctgcatga aagtctttgt tgtctgctgt gtactgagta taataaaagc tgagatcagc   27420
gactactccg gacttccgtg tgttcctgaa tccatcaacc agtccctgtt cttcaccggg   27480
aacgagaccg agctccagct ccagtgtaag ccccacaaga agtacctcac ctggctgttc   27540
cagggctccc cgatcgccgt tgtcaaccac tgcgacaacg acggagtcct gctgagcggc   27600
cctgccaacc ttacttttttc cacccgcaga agcaagctcc agctcttcca acccttcctc   27660
cccgggacct atcagtgcgt ctcgggaccc tgccatcaca ccttccacct gatcccgaat   27720
accacagcgt cgctcccgc tactaacaac caaactaccc accacgcca ccgtcgcgca   27780
ctttcctctg aatctaatac cactaccgga ggtgagctcc gaggtcgacc aacctctggg   27840
attactacg gcccctggga ggtggtgggg ttaatagcgc taggcctagt tgtgggtggg   27900
cttttggctc tctgctacct atacctccct tgctgttcgt acttagtggt gctgtgttgc   27960
tggtttaaga aatggggcag atcaccctag tgagctggga tgtgctggtg gcggtggtgc   28020
tttcgattgt gggactgggc ggcgcggctg tagtgaagga gaaggccgat ccctgcttgc   28080
atttcaatcc cgacaaatgc cagctgagtt ttcagcccga tggcaatcgg tgcgcggtgc   28140
tgatcaagtg cggatgggaa tgcgagaacg tgagaatcga gtacaataac aagactcgga   28200
acaatactct cgcgtccgtg tggcagcccg gggacccga gtggtacacc gtctctgtcc   28260
ccggtgctga cggctccccg cgcaccgtga ataatacttt cattttttgcg cacatgtgcg   28320
acacggtcat gtggatgagc aagcagtacg atatgtggcc cccacacgaag gagaacatcg   28380
tggtcttctc catcgcttac agcctgtgca cggtgctaat caccgctatc gtgtgcctga   28440
gcattcacat gctcatcgct attcgcccca gaaataatgc cgaaaaagag aaacagccat   28500
aacacgtttt ttcacacacc ttgttttttac agacaatgcg tctgttaaat ttttttaaaca   28560
ttgtgctcag tattgcttat gcctctggct atgcaaacat acagaaaacc ctctatgtag   28620
gatctgatga tacactagag ggtacccaat cacaagctag ggtttcatgg tatttttata   28680
aaagctcaga taatcctatt actctttgca aaggtagtca ggggcggaca acaaagccgc   28740
ctatcacatt tagctgtacc agaacaaatc tcacgctttt ctcaattaca aaacaatatg   28800
ctggtatta ttcagtaca aactttcata gtgggcaaga taatattat actgttaagg   28860
tagaaaatcc taccactcct agaactacca ccaccaccac caccaccacc actactgcga   28920
agcccactaa acctaaaact accaagaaaa ccactgtgaa aactacaact agaaccacca   28980
caactacaga aaccaccacc agcacaacac ttgctgcaac tacacacaca cacactgagc   29040
taaccttaca gaccactaat gatttgatag ccctgttgca aaaggggggat aacagccaca   29100
cttccaatga ggagataccc aaatccatga ttggcattat tgttgctgta gtggtgtgca   29160
tgttgatcat cgccttgtgc atggtgtact atgccttctg ctacagaaag cacagactga   29220
acgacaagct ggaacactta ctaagtgttg aattttaatt ttttagaaac atgaagctca   29280
taggcctttt agtttttttct atcattacct ctgctctatg caattctgac aatgaggacg   29340
ttactgtcgt tgtcggatca aattatacac tgaaaggtcc agcgaagggt atgctttcgt   29400
ggtattgctg gtttggaact gacactgatc aaactgagct ttgcaatgca atgaaaggtc   29460
aaataccaac ctcaaaaatt aaacataaat gcaattagta tgacttagta ctactcaata   29520
tcacgaaatc atatgctggc agctattcat gccctggaga tgatgctgag aacatgattt   29580
tttacaaagt aactgttgtt gatcccacta ctccaccacc caccaccaca actactcaca   29640
ccacacacac agaacaaaca ccagaggcag cagaagcaga gttggccttc caggttcacg   29700
gagattcctt tgctgtcaat accccctacac ccgatcatcg gtgtccgggg ctgctagtca   29760
gcggcattgt cggtgtgctt tcgggattag cagtcataat catctgcatg ttcattttttg   29820
cttgctgcta tagaaggctt taccgacaaa aatcagaccc actgctgaac ctctatgttt   29880
aatttttttcc agagccatga aggcagttag cgctctagtt ttttgttctt tgattggcat   29940
tgttttttgc aatcctatta ctagagttag ctttattaaa gatgtgaatg ttactggaggg   30000
gggcaatgtg acactggtag gtgtagaggg tgctaaaaac accacctgga caaaatacca   30060
ccttgggtgg aaagatattt gcaattggag tgtcactgtg tacacatgtg agggagttaa   30120
tcttaccatt gtcaatgcca cctcagctca aaatggtaga attcaaggac aaagtgttag   30180
```

```
tgtgaccagt gatgggtatt tacccaaca tactttatc tatgacgtta aagtcatacc   30240
actgcctacg cctagcccac ctagcaccac tacacaaaca acccacacta cacagacaac   30300
cacatacagt acatcaaatc agcctaccac cactacagca gcagaggttg ccagctcgtc   30360
tggagttcaa gtggcatttt tgttgttgcc cccatctagc agtcccactg ctattaccaa   30420
tgagcagact actgcatttt tgtccactgt cgagagccac accacagcta cctccagtgc   30480
cttctctagc accgccaatc tctcctcgct ttcctctaca ccaatcagtc ccgctactac   30540
tactacccc gctattcttc ccactcccct gaagcaaaca gacggcggca tgcaatggca   30600
gatcaccctg ctcattgtga tcgggttggt catcctagcc gtgttgctct actacatctt   30660
ctgccgccgc attcccaacg cgcaccgcaa gccggtctac aagcccatca ttgtcgggca   30720
gccggagccg cttcaggtgg aaggggggtct aaggaattct ctcttctctt ttacagtatg   30780
gtgattgaac tatgattcct agacaattct tgatcactat tcttatctgc ctcctccaag   30840
tctgtgccac cctcgctctg gtggccaacg ccagtccaga ctgtattggg cccttcgcct   30900
cctacgtgct ctttgccttc atcacctgca tctgctgctg tagcatagtc tgcctgctta   30960
tcaccttctt ccagttcatt gactggatct ttgtgcgcat cgcctacctg cgccaccacc   31020
cccagtaccg cgaccagcga gtggcgcagc tgctcaggct cctctgataa gcatgcgggc   31080
tctgctactt ctcgcgcttc tgctgttagt gctcccccgt cccgttgacc cccggccccc   31140
cactcagtcc cccgaggagg tccgcaaatg caaattccaa gaaccctgga aattcctcaa   31200
atgctaccgc caaaaatcag acatgcatcc cagctgatgc atgatcattg ggatcgtgaa   31260
cattctggcc tgcaccctca tctccttttgt gatttacccc tgctttgact ttggttggaa   31320
ctcgccagag gcgctctatc tcccgcctga acctgacaca ccaccacagc aacctcaggc   31380
acacgcacta ccaccaccac agcctaggcc acaaatacatg cccatattag actatgaggc   31440
cgagccacag cgacccatgc tccccgctat tagttacttc aatctaaccg gcggagatga   31500
ctgacccact ggccaacaac aacgtcaacg accttctcct ggacatggac ggccgcgcct   31560
cggagcagcg actcgcccaa cttcgcattc gccagcagca ggagagagcc gtcaaggagc   31620
tgcaggacgg catagccatc caccagtgca agaaggcat cttctgcctg gtgaaacagg   31680
ccaagatctc ctacgaggtc acccagaccg accatcgcct ctcctacgag ctcctgcagc   31740
agcgccagaa gttcacctgc ctggtcgag tcaaccccat cgtcatcacc cagcagtcgg   31800
gcgataccaa ggggtgcatc cactgctcct gcgactcccc cgactgcgtc cacactctga   31860
tcaagaccct ctgcggcctc cgcgacctcc tccccatgaa ctaatcaccc acttatccag   31920
tgaaataaaa aaataatcat ttgatttgaa ataaagatac aatcatattg atgattttgag   31980
tttaacaaaa ataaagaatc acttacttga aatctgatac caggtctctg tccatatttt   32040
ctgccaacac cacctcactc ccctcttccc agctctggta ctgcaggccc cggcgggctg   32100
caaacttcct ccacacgctg aagggagtgt caaattcctc ctgccctca atcttcattt   32160
tatcttctat cagatgtcca aaaagcgcgt ccgggtgggt gatgactcg accccgtcta   32220
ccccctacgat gcagcaaacg caccgaccgt gcccttcatc aaccccccct tcgtctcttc   32280
agatggattc caagagaagc ccctggggggt gttgtccctg cgactggccg accccgtcac   32340
caccaagaac ggggaaatca ccctcaagct gggagagggg gtggacctcg actcctcggg   32400
aaaactcatc tccaacacgg ccaccaaggc cgctgccct ctcagttttt ccaacaacac   32460
catttccctt aacatggatc acccctttta cactaaagat ggaaattag ccttacaagt   32520
ttctccacca ttaaatatac tgagaacaag cattctaaac acactagctt taggtttggg   32580
atcaggttta ggactccgtg gctctgcctt ggcagtacag ttagtctctc cacttacatt   32640
tgatactgat ggaaacataa agcttacctt agacagaggt ttgcatgtta caacaggaga   32700
tgcaattgaa agcaacataa agctgggctaa aggttaaaaa tttgaagatg gagccatagc   32760
aaccaacatt ggaaatgggt tagagtttgg aagcagtagt acagaaacag gtgtcgatga   32820
tgcttaccca atccaagtta aacttggatc tggccttagc tttgacagta caggagccat   32880
aatggctggt aacaaagaag acgataaact cactttgtgg acaacacctg atccatcacc   32940
aaactgtcaa atactcgcag aaaatgatgc aaaactaacc ctttgcttga ctaaatgtgg   33000
tagtcaaata ctggccactg tgtcagtctt agttgtagga agtggaaacc taaaccccat   33060
tactggcacc gtaagcagtg ctcaggtgtt tctacgtttt gatgcaaacg gtgttctttt   33120
aacagaacat tctacactaa aaaaatactg ggggtatagg cagggagata gcatagatgg   33180
cactccatat cgcaatgctg taggattcat gcccaattta aaagcttatc caaagtcaca   33240
aagttctact actaaaaata atatagtagg gcaagtatac atgaatgag atgtttcaaa   33300
acctatgctt ctcactataa ccctcaatgg tactgatgac agcaacagta catattcaat   33360
gtcattttca tacacctgga ctaatggaag ctatgttgga gcaacatttg gagctaactc   33420
ttataccttc tcctacatcg cccaagaatg aatactgtat cccaccctgc atgcccaacc   33480
ctccccccacc tctgtctata tggaaaactc tgaaacacaa aataaaataa agttcaagtg   33540
ttttattgat tcaacagttt tacaggattc gagcagttat ttttcctcca ccctcccagg   33600
acatggaata caccaccctc tccccccgca cagccttgaa catctgaatg ccattggtga   33660
tggacatgct tttggtctcc acgttccaca cagtttcaga gcgagccagt ctcgggtcgg   33720
tcagggagat gaaaccctcc gggcactccc gcatctgcac ctcacagctc aacagctgag   33780
gattgtcctc ggtggtcggg atcacggtta tctggaagaa gcagaagagc ggcggtggga   33840
atcatagtcc gcgaacggga tcggccgtg tgtcgcatc aggccccgca gcagtcgctg   33900
ccgccgccgc tccgtcaagc tgctgctcag ggggtccggg tccagggact ccctcagcat   33960
gatgcccacg gccctcagca tcagtcgtct ggtgcggcag cagtcgatgc   34020
ctcgctcagg tcgctgcagt acgtgcaaca caggaccacc aggttgttca acagtccata   34080
gttcaacacg ctccagccga aactcatcgc gggaaggatg ctacccacgt ggccgtcgta   34140
ccagatcctc aggtaaatca agtggcgccc cctccagaac acgctgccca tgtacatgat   34200
ctccttggc atgtggcggt tcaccacctc ccggtaccac atcaccctct ggttgaacat   34260
gcagcccccg atgatcctgc ggaaccacag ggccagccgc ggcccgcccg ccatgcagcg   34320
aagagacccc gggtcccggc aatggcaatg gaggacccac cgctcgtacc cgtggatcat   34380
ctgggagctg aacaagtcta tgttggcaca gcacaggcac acgctcatgc atctcttcag   34440
cactctcagc tcctcggggg tcaaaaccat atcccagggc acgggaaact cttgcaggac   34500
agcgaagccc gcagaacagg gcaatcctcg cacataactt acattgtgca tggacagggt   34560
atcgcaatca ggcagcaccg ggtgatcctc caccagagag ggtgtct cggtctcctc   34620
acagcgtggt aaggggggccg gccgatacgg gtgatggcgg gacgcggctg atcgtgttcg   34680
cgaccgtgtc atgatgcagt tgctttcgga catttcgta cttgctgaag cagaacctgg   34740
tccgggcgct gcacaccgat cgccggcggc ggtctcggcg cttggaacgc tcggtgttga   34800
agttgtaaaa cagccactct ctcagaccgt gcagcagatc tagggcctca ggagtgatga   34860
agatcccatc atgcctgatg gctctgatca catcgaccac cgtggaatgg gccagaccca   34920
```

```
gccagatgat gcaattttgt tgggtttcgg tgacggcggg ggagggaaga acaggaagaa    34980
ccatgattaa cttttaatcc aaacggtctc ggagcacttc aaaatgaagg tcgcggagat    35040
ggcacctctc gccccgctg tgttggtgga aaataacagc caggtcaaag gtgatacggt     35100
tctcgagatg ttccacggtg gcttccagca aagcctccac gcgcacatcc agaaacaaga    35160
caatagcgaa agcgggaggg ttctctaatt cctcaatcat catgttacac tcctgcacca    35220
tccccagata attttcattt ttccagcctt gaatgattcg aactagttcc tgaggtaaat    35280
ccaagccagc catgataaag agctcgcgca gagcgccctc caccggcatt cttaagcaca    35340
ccctcataat tccaagatat tctgctcctg gttcacctgc agcagattga caagcgggat    35400
atcaaaatct ctgccgcgat ccctgagctc ctccctcagc aataactgta agtactcttt    35460
catatcctct ccgaaatttt tagccatagg accccagga ataagagaag ggcaagccac     35520
attacagata aaccgaagtc cccccagtg agcattgcca aatgtaagat tgaaataagc     35580
atgctggcta gacccggtga tatcttccag ataactggac agaaaatcgg gcaagcaatt    35640
tttaagaaaa tcaacaaaag aaaaatcttc caggtgcacg tttagggcct cgggaacaaac   35700
gatggagtaa gtgcaagggg tgcgttccag catggttagt tagctgatct gtaaaaaaac    35760
aaaaaataaa acattaaacc atgctagcct ggcgaacagg tgggtaaatc gttctctcca    35820
gcaccaggca ggccacgggg tctccggcgc gaccctcgta aaaattgtcg ctatgattga    35880
aaaccatcac agagagacgt tcccggtggc cggcgtgaat gattcgagaa gaagcataca    35940
ccccggaac attggagtcc gtgagtgaaa aaaagcggcc gaggaagcaa tgaggcacta    36000
caacgctcac tctcaagtcc agcaaagcga tgccatgcgg atgaagcaca aaattttcag    36060
gtgcgtaaaa aatgtaatta ctcccctcct gcacaggcag cgaagctccc gatccctcca    36120
gatacacata caaagcctca gcgtccatag cttaccgagc ggcagcagca gcggcacaca    36180
acaggcgcaa gagtcagaga aaagactgag ctctaacctg ccgcccgct ctctgctcaa     36240
tatatagccc cagatctaca ctgacgtaaa ggccaaagtc taaaaatacc cgccaaataa    36300
tcacacacgc ccagcacacg cccagaaacc ggtgacacac tcaaaaaaat acgcgcactt    36360
cctcaaacgc ccaaactgcc gtcatttccg ggttccacg ctacgtcatc aaaacacgac     36420
tttcaaattc cgtcgaccgt taaaaacgtc acccgccccg cccctaacgg tcgccgctcc    36480
cgcagccaat cagcgccccg catcccaaa ttcaaacagc tcatttgcat attaacgcgc     36540
accaaaagtt tgaggtatat tattgatgat g                                  36571

SEQ ID NO: 3             moltype = DNA  length = 1109
FEATURE                  Location/Qualifiers
misc_feature             1..1109
                         note = Description of Artificial Sequence: Synthetic
                         polynucleotide
source                   1..1109
                         mol_type = other DNA
                         organism = synthetic construct
SEQUENCE: 3
ggagttccgc gttacataac ttacggtaaa tggcccgcct ggctgaccgc ccaacgaccc    60
ccgcccattg acgtcaataa tgacgtatgt tcccatagta acgccaatag ggactttcca    120
ttgacgtcaa tgggtggagt atttacggta aactgcccac ttggcagtac atcaagtgta    180
tcatatgcca agtacgcccc ctattgacgt caatgacggt aaatggcccg cctggcatta    240
tgcccagtac atgaccttat gggactttcc tacttggcag tacatctacg tattagtcat    300
cgctattacc atggtcgagg tgagcccacg ttctgcttc actctcccca tctcccccc      360
ctccccaccc caattttgt attttattat ttttaatta ttttgtgcag cgatgggggc      420
gggggggggg ggggcgcgc gccaggcggg gcggggcggg gcgaggggcg gggcggggcg     480
aggcggagag gtgcggcgc agccaatcag agcggccggc tccgaaagtt tccttttatg    540
gcgaggcggc ggcggcggcg gccctataaa aagcgaagcg ctccctatca gtgatagaga    600
tctccctatc agtgatagag atcgtcgacg agctcgcggc gggcgggagt cgctgcgcgc    660
tgccttcgcc ccgtgccccg ctccgccgcc gcctcgcgcc gcccgcccg gctctgactg     720
accgcgttac taaaaccaggt aagtccggcc tccgcgcccg gttttggcgc ctcccgcggg   780
cgcccccctc ctcacggcga gcgctgccac gtcagacgaa gggcgcagcg agcgtcctga    840
tccttccgcc cggacgctca ggacagcggc ccgctgctca taagactcgg ccttagaacc    900
ccagtatcag cagaaggaca ttttaggacg ggacttgggt gactctaggg cactggtttt    960
ctttccagag agcggaacag gcgaggaaaa gtagtccctt ctcggcgatt ctgcggaggg    1020
atctccgtgg ggcggtgaac gccgatgatg cctctactaa ccatgttcat gttttctttt    1080
tttttctaca ggtcctgggt gacgaacag                                     1109

SEQ ID NO: 4             moltype = DNA  length = 37559
FEATURE                  Location/Qualifiers
misc_feature             1..37559
                         note = Description of Artificial Sequence: Synthetic
                         polynucleotide
source                   1..37559
                         mol_type = other DNA
                         organism = synthetic construct
SEQUENCE: 4
catcatcaat aatataccct attttggatt gaagccaata tgataatgag atgggcggcg    60
cggggcgggg cgcggggcgg gaggcgggtt tggggcggg ccggcgggcg ggggcggtgtg    120
gcggaagtgg actttgtaag tgtggcggat gtgacttgct agtgccgggc gcggtaaaag    180
tgacgttttc cgtgcgcgac aacgcccccg ggaagtgaca ttttttcccgc ggtttttacc    240
ggatgttgta gtgaatttgg gcgtaaccaa gtaagatttg gccattttcg cgggaaaact    300
gaaacgggga agtgaaatct gattaatttt gcgttagtca taccgcgtaa tatttgtcta    360
ggggccgaggg acttggccgg attacgtgga ggactcgtca aggtgttttt tgaggtgaat    420
ttccgcgttc cggtcaaag tctgcgtttt attattatag gatatcccat tgcatacgtt     480
gtatccatat cataatatgt acatttatat tggctcatgt ccaacattac cgccatgttg    540
acattgatta ttgactagtt attaatagta atcaattacg ggtcattag ttcatagccc     600
atatatggag ttccgcgtta cataacttac ggtaaatggc ccgcctggct gaccgcccaa    660
cgacccccgc ccattgacgt caataatgac gtatgttccc atagtaacgc caatagggac    720
```

```
tttccattga cgtcaatggg tggagtattt acggtaaact gcccacttgg cagtacatca  780
agtgtatcat atgccaagta cgcccccta t tgacgtcaat gacggtaaat ggcccgcctg  840
gcattatgcc cagtacatga ccttatggga ctttcctact tggcagtaca tctacgtatt  900
agtcatcgct attaccatgg tgatgcggtt ttggcagtac atcaatgggc gtggatagcg  960
gtttgactca cggggatttc caagtctcca ccccattgac gtcaatggga gtttgttttg 1020
gcaccaaaat caacgggact ttccaaaatg tcgtaacaac tccgccccat tgacgcaaat 1080
gggcggtagg cgtgtacggt gggaggtcta tataagcaga gctctcccta tcagtgatag 1140
agatctccct atcagtgata gagatcgtcg acgagctcgt ttagtgaacc gtcagatcgc 1200
ctggagacgc catccacgct gttttgacct ccatagaaga cacccgggacc gatccagcct 1260
ccgcggccgg gaacgcgtgca ttggaacgcg gattcccgt gccaagagtg agatcttccg 1320
tttatctagg taccagatat cgccaccatg gaactgctga tcctgaaggc caacgccatc 1380
accaccatcc tgaccgccgt gaccttctgc ttcgccagcg ccagaacat caccgaggaa 1440
ttctaccaga gcacctgtag cgccgtgagc aagggctacc tgagcgccct gagaaccggc 1500
tggtacacca gcgtgatcac catcgacctg agcaacatca aagaaaacaa gtgcaacggc 1560
accgacgcca aagtgaagct gatcaagcag gaactggaca agtacaagaa cgccgtgacc 1620
gagctgcagc tgctgatgca gagcacccc gccaccaaca accgggccag acgggagctg 1680
ccccggttca tgaactacac cctgaacaac gccaaaaaga ccaacgtgac cctgagcaag 1740
aagcggaagc ggcggttcct gggctttctg ctgggcgtgg gcagcgccat tgccagcggc 1800
gtggccgtgt ctaaggtgct gcacctggaa ggcgaagtga acaagatcaa gagcgccctg 1860
ctggcacca caaggccgt ggtgtccctg agcaacggcg tgagcgtgct gaccagcaag 1920
gtgctggatc tgaagaacta catcgacaag cagctgctgc ccatcgtgaa caagcagagc 1980
tgcagcatca gcaacatcga gacagtgatc gagttccaag agaagaacaa ccggctgctg 2040
gaaatcaccc gggagttcag cgtgaacgcc ggcgtgacca ccctgtgtc cacctacatg 2100
ctgaccaaca gcgagctgct gagcctgatc aacgacatgc catcaccaa cgaccagaaa 2160
aagctgatga gcaacaacgt gcagatcgtg cggcagcaga gctactccat catgtccatc 2220
atcaaagaag aggtgctggc ctacgtggtg cagctgcccc tgtacggcgt gatcgacacc 2280
ccctgctgga agctgcacac cagccccctg tgcaccacca acaccaaaga gggcagcaac 2340
atctgcctga cccggaccga cagaggctgg tactgcgaca acgccggcag cgtgtcattc 2400
tttccacagg ccgagacatg caaggtgcag agcaaccggg tgttctgcga caccatgaac 2460
agcctgaccc tgcctccga agtgaacctg tgcaacgtga acatcttcaa ccccaagtac 2520
gactgcaaga tcatgacctc caagaccgac gtgtccagct ccgtgatcac ctccctgggc 2580
gccatcgtgt cctgctacgg caagaccaag tgcaccgcca gcaacaagaa ccggggcatc 2640
atcaagacct tcagcaacgg ctgcgactac gtgtccaaca aggggtgga caccgtgtcc 2700
gtgggcaaca ccctgtacta cgtgaacaaa caggaaggca gagcctgta cgtgaagggc 2760
gagcccatca tcaacttcta cgacccctg gtgttccca gcgacgagtt cgacgccagc 2820
atcagccagg tgaacgagaa gatcaaccag agcctggcct tcatccggaa gtccgacgag 2880
ctgctgcaca atgtgaatgc cggcaagtcc accaccaacc ggaagcggag agcccctgtg 2940
aagcagaccc tgaacttcga cctgctgaag ctggccggcg acgtggagag caatcccggc 3000
cctatgccc tgacaaagt gaaactgaac gatcacctga acaaggacca gctgctgtcc 3060
agcagcaagt acaccatcca gcggagcacc ggcgacagca tcgatacccc caactacgac 3120
gtgcagaagc acatcaacaa gctgtgcggc atgctgctga tcacagagga cgccaaccac 3180
aagttcaccg gcctgatcgg catgctgtac gccatgagcc ggctgggccg ggaggacacc 3240
atcaagatcc tgcgggacgc cggctaccac gtgaaggcca atggcgtgga cgtgaccaca 3300
caccggcagg acatcaacgg caaagaaatg aagttcgagg tgctgaccct ggccagcctg 3360
accaccgaga tccagatcaa tatcgagatc gagagccgga agtcctacaa gaaaatgctg 3420
aaagaaatgg gcgaggtggc ccccgagtac agacacgaca gccccgactg cggcatgatc 3480
atcctgtgta tcgccgccct ggtgatcaca aagctggccg ctggcgacag atctggcctg 3540
acagccgtga tcagacgggc caacaatgtg ctgaagaacg agatgaagcg gtacaagggc 3600
ctgctgccca aggacattgc caacagcttc tacgaggtgt cgagaagta ccccacttc 3660
atcgacgtgt cgtgcactt cggcattgcc cagagcagca ccagaggcgg ctccagagtg 3720
gagggcatct tcgccggcct gttcatgaac gcctacggcg ctggccaggt gatgctgaga 3780
tgggcgtgc tggccaagag cgtgaagaac atcatgctgg ccacccgcag cgtgcaggcc 3840
gagatggaac aggtggtgga ggtgtacgag tacgcccaga gctgggcgg agaggccggc 3900
ttctaccaca tcctgaacaa ccctaaggcc tcctgctgt ccctgaccca gttccccac 3960
ttctccagcg tggtgctggg aaatgccgcc ggactggca tcatgggcga gtaccggggc 4020
acccccagaa accaggacct gtacgacgcc gccaaggcct acgccgagca gctgaaagaa 4080
aacggcgtga tcaactacag cgtgctggac ctgaccgctg aggaactgga agccatcaag 4140
caccagctga ccccaagga caacgacgtg gagctggag cggaggatc tggcggcgga 4200
ggcatgagca gacggaaccc ctgcaagttc gagatccggg gccactgcct gaacggcaga 4260
cggtgccact tcagccacaa ctacttcgag tggccccctc atgctctgct ggtgcggcag 4320
aacttcatgc tgaaccggat cctgaagtcc atggacaaga gcatcgacac cctgagcgag 4380
atcagcggag ccgccgagct ggacagaacc gaggaatatg ccctgggcgt ggtgggagtg 4440
ctggaaagct acatcggctc catcaacaac atcacaaagc agagcgcctg cgtggccatg 4500
agcaagctgc tgacagagct gaacaagcga gacatcaaga agctgagga caacgaggaa 4560
ctgaacagcc ccaagatccg ggtgtacaac accgtgatca gctacattga gagcaaccgc 4620
aagaacaaca gcagaccat ccatctgctg aagcggctgc ccgccgacgt gctgaaaaag 4680
accatcaaga cacccctgga catccacaag tccatcacca tcaacaatcc caaagaaagc 4740
accgtgtctg acaccaacga tcacgccaag aacaacgaca ccaactgatg agcgccgcg 4800
atctgctgtg ccttctagtt gccagccatc tgttgtttgc ccctcccccg tgccttcctt 4860
gaccctggaa ggtgccactc ccactgtcct ttcctaataa aatgaggaaa ttgcatcgca 4920
ttgtctgagt aggtgtcatt ctattctggg gggtgggtg gggcaggaca gcaaggggga 4980
ggattgggaa gacaatagca ggcatgctgg ggatgcggtg ggctctatgg ccgatcagcg 5040
atctgctgag tgggtgagtg ggcgtggcct gggtggtca tgaaaatata taagttgggg 5100
gtcttagggt ctctttattt gtgttgcaga gaccgccgga gcatgagcg gagcagcag 5160
cagcagcagt agcagcagcg ccttggatgg cagcatcgtg agcccttatt tgacgacgcg 5220
gatgccccac tgggccgggg tgcgtcagaa tgtgatgggc tccagcatcg acggccgacc 5280
cgtcctgccc gcaaattccg ccacgctgac ctatgcgacc gtcgcgggga cgccgttgga 5340
cgccaccgcc gccgccgccg ccaccgcagc cgcctcggcc gtgcgcagcc tggccacgga 5400
cttttgcatte ctgggaccac tggcgacagg ggctactttct cgggccgctg ctgccgccgt 5460
```

```
tcgcgatgac aagctgaccg ccctgctggc gcagttggat gcgcttactc gggaactggg   5520
tgacctttct cagcaggtca tggccctgcg ccagcaggtc tcctccctgc aagctggcgg   5580
gaatgcttct cccacaaatg ccgtttaaga taaataaaac cagactctgt ttggattaaa   5640
gaaaagtagc aagtgcattg ctctctttat ttcataattt tccgcgcgcg ataggcccta   5700
gaccagcgtt ctcggtcgtt gagggtgcgg tgtatcttct ccaggacgtg gtagaggtgg   5760
ctctggacgt tgagatacat gggcatgagc ccgtcccggg ggtggaggta gcaccactgc   5820
agagcttcat gctccggggt ggtgttgtag atgatccagt cgtagcagga gcgctgggca   5880
tggtgcctaa aaatgtcctt cagcagcagg ccgatggcca gggggaggcc cttggtgtaa   5940
gtgtttacaa aacggttaag ttgggaaggg tgcattcggg gagagatgat gtgcatcttg   6000
gactgtatt ttagattggc gatgtttccg cccagatccc ttctgggatt catgttgtgc   6060
aggaccacca gtacagtgta tccggtgcac ttggggaatt tgtcatgcag cttagaggga   6120
aaaagcgtgga agaacttgga gacgcctttg tggcctccca gattttccat gcattcgtcc   6180
atgatgatgg caatgggccc gcgggaggca gcttgggcaa agatatttct ggggtcgctg   6240
acgtcgtagt tgtgttccag ggtgaggtcg tcataggcca tttttacaaa gcgcgggctg   6300
agggtgcccg actgggggat gatggtcccc tctggccctg gggcgtagtt gccctcgcag   6360
atctgcattt cccaggcctt aatctcggag gggggaatca tatccacctg cggggcgatg   6420
aagaaaacgg tttccggagc cggggagatt aactgggatg agagcaggtt tctaagcagc   6480
tgtgattttc cacaaccggt gggcccataa ataacaccta taaccggttg cagctggtag   6540
tttagagagc tgcagctgcc gtcgtcccgg aggaggggg ccacctcgtt gagcatgtcc   6600
ctgacgcgca tgttctcccc gaccagatcc gccagaaggc gctcgccgcc cagggacagc   6660
agctcttgca aggaagcaaa gttttcagc ggcttgaggc cgtccgccgt gggcatgttt   6720
ttcagggtct ggctcagcag ctccaggcgg tcccagaagct cggtgacgtg ctctacggca   6780
tctctatcca gcatatctcc tcgtttcgcg ggttggggcg actttcgctg tagggcacca   6840
agcggtggtc gtccagcggg gccagagtca tgtccttcca tgggcgcagg gtcctcgtca   6900
gggtggtctg ggtcacggtg aagggggtgcg ctccgggctg agcgcttgcc aagtgcgct   6960
tgaggctggt tctgctggtg ctgaagcgct gccggtcttc gccctgccgg tcggccaggt   7020
agcatttgac catggtgtca tagtccagcc cctccgcggc gtgtcccttg gcgcgcagct   7080
tgcccttgga ggtggcgccg cacgaggggc agagcaggct cttgagcgcg tagagcttgg   7140
gggcgaggaa gaccgattcg ggggagtagg cgtccgcgcc gcagaccccg cacacggtct   7200
cgcactccac cagccaggtg gctcggggcc gcgccggcc aaaaaccagg tttcccccat   7260
gcttttgat gcgtttctta cctcgggtct ccatgaggtg gtgtcccgc tcggtgacga   7320
agaggctgtc cgtgtctccg tagaccgact tgaggggtct tttctccagg ggggtccctc   7380
ggtcttcctc gtagaggaac tcggaccact ctgagacgaa ggcccgcgtc caggccagga   7440
cgaaggaggc tatgtgggag gggtagcggt cgttgtccac taggggggtcc accttctcca   7500
aggtgtgaag acacatgtcg ccttcctcgg cgtccaggaa gtgatggc ttgtaggtgg   7560
aggccacgtg accggggggtt cctgacgggg gggtataaaa ggggtgggg gcgcgctcgt   7620
cgtcactctc ttccgcatcg ctgtctgcga gggccagctg ctgggggtgag tattccctct   7680
cgaaggcggg catgacctcc gcgctgaggt tgtcagtttc caaaaacgag gaggatttga   7740
tgttcacctg tcccgaggtg atacctttga gggtacccgc gtccatctgg tcagaaaaca   7800
cgatcttttt attgtccagc ttggtggcga acgacccgta gaggcgttg gagagcagct   7860
tggcgatgga gcgcagggtc tggttcttgt ccctgtcggc gcgctccttg gccgcgatgt   7920
tgagctgcac gtactcgcgc gcgacgcagc gccactcggg gaagacggtg gtgcgctcgt   7980
cgggcaccag gcgcacggcc cagccgcggt tgtgcaggat gaccaggtcc acgctggtgg   8040
cgacctcgcc gcgcaggcgc tcgttggtcc agcagagacg gccgcccttg cgcgagcaga   8100
aggggggcag ggggtcgagc tgggtctcgt ccgggggtc cgcgtccacg gtgaaaaccc   8160
cggggcgcag gcgcgcgtcg aagtagtcta tcttgcaacc ttgcatgtcc agcgcctgct   8220
gccagtcgcg ggcggcgagc gcgcgtcgt aggggttgag cggcgggcc cagggcatgg   8280
ggtgggtgag tgcggaggcg tacatgccgc agatgtcata gacgtagagg ggctcccgca   8340
ggaccccgat gtaggtgggg tagcagcggc cgccgcggat gctggcgcgc acgtagtcat   8400
acagctcgtg cgagggggcg aggaggtcgg ggcccaggtt ggtgcgggcg gggcgctccg   8460
cgcggaagac gatctgcctg aagatggcat gcgagttgga agatatggtg gggcgctgga   8520
agacgttgaa gctggcgtcc tgcaggccga cggcgtcgcg cacgaaggag gcgtaggagt   8580
cgcgcagctt gtgtaccagc tcggcggtga cctgcacgtc gagcgcgcag tagtcgaggg   8640
tctcgcggat gatgtcatat ttagcctgcc ccttctttt ccacagctcg cggttgagga   8700
caaactcttc gcggtctttc cagtactctt ggatcggaaa accgtccgt tccgaacggt   8760
aagagcctag catgtagaac tggttgacgg cctggtaggc gcagcagccc ttctccacgg   8820
ggagggcgta ggcctgcgcg gccttgcgga gcgaggtgtg ggtcagggcg aaggtgtccc   8880
tgaccatgac tttgaggtac tggtgcttga agtcggagtc gtcgcagccg ccccgctccc   8940
agagcgagaa gtcggtgcgc ttcttggagc ggggggtggg cagagcgaag gtgacatcgt   9000
tgaagaggat tttgcccgcg cggggcatga agttgcggat gatgcggaag ggccccgcag   9060
cttcagagcg gttgttgatg acctgggcgg cgagcacgat ctcgtcgaag ccgttgatgt   9120
tgtgcccac gatgtagagt tccaggaagc ggggccggcc ctttacggtg gcagcttct   9180
ttagctcttc gtaggtgagc tcctcgggcg aggcgaggcc gtgctcggcc agggcccagt   9240
ccgcgaggtg cgggttgtct ctgaggaagg acttccagga gtcgcgggtc aggagggtct   9300
gcaggcggtc tctgaaggtc ctgaactggc ggcccacggc cattttttcg ggggtgatgc   9360
agtagaaggt gagggggtct tgctgccagc ggtcccagtc gagctgcagg gcgaggtcgc   9420
gcgcggcggt gaccaggcgc tcgtcgcccc cgaatttcat gaccagcatg aagggcacga   9480
gctgcttcc gaaggccccc atccaagtgt aggtctctac atcgtaggtg acaaagaggc   9540
gctccgtgcg aggatgcgaa ccgatcggga agaactgaat ctcccgccac cagttggagg   9600
agtggctgtt gatgtggtgg aagtagaagt cccgtcgccg ggccgaacac tcgtgctggc   9660
ttttgtaaaa gcgagcgcag tactggcagc gctgcacggg ctgtacctca tgcacgagat   9720
gcacctttcg cccgcgcacg aggaagccga ggggaaatct gagccccccg cctgctcgc   9780
ggcatgctg gttctcttct actttggatg cgtgtccgtc tccgtctggc tcctcgaggg   9840
gtgttacggt ggagcggacc accacgccgc gcagccgcga gtccagata tcgcgcgcgg   9900
gcggtcggag tttgatgacg acatcgcgca gctgggagct gtccatgtc tggagctccc   9960
gcggcggcgg caggtcagcc gggagttctt gcaggttcac ctgcagagt cgggccaggg  10020
cgcggggcag gtctaggtgg tacctgatct ctagggcgt gttggtggcg gcgtcgatgg  10080
cttgcaggag cccgcagccc cggggggcga cgacggtgcc ccgcggggtg gtggtggtgg  10140
tggcggtgca gctcagaagc ggtgccgcgg gcgggccccc ggaggtaggg ggggctccgg  10200
```

```
tcccgcgggc aggggcggca gcggcacgtc ggcgtggagc gcgggcagga gttggtgctg    10260
tgcccggagg ttgctggcga aggcgacgac gcggcggttg atctcctgga tctggcgcct    10320
ctgcgtgaag acgacgggcc cggtgagctt gaacctgaaa gagagttcga cagaatcaat    10380
ctcggtgtca ttgaccgcgg cctggcgcag gatctcctgc acgtctcccg agttgtcttg    10440
gtaggcgatc tcggccatga actgctcgat ctcttcctcc tggaggtctc cgcgtccggc    10500
gcgttccacg gtggccgcca ggtcgttgga gatgcgcccc atgagctgcg agaaggcgtt    10560
gagtccgccc tcgttccaga ctcggctgta gaccacgccc cctggtcat cgcgggcgcg     10620
catgaccacc tgcgcgaggt tgagctccac gtgccgcgcg aagacggcgt agttgcgcag    10680
acgctggaag aggtagttga gggtggtggc ggtgtgctcg gccacgaaga agttcatgac    10740
ccagcggcgc aacgtggatt cgttgatgtc ccccaaggcc tccagccgtt ccatggcctc    10800
gtagaagtcc acggcgaagt tgaaaaactg ggagttgcgc gccgacacgg tcaactcctc    10860
ctccagaaga cggatgagct cggcgacggt gtcgcgcacc tcgcgctcga aggctatggg    10920
gatctcttcc tccgctagca tcaccacctc ctcctcttcc tcctcttctg gcacttccat    10980
gatggcttcc tcctcttcgg ggggtggcgg cggcggcggt ggggagggg gcgctctgcg     11040
ccggcggcgg cgcaccggga ggcggtccac gaagcgcgcg atcatctccc cgcggcggcg    11100
gcgcatggtc tcggtgacgg cgcggccgtt ctcccggggg cgcagttgga agacgccgcc    11160
ggacatctgg tgctggggcg ggtggccgtg aggcagcgag acggcgctga cgatgcatct    11220
caacaattgc tgcgtaggta cgccgccgag ggacctgagg gagtccatat ccaccggatc    11280
cgaaaacctt tcgaggaagg cgtctaacca gtcgcagtcg caaggtaggc tgagcaccgt    11340
ggcgggcggc gggggtggg gggagtgtct ggcggaggtg ctgctgatga tgtaattgaa    11400
gtaggcggac ttgacacggc ggatggtcga caggagcacc atgtccttgg gtccggcctg    11460
ctggatgcgg aggcgtcgg ctatgcccca ggcttcgttc tggcatcggc gcaggtcctt    11520
gtagtagtct tgcatgagcc tttccaccgg cacctcttct ccttcctctt ctgcttcttc    11580
catgtctgct tcggccctgg ggcggcgccg cgcccccctg cccccatgc gcgtgacccc     11640
gaaccccctg agcggttgga gcaggccag gtcggcgacg acgcgctcgg ccaggatggc    11700
ctgctgcacc tgcgtgaggg tggttttggaa gtcatccaaa tccacgaagc ggtaggtaggc  11760
gcccgtgttg atggtgtagg tgcagttggc catgacggac cagttgacgg tctggtggcc    11820
cggttgcgac atctcggtgt acctgagtcg cgagtaggcg cgggagtcga agacgtagtc    11880
gttgcaagtc cgcaccaggt actggtagcc caccaggaag tgcggcggcg gctggcggta    11940
gagggccag cgcagggtgg cgggggctcc ggggggcagg tcttccagca tgaggcggtg     12000
gtaggcgtag atgtacctgg acatccaggt gataccgcg gcggtggtgg aggcgcggg     12060
gaagtcgcgc acccggttcc agatgttgcg caggggcaga aagtgctcca tggtaggcgt    12120
gctctgtcca gtcagacgcg cgcagtcgtt gatactctag accagggaaa acgaaagccg    12180
gtcagcgggc actcttccgt ggtctggtga atagatcgca agggtatcat ggcggagggc    12240
ctcggttcga gccccgggtc cgggccggac ggtccgccat gatccacgcg gttaccgccc    12300
gcgtgtcgaa cccaggtgtg cgacgtcaga caacggtgga gtgttccttt tggcgttttt    12360
ctggccgggc gccggcgccg cgtaagagac taagccgcga aagcgaaagc agtaagtggc    12420
tcgctcccg tagccggagg gatccttgct aagggttgcg ttgcggcgaa ccccggttcg     12480
aatccgctac tcgggccggc cggacccgcg gctaaggtgt tggattggcc tcccctcgt    12540
ataaagaccc cgcttgcgga ttgactccgg acacggggac gagcccctt tatttttgct     12600
ttcccagat gcatccggtg ctgcggcaga tgcgcccccc gcccagcag cagcaacaac      12660
accagcaaga gcggcagcaa cagcagcggg agtcatgcag ggcccctca cccaccctcg     12720
gcgggccag cacctcggcg tccgcgccg tgtctggcgc ctgcgcgggc gcgggggcg       12780
cggctgacga ccccgaggag ccccgcggc gcagggccaa acactacctg gacctggagg     12840
agggcgaggg cctggcgcgg ctgggggcgc cgtctcccga gcgccaccg cggtggcagc     12900
tgaagcgcga ctcgcgcgag gcgtacgtgc ctcggcagaa cctgttcagg gaccgcgcgg    12960
gcgaggagcc cgaggagatg cggacagga ggttcagcgc agggcgggag ctgcggcagg     13020
ggctgaaccg cgagcggctg ctgcgcgagg aggactttga gcccgacgcg cggacgggga    13080
tcagccccgc gcgcgcgcac gtggcggccg ccgacctggt gacggcgtac gagcagacgg    13140
tgaaccagga gatcaacttc caaaagagtt tcaacaacca cgtgcgcacg ctggtggcgc    13200
gcgagaggt gaccatcggg ctgatgcacc tgtgggactt tgtaagcgcg ctggtggcga     13260
accccaacag caagcctctg acggcgcagc tgttcctgat agtgcagcac agcagggaca    13320
acgaggcgtt tagggacgcg ctgctgaaca tcaccgagcc cgagggtcgg tggctgctgg    13380
acctgattaa catcctgcag agcatagtgg tgcaggagcg cagcctgagc ctggccgaca    13440
aggtgccgc catcaactac tcgatgctga gcctgggcaa gttttacgcg gccaagatct     13500
accagacgcc gtacgtgccc atagacaagg aggtgaagat cgacggtttt tacatgcgca    13560
tggcgctgaa ggtgctcacc ctgagcgacg acctgggcgt gtaccgcaac gagcgcatcc    13620
acaaggccgt gagcgtgagc cggcggcgcg agctgagcga ccgcgagctg atgcacagcc    13680
tgcagcgggc gctggcgggc gccggcagcg gcgacaggga ggcggagtcc tacttcgatg    13740
cgggggcgg cctgcgctgg gcgcccagcc gggccgcct gggggccgcg ggggtccgcg     13800
aggactatga cgaggacggc gaggaggatg aggagtacga gctagaggag ggcgagtacc    13860
tggactaaac cgcgggtggt gtttccggta gatgcaagac ccgaacgtgg tgacccggc     13920
gctgcgggcg gctctgcaga gccagccgtc cggccttaac tcctcagacg actggcgaca    13980
ggtcatggac cgcatcatgt cgctgacggc gcgtaaccgg gcgttcc gcagcagcc        14040
gcaggccaac aggctctccg ccatcctgga ggcggtggtg cctgcgcgct cgaaccccac    14100
gcacgagaag gtgctggcca tagtgaacgc gctggccgag aacagggcca tccgcccgga    14160
cgaggccggg ctggtgtacg acgcgctgct gcagcgcgtg gcccgctaca acagcggcaa    14220
cgtgcagacc aacctggacc ggctggtggg ggacgtcgcg gaggcggtgg cgcagcgcga    14280
gcgcgcgggat cggcagggca acctgggctc catgtggcgc ctgaatgcct tcctgagcac    14340
gcagccggcc aacgtgccgc gggggcagga agactacacc aactttgtga gcgcgctgcg    14400
gctgatggtg accgagaccc cccagagcga ggtgtaccag tcgggcccgg actacttctt    14460
ccagaccagc agacagggcc tgcagacggt gaacctgagc caggctttca agaacctgcg    14520
ggggctgtgg ggcgtgaagg cgcccaccgg cgaccggggcc acgtgtcca gctgctgac     14580
gcccaactcg cgcctctgc tgctgctgat ccgccgttc acggacagcg acggcgtgtg     14640
ccgggacacc tacctgggc acctgctgac cctgtaccgc gaggccatcg gcaggcgca     14700
ggtggacgag cacaccttcc aggagatcac cagcgtgagc cgcgcgctgg ggcaggagga    14760
cacgagcagc ctgaggcga ctctgaacta cctgctgacc aaccggcggc agaagattcc     14820
ctcgctgcac agcctgacct ccgaggagga gcgcatcttg cgctacgtgc agcagagcgt    14880
gagcctgaac ctgatgcgcg acggggtgac gcccagcgtg gcgctggaca tgaccgcgcg    14940
```

```
caacatggaa ccgggcatgt acgccgcgca ccggccttac atcaaccgcc tgatggacta  15000
cctgcatcgc gcggcggccg tgaacccgga gtactttacc aacgccatcc tgaacccgca  15060
ctggctcccg ccgcccgggt tctacagcgg gggcttcgag gtcccggaga ccaacgatgg  15120
cttcctgtgg gacgacatgg acgacagcgt gttctccccg cggccgcagg cgctggcgga  15180
agcgtccctg ctgcgtccca agaaggagga ggaggaggga gcgagtccgc gccgcggcag  15240
cagcggcgtg gcttctctgt ccgagctggg ggcggcagcc gccgcgcgcc ccgggtccct  15300
gggcggcagc ccctttccga gcctggtggg gtctctgcac agcgagcgca ccacccgccc  15360
tcggctgctg ggcgaggacg agtacctgaa taactccctg ctgcagccgg tgcgggagaa  15420
aaacctgcct cccgccttcc ccaacaacgg gatagagagc ctggtggaca agatgagcag  15480
atggaagacc tatgcgcagg agcacaggga cgcgcctggc ctccggccgc ccacgcggcg  15540
ccagcgccac gaccggcagc gggggctggt gtgggatgac gaggactccg cggacgatag  15600
cagcgtgctg gacctgggag ggagcggcaa cccgttcgcg cacctgcgcc cccgcctggg  15660
gaggatgttt taaaaaaaaa aaaaaaagc aagaagcatg atgcaaaat taaataaaac  15720
tcaccaaggc catggcgacc gagcgttggt ttcttgtgtt ccctttcagt a tgcggcgcag  15780
ggcgatgtac caggagggac ctcctcctc ttacgagag gtggtgggcg gcggcggc  15840
ggcgccctct tctcccttg cgtcgcagct gctggagccg ccgtacgtgc ctccgcgcta  15900
cctgcggcct acgggggga gaaacagcat ccgttactcg gagctggcgc ccctgttcga  15960
caccacccgg gtgtacctgg tggacaacaa gtccggcgag ggcctccc tgaactacca  16020
gaacgaccac agcaattttt tgaccacggt catccagaac aatgactaca gcccgagcga  16080
ggccagcacc cagaccatca atctggatga ccggtcgcac tggggcggcg acctgaaaac  16140
catcctgcac accaacatgc caacgtgaa cgagttcatg ttcaccaata agttcaaggc  16200
gcgggtgatg gtgtcgcgct cgcacaccaa ggaagccggg gtggagctga agtacgagtg  16260
ggtggagttc gagctgccag agggcaacta ctccgagacc atgaccattg acctgatgaa  16320
caacgcgatc gtggagcact atctgaaagt gggcaggcag aacggggtcc tggagagcga  16380
catcgggtc aagttcgaca ccaggaactt ccgcctgggg ctggaccccg tgaccgggct  16440
ggttatgccc ggggtgtaca ccaacgagc cttccatccc gacatcatcc tgctgcccgg  16500
ctgcggggtg gacttcactt acagccgcct gagcaacctc ctgggcatcc gcaagcggca  16560
gccttccag gagggcttca ggatcaccta cgaggacctg aggggggca acatccccgc  16620
gctcctcgat gtggaggcct accaggatag cttgaaggaa aatgaggcgg acaggaggga  16680
taccgccccc gccgcctccg ccgccgccga gcagggcgag gatgctgctg acaccgcggc  16740
cgcggacggg gcagaggccg acccgctat gtgggtggag gctcccgagc aggaggagga  16800
catgaatgac agtgcggtgc gcggagacac cttcgtcacc cgggggggagg aaaagcaagc  16860
ggaggccgag gccgcggccg aggaaaagca actggcggca gcagcggcgg cggcggcgtt  16920
ggcgcgcgcg gaggctgagt ctgagggac caagcccgc aaggagcccg tgattaagcc  16980
cctgaccgaa gatagcaaga agcgacgtta caacctgctc aaggacagca ccaacaccgc  17040
gtaccgcagc tggtacctgg cctacaacta cggcgacccg tcgacggggg tgcgctcctg  17100
gaccctgctg tgcacgccgg acgtgacctg cggctcggag caggtgtact ggtcgctgcc  17160
cgacatgatg caagaccccg tgaccttccg ctccacgcgg caggtcagca acttcccggt  17220
ggtgggcgcc gagctgctgc ccgtgcactc caagagcttc tacaacgacg aggccgtcta  17280
ctcccagctc atccgccagt tcacctctct gacccacgtg ttcaatcgct ttcctgagaa  17340
ccagattctg gcgcgcccgc ccgcccccac catcaccacc gtcagtgaaa acgttcctgc  17400
tctcacagat cacgggacgc taccgctgcg caacagcatc ggaggagtcc agcgagtgac  17460
cgttactgac gccagacgcc gcacctgccc ctacgtttac aaggccttgg gcatagtctc  17520
gccgcgcgtc ctttcagcc gcactttttg agcaacacca ccatcatgtc catcctgatc  17580
tcacccagca ataactccgg ctggggactg ctgcgcgcgc ccagcaagat gttcggaggg  17640
gcgaggaagc gttccgagca gcaccccgtg cgcgtgcgcg ggcacttccg cgccccctgg  17700
ggagcgcaca aacgggccg cgcggggcgc accaccgtgg acgacgccat cgactcggtg  17760
gtggagcagg cgcgcaacta caggcccgcg gtctctaccg tggacgcggc catccagacc  17820
gtggtgcggg gcgcgcggcg gtacgccaag ctgaagagcc gccggaagcg cgtgcccgc  17880
cgccaccgcc gccgacccgg ggccgccgcc aaacgcgccg ccgcggccct gcttcgccgg  17940
gccaagcgca cgggccgccg cgccgccatg agggccgcgc gccgctttggc cgccggcatc  18000
accgccgcca ccatgccccc ccgtaccgga agacgcgcgg ccgccgccgc cgccgccgcg  18060
atcagtgaca tggccagcag gcgccgggc aacgtgtact gggtgcgcga ctcggtgacc  18120
ggcacgcgcg tgcccgtgcg cttccgcccc ccgcggactt gagatgatgt gaaaaaacaa  18180
cactgagtct cctgctgttg tgtgtatccc agcggcgggg gcgcgcgcag cgtcatgtcc  18240
aagcgcaaaa tcaaagaaga gatgctccag gtcgtcgcgc cggagatcta tgggcccccg  18300
aagaaggaag agcaggattc gaagcccgc aagataaagc gggtcaaaaa gaaaagaaa  18360
gatgatgacg atgccgatgg ggaggtggag ttcctgcgcg ccacggcgcc caggcgcccg  18420
gtgcagtgga agggccggcg cgtaaagcgc gtcctgcgcc ccggcaccgc ggtggtcttc  18480
acgcccggcg agcgctccac ccggacttc aagcgcgtct atgacgaggt gtacgcgac  18540
gaagacctgc tggagcaggc caacgagcgc ttcgagagt ttgcttacgg gaagcgtcag  18600
cgggcgctgg ggaaggagga cctgctggcg ctgccgctgg accagggcaa ccccacccc  18660
agtctgaagc ccgtgaccct gcagcaggtg ctgccgagca gcgcaccctc cgaggcgaag  18720
cgggtctga agcgcgaggg cggcgacctg gcgcccaag tgcagctcat ggtgccaag  18780
cggcagaggc tggaggatgt gctggagaaa atgaaagtag accccggtct gcagccggac  18840
atcagggtcc gccccatcaa gcaggtggcc ccgggcctcg gcgtgcagac cgtggacgtg  18900
gtcatcccca ccggcaactc cccgccgcc gccaccacta ccgctgcctc cacggacatg  18960
gagacacaga ccgatcccgc cgcagccgca gccgcagccgc ccgccgcgac ctcctcggcg  19020
gaggtgcaga cggaccctg gctgccgccg cgatgtcag ctccccgcc gcgtcgccgg  19080
cgcaggaagt acggcgccgc caacgcgctc ctgcccgagt acgccttgca tccttccatc  19140
gcgcccaccc ccggctaccg aggctatacc taccccgcc gaaagagcca gggttccacc  19200
cgccgtcccc gccgacgcgc cgccgccacc acccgccgcc gccgccgcag acgcagccc  19260
gcactggctc cagtctccgt gaggaaagtg gcgcgcgacg acacaccct ggtgctgccc  19320
agggcgtga ccaccccag catcgtttaa aagcctgttg tggttcttgc agatatggcg  19380
ctcacttgcc gcctccgttt cccggtgccg ggataccgag gaggaagatc gcgccgcagg  19440
aggggtctgg ccggccgcgg cctgagcgga ggcagccgcc gcgcgcaccg gcggcgacgc  19500
gccaccagcc gacgcatgcg cggcggggtg ctgcccctgt taatcccct gatcgccgcg  19560
gcgatcggcc ccgtgcccgg gatcgcctcc gtggccttgc aagcgtccca gaggcattga  19620
cagacttgca aacttgcaaa tatggaaaaa aaaacccaa taaaaaagtc tagactctca  19680
```

```
cgctcgcttg gtcctgtgac tattttgtag aatggaagac atcaactttg cgtcgctggc   19740
cccgcgtcac ggctcgcgcc cgttcctggg acactggaac gatatcggca ccagcaacat   19800
gagcggtggc gccttcagtt ggggctctct gtggagcggc attaaaagta tcgggtctgc   19860
cgttaaaaat tacggctccc gggcctggaa cagcagcacg ggccagatgt tgagagacaa   19920
gttgaaagag cagaacttcc agcagaaggt ggtggaggc ctggcctccg gcatcaacgg   19980
ggtggtggac ctggccaacc aggccgtgca gaataagatc aacagcagac tggaccccg    20040
gccgccggtg gaggaggtgc cgccggcgct ggagacggtg tccccgatg ggcgtggcga    20100
gaagcgcccg cggcccgata gggaagagac cactctggtc acgcagaccg atgagccgcc   20160
cccgtatgag gaggccctga agcaaggtct gcccaccacg cggcccatcg cgcccatgcc   20220
caccgggggtg gtgggccgcc acaccccgc cacgctggac ttgcctccgc ccgccgatgt    20280
gccgcagcag cagaaggcgg cacagccggg cccgcccgcg accgcctccc gttcctccgc   20340
cggtcctctg cgccgcgcgg ccagcggccc ccgcggggg gtcgcgaggc acggcaactg    20400
gcagagcacg ctgaacagca tcgtgggtct ggggtgcgg tccgtgaagc gccgccgatg    20460
ctactgaata gcttagctaa cgtgttgtat gtgtgtatgc gccctatgtc gccgccagag   20520
gagctgctga gtcgccgccg ttcgcgcgcc caccaccacc gccactccgc ccctcaagat   20580
ggcgacccca tcgatgatgc cgcagtggtc gtacatgcac atctcgggcc aggacgcctc   20640
ggagtacctg agcccgggc tggtgcagtt cgcccgcgcc accgagagct acttcagcct   20700
gagtaacaag tttaggaacc ccacggtggc gcccacgcac gatgtgacca ccgaccggtc   20760
tcagcgcctg acgctgcggt tcattcccgt ggaccgcgag gacaccgcgt actcgtacaa   20820
ggcgcggttc accctggccg tgggcgacaa ccgcgtgctg gacatggcct ccacctactt   20880
tgacatccgc ggggtgctgg accggggtcc cactttcaag ccctactctg gcaccgccta   20940
caactccctg gcccccaagg gcgctcccaa ctcctgcgag tgggagcaag aggaaactca   21000
ggcagttgaa gaagcagcag aagaggaaga agaagatgct gacggtcaag ctgaggaaga   21060
gcaagcagct accaaaaaga ctcatgtata tgctcaggct ccccttctg gcgaaaaaat    21120
tagtaaagat ggtctgcaaa taggaacgga cgctacagct acagaacaaa aacctattta   21180
tgcagaccct acattccagc ccgaacccca aatcggggag tcccagtgga atgaggcaga   21240
tgctacagtc gccggcggta gagtgctaaa gaaatctact cccatgaaac catgctatgg   21300
ttcctatgca agaccccaca atgctaatgg aggtcagggt gtactaacgg caaatgccca   21360
gggacagcta gaatctcagg ttgaaatgca attcttttca acttctgaaa cgcccgtaa    21420
cgaggctaac aacattcagc ccaaattggt gctgtatagt gaggatgtgc acatggagac   21480
cccggatacg caccttttctt acaagcccgc aaaaagcgat gacaattcaa aaatcatgct   21540
gggtcagcag tccatgccca acagacctaa ttacatcggc ttcagagaca ctttatcgg    21600
cctcatgtat tacaatagca ctggcaacat gggagtgctt gcaggtcagg cctctcagtt   21660
gaatgcagtg gtggacttgc aagacagaaa cacagaactg tcctaccagc tcttgcttga   21720
ttccatgggt gacagaacca gatacttttc catgtggaat caggcagtgg acagttatga   21780
cccagatgtt agaattattg aaaatcatgg aactgaagac gagctcccca actattgttt   21840
ccctctgggg ggcataggg taactgacac ttaccaggct gttaaaacca acaatggcaa    21900
taacgggggc caggtgactt ggacaaaaga tgaaacttttt gcagatcgca atgaaatagg   21960
ggtgggaaac aatttcgcta tggagatcaa cctcagtgcc aacctgtgga gaaacttcct   22020
gtactccaac gtggcgctgt acctaccaga caagcttaag tacaaccct ccaatgtgga    22080
catctctgac aaccccaaca cctacgatta catgaacaag cgagtggtgg ccccgggcct   22140
ggtggactgc tacatcaacc tgggcgcgcg ctggtcgctg gactacatgg acaacgtcaa   22200
ccccttcaac caccaccgca atgcgggcct gcgctacgtc tgggcaacgg   22260
gcgctacgtg cccttccaca tccaggtgcc ccagaagttc tttgccatca gaaacctcct   22320
cctcctgccg ggtcctaca cctacgagtg gaacttcagg aaggatgtca acatggtcct    22380
ccagagctct ctgggtaacg atctcagggt ggacggggcc agcatcaagt tcgagagcat   22440
ctgcctctac gccaccttct tccccatggc ccacaacacg gcctccacgc tcgaggccat   22500
gctcaggaac gacaccaacg accagtcctt caatgactac ctctccgccg ccaacatgct   22560
ctaccccata cccgccaacg ccaccaacgt ccccatctcc atccctcgc gcaactgggc    22620
ggccttccgc ggctgggcct tcacccgcct caagaccaag gagacccct ccctgggctc    22680
gggattcgac ccctactaca cctactcggg ctccattccc tacctggacg gcaccttcta   22740
cctcaaccac actttcaaga aggtctcggt caccttcgac tcctcggtca gctggccggg    22800
caacgaccgt ctgctcaccc ccaagagtt cgagatcaag cgtcggtcg acggggaggg    22860
ctacaacgtg gcccagtgca acatgaccaa ggactggttc ctggtccaga tgctggccaa   22920
ctacaacatc ggctaccagg gcttctacat cccagagagc tacaaggaca ggatgtactc   22980
cttcttcagg aacttccagc ccatgagccg gcaggtggtg gaccagacca agtacaagga   23040
ctaccaggag gtgggcatca tccaccagca caacaactcg ggcttcgtgg gctacctcgc   23100
ccccaccatg cgcgagggac aggcctaccc cgccaacttc ccctatccgc tcataggcaa   23160
gaccgcggtc gacagcatca cccagaaaaa gttcctctgc gaccgcaccc tctgcgcat    23220
ccccttctcc agcaacttca tgtccatggg tgcgctctcg gacctgggcc agaacttgct   23280
ctacgccaac tccgcccacg ccctcgacat gaccttcgag gtcgacccca tggacgagcc   23340
cacccttctc tatgttctgt tcgaagtctt tgacgtggtc cgggtccacc agccgcaccg   23400
cggcgtcatc gagaccgtgt acctgcgtac gcccttctcg gccggcaacg ccaccaccta   23460
aagaagcaag ccgcagtcat cgccgcctgc atgccgtcgg gttccaccga gcaagactcc   23520
agggccatcg tcagagacct gggatgcggg ccctattttt tggcaccttt cgacaagcgc   23580
ttccctggct ttgtctcccc acacaagctg gcctgcgcca tcgtcaacac ggccggccgc   23640
gagaccgggg gcgtgcactg gctggccttc gcctggaacc cgcgctccaa acatgcttc    23700
ctctttgacc ccttcggctt tcggaccag cggctcaagc aaatctacga gttcgagtac    23760
gagggcttgc tgcgtcgcag tgccatcgcc tcctcgcccg accgctgcgt caccctcgaa   23820
aagtccaccc agaccgtgca ggggcccgac tcggccgcct gcggtctctt ctgctgcatg   23880
tttctgcacg cctttgtgca ctggcctcag agtccatgg accgcaaccc caccatgaac   23940
ttgctgacgg gggtgcccaa ctccatgctc cagagccccc aggtcgagcc cccctgcgc    24000
cgcaaccagg agcagctcta cagcttcctg gagcgccact cgcttacttt ccgccgccac   24060
agcgcacaga tcaggagggc caccctcttc tgccacttgg aagagatgca agaagggtaa   24120
taacgatgta cacacttttt ttctcaataa atgcatctt tttatttata caagctctct   24180
ggggtattca tttcccacca ccaccgccg tgtcgccat ctggctctat ttagaaatcg    24240
aaaggggttct gccgggagtc gccgtgcgcc acgggcaggg acacgttgcg atactggtag   24300
cgggtgcccc acttgaactc gggcaccacc aggcgaggca gctcgggaa gttttcgctc    24360
cacaggctgc gggtcagcac cagcgcgttc atcaggtcgg gcgccgagat cttgaagtcg   24420
```

-continued

```
cagttggggc cgccgccctg cgcgcgcgag ttgcggtaca ccgggttgca gcactggaac   24480
accaacagcg ccgggtgctt cacgctggcc agcacgctgc ggtcggagat cagctcggcg   24540
tccaggtcct ccgcgttgct cagcgcgaac ggggtcatct tgggcacttg ccgcccagg    24600
aagggcgcgt gccccggttt cgagttgcag tcgcagcgca gcgggatcag caggtgcccg   24660
tgcccggact cggcgttggg gtacagcgcg cgcatgaagg cctgcatctg gcggaaggcc   24720
atctgggcct tggcgccctc cgagaagaac atgccgcagg acttgcccga gaactggttt   24780
gcggggcagc tggcgtcgtg caggcagcag cgcgcgtcgg tgttggcgat ctgcaccacg   24840
ttgcgccccc accggttctt cacgatcttg gccttggacg attgctcctt cagcgcgcgc   24900
tgcccgttct cgctggtcac atccatctcg atcacatgtt ccttgttcac catgctgctg   24960
ccgtgcagac acttcagctc gccctccgtc tcggtgcagc ggtgctgcca cagcgcgcag   25020
cccgtgggct cgaaagactt gtaggtcacc tccgcgaagg actgcaggta ccctgcaaa    25080
aagcggccca tcatggtcac gaaggtcttg ttgctgctga aggtcagctg cagcccgcgg   25140
tgctcctcgt tcagccaggt cttgcacacg gccgccagcg cctccacctg gtcgggcagc   25200
atcttgaagt tcaccttcag ctcattctcc acgtggtact tgtccatcag cgtgcgcgcc   25260
gcctccatgc ccttctccca ggccgacacc agcggcaggc tcacggggtt cttcaccatc   25320
accgtggccg ccgcctccgc cgcgctttcg ctttccgccc cgctgttctc ttcctcttcc   25380
tcctcttcct cgccgccgcc cactcgcagc ccccgcacca cggggtcgtc ttcctgcagg   25440
cgctgcacct tgcgcttgcc gttgcgcccc tgcttgatgc gcacgggcgg gttgctgaag   25500
cccaccatca ccagcgcggc ctcttcttgc tcgtcctcgc tgtccagaat gacctccggg   25560
gagggggggt tggtcatcct cagtaccgag gcacgcttct ttttcttcct gggggcgttc   25620
gccagctccg cggctgcggc cgctgccgag gtcgaaggcc gagggctggg cgtgcgcggc   25680
accagcgcgt cctgcgagcc gtcctcgtcc tcctcggact cgagacggag gcgggcccgc   25740
ttcttcgggg gcgcgcgggg cggcggaggc ggcggcggcg acggagacgg ggacgagaca   25800
tcgtccaggg tgggtggacg gcgggccgcg ccgtccgc gctcgggggt ggtctcgcgc     25860
tggtcctctt cccgactggc catctcccac tgctccttct cctataggca gaaagagatc   25920
atggagtctc tcatgcgagt cgagaaggag gaggacagcc taaccgcccc ctctgagccc   25980
tccaccaccg ccgccaccac cgccaatgcc gccgcggacg acgcgcccac cgagaccacc   26040
gccagtacca ccctccccag cgacgcaccc ccgtcgaga atgaagtgct gatcgagcag    26100
gacccggggt ttgtgagcgg agaggaggat gaggtggatg agaaggagaa ggaggaggtc   26160
gccgcctcag tgccaaaaga ggataaaaag caagaccagg acgacgcaga taaggatgag   26220
acagcagtcg ggcgggggaa cggaagccat gatgctgatg acgctacct agacgtggga    26280
gacgacgtgc tgcttaagca cctgcaccgc cagtgcgtca tcgtctgcga cgcgctgcag   26340
gagcgctgcg aagtgcccct ggacgtggcg gaggtcagcc gcgcctacga gcggcacctc   26400
ttcgccgccc acgtgccccc caagcgccgg gagaacgcca cctgcgagcc caaccgcgt    26460
ctcaacttct acccggtctt cgcggtaccc gaggtgctgg ccacctacca catcttttc    26520
caaaactgca agatcccctc tcctgccgc gccaaccgca cccgcgccga caaaccctg     26580
accctgcggc agggcgccca catacctgat atcgcctctc tggaggaagt gcccaagatc   26640
ttcgagggtc tcggtcgcga cgagaaacgg gcggcgaacg ctctgcacgg agacagcgaa   26700
aacgagagtc actcggggt gctggtggag ctcgagggcg acaacgcgcg cctggccgta    26760
ctcaagcgca gcatagaggt cacccacttt gcctacccgg cgctcaacct gcccccaag    26820
gtcatgagtg tggtcatggg cgagctcatc atgcgccgcg cccagcccct ggccgcggat   26880
gcaaacttgc aagagtcctc cgaggaaggc ctgcccgcgg tcagcgacga gcagctggcg   26940
cgctgctgg agaccgcga ccccgcgcag ctggaggagc ggcgcaagct catgatgcgc     27000
gcggtgctgg tcaccgtgga gctcgagtgt ctgcagcgct tcttcgcgga ccccgagatg   27060
cagcgcaagc tcgaggagac cctgcactac accttccgcc agggctacgt gcgccaggcc   27120
tgcaagatct ccaacgtgga gctctgcaac ctggtctcct acctgggcat cctgcacgag   27180
aaccgcctcg ggcagaacgt cctgcactcc accctcaaag gggaggccgg ccgcgactac   27240
atccgcgact gcgcctacct cttcctctgc tacacctggc agacggccat ggggtctgg    27300
cagcagtgcc tggaggagcg caacctcaag gagctggaaa agctcctcaa gcgcaccctc   27360
agggacctct ggacgggctt caacgagcgc tcggtggccg ccgcgctggc ggacatcatc   27420
tttcccgagc gcctgctcaa gaccctgcag cagggcctgc ccgacttcac cagccagagc   27480
atgctgcaga acttcaggac tttcatcctg gagcgctcgg gcatcctgcc ggccacttgc   27540
tgcgcgctgc ccagcgactt cgtgcccatc aagtacaggg agtgcccgcc gccgctctgg   27600
ggccactgct acctcttcca gctggccaac tacctcgcct accactcgga cctcatggaa   27660
gacgtgagcg gcgagggcct ggtcgagtgc cactgccgct gcaaccttcg cacgccccac   27720
cgctctctag tctgcaaccc cagctgctc agcgagagtc agattatcgg taccttcgag    27780
ctgcagggtc cctcgcctga cgagaagtcc gcggctccag ggctgaaact cactccgggg   27840
ctgtggactt ccgcctacct acgcaaattt gtacctgagg actaccacgc ccacgagatc   27900
aggttctacg aagaccaatc ccgcccgccc aaggcggagc tcaccgcctg cgtcatcacc   27960
caggggcaca tcctgggcca attgcaagcc atcaacaaag cccgccgaga gttcttgctg   28020
aaaaagggtc gggggggtgta cctgaccccc cagtccggcg aggagctaaa cccgctaccc   28080
ccgccgccgc cccagcagcg ggaccttgct tccaggatg gcacccagaa agaagcagca    28140
gccgccgccg ccgccgcagc catacatgct tctggaggaa gaggaggagg actgggacag   28200
tcaggcagag gaggtttcgg acgaggagca ggaggagagt atggaagact ggaggaggag   28260
cagcagccta gacgaggaag cttcagaggc cgaagaggtc gcagacgcaa caccatcgcc   28320
ctcggtcgca gccccctcgc cggggcccct gaaatcctcc gaacccagca ccagcgctat   28380
aacctccgct cctccggcgc cggcgccacc cgcccgcaga cccaaccgta gatgggacac   28440
cacaggaacc ggggtcggta agtccaagtg cccgccgccc ccaccgcagc agcagcaga    28500
gcagcgccag ggctaccgct cgtgcgcggg gcacaagaac ccatagtcg cctgcttgca    28560
agactgcggg ggcaacatct ctttcgcccg ccgcttcctg ctattccacc acggggtcgc   28620
ctttccccgc aatgtcctgc attactaccg tcatctctac agcccctact gcagcggcga   28680
cccagaggcg gcagcggcag ccacagcggc gaccaccacc taggaagata tcctccgcgg   28740
gcaagacagc ggcagcagcg gccaggagac ccgcggcagc agcggcggga gcggtgggcg   28800
cactgcgcct ctcgcccaac gaaccctct cgaccggga gctcagacac aggatcttcc     28860
ccactttgta tgccatcttc aacagagca gaggccagga gcaggagctg aaaataaaaa     28920
acagatctct gcgctccctc acccgcagct gtctgtatca caaaagcgaa gatcagcttc   28980
ggcgcacgct ggaggacgcg gaggcactct tcagcaaata ctgcgcgctc actcttaaag   29040
actagctccg cgcccttctc gaattaggc gggagaaaac tacgtcatcg ccggccgccg    29100
cccagcccgc ccagccgaga tgagcaaaga gattcccacg ccatacatgt ggagctacca   29160
```

```
gccgcagatg ggactcgcgg cgggagcggc ccaggactac tccacccgca tgaactacat  29220
gagcgcggga ccccacatga tctcacaggt caacgggatc cgcgcccagc gaaaccaaat  29280
actgctggaa caggcggcca tcaccgccac gccccgccat aatctcaacc cccgaaattg  29340
gcccgccgcc ctcgtgtacc aggaaacccc ctccgccacc accgtactac ttccgcgtga  29400
cgcccaggcc gaagtccaga tgactaactc aggggcgacg ctcgcgggcg gctttcgtca  29460
cggggcgcgg ccgctccgac caggtataag acacctgatg atcagaggcc gaggtatcca  29520
gctcaacgac gagtcggtga gctcttcgct cggtctccgt ccggacggaa ctttccagct  29580
cgccggatcc ggccgctctt cgttcacgcc ccgccaggcg tacctgactc tgcagacctc  29640
gtcctcggag ccccgctccg gcggcatcgg aaccctccag ttcgtggagg agttcgtgcc  29700
ctcggtctac ttcaacccct tctcgggacc tccccgacgc taccccgacc agttcattcc  29760
gaactttgac gcggtgaagg actcggcgga cggctacgac tgaatgtcag gtgtcgaggc  29820
agagcagctt cgcctgagac acctcgagca ctgccgccgc cacaagtgct cgcccgcgg  29880
ttctggtgag ttctgctact ttcagctacc cgaggagcat accgagggc cggcgcacgg  29940
cgtccgcctg accaccagg gcgaggttac ctgttccctc atccgggagt ttaccctccg  30000
tccccttgcta gtggagcggg agcggggtcc ctgtgtccta actatcgcct gcaactgccc  30060
taaccctgga ttacatcaag atctttgctg tcatctctgt gctgagttta ataaacgctg  30120
agatcagaat ctactgggc tcctgtcgcc atcctgtgaa cgccaccgtc ttcacccacc  30180
ccgaccaggc ccaggcgaac ctcacctgcg gtctgcatcg gagggccaag aagtacctca  30240
cctggtactt caacggcacc ccctttgtgg tttacaacag cttcgacggg gacggagtct  30300
ccctgaaaga ccagctctcc ggtctcagct actccatcca caagaacacc accctccaac  30360
tcttccctcc ctacctgccg ggaacctacg agtgcgtcac cggccgctgc acccacctca  30420
cccgctgat cgtaaaccag agctttccgg gaacagataa ctccctcttc cccagaacag  30480
gaggtgagct caggaaactc cccggggacc agggcggaga cgtaccttcg acccttgtgg  30540
ggttaggatt ttttattacc gggttgctgg ctcttttaat caaagtttcc ttgagatttg  30600
ttctttcctt ctacgtgtat gaacacctca acctccaata actctaccct tcttcggaa  30660
tcaggtgact tctctgaaat cgggcttggt gtgctgctta ctctgttgat tttttttctt  30720
atcatactca gccttctgtg cctcaggctc gccgctgct cgcacacat ctatatctac  30780
tgctggttgc tcaagtgcag gggtcgccac ccaagatgaa caggtacatg gtcctatcga  30840
tcctaggcct gctggccctg gcggcctgca gcgccgccaa aaaagagatt accttgagg  30900
agcccgcttg caatgtaact ttcaagcccg agggtgacca atgcaccacc ctcgtcaaat  30960
gcgttaccaa tcatgagagg ctgcgcatcg actacaaaaa caaaactggc cagtttgcgg  31020
tctatagtgt gtttacgccc ggagacccct ctaactactc tgtcaccgtc ttccagggcg  31080
gacagtctaa gatattcaat tacactttcc cttttatga gttatgcgat gcggtcatgt  31140
acatgtcaaa acagtacaac ctgtggcctc cctctcccca ggcgtgtgtg gaaaatactg  31200
ggtcttactg ctgtatggct ttcgcaatca ctacgctcgc tctaatctgc acggtgctat  31260
acataaaatt caggcagagg cgaatctttta tcgatgaaaa gaaatgcct tgatcgctaa  31320
caccggcttt ctatctgcag aatgaatgca atcacctccc tactaatcac caccaccctc  31380
cttgcgattg cccatgggtt gacacgaatc gaagtgccag tggggtccaa tgtcaccatg  31440
gtgggcccg ccggcaattc caccctcatg tgggaaaaat ttgtccgcaa tcaatgggtt  31500
catttctgct ctaaccgaat cagtatcaag cccagagcca tctgcgatgg gcaaaatcta  31560
actctgatca atgtgcaaat gatggatgct gggtactatt acgggcagcg gggagaaatc  31620
attaattact ggcgaccca caaggactac atgctgcatg tagtcgaggc acttcccact  31680
accaccccca ctaccacctc tccaccacc accaccacta ctactactac tactactact  31740
actactacta ccactaccgc tgcccgccat cccgcaaaa gcaccatgat tagcacaaag  31800
ccccctcgtg ctcactccca cgccggcggg cccatcggtg cgacctcaga aaccaccgag  31860
cttttgcttct gccaatgcac taacgccagc gctcatgaac tgttcgacct ggagaatgag  31920
gatgtccagc agagctccgc ttgcctgacc caggaggctg tggagcccgt tgccctgaag  31980
cagatcggtg attcaataat tgactcttct tcttttgcca ctcccgaata ccctcccgat  32040
tctactttcc acatcacggg taccaaagac cctaacctct cttttacct gatgctgctg  32100
ctctgtatct ctgtggtctc ttccgcgctg atgttactgg ggatgttctg ctgcctgatc  32160
tgccgcagaa agagaaaagc tcgctctcag ggccaaccac tgatgcccctt ccctacccc  32220
ccggattttg cagataacaa gatatgagct cgctgctgac actaaccgct ttactagccc  32280
gcgctctaac ccttgtcgct tgcgactcga gattccacaa tgtcacagct gtggcaggag  32340
aaaatgttac tttcaactcc acggccgata cccagtggtc gtggagtggc tcaggtagct  32400
acttaactat ctgcaaatagc tccacttccc ccggcatatc ccaaccaag taccaatgca  32460
atgccagcct gttcaccctc atcaacgctt ccaccctgca caatggactc tatgtaggct  32520
atgtacccctt tggtgggcaa ggaaagaccc acgcttacaa cctggaagtt cgccagccca  32580
gaaccactac ccaagcttct cccaccacca ccaccaccac caccatcacc agcagcagca  32640
gcagcagcca ccacagcagc agcagcagat tattgacttt ggttttggcc agctcatctg  32700
ccgctaccca ggccatctac agctctgtgc ccgaaaccac tcagatccac cgcccagaaa  32760
cgaccaccgc caccacccta cacacctcca cgcatcagat gccgaccaac atcacccct  32820
tggctcttca aatgggactt acaagcccca ctccaaaacc agtggatgcg gccgaggtct  32880
ccgcccctcgt caatgactgg gcggggctgg gaatgtggtg gttcgccata ggcatgatgg  32940
cgctcgcct gcttctgctc tggctcatct gctgcctcca ccgcaggcga gcagaccccc  33000
ccatctatag acccatcatt gtcctgaacc ccgataatga tgggatccat agattggatg  33060
gcctgaaaaa cctacttttt tcttttacag tatgataaat tgagacatgc ctcgcatttt  33120
cttgtacatg ttccttctcc cacctttct ggggtgttct acgctggccg ctgtgtctca  33180
cctggaggta gactgcctct caccccttcac tgtctacctg ctttacggat tggtcacct  33240
cactctcatc tgcagcctaa tcacagtaat catcgcctc atccagtgca ttgattacat  33300
ctgtgtgcgc ctcgcatact tcagacacca cccgcagtac cgagacagga acattgccca  33360
acttctaaga ctgctctaat catgcataag actgtgatct gccttctgat cctctgcatc  33420
ctgcccaccc tcacctcctg ccagtacacc acaaaatctc cgcgcaaaag acatgcctcc  33480
tgccgcttca cccaactgtg gaatatacccc aaatgctaca acgaaagag cgagctctcc  33540
gaagcttggc tgtatgggt catctgtgtc ttagttttt gcagcactgt ctttgccctc  33600
ataatctacc cctactttga tttgggatgg aacgcgatcg atgccatgaa ttaccccacc  33660
tttcccgcac ccgagataat tccactgcga caagttgtac ccgttgtcgt taatcaacgc  33720
ccccccatccc ctacgcccac tgaaatcagc tactttaacc taacaggcgg agatgactga  33780
cgccctagat ctagaaatgg acggcatcag taccgagcag cgtctcctag agaggcgcag  33840
gcaggcggct gagcaagagc gcctcaatca ggagctccga gatctcgtta acctgcacca  33900
```

```
gtgcaaaaga ggcatctttt gtctggtaaa gcaggccaaa gtcacctacg agaagaccgg    33960
caacagccac cgcctcagtt acaaattgcc cacccagcgc cagaagctgg tgctcatggt    34020
gggtgagaat cccatcaccg tcacccagca ctcggtagag accgaggggt gtctgcactc    34080
cccctgtcgg ggtccagaag acctctgcac cctggtaaag accctgtgcg gtctcagaga    34140
tttagtcccc tttaactaat caaacactgg aatcaataaa aagaatcact tacttaaaat    34200
cagacagcag gtctctgtcc agtttattca gcagccctc cttccctcc tcccaactct    34260
ggtactccaa acgccttctg gcggcaaact tcctccacac cctgaaggga atgtcagatt    34320
cttgctcctg tccctccgca cccactatct tcatgttgtt gcagatgaag cgcaccaaaa    34380
cgtctgacga gagcttcaac cccgtgtacc cctatgacac ggaaagcggc cctccctccg    34440
tcccttcct cacccctccc ttcgtgtctc ccgatggatt ccaagaaagt cccccaggg    34500
tcctgtctct gaacctggcc gagccctgg tcacttccca cggcatgctc gccctgaaaa    34560
tgggaagtgg cctctccctg gacgacgctg gcaacctcac ctctcaagat atcaccaccg    34620
ctagccctcc cctcaaaaaa accaagacca acctcagcct agaaacctca tcccccatca    34680
ctgtgagcac ctcaggcgcc ctcaccgtag cagccgccgc tccctggcg gtggccggca    34740
cctccctcac catgcaatca gaggccccc tgacagtaca ggatgcaaaa ctcaccctgg    34800
ccaccaaagg cccctgacc gtgtctgaag gcaaactggc cttgcaaaca tcggcccgc    34860
tgacggccgc tgacagcagc accctcacag tcagtgccac accaccctt agcacaagca    34920
atggcagctt gggtattgac atgcaagccc ccatttacac caccaatgga aaactaggac    34980
ttaactttgg cgctcccctg catgtggtag acagcctaaa tgcactgact gtagttactg    35040
gccaaggtct tacgataaac ggaacagccc tacaaactag agtctcaggt gccctcaact    35100
atgacacatc aggaaaccta gaattgagag ctgcagggg tatgcgagtt gatgcaaatg    35160
gtcaacttat ccttgatgta gcttacccat ttgatgcaca aaacaatctc agccttaggc    35220
ttggacaggg accctgtttt gttaactctg cccacaactt ggatgttaac tacaacagag    35280
gcctctacct gttcacatct ggaaatacca aaaagctaga agttaatatc aaaacagcca    35340
agggtctcat ttatgatgac actgctatag caatcaatgc gggtgatggg ctacagtttg    35400
actcaggctc agatacaaat ccattaaaaa ctaaacttgg attaggactg gattatgact    35460
ccagcagagc cataattgct aaactgggaa ctggcctaag ctttgacaac acaggtgcca    35520
tcacagtagg caacaaaaat gatgacaagc ttaccttgtg gaccacacca gacccatccc    35580
ctaactgtag aatctattca gagaaagatg ctaaattcac acttgttttg actaaatgcg    35640
gcagtcaggt gttggccagc gtttctgttt tatctgtaaa agtagccgt gcgcccatca    35700
gtggcacagt aactagtgct cagattgtcc tcagatttga tgaaaatgga gttctactaa    35760
gcaattcttc ccttgaccct caatactgga actacagaaa aggtgacctt acagagggca    35820
ctgcatatac caacgcagtg ggatttatgc ccaacctcac agcatccca aaaacacaga    35880
gccaaactgc taaaagcaac attgtaagtc aggtttactt gaatggggac aaatccaaac    35940
ccatgaccct caccattacc ctcaatgaa ctaatgaaac aggagatgcc acagtaagca    36000
cttactccat gtcattctca tggaactgga atggaagtaa ttacattaat gaaacgttcc    36060
aaaccaactc cttcaccttc tcctacatcg cccaagaata aaaagcatga cgctgttgat    36120
ttgattcaat gtgtttctgt tttattttca agcacaacaa aatcattcaa gtcattcttc    36180
catcttagct taatagacac agtagcttaa tagacccagt agtgcaaagc cccattctag    36240
cttataacta gtgagaagt actcgcctac atggggtag agtcataatc gtgcatcagg    36300
atagggcggt ggtgctgcag cagcgcgcga ataaactgct gccgccgccg ctccgtcctg    36360
caggaataca acatggcagt ggtctcctca gcgatgattc gcaccgcccg cagcataagg    36420
cgccttgtcc tccgggcaca gcagcgcacc ctgatctcac ttaaatcgac acagtaactg    36480
cagcacagca ccacaatatt gttcaaaatc ccacagtgca aggcgctgta tccaaagctc    36540
atggcgggga ccacagaacc cacgtggcca tcataccaca agcgcaggta gattaagtgg    36600
cgaccctca taaacacgct ggacataaac attacctctt ttggcatgtt gtaattcacc    36660
acctccggt accatataa cctctgatta aactggcgc catccaccac catcctaaac    36720
cagctggcca aaacctgccc gccggctata cactgcaggg aaccgggact ggaaccaatga    36780
cagtggagag cccaggactc gtaaccatgg atcatcatgc tcgtcatgat atcaatgttg    36840
gcacaacaca ggcacacgtg catacacttc ctcaggatta caagctcctc ccgcgttaga    36900
accatatccc agggaacaac tcattcctga atcagcgtaa atcccacact gcagggaaga    36960
cctcgcacgt aactcacgtt gtgcattgtc aaagtgttac attcgggcag cagcggatga    37020
tcctccagta tggtagcgcg ggtttctgtc tcaaaaggag gtagcgatc cctactgtac    37080
ggagtgcgcc gagacaaccg agatcgtgtt ggtcgtagtg tcatgccaaa tggaacgccg    37140
gacgtagtca tatttcctga agtcttagat ctctcaaacg agcaccagca ccaacacttc    37200
gcagtgtaaa aggccaagtg ccgagagagt atatatagga ataaaagtg acgtaaacgg    37260
gcaaagtcca aaaaacgccc agaaaaaccg cacgcgaacc tacgcccgaa acgaaagcc    37320
aaaaaacact agacactccc ttccggcgtc aacttccgct ttcccacgct acgtcacttg    37380
ccccagtcaa acaaactaca tatcccgaac ttccaagtcg ccacgcccaa aacaccgcct    37440
acacctcccc gcccgccggc ccgcccccaa acccgcctcc cgcccgcgc cccgcccgc    37500
gccgcccatc tcattatcat attggcttca atccaaaata aggtatatta ttgatgatg    37559
```

```
SEQ ID NO: 5          moltype = AA   length = 1145
FEATURE               Location/Qualifiers
REGION                1..1145
                      note = Description of Artificial Sequence: Synthetic
                      polypeptide
source                1..1145
                      mol_type = protein
                      organism = synthetic construct
SEQUENCE: 5
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVSKVLHL EGEVNKIKSA LLSTNKAVVS   180
LSNGVSVLTS KVLDLKNYID KQLLPIVNKQ SCSISNIETV IEFQQKNNRL LEITREFSVN   240
AGVTTPVSTY MLTNSELLSL NDMPITNDQK KLMSNNVQIV RQQSYSIMSI IKEEVLAYVV   300
QLPLYGVIDT PCWKLHTSPL CTTNTKEGSN ICLTRTDRGW YCDNAGSVSF FPQAETCKVQ   360
SNRVFCDTMN SLTLPSEVNL CNVDIFNPKY DCKIMTSKTD VSSSVITSLG AIVSCYGKTK   420
CTASNKNRGI IKTFSNGCDY VSNKGVDTVS VGNTLYYVNK QEGKSLYVKG EPIINFYDPL   480
```

```
VFPSDEFDAS ISQVNEKINQ SLAFIRKSDE LLHNVNAGKS TTNRKRRAPV KQTLNFDLLK    540
LAGDVESNPG PMALSKVKLN DTLNKDQLLS SSKYTIQRST GDSIDTPNYD VQKHINKLCG    600
MLLITEDANH KFTGLIGMLY AMSRLGREDT IKILRDAGYH VKANGVDTT HRQDINGKEM     660
KFEVLTLASL TTEIQINIEI ESRKSYKKML KEMGEVAPEY RHDSPDCGMI ILCIAALVIT    720
KLAAGDRSGL TAVIRRANNV LKNEMKRYKG LLPKDIANSF YEVFEKYPHF IDVFVHFGIA    780
QSSTRGGSRV EGIFAGLFMN AYGAGQVMLR WGVLAKSVKN IMLGHASVQA EMEQVVEVYE    840
YAQKLGGEAG FYHILNNPKA SLLSLTQFPH FSSVVLGNAA GLGIMGEYRG TPRNQDLYDA    900
AKAYAEQLKE NGVINYSVLD LTAEELEAIK HQLNPKDNDV ELGGGGSGGG GMSRRNPCKF    960
EIRGHCLNGK RCHFSHNYFE WPPHALLVRQ NFMLNRILKS MDKSIDTLSE ISGAAELDRT   1020
EEYALGVVGV LESYIGSINN ITKQSACVAM SKLLTELNSD DIKKLRDNEE LNSPKIRVYN   1080
TVISYIESNR KNNKQTIHLL KRLPADVLKK TIKNTLDIHK SITINNPKES TVSDTNDHAK   1140
NNDTT                                                              1145

SEQ ID NO: 6              moltype = DNA   length = 1187
FEATURE                   Location/Qualifiers
misc_feature              1..1187
                          note = Description of Artificial Sequence: Synthetic
                          polynucleotide
source                    1..1187
                          mol_type = other DNA
                          organism = synthetic construct
SEQUENCE: 6
ccattgcata cgttgtatcc atatcataat atgtacattt atattggctc atgtccaaca     60
ttaccgccat gttgacattg attattgact agttattaat agtaatcaat tacggggtca    120
ttagttcata gcccatatat ggagttccgc gttacataac ttacggtaaa tggcccgcct    180
ggctgaccgc ccaacgaccc ccgcccattg acgtcaataa tgacgtatgt tcccatagta    240
acgccaatag ggactttcca ttgacgtcaa tgggtggagt atttacggta aactgcccac    300
ttggcagtac atcaagtgta tcatatgcca agtacgcccc ctattgacgt caatgacggt    360
aaatggcccg cctggcatta tgcccagtac atgaccttat gggactttcc tacttggcag    420
tacatctacg tattagtcat cgctattacc atggtgatgc ggttttggca gtacatcaat    480
gggcgtggat agcggtttga ctcacgggga tttccaagtc tccacccat tgacgtcaat    540
gggagtttgt tttggcacca aaatcaacgg gactttccaa aatgtcgtaa caactccgcc    600
ccattgacgc aaatgggcgg taggcgtgta cggtgggagg tctatataag gcgaagcgct    660
ccctatcagt gatagagatc tccctatcag tgatagagat cgtcgacgag ctcgcggcgg    720
gcgggagtcg ctgcgcgctg ccttcgcccc gtgccccgct ccgccgccgc ctcgcgccgc    780
ccgccccggc tctgactgac cgcgttacta aacaggtaaa gtccggcctc cgcgccgggt    840
tttggcgcct cccgcgggcg ccccctcct cacggcgagc gctgccacgt cagacgaagg    900
gcgcagcgag cgtcctgatc cttccgcccg dacgctcagg acagcggccc gctgctcata    960
agactcgtac ttagaacccc agtatcagca gaaggacatt ttaggacgag acttgggtga   1020
ctctagggca ctggtttct ttccagagag cggaacaggc gaggaaaagt agtcccttcc    1080
cggcgattct gcggagggat ctccgtgggg cggtgaacgc cgatgatgcc tctactaacc   1140
atgttcatgt tttcttttt tttctacagg tcctgggtga cgaacag                  1187

SEQ ID NO: 7              moltype = DNA   length = 2908
FEATURE                   Location/Qualifiers
misc_feature              1..2908
                          note = Description of Artificial Sequence: Synthetic
                          polynucleotide
source                    1..2908
                          mol_type = other DNA
                          organism = synthetic construct
SEQUENCE: 7
ccattgcata cgttgtatcc atatcataat atgtacattt atattggctc atgtccaaca     60
ttaccgccat gttgacattg attattgact agttattaat agtaatcaat tacggggtca    120
ttagttcata gcccatatat ggagttccgc gttacataac ttacggtaaa tggcccgcct    180
ggctgaccgc ccaacgaccc ccgcccattg acgtcaataa tgacgtatgt tcccatagta    240
acgccaatag ggactttcca ttgacgtcaa tgggtggagt atttacggta aactgcccac    300
ttggcagtac atcaagtgta tcatatgcca agtacgcccc ctattgacgt caatgacggt    360
aaatggcccg cctggcatta tgcccagtac atgaccttat gggactttcc tacttggcag    420
tacatctacg tattagtcat cgctattacc atggtgatgc ggttttggca gtacatcaat    480
gggcgtggat agcggtttga ctcacgggga tttccaagtc tccacccat tgacgtcaat    540
gggagtttgt tttggcacca aaatcaacgg gactttccaa aatgtcgtaa caactccgcc    600
ccattgacgc aaatgggcgg taggcgtgta cggtgggagg tctatataag cagagctctc    660
cctatcagtg atagagatct ccctatcagt gatagagatc gtcgacgagc tcgtttagtg    720
aaccgtcaga tcgcctggag acgccatcca cgctgttttg acctccatag aagacaccgg    780
gaccgatcca gcctccgcgg ccgggaacgg tgcattggaa cgcggattcc ccgtgccaag    840
agtgagatct tccgttatc taggtaccag atatcgccac catggcctg agcaaagtga     900
aactgaacga tacactgaac aaggaccagc tgctgtccag cagcaagtac accatccagc    960
ggagcaccgg cgacagcatc gataccccca ctacgacgtc gcagaagcac atcaacaagc   1020
tgtgcggcat gctgctgatc acagaggacg ccaaccacaa gttcaccggc ctgatcggca   1080
tgctgtacgc catgagccgg ctgggccggg aggacaccat caagatcctg cgggacgccg   1140
gctaccacgt gaaggccaat ggcgtggacg tgaccacaca ccggcaggac atcaacggca   1200
aagaaatgaa gttcgaggtg ctgaccctgg ccagcctgac caccgagatc cagatcaata   1260
tcgagatcga gagccggaag tcctacaaga aaatgctgaa agaaatgggc gaggttgccc   1320
ccgagtacag acacgacagc cccgactgcg gcatgatcat cctctgtatc gccgcccgg    1380
tgatcacaaa gctggccgct ggcgacagat ctggcctgac agcgtgatc agacgggcca   1440
acaatgtgct gaagaacgag atgaagcggt acaagggcct gctgcccaag gacattgcca   1500
acagcttcta cgaggtgttc gagaagtacc ccacttcat cgacgtgttc gtgcacttcg   1560
gcattgccca gagcagcacc agaggcggct ccagagtgga gggcatcttc gccggcctgt   1620
```

```
tcatgaacgc ctacggcgct ggccaggtga tgctgagatg gggcgtgctg ccaagagcg    1680
tgaagaacat catgctgggc cacgccagcg tgcaggccga gatggaacag gtggtggagg    1740
tgtacgagta cgcccagaag ctgggcgagg aggccggctt ctaccacatc ctgaacaacc    1800
ctaaggcctc cctgctgtcc ctgacccagt tccccccactt ctccagcgtg gtgctgggaa    1860
atgccggacg actgggcatc atgggcgagt accggggcac ccccagaaac caggacctgt    1920
acgacgccgc caaggcctac gccgagcagc tgaaagaaaa cggcgtgatc aactacagcg    1980
tgctggacct gaccgctgag gaactggaag ccatcaagca ccagctgaac cccaaggaca    2040
acgacgtgga gctgggaggc ggaggatctg gcggcgagg catgagcaga cggaacccct    2100
gcaagttcga gatccgggc cactgcctga cggcaagcg gtgccacttc agccacaact    2160
acttcgagtg gcccctcat gctctgctgg tgcggcagaa cttcatgctg aacggatcc    2220
tgaagtccat ggacaagagc atcgacaccc tgagcgagat cagcggagcc gccgagctgg    2280
acagaaccga ggaatatgcc ctgggcgtgg tgggagtgct ggaaagctac atcggctcca    2340
tcaacaacat cacaaagcag agcgcctgcg tggccatgag caagctgctg acagagctga    2400
acagcgacga catcaagaag ctgaggggaca acgaggaact gaacagcccc aagatcctgc    2460
tgtacaacac cgtgatcagc tacattgaga gcaaccgcaa gaacaacaag cagaccatcc    2520
atctgctgaa gcggctgccc gccgacgtgc tgaaaaagac catcaagaac ccctggaca    2580
tccacaagtc catcaccatc aacaatccca agaaagcac gtgtctgac accaacgatc    2640
acgccaagaa caacgacacc acctgatgag cggccgcat ctgctgtgcc ttctagttgc    2700
cagccatctg ttgttgccc ctcccccgtg ccttccttga ccctggaagg tgccactccc    2760
actgtccttt cctaataaaa tgaggaaatt gcatcgcatt gtctgagtag gtgtcattct    2820
attctggggg gtgggtggg gcaggacagc aaggggagg attgggaaga caatagcagg    2880
catgctgggg atgcggtggg ctctatgg                                        2908

SEQ ID NO: 8            moltype = AA  length = 594
FEATURE                 Location/Qualifiers
REGION                  1..594
                        note = Description of Artificial Sequence: Synthetic
                         polypeptide
source                  1..594
                        mol_type = protein
                        organism = synthetic construct
SEQUENCE: 8
MALSKVKLND TLNKDQLLSS SKYTIQRSTG DSIDTPNYDV QKHINKLCGM LLITEDANHK   60
FTGLIGMLYA MSRLGREDTI KILRDAGYHV KANGVDVTTH RQDINGKEMK FEVLTLASLT   120
TEIQINIEIE SRKSYKKMLK EMGEVAPEYR HDSPDCGMII LCIAALVITK LAAGDRSGLT   180
AVIRRANNVL KNEMKRYKGL LPKDIANSFY EVFEKYPHFI DVFVHFGIAQ SSTRGGSRVE   240
GIFAGLFMNA YGAGQVMLRW GVLAKSVKNI MLGHASVQAE MEQVVEVYEY AQKLGGEAGF   300
YHILNNPKAS LLSLTQFPHF SSVVLGNAAG LGIMGEYRGT PRNQDLYDAA KAYAEQLKEN   360
GVINYSVLDL TAEELEAIKH QLNPKDNDVE LGGGGSGGGG MSRRNPCKFE IRGHCLNGKR   420
CHFSHNYFEW PPHALLVRQN FMLNRILKSM DKSIDTLSEI SGAAELDRTE EYALGVVGVL   480
ESYIGSINNI TKQSACVAMS KLLTELNSDD IKKLRDNEEL NSPKIRVYNT VISYIESNRK   540
NNKQTIHLLK RLPADVLKKT IKNTLDIHKS ITINNPKEST VSDTNDHAKN NDTT          594

SEQ ID NO: 9            moltype = DNA  length = 3617
FEATURE                 Location/Qualifiers
misc_feature            1..3617
                        note = Description of Artificial Sequence: Synthetic
                         polynucleotide
source                  1..3617
                        mol_type = other DNA
                        organism = synthetic construct
SEQUENCE: 9
ccattgcata cgttgtatcc atatcataat atgtacattt atattggctc atgtccaaca    60
ttaccgccat gttgacattg attattgact agttattaat agtaatcaat tacggggtca   120
ttagttcata gcccatatat ggagttccgc gttacataac ttacggtaaa tggcccgcct   180
ggctgaccgc ccaacgaccc ccgcccattg acgtcaataa tgacgtatgt tcccatagta   240
acgccaatag ggactttcca ttgacgtcaa tgggtggagt atttacggta aactgcccac   300
ttggcagtac atcaagtgta tcatatgcca agtacgcccc ctattgacgt caatgacggt   360
aaatggcccg cctggcatta tgcccagtac atgaccttat gggactttcc tacttggcag   420
tacatctacg tattagtcat cgctattacc atggtgatgc ggttttggca gtacatcaat   480
gggcgtggat agcggtttga ctcacgggga tttccaagtc tccacccat tgacgtcaat   540
gggagtttgt tttggcacca aaatcaacgg gactttccaa aatgtcgtaa caactccgcc   600
ccattgacgc aaatgggcgg taggcgtgta cggtgggagg tctatataag cgaagcgct    660
ccctatcagt gatagagatc tccctatcag tgatagacga tcgacgagtc tcgcggcgg   720
gcgggagtcg ctgcgcgctg ccttcgcccc gtgccccgct ccgccgcgc ctcgcgccgc    780
ccgccccggc tctgactgac cgcgttacta aacacaggta agtgccgcc tcgcgccggt   840
tttgcgcgcct cccgcgggcg ccccctcct cacgggcagc gctgccacgt cagacgaagg    900
gcgcagcgag cgtcctgatc cttccgcccg gacgctcagg acagcggccc gctgctcata    960
agactcggcc ttagaaccc agtatcagca aaggacatt ttaggacggg acttgggtga   1020
ctctagggca ctggtttct ttccagagag cggaacaggc gaggaaaagt agtcccttct   1080
cggcgattct gcggagggat ctcgtgggg cggtgaacgc catgatgcc tctactaacc   1140
atgttcatgt tttctttttt tttctacagg tcctgggtga cgaacaggat atcgccacca   1200
tggaactgct gatcctgaag gccaacgcca tcaccatt cctgaccgcc gtgacctttct   1260
gcttcgccag cgcccagaac atcaccgagg aattctcaca gaagaccgtg agcgcgtga   1320
gcaaggcta cctgagcgcc ctgagaaccg gctggtacac cagcgtgatc accatcgagc   1380
tgagcaacat caaagaaac aagtgcacg gcaccgacgc caaagtgaag ctgatcaagc   1440
aggaactgga caagtacaag aacgccgtga ccgagctgca gctgctgatg cagagcaccc   1500
ccgccaccaa caaccgggcc agacgggagc tgccccggt catgaactac accctgaaca   1560
acgccaaaaa gaccaacgtg accctgagca agaagcggaa cgcgcggtc ctgggctttc   1620
```

```
tgctgggcgt gggcagcgcc attgccagcg gcgtggccgt gtctaaggtg ctgcacctgg   1680
aaggcgaagt gaacaagatc aagagcgccc tgctgagcac caacaaggcc gtggtgtccc   1740
tgagcaacgg cgtgagcgtg ctgaccagca aggtgctgga tctgaagaac tacatcgaca   1800
agcagctgct gcccatcgtg aacaagcaga gctgcagcat cagcaacatc gagacagtga   1860
tcgagttcca gcagaagaac aaccggctgc tggaaatcac ccgggagttc agcgtgaacg   1920
ccggcgtgac caccectgtg tccacctaca tgctgaccaa cagcgagctg ctgagcctga   1980
tcaacgacat gcccatcacc aacgaccaga aaaagctgat gagcaacaac gtgcagatcg   2040
tgcggcagca gagctactcc atcatgtcca tcatcaaaga agaggtgctg gcctacgtgg   2100
tgcagctgcc cctgtacggc gtgatcgaca cccctgctg gaagctgcac accagcccc    2160
tgtgcaccac caacaccaaa gagggcagca acatctgcct gacccggacc gacagaggct   2220
ggtactgcga caacgccggc agcgtgtcat tctttccaca ggccgagaca tgcaaggtgc   2280
agagcaaccg ggtgttctgc gacaccatga acagcctgac cctgccctcc gaagtgaacc   2340
tgtgcaacgt ggacatcttc aaccccaagt acgactgcaa gatcatgacc tccaagaccg   2400
acgtgtccag ctccgtgatc acctccctgg gcgccatcgt gtcctgctac ggcaagacca   2460
agtgcaccgc cagcaacaag aaccgggca tcatcaagac cttcagcaac ggctgcgact   2520
acgtgtccaa caaggggtg gacaccgtgt ccgtgggcaa cacectgtac tacgtgaaca   2580
aacaggaagg caagagcctg tacgtgaagg gcgagcccat catcaacttc tacgaccccc   2640
tggtgttccc cagcgacgag ttcgacgcca gcatcagcca ggtgaacgag aagatcaacc   2700
agagcctggc cttcatccgg aagtccgacg agctgctgca caatgtgaat gccggccaagt   2760
ccaccaccaa ctgatgagcg gccatctaat caacctctgg attacaaaat tgtgaaaga    2820
ttgactggta ttcttaacta tgttgctcct tttacgctat gtggatacgc tgctttaatg   2880
cctttgtatc atgctattgc ttcccgtatg gctttcattt tctcctcctt gtataaatcc   2940
tggttgctgt ctctttatga ggagttgtgg cccgttgtca ggcaacgtgg cgtggtgtgc   3000
actgtgtttg ctgacgcaac ccccactggt tggggcattg ccaccacctg tcagctcctt   3060
tccgggactt tcgctttccc cctccctatt gccacgcgg aactcatcgc cgcctgcctt    3120
gcccgctgct ggacagggtc tcggctgttg ggcactgaca attccgtgt gttgtcgggg    3180
aaatcatcgt cctttccttg gctgctcgcc tgtgttgcca cctggattct gcgcgggacg   3240
tccttctgct acgtccctt ggccctcaat ccagcggacc ttccttccg cggcctgctg     3300
ccggctctgc ggcctcttcc gcgtcttcgc cttcgccctc agacgagtcg gatctccctt   3360
tgggccgcct ccccgcctgc ggccgcgatc tgctgtgcct tctagttgcc agccatctgt   3420
tgtttgcccc tccccgtgc cttccttgac cctggaaggt gccactccca ctgtcctttc    3480
ctaataaaat gaggaaattg catcgcattg tctgagtagg tgtcattcta ttctgggggg   3540
tggggtgggg caggacagca agggggagga ttgggaagac aatagcaggc atgctgggga   3600
tgcggtgggc tctatgg                                                3617

SEQ ID NO: 10          moltype = AA  length = 524
FEATURE                Location/Qualifiers
REGION                 1..524
                       note = Description of Artificial Sequence: Synthetic
                        polypeptide
source                 1..524
                       mol_type = protein
                       organism = synthetic construct
SEQUENCE: 10
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVSKVLHL EGEVNKIKSA LLSTNKAVVS   180
LSNGVSVLTS KVLDLKNYID KQLLPIVNKQ SCSISNIETV IEFQQKNNRL LEITREFSVN   240
AGVTTPVSTY MLTNSELLSL INDMPITNDQ KKLMSNNVQI VRQQSYSIMS IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLHNVNAGK STTN                   524

SEQ ID NO: 11          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 11
GGGSGGG                                                              7

SEQ ID NO: 12          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 12
GGGGSGGGG                                                            9
```

The invention claimed is:

1. A simian adenoviral vector comprising two expression cassettes, wherein each expression cassette comprises a transgene and a promoter, and wherein the first expression cassette is inserted in the E1 region of the simian adenoviral vector, and the second expression cassette is inserted in a region of the adenoviral vector that is compatible with vector replication; the transgene of the first and second expression cassettes encode an antigen; and the first expression cassette and/or the second expression cassette comprises an enhanced human CMV promoter having a nucleic acid sequence having at least about 90% sequence identity to SEQ ID NO: 6.

2. The simian adenoviral vector of claim 1, wherein the second expression cassette is inserted in the E3 region of the simian adenoviral vector.

3. The simian adenoviral vector of claim 1, wherein the second expression cassette is inserted in the HE1 region of the simian adenoviral vector.

4. The simian adenoviral vector of claim 1, wherein the second expression cassette is inserted in the HE2 region of the simian adenoviral vector.

5. The simian adenoviral vector of claim 1, wherein the vector is a chimpanzee adenoviral vector.

6. The simian adenoviral vector of claim 1, wherein the vector is an adenovirus.

7. The simian adenoviral vector of claim 6, wherein the vector is ChAd155.

8. The simian adenoviral vector of claim 6, wherein the vector is ChAd83.

9. The simian adenoviral vector of claim 1, wherein the enhanced hCMV promoter has a nucleic acid sequence having at least about 95%, at least about 96%, at least about 97%, at least about 98%, or at least about 99% sequence identity to SEQ ID NO: 6.

10. The simian adenoviral vector of claim 1, wherein, the promoter comprises or consists of a nucleic acid sequence of SEQ ID NO: 6.

11. The simian adenoviral vector of claim 1, wherein the first and second expression cassettes comprise different promoters.

12. The simian adenoviral vector of claim 1, wherein the adenoviral vector is capable of infecting a mammalian cell.

13. The simian adenoviral vector of claim 1, wherein the first and/or second expression cassette further comprises a posttranscriptional regulatory element.

14. The simian adenoviral vector of claim 13, wherein the posttranscriptional regulatory element is a Woodchuck Hepatitis Posttranscriptional Regulatory Element.

15. A composition comprising a simian adenoviral vector of claim 1 and a pharmaceutically acceptable excipient.

16. A simian adenoviral vector according to claim 1 for the therapy or prophylaxis of a disease.

17. A method of inducing an immune response in a subject comprising administering the simian adenoviral vector according to claim 1 to the subject.

18. A method of inducing an immune response in a subject comprising administering the composition according to claim 15 to the subject.

* * * * *